(12) United States Patent
Medin et al.

(10) Patent No.: US 12,239,693 B2
(45) Date of Patent: Mar. 4, 2025

(54) USE OF LENTIVECTOR-TRANSDUCED T-Rapa CELLS FOR AMELIORATION OF LYSOSOMAL STORAGE DISORDERS

(71) Applicant: The Medical College of Wisconsin, Inc., Milwaukee, WI (US)

(72) Inventors: Jeffrey A. Medin, Shorewood, WI (US); Daniel H. Fowler, Milwaukee, WI (US); Murtaza S. Nagree, Milwaukee, WI (US); Tania Felizardo, Milwaukee, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 1005 days.

(21) Appl. No.: 17/050,949

(22) PCT Filed: Apr. 29, 2019

(86) PCT No.: PCT/US2019/029639
§ 371 (c)(1),
(2) Date: Oct. 27, 2020

(87) PCT Pub. No.: WO2019/210301
PCT Pub. Date: Oct. 31, 2019

(65) Prior Publication Data
US 2021/0322472 A1 Oct. 21, 2021

Related U.S. Application Data

(60) Provisional application No. 62/663,786, filed on Apr. 27, 2018.

(51) Int. Cl.
| | |
|---|---|
| C12N 15/86 | (2006.01) |
| A61K 35/17 | (2015.01) |
| A61K 38/44 | (2006.01) |
| A61K 38/47 | (2006.01) |
| A61K 39/00 | (2006.01) |
| A61P 43/00 | (2006.01) |
| C12N 5/0783 | (2010.01) |
| C12N 15/63 | (2006.01) |
| C12N 15/79 | (2006.01) |

(52) U.S. Cl.
CPC ............ *A61K 38/443* (2013.01); *A61K 38/47* (2013.01); *A61K 39/4611* (2023.05); *A61K 39/464* (2023.05); *A61P 43/00* (2018.01); *C12N 5/0636* (2013.01); *C12N 15/86* (2013.01); *A61K 2239/31* (2023.05); *A61K 2239/38* (2023.05); *C12N 15/79* (2013.01); *C12N 2510/00* (2013.01); *C12Y 101/01205* (2013.01); *C12Y 302/01022* (2013.01)

(58) Field of Classification Search
CPC ........ C12N 15/79; C12N 15/85; C12N 15/86; C12N 15/63; C12N 5/0636; C12N 2510/00; A61K 35/17; C07H 21/04
See application file for complete search history.

(56) References Cited

U.S. PATENT DOCUMENTS

| | | |
|---|---|---|
| 6,013,516 A | 1/2000 | Verma et al. |
| 6,207,455 B1 | 3/2001 | Chang |
| 6,235,522 B1 | 5/2001 | Kingsman et al. |
| 6,277,633 B1 | 8/2001 | Olsen |
| 6,326,007 B1 | 12/2001 | Yilma et al. |
| 6,627,442 B1 | 9/2003 | Humeau et al. |
| 7,045,508 B2 | 5/2006 | Scaria |
| 7,575,924 B2 | 8/2009 | Trono et al. |
| 7,968,332 B2 | 6/2011 | Charneau et al. |
| 8,329,462 B2 | 12/2012 | Trono et al. |
| 8,349,606 B2 | 1/2013 | Charneau et al. |
| 8,551,773 B2 | 10/2013 | Trono et al. |
| 8,652,807 B2 | 2/2014 | Charneau et al. |
| 9,023,646 B2 | 5/2015 | Trono et al. |
| 9,387,236 B2 | 7/2016 | Olmstead |
| 9,476,062 B2 | 10/2016 | Trono et al. |
| 9,662,375 B2 | 5/2017 | Jensen et al. |
| 9,988,644 B2 | 6/2018 | Heffner et al. |
| 10,501,759 B2 | 12/2019 | Heffner et al. |
| 10,532,085 B2 | 1/2020 | Jensen et al. |
| 10,584,351 B2 | 3/2020 | Roeth et al. |
| 10,907,177 B2 | 2/2021 | Heffner et al. |
| 11,149,285 B2 | 10/2021 | Tubert et al. |
| 11,571,407 B2 | 2/2023 | Farrera-Sinfreu et al. |
| 11,834,668 B2 | 12/2023 | Heffner et al. |
| 2002/0123471 A1 | 9/2002 | Uberla |
| 2012/0315263 A1 | 12/2012 | Olmstead |

(Continued)

FOREIGN PATENT DOCUMENTS

| | | |
|---|---|---|
| EP | 3293259 A1 | 3/2018 |
| WO | 9904026 A2 | 1/1991 |

(Continued)

OTHER PUBLICATIONS

Wu et al., 2012 (Aging Research reviews, vol. 11, p. 32-40).*
Agrahari et al., 2017 (Expert Opinion on Drug Delivery, vol. 14, No. 10, p. 1145-1162).*
Ikonomou et al., 2017 (Am J Respir Crit Care Med, vol. 195, p. 13-14).*
Domm et al., 2021 (Molecular Genetics and Metabolism, vol. 134, p. 117-131).*
Ikehara et al., 2013 (Frontier in Cell and Developmental Biology, vol. 1, Article 2, p. 1-2).*
Cooper et al., 2015 (International Journal of Surgery, vol. 23, p. 211-216).*

(Continued)

*Primary Examiner* — Shin Lin Chen
(74) *Attorney, Agent, or Firm* — Quarles & Brady LLP

(57) ABSTRACT

The present disclosure provides methods of treating lysosomal storage disorders, e.g., Fabry disease, Gaucher disease, Farber disease, and Pompe disease. The method comprises producing vector-transduced T-Rapa cells that express a transgene of interest and administering the cells to a patient in need thereof. The T-Rapa cells may be transduced with a dual promoter lentivirus vector.

12 Claims, 29 Drawing Sheets
Specification includes a Sequence Listing.

(56) References Cited

U.S. PATENT DOCUMENTS

| | | |
|---|---|---|
| 2013/0195800 A1 | 8/2013 | Roeth et al. |
| 2013/0230506 A1 | 9/2013 | Jensen et al. |
| 2014/0010861 A1 | 1/2014 | Bancel et al. |
| 2014/0234278 A1 | 8/2014 | Heffner et al. |
| 2016/0208285 A1 | 7/2016 | Roeth et al. |
| 2016/0296563 A1 | 10/2016 | Sourdive et al. |
| 2016/0317489 A1 | 11/2016 | Farrera-Sinfreu et al. |
| 2016/0317627 A1 | 11/2016 | Olmstead |
| 2017/0056558 A1 | 3/2017 | Kajaste-Rudnitski |
| 2017/0088859 A1 | 3/2017 | Bosch Tubert et al. |
| 2017/0165303 A1 | 6/2017 | Olmstead |
| 2017/0266263 A1 | 9/2017 | Jensen et al. |
| 2017/0360900 A1 | 12/2017 | Agard et al. |
| 2018/0002719 A1 | 1/2018 | Roeth et al. |
| 2018/0363004 A1 | 12/2018 | Heffner et al. |
| 2020/0048657 A1 | 2/2020 | Heffner et al. |
| 2020/0121740 A1 | 4/2020 | Olmstead |
| 2020/0181582 A1 | 6/2020 | Medin |
| 2020/0188492 A1 | 6/2020 | Jensen et al. |
| 2020/0239906 A1 | 7/2020 | Roeth et al. |
| 2021/0171980 A1 | 6/2021 | Heffner et al. |
| 2022/0374361 A1 | 11/2022 | Jensen et al. |

FOREIGN PATENT DOCUMENTS

| | | | |
|---|---|---|---|
| WO | 0134843 | A1 | 5/2001 |
| WO | 03029412 | A2 | 4/2003 |
| WO | 03029414 | A2 | 4/2003 |
| WO | 2009114942 | A1 | 9/2009 |
| WO | 2016183593 | A2 | 11/2016 |
| WO | 2017093464 | A1 | 6/2017 |
| WO | 2018132667 | A1 | 7/2018 |
| WO | 2019046815 | A1 | 3/2019 |

OTHER PUBLICATIONS

Liu et al., 2017 (Frontiers in Immunology, vol. 8, article 645, p. 1-6).*

National Institute of Neurological Disorders and Stroke (NINDS), 2023 (Fabry Disease, p. 1-2).*

Huang et al., Jun. 2017 (Molecular Therapy: Methods & Clinical Development, vol. 5, p. 241-258).*

Nagree, M. et al., Expert Opinion on Biological Therapy, vol. 19, No. 7, 2019, pp. 655-670.

Sands, M. et al., Molecular Therapy, vol. 13, No. 5, May 2006, pp. 839-849.

Dahl, M. et al., Molecular Therapy, vol. 23, No. 5, May 2015, pp. 835-844.

Harrison, F. et al., Molecular Therapy, vol. 21, No. 2, Feb. 2013, pp. 433-444.

Dunbar, C. et al., Human Gene Therapy, vol. 9, No. 17, Nov. 20, 1998, pp. 2629-2640.

Biffi, A. et al., Science, American Association for the Advancement of Science, vol. 341, No. 6148, Aug. 23, 2013, pp. 1-16.

Fowler, D. H., et al. "Phase 2 clinical trial of rapamycin-resistant donor CD4+ Th2/Th1 (T-Rapa) cells after low-intensity allogeneic hematopoietic cell transplantation." Blood 121.15 (2013): 2864-2874.

Huang, J., et al. "Lentivector iterations and pre-clinical scale-up/toxicity testing: Targeting mobilized CD34+ cells for correction of Fabry disease." Molecular Therapy—Methods & Clinical Development 5 (2017): 241-258.

International Searching Authority. International Search Report and Written Opinion for application PCT/US2019/029639. Mailed on Jul. 15, 2019. 16 pages.

Miller, J. J., et al. "Glycolipid Storage and Phenotypes in a New Rat Model of Fabry Disease." The FASEB Journal 31 (2017): 953-2.

Naldini, L., et al. "In vivo gene delivery and stable transduction of nondividing cells by a lentiviral vector." Science 272.5259 (1996): 263-267.

Pacienza, N., et al. (2012). Lentivector Transduction Improves Outcomes Over Transplantation of Human HSCs Alone in NOD/SCID/Fabry Mice. Molecular Therapy, 20(7), 1454-1461.

Rombach, S. M., et al. "Long term enzyme replacement therapy for Fabry disease: effectiveness on kidney, heart and brain." Orphanet journal of rare diseases 8.1 (2013): 1-9.

Wang, J.C., et al. (2013). Engineering lentiviral vectors for modulation of dendritic cell apoptotic pathways. Virol. J. 10, 240.

Yoshimitsu, M., et al. "Bioluminescent imaging of a marking transgene and correction of Fabry mice by neonatal injection of recombinant lentiviral vectors." Proceedings of the National Academy of Sciences 101.48 (2004): 16909-16914.

Zufferey, R., et al. "Multiply attenuated lentiviral vector achieves efficient gene delivery in vivo." Nature biotechnology 15.9 (1997): 871-875.

Brady, R. et al., Enzymatic Defect in Fabry's Disease: Ceramidetrihexosidase Deficiency, New England Journal of Medicine, 1967, 276(21):1163-1167.

Brady, R. et al., Replacement Therapy for Inherited Enzyme Deficiency: Use of Purified Ceramidetrihexosidase in Fabry's Disease, New England Journal of Medicine, 1973, 289:9-14.

Gargulak, K. et al., Post-Infusion Cell Enrichment: Gaucher Disease as a Model, Molecular Therapy, 2018, 26 (5S1):253-254.

Jonnalagadda, M. et al., Engineering Human T Cells for Resistance to Methotrexate and Mycophenolate Mofetil as an In Vivo Cell Selection Strategy, PloS One, 2013, 8(6):e65519, pp. 1-10.

Kim, E. et al., Long-Term Expression of the Human Glucocerebrosidase Gene In Vivo After Transplantation of Bone-Marrow-Derived Cells Transformed with a Lentivirus Vector, Journal of Gene Medicine, 2005, 7:878-887.

Medin, J. et al., Correction in Trans for Fabry Disease: Expression, Secretion and Uptake of Alpha-Galactosidase A in Patient-Derived Cells Driven by a High-Titer Recombinant Retroviral Vector, Proceedings of the National Academy of Sciences, 1996, 93:7917-7922.

Nagree, M. et al., Towards In Vivo Amplification: Overcoming Hurdles in the Use of Hematopoietic Stem Cells in Transplantation and Gene Therapy, World Journal of Stem Cells, 2015, 7(11):1233-1250.

Nagree, M. et al., In Vivo Enrichment of Transduced Cells to Enhance Gene Therapy for Fabry Disease, Molecular Genetics and Metabolism, 2018, 123:S102-S103.

Nagree, M. et al., An In Vivo Enrichment Platform to Enhance Hematopoietic Cell-Directed Gene Therapy, Molecular Therapy, 2018, 26(5S1):253.

Sangiolo, D. et al., Lentiviral Vector Conferring Resistance to Mycophenolate Mofetil and Sensitivity to Ganciclovir for In Vivo T-cell Selection, Gene Therapy, 2007, 14:1549-1554.

Shi, Q. et al., Lentivirus-Mediated Platelet-Derived Factor VIII Gene Therapy in Murine Haemophilia A, Journal of Thrombosis and Haemostasis, 2007, 5:352-361.

Singh, R. et al., Protein Engineering Approaches in the Post-Genomic Era, Current Protein and Peptide Science, 2017, 18:1-11.

Yam, P. et al., Ex Vivo Selection and Expansion of Cells Based on Expression of a Mutated Inosine Monophosphate Dehydrogenase 2 after HIV Vector Transduction: Effects on Lymphocytes, Monocytes, and CD34+ Stem Cells, Molecular Therapy, 2006, 14(2):236-244.

Yu, X. et al., Lentiviral Vectors with Two Independent Internal Promoters Transfer High-Level Expression of Multiple Transgenes to Human Hematopoietic Stem-Progenitor Cells, Molecular Therapy, 2003, 7(6):827-838.

Zhang, M. et al., Propagated Perturbations from a Peripheral Mutation Show Interactions Supporting WW Domain Thermostability, Structure, 2018, 26:1474-1485.

China National Intellectual Property Administration, First Office Action and Search Report, Application No. 201980043179.X, Jan. 31, 2024, 21 pages.

European Patent Office, Extended European Search Report, Application No. 23190055.6, Feb. 6, 2024, 7 pages.

* cited by examiner

A. α-gal A in cell lysates (inside cells)

B. α-gal A in supernatant (secreted from cells)

Raw activity data for all mice engrafted

| Cells | Mouse | nmols/hr/mL | Engraftment %hCD3 | |
|---|---|---|---|---|
| NT | ND2-1 ♀#3 | 1.056 | 69.7 | |
| NT | ND2-1 ♀#4 | 0.225 | 67.5 | |
| NT | ND2-2 ♀#3 | 1.177 | 54.1 | |
| NT | ND2-2 ♂#3 | 1.294 | 69.8 | Healthy Donor |
| LV/AGA | ND2-1 ♀#1 | 14.882 | 64 | |
| LV/AGA | ND2-1 ♀#5 | 26.658 | 92.3 | |
| LV/AGA | ND2-1 ♂#2 | 0.530 | 10.2 | |
| LV/AGA | ND2-2 ♀#2 | 31.113 | 14.6 | |
| LV/AGA | ND2-2 ♂#1 | 8.254 | 3.19 | |

| Cells | Mouse | nmols/hr/mL | Engraftment %hCD3 | |
|---|---|---|---|---|
| NT | FD2-2 ♂#1 | 0.171 | 93.70 | |
| NT | FD2-2 ♂#2 | 0.159 | 96.90 | |
| NT | FD2-1 ♀#4 | 0.073 | 93.80 | |
| NT | FD2-1 ♂#1 | 0.184 | 93.90 | |
| LV/AGA | FD2-2 ♂#4 | 2.749 | 93.80 | Fabry Donor |
| LV/AGA | FD2-2 ♀#2 | 3.771 | 80.70 | |
| LV/AGA | FD2-1 ♀#2 | 0.811 | 14.40 | |
| LV/AGA | FD2-1 ♀#5 | 4.940 | 86.60 | |
| LV/AGA | FD2-1 ♂#4 | 1.350 | 29.10 | |

FIG. 8

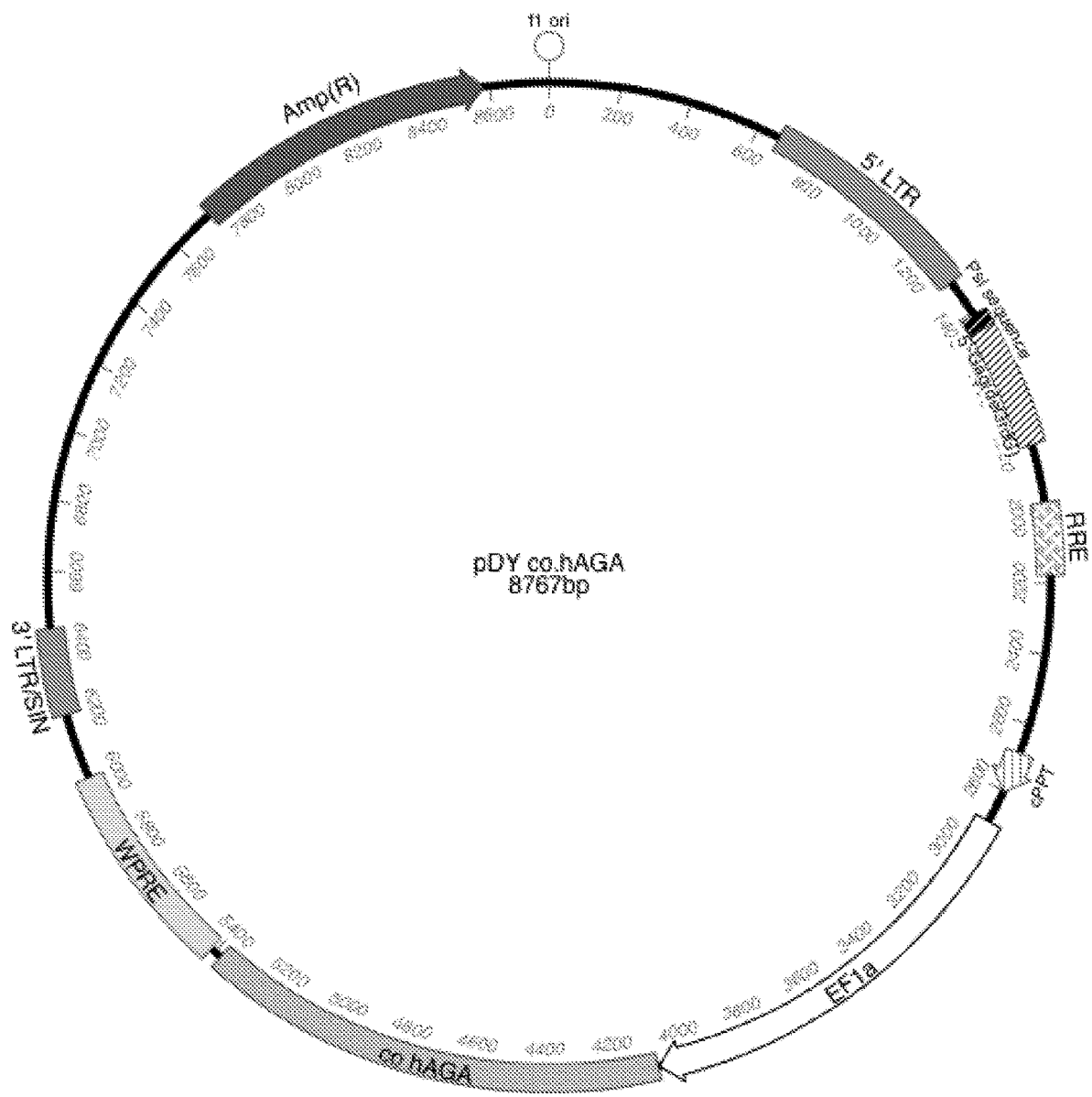
FIG. 13A (lentiviral vector containing AGA which can express α-gal A)

FIG. 13B (dual promoter AGA/IY)

(Lentiviral vector encoding human GBA, SEQ ID NO:4)

(Lentiviral vector encoding human ASAH1, SEQ ID NO:5)

(Lentiviral vector encoding human GAA, SEQ ID NO:6)

USE OF LENTIVECTOR-TRANSDUCED T-Rapa CELLS FOR AMELIORATION OF LYSOSOMAL STORAGE DISORDERS

CROSS-REFERENCE TO RELATED APPLICATIONS

This application claims priority to U.S. Provisional Application No. 62/663,786, filed on Apr. 27, 2018, the contents of which are incorporated by reference in its entirety.

STATEMENT REGARDING FEDERALLY SPONSORED RESEARCH

This invention was made with government support under Project Number ZIA BC 011219 awarded by the National Cancer Institute. The government has certain rights in the invention.

BACKGROUND OF THE INVENTION

The field of the invention is treatment of lysosomal storage disorders (LSD, lysosomal storage diseases). LSD are associated with dysregulation or deficiency of a single protein (such as Fabry disease) or combinations of an enzyme deficiency and co-activator proteins.

Lysosomes are membrane-bound organelles in eukaryotic cells that contain more than 60 different enzymes capable of digesting nearly any biomolecule. They carry out many critical biological functions, including acting as the cell's waste disposal system by digesting unwanted materials in the cytoplasm, both from outside of the cell and obsolete components inside the cell. Lysosomal Storage Disorders (LSD) are a group of more than 60 rare inherited metabolic disorders that result from lysosome dysfunction, usually as a consequence of a deficiency in a single enzyme required for the intracellular digestion of lipids, glycoproteins or polysaccharides. As a result of such deficiencies, the molecules that would normally be degraded accumulate inside the cell, leading to dysfunction or death of the cell.

Fabry disease is a LSD resulting from a deficiency in the enzyme α-galactosidase A (α-gal A encoded by the AGA transgene), an enzyme that hydrolyses α-galactose from glycosphingolipids, in particular globotriaosylceramide ($Gb_3$).

The standard-of-care treatment for Fabry disease is enzyme replacement therapy (ERT). The efficacy of ERT is outlined by Rombach et al. (Orphanet J Rare Dis. 8:47-10.1186/1750-1172-8-47 (2013)). While some benefits can be obtained, disease progression is not halted. ERT requires lengthy intravenous infusions of recombinant α-gal A administered every couple of weeks, often at an outpatient center. Fabry patients often require treatment for pain, gastrointestinal dysfunction, arrhythmias and other heart problems, as well as needing blood thinners and blood pressure medications to protect kidney functions. Although Fabry disease is relatively rare, there are about 4000 patients in the US, treatment costs are on the order of $300,000/year/patient ($1.2 B/year for all US patients).

Hematopoietic stem cells (HSCs) are "multipotent" cells residing in bone marrow that can ultimately differentiate into all blood cell types. A characteristic of HSCs is their expression of a cell surface glycoprotein called CD34, and such cells are sometimes referred to as CD34+ hematopoietic cells, or more simply as CD34+ HSCs. Clinically, the presence of CD34 on HSCs can be used to facilitate selective enrichment of HSCs for bone marrow transplants. In addition, CD34+ HSCs have been used experimentally to treat a variety of non-hematopoietic diseases including spinal cord injuries, liver cirrhosis, and peripheral vascular disease. HSCs can be harvested from bone marrow, but may also be harvested from peripheral blood after treatment with certain drugs to 'mobilize' them. Thus, HSCs can be harvested from blood (e.g., by apheresis). HSCs are also "mobile", meaning that they can move from bone marrow into the blood stream to different sites in the body. HSCs can be administered by injection into the blood stream in order to repopulate bone marrow.

The inventors have previously used HSCs harvested from Fabry patients to genetically modify the HSCs to produce α-gal A, the enzyme deficient in patients with Fabry disease. These genetically modified HSCs are infused back into the same patients (autologous grafts) after patients have been "conditioned" by drug regimens to ablate the endogenous HSCs in order to improve the success of the therapy.

Upon re-introduction of the patient's modified cells back into the patient, the genetically modified HSCs will populate all downstream lineages of the hematopoietic system and then circulate throughout the body. The modified cells secrete a form of α-gal A with a molecular "tag" (mannose-6-phosphate) which enables uncorrected "bystander" cells in the patient to take up and transport the α-gal A intracellularly into their lysosomes, where they compensate for the patient's α-gal A deficiency, and effectively degrade the accumulated glycosphingolipids. This method is undergoing clinical trials in Canada (ClinicalTrials.gov #NCT02800070).

The core tenet of the prior protocol is that the genetically modified HSCs will differentiate into all possible blood cell (hematopoietic) lineages and circulate throughout the body. However, due to inefficiency of engraftment, it is necessary to condition recipients by hematologic ablation. The degree of ablation can determine the efficiency of engraftment in most cases. In addition, there is a limitation on the numbers of transduced bonafide stem cells that can be obtained and employed to correct the disease. Even using autologous grafts, additional rounds of transplantation may be necessary to effectively treat the disease.

Thus, there is a need to fine a renewable source of cells within a subject that can be used for therapy and will require minimal or no ablation of the patient.

SUMMARY OF THE INVENTION

The present invention overcomes the aforementioned drawbacks by providing methods of treating lysosomal storage disorders.

In one aspect, the disclosure provides a method of treating a lysosomal storage disorder in a subject, the method comprising the steps of: (a) conditioning T-cells from the subject or suitable donor with rapamycin ex vivo to generate T-Rapa cells; (b) transducing the T-cells in vitro with a vector comprising a transgene of interest that encodes an enzyme associated with a lysosomal storage disorder; and (c) administering the transduced T-Rapa cells to the subject, wherein the T-Rapa cells express the enzyme associated with the lysosomal storage disorder in the subject and reduce one or more symptoms of the lysosomal storage disorder. In some aspect, the method after step (b) comprises expanding the vector-transduced T-Rapa cells by culturing in vitro, and step (c) comprises administering the transduced and expanded T-Rapa cells to the subject.

In another aspect, the disclosure provides a method of treating a lysosomal storage disorder in a subject, the method comprising the steps of: (a) obtaining T-cells from the subject or a suitable donor, (b) conditioning the T-cells with rapamycin ex vivo to generate T-Rapa cells; (c) transducing the T-cells in vitro with a vector that expresses the transgene of interest in the T-Rapa cells; (d) in vitro expanding the vector-transduced T-Rapa cells in culture, and (e) administering T-Rapa cells into the subject, wherein the T-Rapa cells express the transgene of interest in the subject and reduce one or more symptoms of the lysosomal storage disorder.

In some embodiments, the administering step is by transfusion or intravenous injection.

In some aspects the method further comprises maintaining and expanding the vector-transduced T-Rapa cells in in vitro culture and storing a portion of the vector-transduced T-Rapa cells for future administration to the subject.

In another aspect, the disclosure provides a method of producing a population of transduced T-Rapa cells that express an enzyme encoded by a transgene of interest for the treatment of a lysosomal storage disorder, the method comprising: (a) conditioning T-cells from a subject or a suitable donor with rapamycin, producing a population of T-Rapa cells; and (b) transducing the T-Rapa cells in vitro with a vector comprising the transgene of interest to produce a population of transduced T-Rapa cells. This method produces transduced T-Rapa cells able to express the protein (e.g. enzyme) encoded by the transgene of interest. In some aspects, the method further comprises (c) in vitro expanding the vector-transduced T-Rapa cells in culture.

In another aspect, the disclosure provides a method of producing a population of transduced T-Rapa cells that express a transgene of interest for the treatment of a lysosomal storage disorder, the method comprising: (a) obtaining T-cells from the subject or a suitable donor, (b) conditioning the T-cells with rapamycin, producing T-Rapa cells; and (c) transducing the T-Rapa cells in vitro with a vector that expresses a transgene of interest in the T-Rapa cell. In some aspects, the method further comprises (d) in vitro expanding the vector-transduced T-Rapa cells in culture.

In yet another aspect, the disclosure provides a method of treating a subject with Fabry disease, the method comprising administering an effective amount of the transduced T-Rapa cells made by the method described herein that express α-gal A to treat one or more symptoms of Fabry disease.

In another aspect, the disclosure provides a population of transduced T-Rapa cells that express a protein encoded by a transgene of interest. In one aspect, the disclosure provides a population of transduced T-Rapa cells that express α-gal A. In another aspect, the disclosure provides a population of transduced T-Rapa cells that express β-glucocerebrosidase. In another aspect, the disclosure provides a population of transduced T-Rapa cells that express acid ceramidase. In another aspect, the disclosure provides a population of transduce T-Rapa cells that express acid α-glucosidase.

In yet another aspect, the disclosure provides a method of treating a subject with Gaucher disease, the method comprising administering an effective amount of the transduced T-Rapa cells that express GBA to treat one or more symptoms of Gaucher disease.

In yet another aspect, the disclosure provides a method of treating a subject with Farber disease, the method comprising administering an effective amount of the transduced T-Rapa cells that express ASAH1 to treat one or more symptoms of Farber disease.

In a further aspect, the disclosure provides a method of treating a subject with Pompe disease, the method comprising administering an effective amount of the transduced T-Rapa cells that express GAA to treat one or more symptoms of Pompe disease.

In yet another aspect, the disclosure provides a method of treating a subject with a lysosomal storage disorder, the method comprising administering transduced T-Rapa cells expressing a transgene associated with treatment of the lysosomal storage disorder in an effective amount to treat one or more symptom of the lysosomal storage disorder.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

BRIEF DESCRIPTION OF THE DRAWINGS

FIG. 8 is the raw data from the mouse experiments of Example 5 and FIG. 7.

Figure 12A:
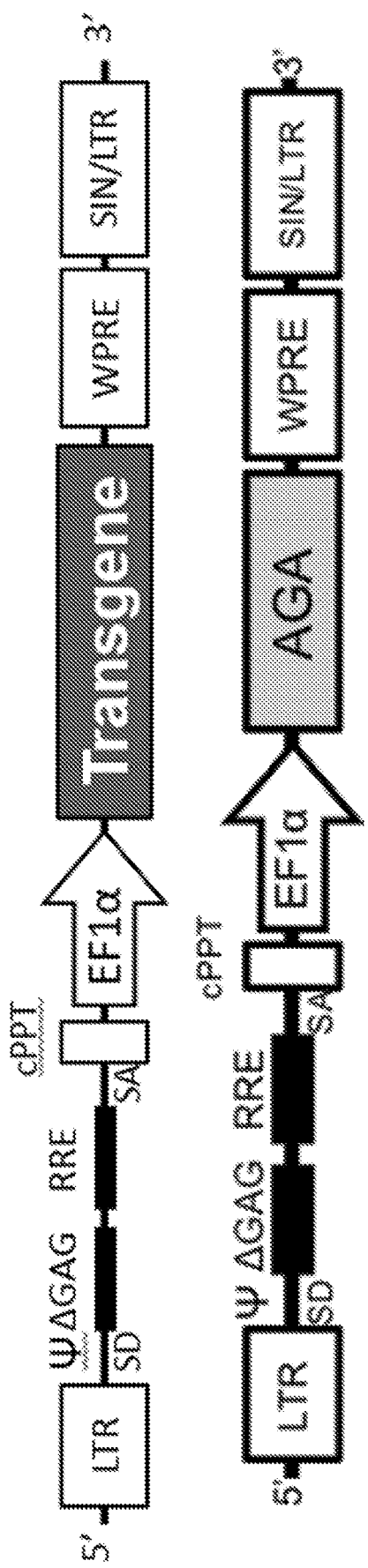
FIG. 12A is a schematic of a suitable lentiviral vector able to be used in the present methods; pDY/CO.α-galA (i.e., LV/AGA) to express α-gal A. LTR, long terminal repeat, Ψ, HIV packaging signal; SD, 5' splice donor site; ΔGAG, truncated portion of HIV-1 group specific antigen gene; RRE, Rev-response element; SA, 3' splice acceptor site; cPPT, central polypurine tract; EF-1α, elongation factor 1 a promoter; CO.α-gal A, codon-optimized cDNA of the human GLA gene encoding the wild-type α-gal A enzyme; WPRE, woodchuck hepatitis virus post-transcriptional regulatory element; SIN/LTR, self-inactivating LTR.
Figure 12B:
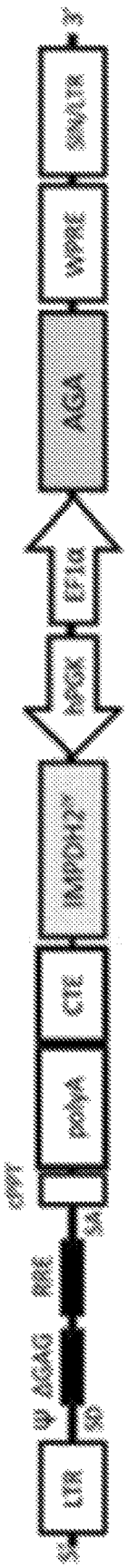
FIG. 12B is a schematic of a dual promoter lentiviral vector containing codon optimized and mutated IMPDH2 cDNA sequence (IMPDH2(IY)) and AGA codon optimized transgene as described in FIG. 12A.
Figure 12C:
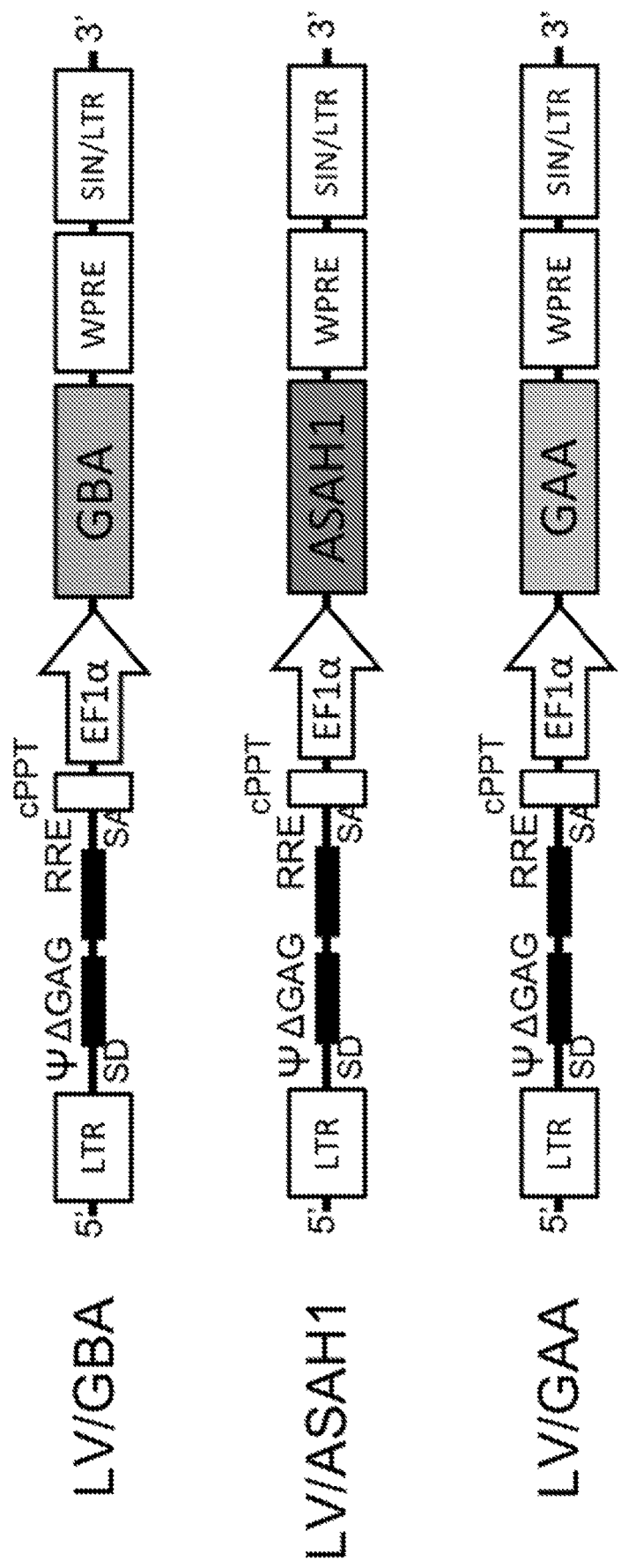

FIG. 12C shows exemplary schema of lentiviral vectors containing the GBA, ASAH1 and GAA gene, respectively.

FIG. 13A is the plasmid map of the lentiviral vector expressing α-gal A (SEQ ID NO:3).

FIG. 13B is a plasmid map of dual promoter lentiviral vector containing the mutant IMPDH2 gene (IMPDH2(IY)) and AGA codon optimized gene (vector: SEQ ID NO:4).

Figure 13C:
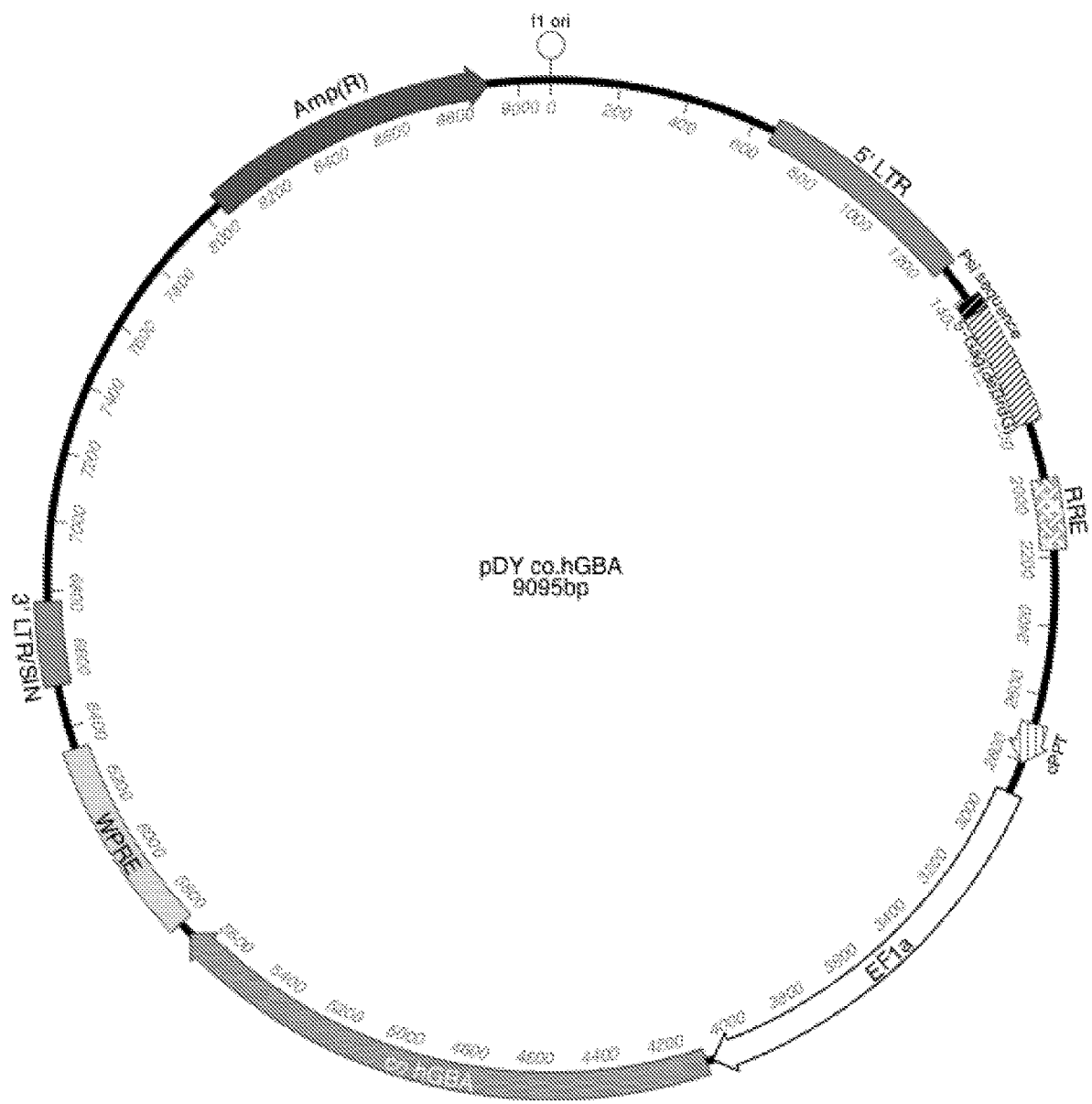

FIG. 13C is a plasmid map made of the lentiviral vector containing a wild-type codon optimized GBA transgene (SEQ ID NO:4).

Figure 13D:
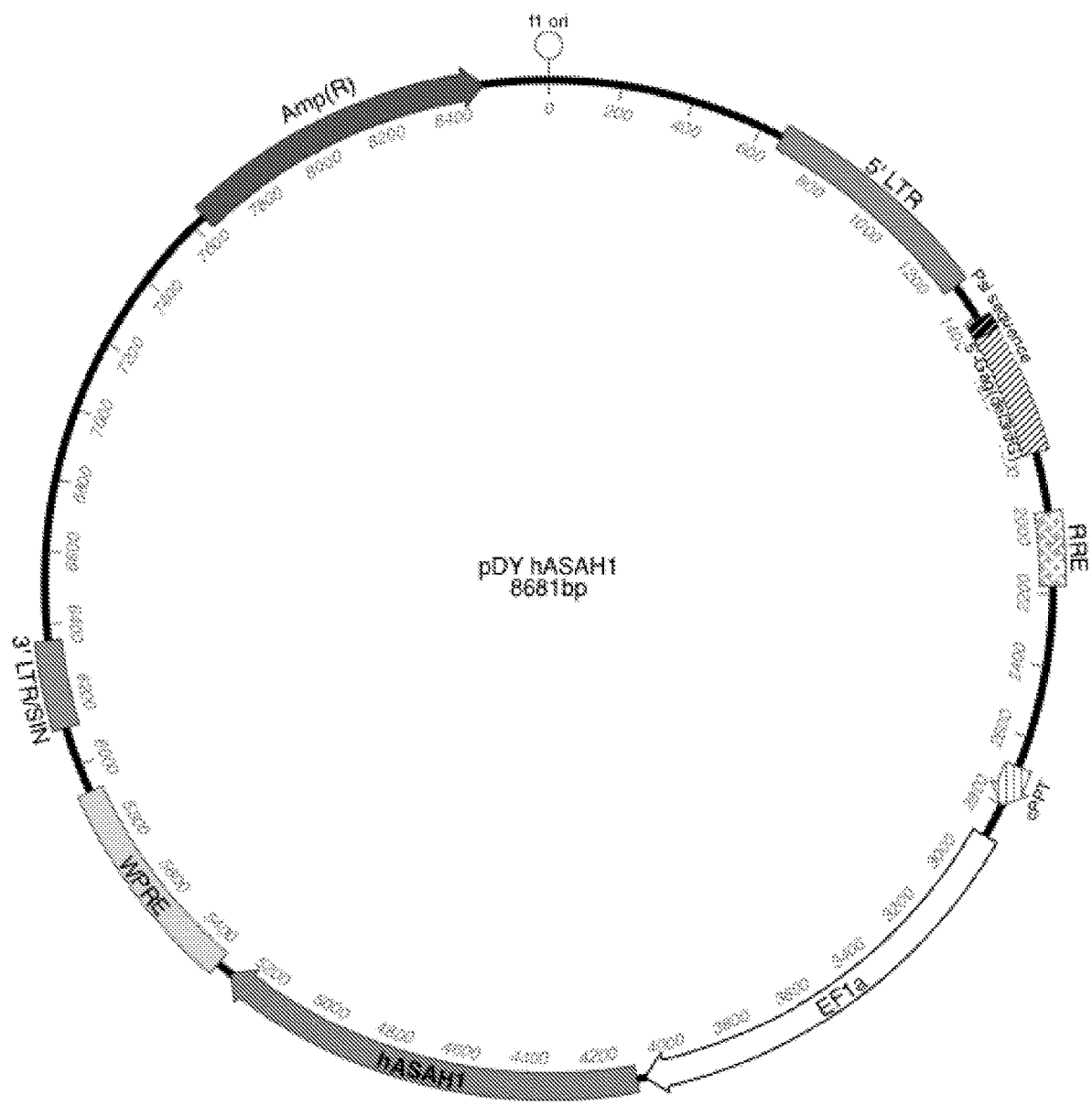

FIG. 13D is a plasmid map of the lentiviral vector containing a wild-type ASAH1 transgene (SEQ ID NO5).

Figure 13E:
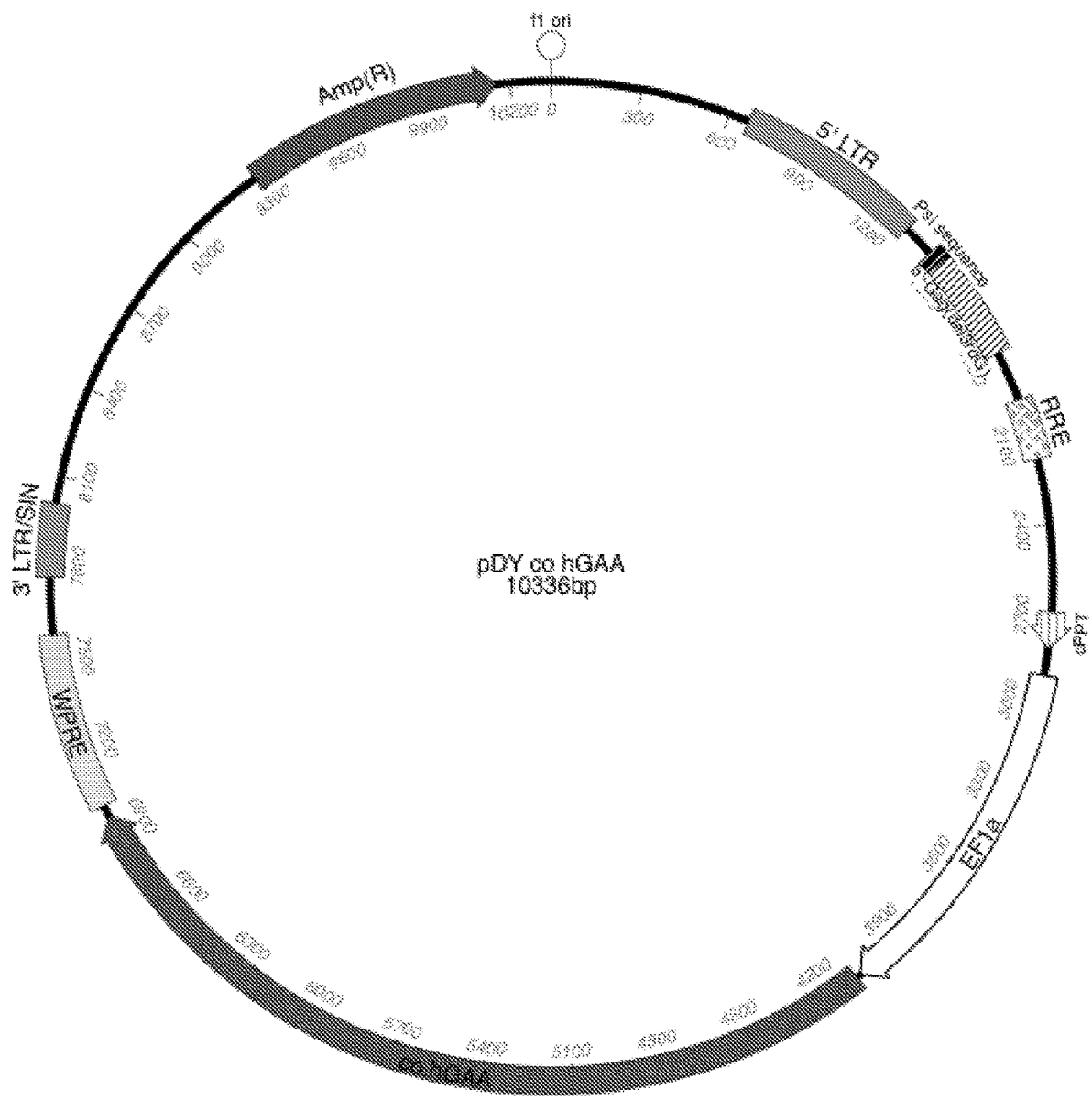

FIG. 13E is a plasmid map of the lentiviral vector containing a wild-type codon optimized GAA transgene (SEQ ID NO:6).

Figure 14:
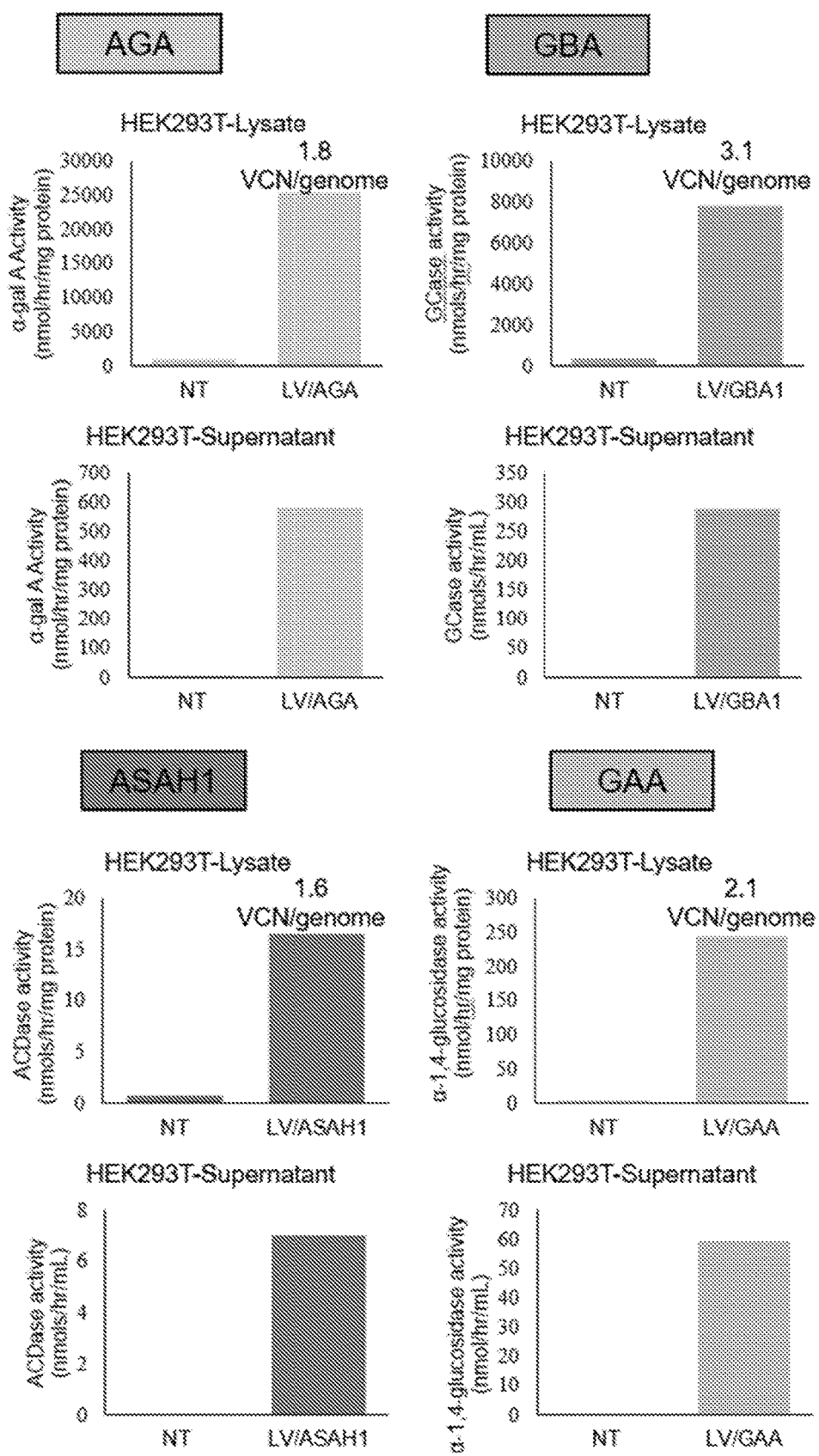

FIG. 14 demonstrates the ability of the lentiviruses encoding AGA, GBA, ASAH1 or GM to express and produce the corresponding enzyme within transduced HEK293T cells.

Figure 15:
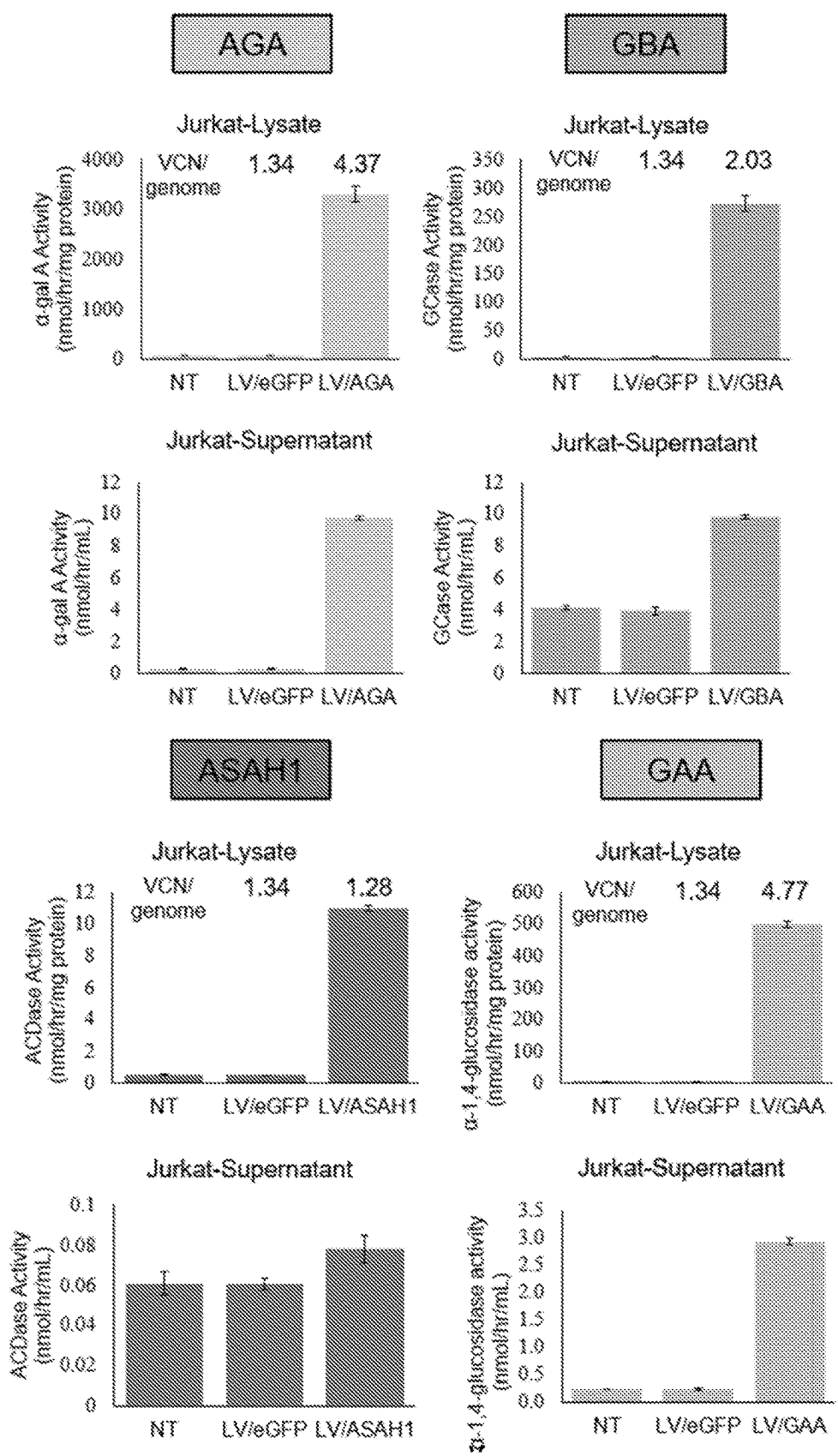

FIG. 15 demonstrates the ability of the lentiviruses encoding the enzymes of the transgenes AGA, GBA, ASAH1 or GM to express and secrete the corresponding enzyme within transduced Jurkat cells.

Figure 16:
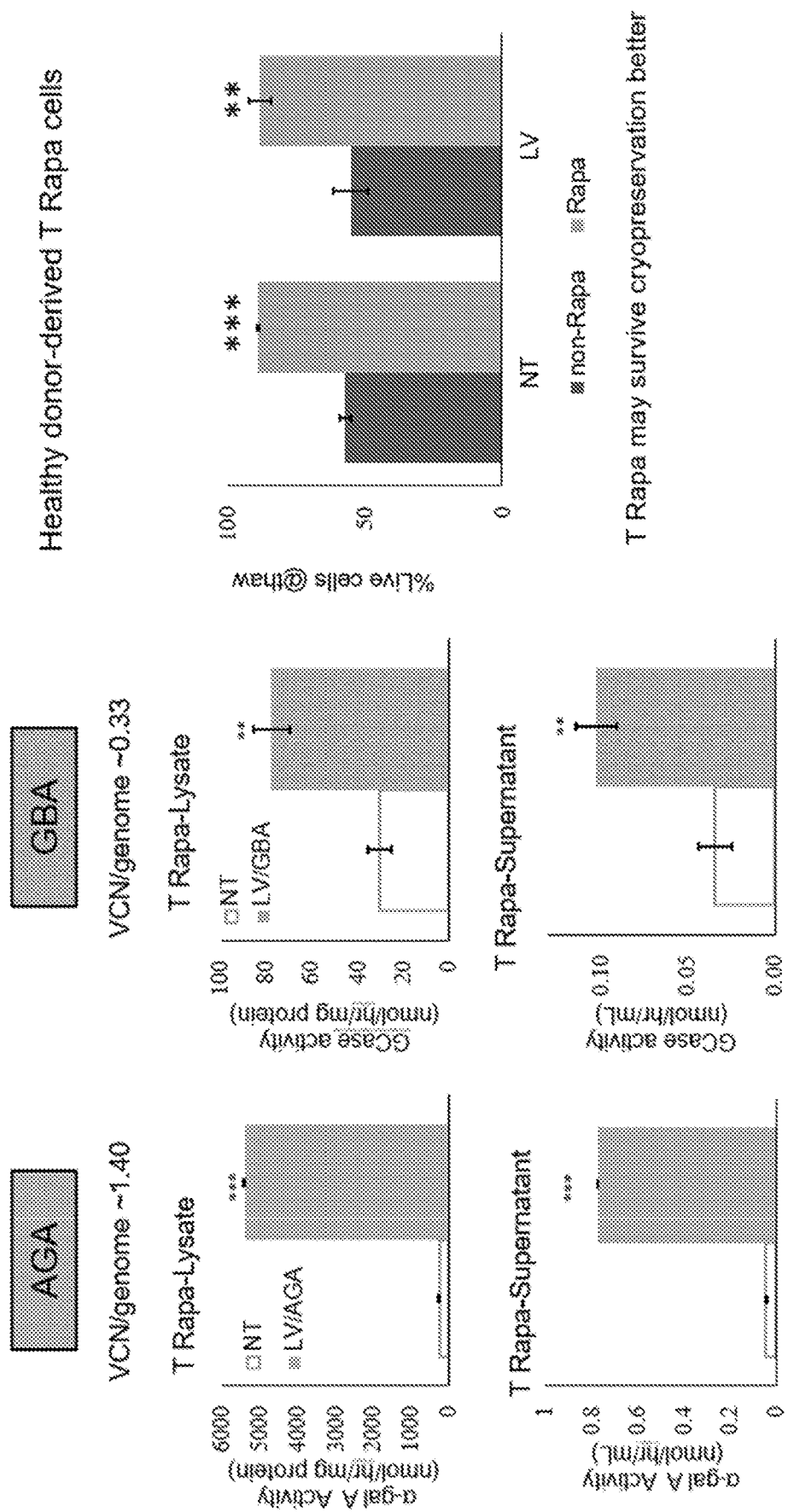

FIG. 16 demonstrates the ability of the lentivirus vectors encoding the enzyme associated with either AGA transgene or GBA transgene to be transduced into T-Rapa cells (from healthy donors), and the ability of the T-Rapa cells to survive cryopreservation and subsequent thawing.

Figure 17:
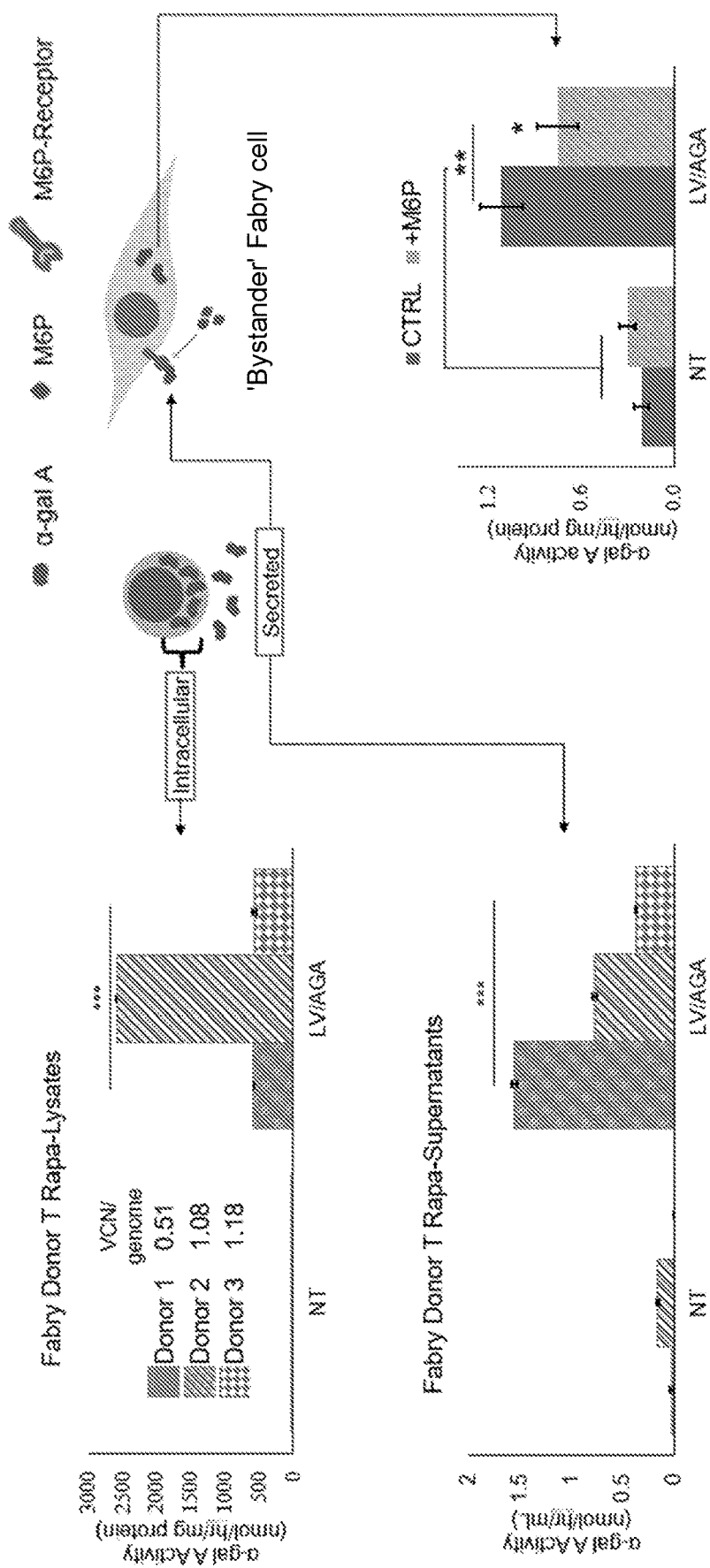

FIG. 17 demonstrates transduced T-Rapa cells derived from Fabry patients are able to produce α-gal A after transduction (left panel) and that α-gal A produced from Fabry patient transduced T-Rapa cells can be taken up by patient cells due to their molecular 'tag' (right panel).

Figure 18:
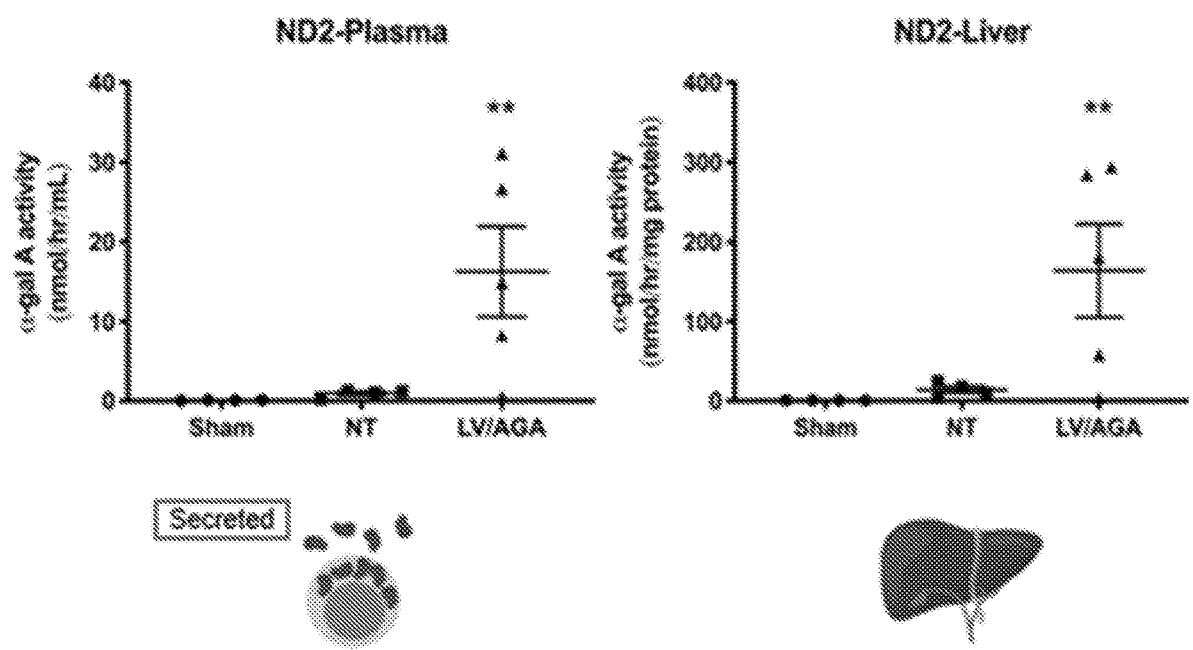
Figure 18:
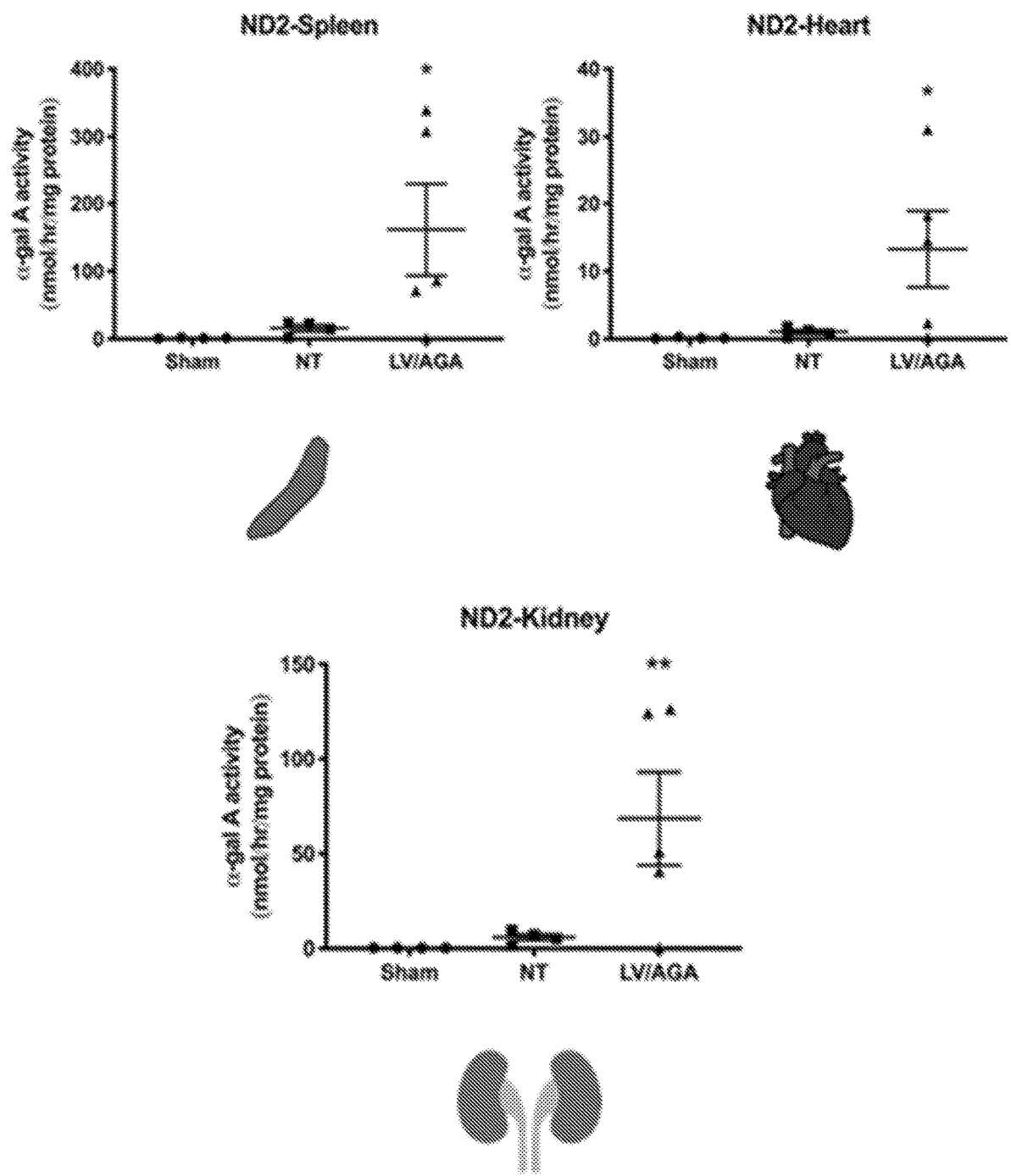

FIG. 18 demonstrates the ability of human transduced T-Rapa cells to produce enzyme in vivo when transplanted into immunocompromised Fabry mice after conditioning. Engraftment was confirmed by detecting hCD3/hCD4 in peripheral blood. α-gal A activity was detectable in vivo 4 weeks after xenograft of transduced healthy donor T-Rapa (n=4-5) in plasma or lysates of the indicated tissue (liver, spleen, heart or kidney).

Figure 19:
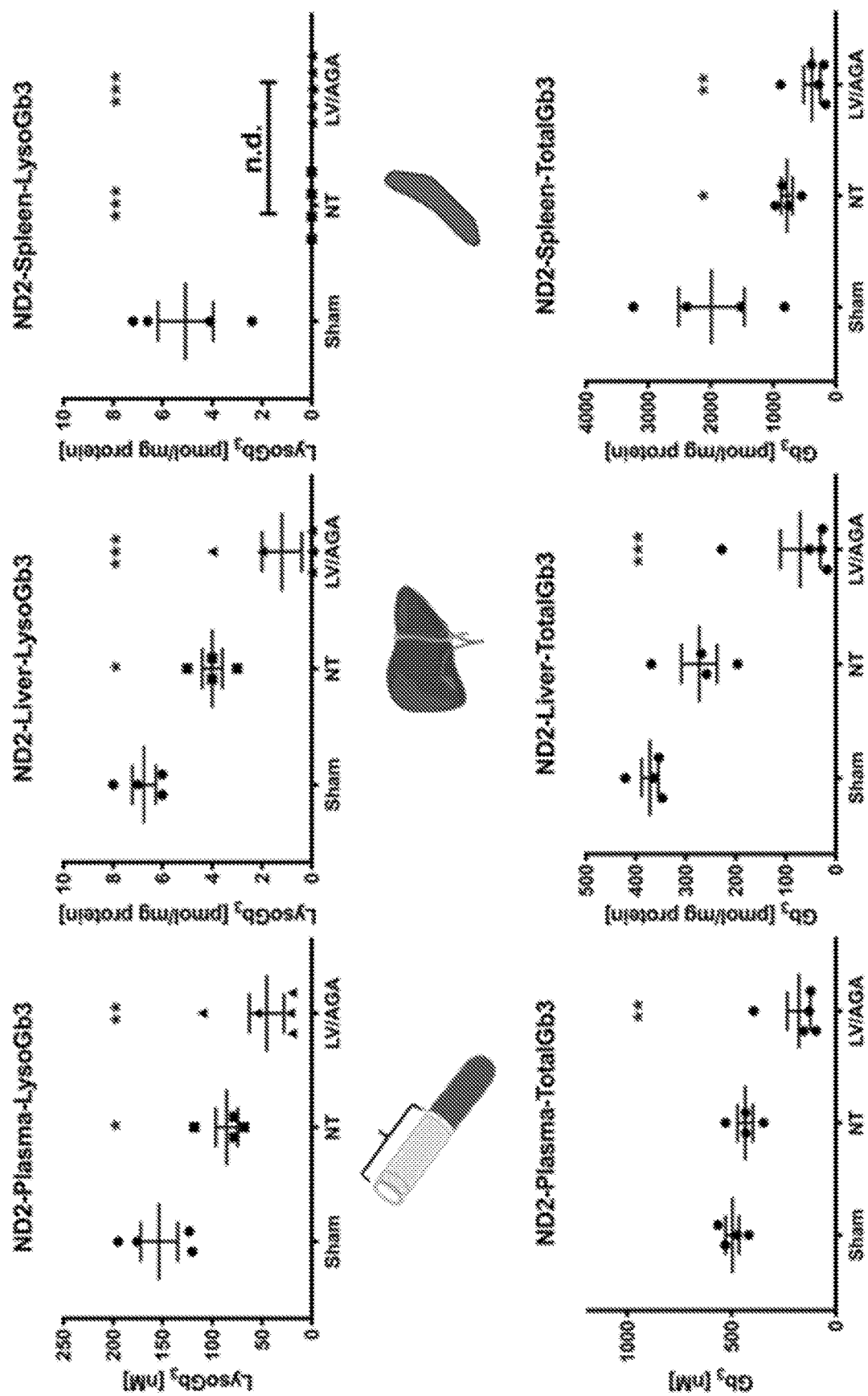
Figure 19:
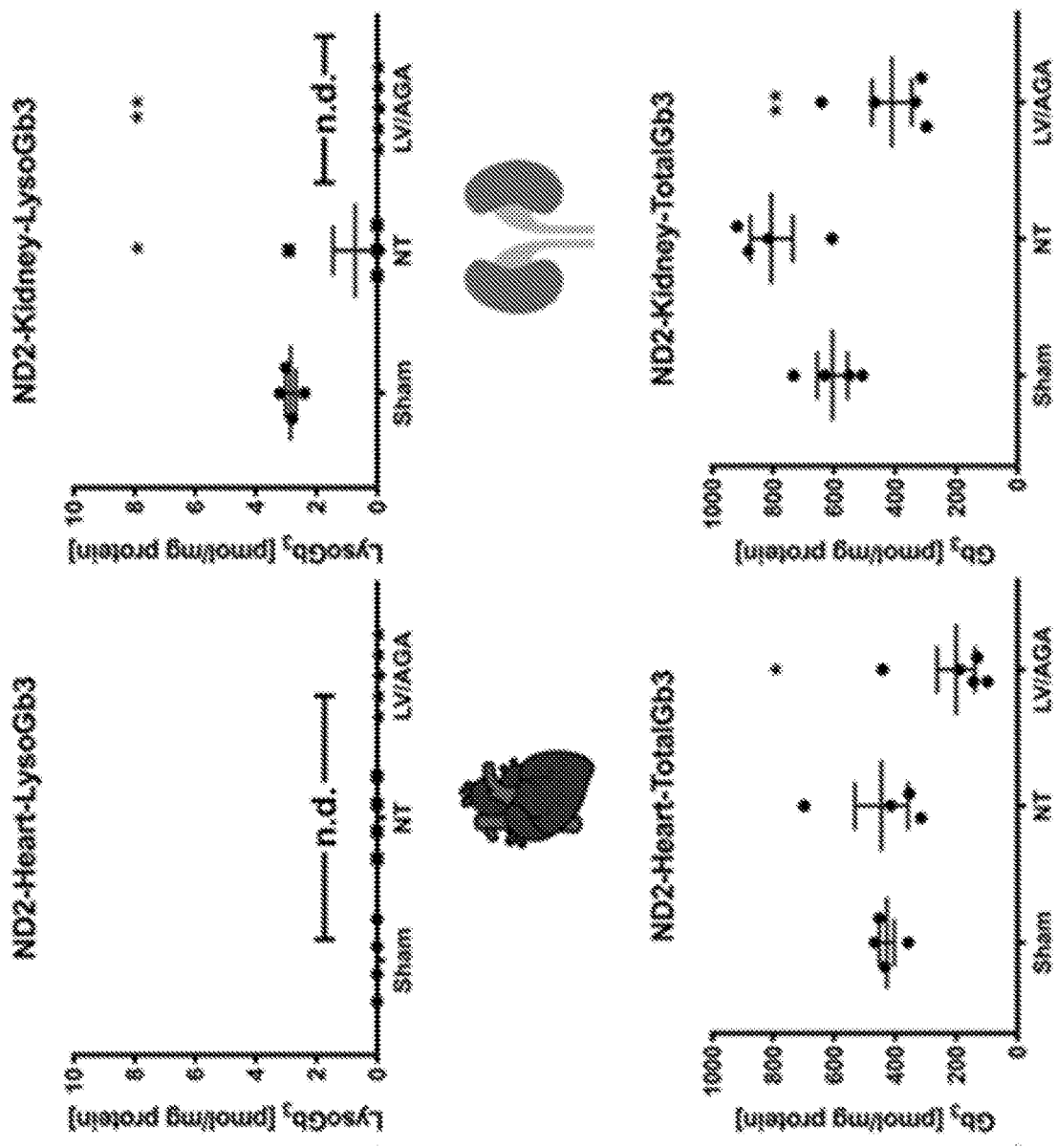

FIG. 19 demonstrates the ability of the lentiviral transduced human T-Rapa cells to reduce substrate globotriaosylceramide ($Gb_3$) (the primary substrate that accumulates in Fabry mice) after transplant into immunocompromised Fabry mice.

Figure 20:
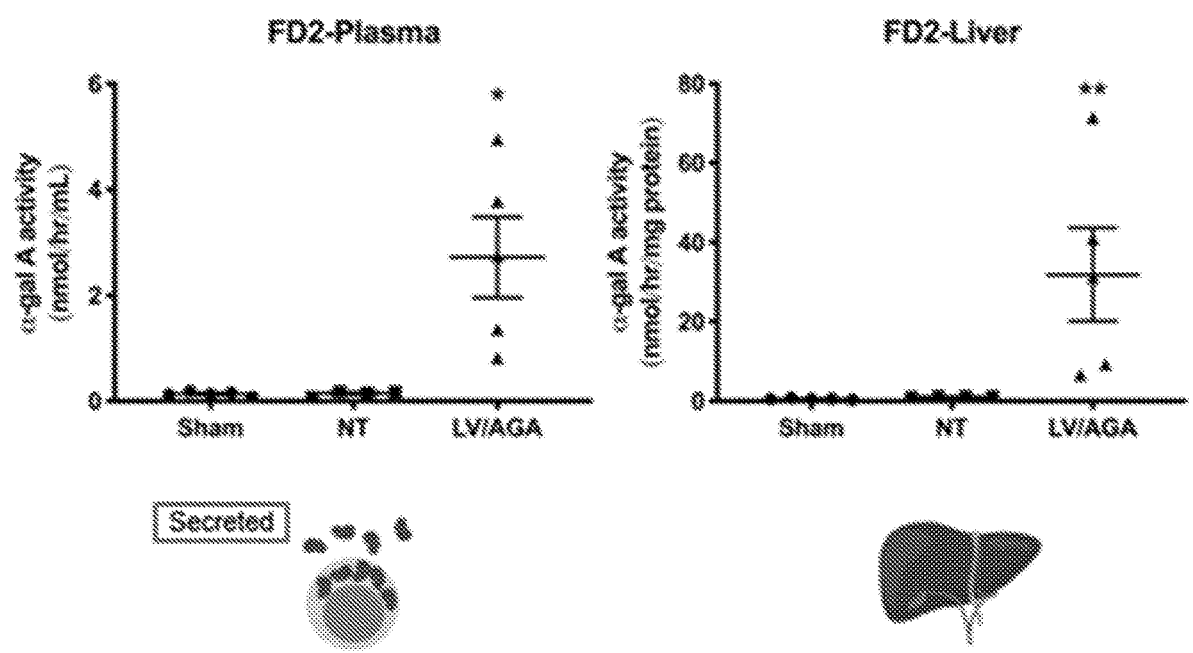
Figure 20:
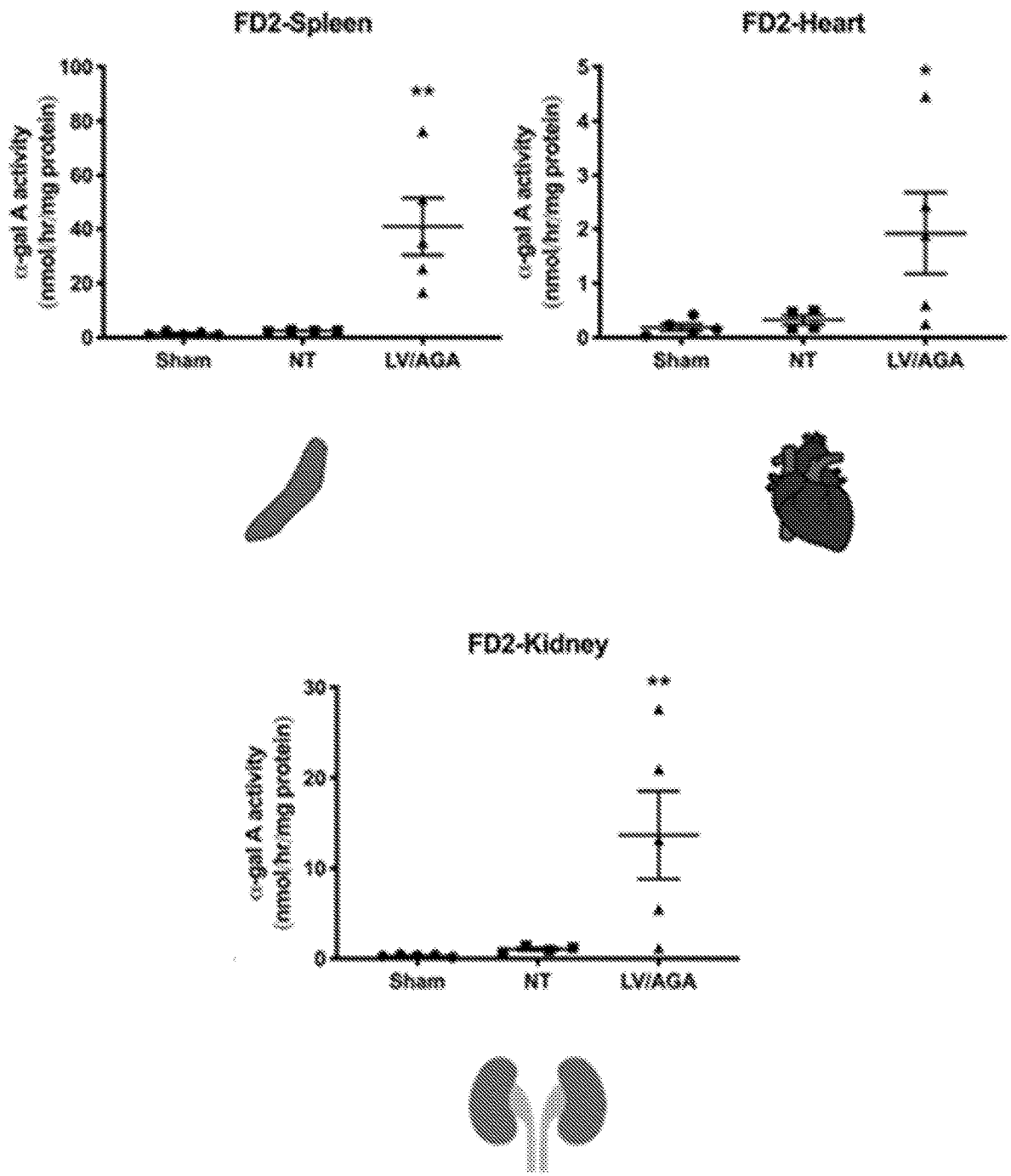

FIG. 20 demonstrates the ability of the Fabry patient T-Rapa cells transduced with the lentivirus encoding AGA to be able to secrete α-gal A in vivo. α-gal A activity is detectable in vivo 4 weeks after xenograft of transduced Fabry donor T Rapa (n=4-5) in the indicated tissues.

Figure 21:
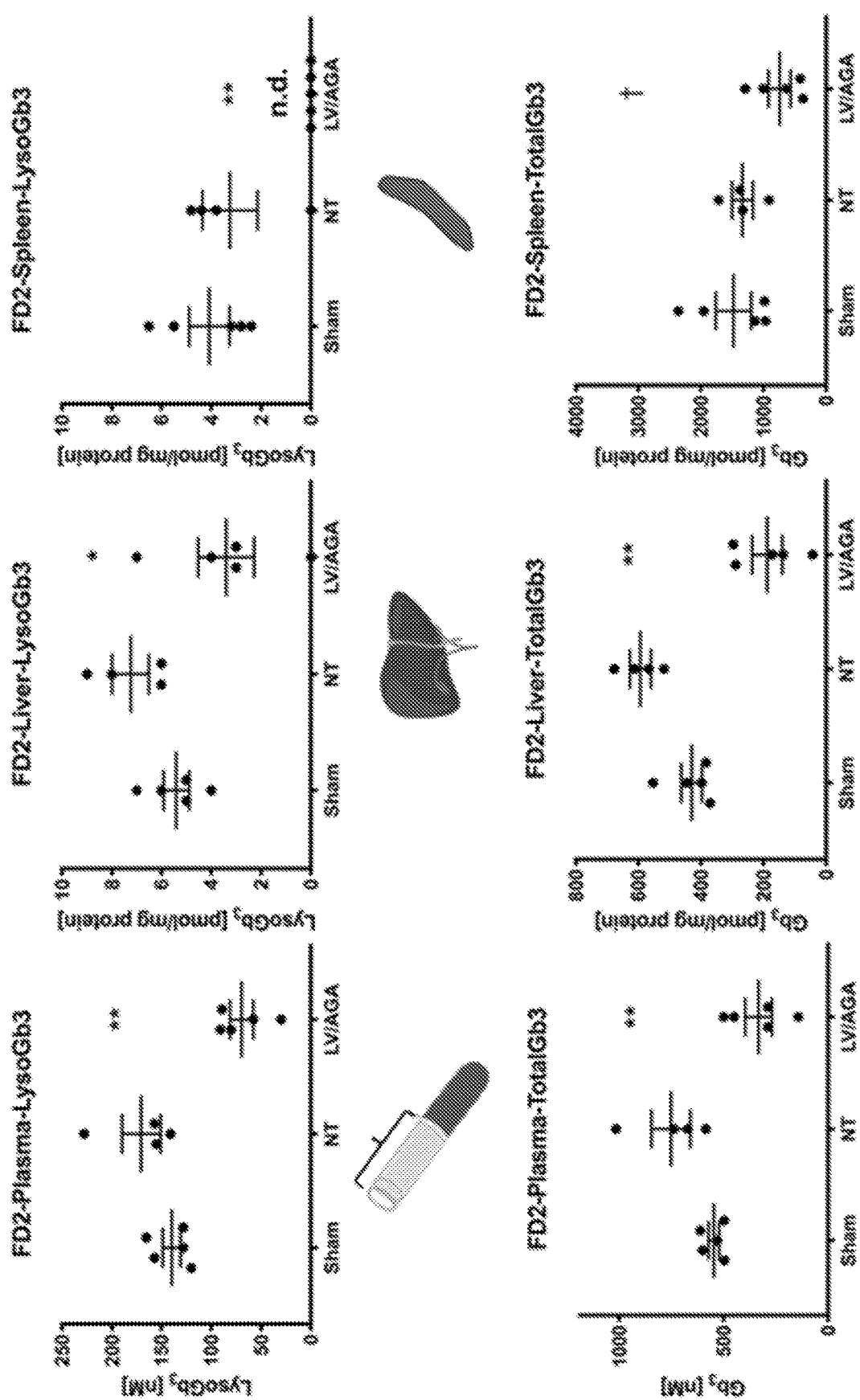
Figure 21:
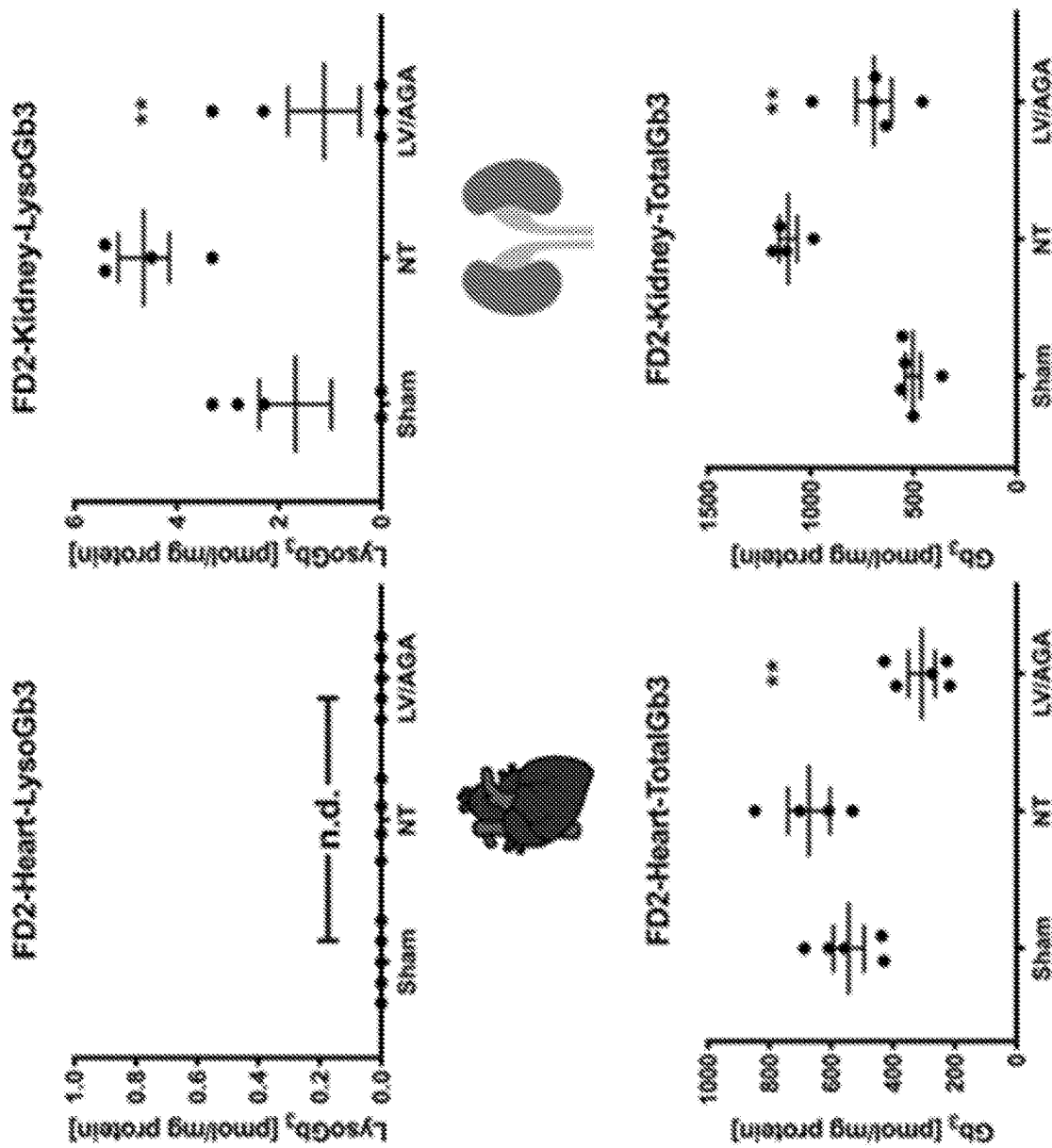

FIG. 21 demonstrates the ability of the lentiviral transduced Fabry patient T-Rapa cells to reduce substrate globotriaosylceramide ($Gb_3$) (the primary substrate that accumulates in Fabry mice) after transplant into immunocompromised Fabry mice.

DETAILED DESCRIPTION OF THE INVENTION

Prior methods of using hematopoietic stem cell (HSC)-directed gene therapy are being tested in amenable lysosomal storage deficiencies which are caused by a single enzyme deficiency. As an example, the inventors are currently conducting a phase I clinical trial (NCT02800070) aimed at treating patients with Fabry disease (FD) by gene transfer. FD is an α-galactosidase A (α-gal A) deficiency in which globotriaosylceramide ($Gb_3$) and other metabolites accumulate. In this prior protocol, CD34+ hematopoietic cells are transduced ex vivo with a recombinant lentivirus (LV) engineered to overexpress α-gal A. These cells are then returned to the patient. Cells derived from the vector-transduced HSCs, including leukocytes, can secrete α-gal A and uncorrected cells within the patient can take up the secreted α-gal A, a process termed "cross-correction". For efficient engraftment, patients receive conditioning regimens (e.g., ablation) that can be problematic. In addition, HSCs must be mobilized to peripheral blood with drugs and collected via apheresis. Alternative circulating cell populations that are easier to obtain and transplant are more desirable to use to deliver therapeutic cargo systemically.

The present disclosure provides improved methods of treating a lysosomal storage disorders, particularly Fabry disease (Online Mendelian Inheritance in Man (OMIM) ID #301500, Gaucher disease (OMIM ID #230800, 230900, 231000, 231005), Farber disease (OMIM ID #228000), and Pompe disease (OMIM ID #232300)). Particularly, the present invention describes the use of autologous or donor (non-autologous) $CD4^+$ T-Rapa cells to deliver therapeutic transgene products systemically. T-Rapa cells can be manufactured from peripheral blood cells of affected patients or normal donors (ND) and can be productively transduced with a vector (e.g., lentiviral vector) comprising a transgene (e.g. sequence encoding an enzyme) lacking in the disease, for example, but not limited to, the enzymes α-gal A for Fabry disease, beta-glucocerebrosidase (GBA, β-Glucocerebrosidase, acid β-glucosidase, D-glucosyl-N-acylsphingosine glucohydrolase, or GCase, which can be used interchangeably) for Gaucher disease, acid ceramidase (encoded by the ASAH1 transgene) for Farber disease, and acid α-glucosidase (encoded by GM transgene, also known as acid maltase) for Pompe disease. The present disclosure provides an improved method that uses cells obtained from the peripheral blood (e.g. T-cells) and can provide a population of transduced T-Rapa cells expressing the enzyme that can be stored and infused at any time to boost in vivo circulating transgene-producing T-Rapa cells when needed. Further, the method requires low, if any, ablation to provide efficient engraftment into the subject.

T-cells are natural protein-secreting machines and are already employed in many clinical trials. Unlike HSCs, T-cells can be obtained from peripheral blood (PB) without mobilization and can be expanded exponentially in culture. Ex vivo treatment with rapamycin elicits numerous changes in T-cells (e.g., CD4+ T-cells) that, in sum, endow them with a pro-engraftment and anti-apoptotic phenotype. These are termed T-Rapa cells. More about T-Rapa cells can be found in Fowler et al. ("Phase 2 clinical trial of rapamycin-resistant donor CD4+Th2/Th1 (T-Rapa) cells after low-intensity allogeneic hematopoietic cell transplantation," Blood (2013) 11: 121 (15):2864-2874), the contents of which are incorporated by reference in its entirety. Successful allotransplantation of donor T-Rapa cells requires less host conditioning (lymphocyte-specific, myeloid sparing) that results in the creation of sufficient immune space for T-cell engraftment while causing minimal host myeloid cell depletion. This method of host conditioning and T-cell-driven gene therapy is substantially different from HSC-driven gene therapy, which typically requires relatively intense myeloid cell depletion. Not to be bound by any theory, but it is advantageous to administer gene therapy via T-cells rather than HSC from several perspectives, including the fact that reduction in myeloid cell depletion: will reduce infectious complications that are associated with myeloid depletion; allow gene therapy to be performed in the outpatient setting, which will lower treatment morbidity and cost; and will allow repetitive dosing of gene therapy, which will ultimately improve efficacy.

As demonstrated in the Examples, after in vitro expansion for 2 weeks, transduced T-Rapa cells continue to secrete the transgene-product (e.g. enzyme, such as α-gal A) in the absence of stimulation in vitro. Transduced and control T-Rapa cells from FD patients and normal donors were xenografted into NOD/SCID/Aga$^{-/-}$ mice (NSF). Higher α-gal A activity was detected in plasma and organs of mice given LV-modified cells. Vector copy number analyses suggest stable transduction. NSF mice receiving transduced cells also exhibited reduced $Gb_3$ levels, demonstrating the ability of the enzyme being expressed from the transduced T-Rapa cells to reduce the in vivo substrate target.

The Examples demonstrate the in vitro development of lentiviral-transduced T-Rapa cells that can lead to increased enzyme activity and secretion of enzymes from cells. While the Examples demonstrate the use of lentiviral-transduced T-Rapa cells that increase α-gal A activity which can be used to treat Fabry disease, lentiviral-transduced T-Rapa cells can be used for expressing other enzymes to treat other lysosomal storage disorders, as shown in FIGS. 14 and 15 for the transgenes GBA, ASAH1 and GAA.

In one embodiment, the disclosure provides a method of treating a lysosomal storage disorder in a subject, the method comprising the steps of: (a) conditioning T-cells from the subject or suitable donor with rapamycin ex vivo to generate T-Rapa cells; (b) transducing the T-cells in vitro with a vector comprising a transgene of interest that encodes an enzyme associated with a lysosomal storage disorder; and (c) administering the transduced T-Rapa cells to the subject, wherein the T-Rapa cells express the enzyme associated with a lysosomal storage disorder in the subject and reduce one or more symptoms of the lysosomal storage disorder. In some embodiment, the method after step (b) comprises expanding the vector-transduced T-Rapa cells by culturing in vitro before administering the transduced and expanded T-Rapa cells in step (c)

Suitable methods of administering the transduced T-Rapa cells are known in the art, and include, transfusion and intravenous administration.

In one embodiment, the disclosure provides a method of treating a lysosomal storage disorder in a subject. The method comprising the steps of: (a) conditioning T-cells with an effective amount of rapamycin ex vivo to produce T-Rapa cells; (b) transducing the T-Rapa cells in vitro with a vector that comprises the transgene of interest that encodes the enzyme associated with the lysosomal storage disease; (c) expanding the vector-transduced T-Rapa cells in in vitro culture, and (d) administering the transduced T-Rapa cells into the subject, wherein the T-Rapa cells express the protein encoded by the transgene of interest in the subject and can subsequently reduce one or more symptoms of the lysosomal storage disorder.

In another embodiment, the disclosure provides a method of treating a lysosomal storage disorder in a subject. The method comprising the steps of: (a) obtaining T-cells from the subject or a suitable donor, (b) conditioning the T-cells with rapamycin ex vivo to produce T-Rapa cells; (c) transducing the T-Rapa cells in vitro with a vector that expresses the transgene of interest when functionally present in the T-Rapa cells; (d) expanding the vector-transduced T-Rapa cells in in vitro culture, and (e) administering the transduced T-Rapa cells into the subject, wherein the T-Rapa cells express the protein encoded by the transgene of interest in the subject and can subsequently reduce one or more symptoms of the lysosomal storage disorder.

Suitable methods of obtaining T-cells (e.g., CD4+ T-cells) from a subject are known in the art including standard outpatient blood draws or apheresis. In one embodiment, obtaining T-cells comprises detecting and isolating CD4+ T-cells from a peripheral blood sample of a subject or suitable donor. Suitable methods of detecting and isolating CD4+ T-cells from peripheral blood are known in the art and include, but are not limited to, for example, flow cytometric cell sorting, including fluorescence-activated cell sorting (FACS), or magnetic separation with the use of magnetic beads that recognize T-cells, including magnet-assisted cell sorting (MACS). In suitable embodiments, antibodies specific to CD4 that may be, in some examples, attached to magnetic beads, and are used to separate CD4+ T-cells from other cells found in peripheral blood. Alternatively, negative selection can be used to deplete the CD4− cells, allowing for the enrichment of CD4+ cells. An advantage of the methods of the current technology are that CD4+ T-cells for use in the methods can be obtained from a peripheral blood sample obtained from an outpatient blood draw and do not require any priming or other treatment steps prior to the isolation of the peripheral blood. In some embodiments, the isolated CD4+ T-cells used in the methods are at least about 70% CD4+ (70% pure), more preferably at least about 75% CD4+ (75% pure), alternatively at least about 80% CD4+ (80% pure), alternatively at least about 85% (85% pure), at least about 90% CD4+ (90% pure), at least about 95% CD4+ (95% pure).

In some embodiments, once the CD4+ T-cells are isolated, the CD4+ T-cells are cultured in vitro to expand the cells.

In some embodiments, once isolated, the isolated CD4+ T-cells are conditioned/treated with rapamycin to form T-Rapa cells. Suitably, the T-cells may be conditioned/treated with rapamycin before transduction with the vector comprising the transgene (e.g. AGA, GAA, ASAH1, and GBA transgene) or other appropriate therapeutic construct. Methods of conditioning T-cells to form T-Rapa cells is known in the art and described in Fowler et al. 2013, the contents of which are incorporated by reference in its entirety. Suitably, the isolated T-cells are cultured in chemically defined medium comprising cytokines and rapamycin in a suitable amount to transform the T-cells into rapamycin resistant T-cells (T-Rapa cells).

Suitable amounts of rapamycin to transform T-cells into T-Rapa cells include, but are not limited to, a concentration of about 0.1 micromolar to about 2 micromolar, (0.1-2 μM), alternatively from about 0.8-1.5 micromolar. Lower concentrations of rapamycin such as 0.1 micromolar can be used; however, lowering the concentration of rapamycin can deteriorate the ability to grow rapamycin-resistant T-cells, and as such, a preferred concentration of rapamycin is about 1 micromolar. Increasing the rapamycin concentration above 1 micromolar has limited feasibility because the drug is not fully solubilized in conventional media above this concentration. As such, concentrations around 1 micromolar are optimal for achievement of the rapamycin resistance (T-Rapa) phenotype.

Once T-Rapa cells are derived, the T-Rapa cells are transduced in vitro with a vector that allows expression of the transgene of interest. Suitable transgenes of interest will depend on the lysosomal storage disorder being treated.

Suitable vectors are known in the art and contain the necessary elements in order for the gene encoded within the vector to be expressed in the host cell. The term "vector"

refers to a nucleic acid molecule or genetic construct capable of transporting another nucleic acid to which it has been linked. One type of vector is a "plasmid", which refers to a circular double stranded DNA loop into which additional DNA segments may be ligated, specifically exogenous DNA segments encoding the targeted protein. Another type of vector is a viral vector, wherein additional DNA segments may be ligated into the viral genome. Certain vectors are capable of autonomous replication in a host cell into which they are introduced. Other vectors can be integrated into the genome of a host cell upon introduction into the host cell, and thereby are replicated along with the host genome (e.g. lentiviral vectors). Moreover, certain vectors are capable of directing the expression of exogenous genes to which they are operatively linked. Such vectors are referred to herein as "recombinant expression vectors" (or simply, "expression vectors" or "vectors"). In general, vectors of utility in recombinant DNA techniques are often in the form of plasmids. In the present specification "vector" include expression vectors, such as viral vectors (e.g., replication defective retroviruses (including lentiviruses), adenoviruses and adeno-associated viruses), which serve equivalent functions. Methods of using viral vectors to transduce cells are known in the art along with the methods of producing the viruses to infect or transduce the cells.

The vectors are heterogeneous exogenous constructs containing sequences from two or more different sources. Suitable vectors include, but are not limited to, plasmids, expression vectors, lentiviruses (lentiviral vectors), adeno-associated viral vectors (rAAV) among others and includes constructs that are able to express the protein encoded by the gene of interest (e.g. AGA transgene). A preferred vector is a lentiviral vector. Suitable methods of making lentiviral vector particles are known in the art and one embodiment is described in the Examples. While specific lentiviral vectors have been used in the examples, the vectors are not limited to these embodiments and any lentiviral vectors or other vectors capable of expressing the transgene of interest are contemplated for use in the practice of the current invention.

A vector can preferably transduce, transform or infect a cell, thereby causing the cell to express the nucleic acids and/or proteins encoded by the vector.

The transgene or transgenes of interest may be able to express any protein or enzyme that is associated with a disease or disorder, in some instances, the transgene expresses an enzyme or protein associated with a lysosomal storage disorder.

Suitable lysosomal storage disorders and suitable transgene of interest to target for the lysosomal storage disorders can be found in Table 1. In one embodiment, the lysosomal storage disorder and transgene are selected from Table 1.

| Lysosomal Disorder | Transgene of interest | Sequence ID (nucleotide) |
|---|---|---|
| Fabry disease | AGA | SEQ ID NO: 1 |
| Gaucher disease | GBA | SEQ ID NO: 7 |
| Farber disease | ASAH1 | SEQ ID NO: 8 |
| Pompe disease | GAA | SEQ ID NO: 9 |

In one embodiment, the lysosomal storage disorder is selected from the group consisting of Fabry disease, Gaucher disease, Farber disease, and Pompe disease.

In one embodiment, the vector is a lentiviral vector containing a transgene for expression of α-galactosidase A (α-gal A) for the treatment of Fabry disease. As used herein, the term alpha-gal or α-gal A are used interchangeably to refer to α-galactosidase A enzyme (protein).

Fabry Disease

Suitable methods of cloning the transgene of interest, for example, the codon optimized AGA transgene (SEQ ID NO:1) into an exogenous expression vector (for example a lentiviral vector) are known in the art for producing functional vector to engineer T-Rapa cells to express α-gal A for treatment of Fabry disease. In a preferred embodiment, a suitable expression vector includes, for example, a lentiviral vector, for example, pDY/CO.α-galA (i.e., LV/AGA) (SEQ ID NO:2).

Suitably, the AGA transgene will have at least 80% similarity to the SEQ ID NO:1, alternatively at least 85% sequence similarity to SEQ ID NO:1, alternatively at least 90% sequence similarity to SEQ ID NO:1, alternatively at least 95% sequence similarity to SEQ ID NO:1, alternatively at least 98% sequence similarity to SEQ ID NO:1, alternatively at least 99% sequence similarity to SEQ ID NO:1, alternatively at least 100% sequence similarity to SEQ ID NO:1. Suitable lentiviral vectors for the treatment of Fabry disease include the vector of SEQ ID NO:2, and includes vectors that will have at least 80% similarity to the SEQ ID NO:2, alternatively at least 85% sequence similarity to SEQ ID NO:2, alternatively at least 90% sequence similarity to SEQ ID NO:2, alternatively at least 95% sequence similarity to SEQ ID NO:2, alternatively at least 98% sequence similarity to SEQ ID NO:2, alternatively at least 99% sequence similarity to SEQ ID NO:2, alternatively at least 100% sequence similarity to SEQ ID NO:2.

In some embodiments, a dual promoter lentiviral vector may be used that allows for the expression of more than one gene of interest. For example, a dual promoter lentiviral vector may express the transgene of interest to treat one lysosomal storage disorder and another protein of interest to treat the same or different disease. Alternatively, the dual promoter lentiviral vector may be able to express the transgene of interest and a second protein that helps to promote the survival or selection of the transduced T-Rapa cells, either in vitro or in vivo. For exemplary purposes only, one suitable dual promoter vector is LV/AGA+(IY) (SEQ ID NO:3, FIG. 13B), as described in Provisional Application No. 62/516,022, the contents of which are incorporated by reference in its entirety. In one suitable embodiment, the T-Rapa cells are transduced with a lentiviral vector as depicted in FIG. 12. In another embodiment, the T-Rapa cells are transduced with a dual promoter lentivirus vector that expresses α-galactosidase A and a mutant form of inosine-5'-monophosphate dehydrogenase 2 (IMPDH2(IY)) (e.g., vector encoded by SEQ ID NO:3). Use of such a lentiviral vector will allow for further enrichment of the transduced T-Rapa cells in vivo in the subject by the treatment of the subject with an effective amount of mycophenolate mofetil (MMF) or mycophenolic acid (MPA) sufficient to enrich the population of lentivirus vector transduced T-Rapa cells in the subject.

The primary consequence of MPA/MMF administration is T and B cell depletion. By expressing IMPDH2 (IY), T-Rapa cells that were transduced are resistant to MPA/MMF. Treatment with low doses of MMF can increase the number of therapeutic T-Rapa, without affecting the original engraftment, while causing minimal or no toxicity. This, in turn, increases the total number of circulating cells that are expressing and secreting the transgene, for example, α-galactosidase A, which can lead to better correction of the disease. The current method gives a way to enrich for transduced cells in vivo and allows some gating as to how selective and strong that enrichment is depending on the administration of the MMF. The present methods also allow for cells harboring this lentiviral vector to be enriched for even years down the road to renew the correcting cell population expressing the transgene of interest.

In suitable embodiments, the MMF is administered at an effective dosage. An "effective dosage" refers to a dosage that allows for selective enrichment of T-Rapa cells that express the transgene via the lentiviral vector with minimal side effects. In one embodiment, the effective dosage is a low dosage. Suitable low dosages include, but are not limited to, for example, 0.1-5 mg/kg body weight given TID (three times a day), alternatively include from about 0.1-3 mg/kg body weight given TID. Alternatively, the effective dose may include higher doses of MMF. Suitable higher dosage of MMF for practice of this invention include MMF in an amount of about 5-10 mg/kg body weight TID (three times a day), alternatively 1000 mg given BID (two times a day). Suitably, an "effective amount" of MMF will result in a blood concentration within the subject of about 0.4 to about 2 μM free mycophenolic acid (MPA). Suitable dosages to obtain this blood concentration are readily determined by a physician treating the subject. MMF may also be substituted for mycophenolic acid (MPA) formulations (Myfortic, Novartis, or approved generic).

Gaucher Disease

In some embodiments, the lysosomal storage disorder is Gaucher disease. In Gaucher disease, mutations in the GBA gene greatly reduce or eliminate the activity of β-glucocerebrosidase, which breaks down waxy substances of the lipid class glycosphingolipids called glucocerebrosides into a sugar (glucose) and ceramide, another sphingolipid. Without enough of this enzyme, glucocerebroside and related substances can build up to toxic levels within cells. Tissues and organs are damaged by the abnormal accumulation and storage of these substances, causing the characteristic features of Gaucher disease. Suitable embodiments of the present invention provide for T-Rapa cells expressing GBA for the treatment of Gaucher disease. In one embodiment, a lentiviral vector comprises the transgene (e.g., GBA transgene) that allows for expression of 13-Glucocerebrosidase (e.g. GBA transgene found in SEQ ID NO:7) in the transduced cells. Suitably, the GBA transgene will have at least 80% similarity to the SEQ ID NO:7, alternatively at least 85% sequence similarity to SEQ ID NO:7, alternatively at least 90% sequence similarity to SEQ ID NO:7, alternatively at least 95% sequence similarity to SEQ ID NO:7 alternatively at least 98% sequence similarity to SEQ ID NO:7, alternatively at least 99% sequence similarity to SEQ ID NO:7, alternatively at least 100% sequence similarity to SEQ ID NO:7.

In one embodiment, the vector is a lentiviral vector that comprises the transgene GBA of SEQ ID NO:7 or a sequence with at least 80% identity to SEQ ID NO:7.

Suitable sequence for the lentiviral vector comprising GBA is found in SEQ ID NO:4 and depicted in FIG. 13C, or a sequence that will have at least 75% similarity to SEQ ID NO:4, alternatively at least 80% similarity to the SEQ ID NO:4, alternatively at least 85% sequence similarity to SEQ ID NO:4, alternatively at least 90% sequence similarity to SEQ ID NO:4, alternatively at least 95% sequence similarity to SEQ ID NO:4, alternatively at least 98% sequence similarity to SEQ ID NO:4, alternatively at least 99% sequence similarity to SEQ ID NO:4, alternatively at least 100% sequence similarity to SEQ ID NO:4. Other suitable vectors that encode for the expression of the 13-Glucocerebrosidase protein are contemplated herein.

Farber Disease

In some embodiments, the lysosomal storage disorder is Farber disease (also known as Farber's lipogranulomatosis, ceramidase deficiency, "Fibrocytic dysmucopolysaccharidosis," and "Lipogranulomatosis") and the transgene ASAH1 expresses N-Acylsphingosine Amidohydrolase 1 or acid ceramidase (used interchangeably herein). Farber disease is an extremely rare autosomal recessive lysosomal storage disorder marked by a deficiency in the enzyme acid ceramidase that causes an accumulation of a waxy class of lipids known as sphingolipids, in particular ceramide, leading to abnormalities in the joints, liver, throat, visceral tissues and central nervous system. Suitable embodiments provide T-Rapa cells expressing N-Acylsphingosine Amidohydrolase 1 for the treatment of Farber disease. Suitable vectors, preferably a lentiviral vector, are used to express N-Acylsphingosine Amidohydrolase 1 within the T-Rapa cells. As used in the present invention, a suitable vector, preferably a lentiviral vector can be used to express N-Acylsphingosine Amidohydrolase 1 in the T-Rapa cells. For example, a suitable vector can express N-Acylsphingosine Amidohydrolase 1 using the ASAH1 transgene of SEQ ID NO:8 or a sequence having 80% similarity to SEQ ID NO:8. Suitably, the ASAH1 transgene will have at least 80% similarity to the SEQ ID NO:8, alternatively at least 85% sequence similarity to SEQ ID NO:8, alternatively at least 90% sequence similarity to SEQ ID NO:8, alternatively at least 95% sequence similarity to SEQ ID NO:8, alternatively at least 98% sequence similarity to SEQ ID NO:8, alternatively at least 99% sequence similarity to SEQ ID NO:8, alternatively at least 100% sequence similarity to SEQ ID NO:8.

A suitable lentiviral vector includes the vector depicted in FIG. 13D and in SEQ ID NO:5. Suitable sequence for the lentiviral vector comprising ASAH1 transgene found in SEQ ID NO:5, or a sequence that will have at least 75% similarity to SEQ ID NO:5, alternatively at least 80% similarity to the SEQ ID NO:5, alternatively at least 85% sequence similarity to SEQ ID NO:5, alternatively at least 90% sequence similarity to SEQ ID NO:5, alternatively at least 95% sequence similarity to SEQ ID NO:5, alternatively at least 98% sequence similarity to SEQ ID NO:5, alternatively at least 99% sequence similarity to SEQ ID NO:5, alternatively at least 100% sequence similarity to SEQ ID NO:5. Other suitable vectors that encode for the expression of the N-Acylsphingosine Amidohydrolase 1 protein are contemplated herein.

Pompe Disease

In another embodiment, the present invention provides vectors and T-Rapa cells expressing acid α-glucosidase (encoded by the GM transgene) for the treatment of Pompe disease. Pompe disease is an inherited disorder resulting from the inability to breakdown a complex sugar called glycogen in lysosomes of the body's cells resulting in accumulation of glycogen in certain organs and tissues, especially muscles, which impairs their ability to function normally. Mutations within the GAA gene cause Pompe disease as the GAA gene provides instructions for producing an enzyme called acid α-glucosidase (also known as acid maltase). This enzyme is active in lysosomes which serve as recycling centers within cells. The enzyme normally breaks down glycogen in lysosomes into a simpler sugar called glucose, which is the main energy source for most cells. In some embodiments, T-Rapa cells expressing acid α-glucosidase are used to treat a subject having Pompe disease. As described above, vectors, preferably lentiviral vectors can be used to express acid α-glucosidase via the GAA transgene within the T-Rapa cells for subsequent secretion by them. In one embodiment, the vectors, preferably lentiviral vectors comprise the GAA transgene of SEQ ID NO:9 or a sequence at least 80% similar to SEQ ID NO:9. Suitably, the GAA transgene will have at least 80% similarity to the SEQ ID NO:9, alternatively at least 85% sequence similarity to SEQ ID NO:9, alternatively at least 90% sequence similarity to SEQ ID NO:9, alternatively at least 95% sequence similarity to SEQ ID NO:9, alternatively at least 98% sequence similarity to SEQ ID NO:9, alternatively at least 99% sequence similarity to SEQ ID NO:9, alternatively at least 100% sequence similarity to SEQ ID NO:9.

In one embodiment, the suitable lentiviral vector is shown in FIG. 13E and SEQ ID NO:6. Suitable sequence for the lentiviral vector comprising GM is found in SEQ ID NO:6, or a sequence that will have at least 75% similarity to SEQ ID NO:6, alternatively at least 80% similarity to the SEQ ID NO:6, alternatively at least 85% sequence similarity to SEQ ID NO:6, alternatively at least 90% sequence similarity to SEQ ID NO:6, alternatively at least 95% sequence similarity to SEQ ID NO:6, alternatively at least 98% sequence similarity to SEQ ID NO:6, alternatively at least 99% sequence similarity to SEQ ID NO:6, alternatively at least 100% sequence similarity to SEQ ID NO:6. Other suitable vectors that encode for the expression of a form of acid α-glucosidase protein are contemplated herein.

Other lysosomal disorders listed in Table 1 are contemplated to be treated by the methods described herein.

"Percentage of sequence identity" or "sequence similarity" is determined by comparing two optimally aligned sequences over a comparison window, wherein the portion of the polynucleotide sequence in the comparison window may comprise substitutions, or additions or deletions (i.e., gaps) as compared to the reference sequence (which does not comprise substitutions, additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "similarity" of polynucleotide sequences means that a polynucleotide comprises a sequence that has at least 80% sequence identity. Suitable sequence similarity allows for small changes in the transgene that do not affect the function of the protein expressed by the transgene. Alternatively, percent identity can be any integer from 75% to 100%. More preferred embodiments include at least: 75%, 80%, 85%, 86%, 87%, 88%, 89%, 90%, 91%, 92%, 93%, 94%, 95%, 96%, 97%, 98% or 99% compared to a reference sequence using programs such as BLAST using standard parameters. These values can be appropriately adjusted to determine corresponding identity of proteins encoded by two nucleotide sequences by taking into account codon degeneracy, amino acid similarity, reading frame positioning and the like.

Suitable amounts of lentivirus able to transduce T-Rapa cells include, for example, using a MOI (multiplicity of infection) of 1-100, preferably an MOI of 1-30, alternatively 1-60. The T-Rapa cells may be exposed to the lentivirus for 10-24 hours, suitably about 12-16 hours. The T-Rapa cells may be transduced consecutively 1-3 times for exposure times listed herein, suitably 1 time. Cytokines may be added to the culture medium during transduction. After transduction, the cells can be either transferred back into the patient or cryopreserved for later transplantation, or a combination of both. In some instances, the transduced cells may be cultured for a number of days before being transferred or cryopreserved. Suitable methods of cryopreservation are known in the art.

Other suitable vectors are known in the art and can be used to transduce the cell including AAV vectors, and the like. Any vector that is able to allow for stable expression of the enzyme encoded by the transgene of interest is contemplated for use herein.

In some embodiments, the transduced T-Rapa cells are expanded in culture and cryopreserved at various stages of culture. Suitable methods of cryopreservation include, but are not limited to, suspending the cells in a cryopreservation medium and storing the cells at −80° C. to −196° C., preferably below −80° C. Suitable cryopreservation media are known in the art and may comprise some combination of base medium, cryopreservative (e.g., DMSO) and a protein source. For example, a suitable cryopreservation medium may comprise complete medium and 10% glycerol, complete medium containing 10% DMSO (dimethlysulfoxide), or 45% cell-conditioned medium with 45% fresh medium and 10% glycerol or DMSO. In alternative embodiments, the cryopreservation medium may be serum free, for example, comprises 46.25% cell-conditioned serum-free medium with 46.25% fresh serum-free medium and 7.5% DMSO.

Suitable chemically defined medium for culturing T-cells are known in the art and include, but are not limited to, commercial nutrient-rich media such as X-Vivo 20. Suitably, the chemically defined medium is further supplemented with cytokines. Preferably, in one embodiment, recombinant human IL-2 (rhu IL-2) and recombinant human IL-4 (rhu IL-4) cytokines are used to supplement the medium. Suitable amount of the recombinant cytokines include about 10-100 IU/mL of IL-2, preferably about 20 IU/mL of IL-2 and about 500-2000 IU/mL of IL-4, preferably about 1000 IU/mL IL-4.

In some embodiments, the transduced T-Rapa cells are expanded in vitro. During expansion, the transduced T-Rapa cells may be cultured in chemically defined medium supplemented with cytokines as described herein. Suitably, the transduced T-Rapa cells may be cultured for at least one day, and suitably may be cultured for at least 2 weeks, alternatively at least 4 weeks, alternatively at least 6 weeks.

The transduced T-Rapa cells may be maintained and expanded in vitro in culture for at least 5 passages, alternatively at least 10 passages, alternatively at least 15 passages, alternatively at least 20 passages. The transduced T-Rapa cells may be cryopreserved at any passage after transduction.

The present disclosure contemplates populations of transduced T-Rapa cells that express the protein encoded by a transgene of interest and any methods of use thereof. For example, the present disclosure provides a population of transduced T-Rapa cells that express a protein encoded by the transgene of interest. In one embodiment, the disclosure provides a population of transduced T-Rapa cells that express α-gal A. In another aspect, the discourse provides a population of transduced T-Rapa cells that express β-glucocerebrosidase. In another aspect, the disclosure provides a population of transduced T-Rapa cells that express acid ceramidase. In another aspect, the disclosure provides a population of transduced T-Rapa cells that express acid α-glucosidase.

Suitably, the transduced T-Rapa cells are administered into the subject having a lysosomal storage disorder in an amount effective to reduce one or more symptoms of the lysosomal storage disorder (e.g. Fabry disease). Suitable methods of administering the transduced T-Rapa cells are known in the art, and include, but are not limited to, intravenous injection and transfusion.

The transduced T-Rapa cells may be administered at least once, and suitably will be administered at subsequent times at which increased expression of the enzyme or protein of interest (e.g. α-gal A expression) are needed to treat one or more symptom of the lysosomal storage disorder (e.g. Fabry disease). A skilled artisan familiar with lysosomal storage disorders will appreciate monitoring enzyme (e.g. α-gal A) production and the necessity for additional administrations.

The term "subject" or "patient" are used interchangeably and refer to a mammalian subject, for example, a mouse, a rat, a monkey, a human, etc. In a preferred embodiment, the subject is a human. It is contemplated that the subject or patient may have already been treated with one or more therapies for the lysosomal storage disorder before undergoing the treatment contemplated herein. For example, patients treated with exogenous enzymes or by prior methods of using transduced HSC cells are contemplated as subjects for use of the present invention.

The host cell is suitably a T-cell, for example CD4+ T-cells. Although the examples provided here describe the use of CD4+ T-cells, in some embodiments, it may be advantageous to manufacture a mixed population of CD4+ and CD8+ T-cells that secrete the therapeutic protein (transgene of interest). Further, in one embodiment, the T-cells are skewed toward Th2 cytokine phenotype, in some embodiments, it may be advantageous to manufacture T-cells skewed towards other phenotypes such as Th1, Th17, or a regulatory T-cell subset.

Suitable methods of producing a population of transduced T-Rapa cells are provided herein.

In some embodiments, the transduced T-Rapa cells are administered to the subject with a pharmaceutically acceptable carrier or excipient.

A "pharmaceutically acceptable carrier" means any conventional pharmaceutically acceptable carrier, vehicle, or excipient that is used in the art for production and administration of compositions to a subject. Pharmaceutically acceptable carriers are typically non-toxic, inert, solid or liquid carriers which are physiologically balanced. Typically, buffered saline or other saline solutions are physiologically acceptable carriers. Water is not contemplated as a suitable physiologically acceptable carrier. In some embodiments, additional components may be added to preserve the structure and function of the T-Rapa cells of the present invention, but are physiologically acceptable for administration to a subject.

The present invention has been described in terms of one or more preferred embodiments, and it should be appreciated that many equivalents, alternatives, variations, and modifications, aside from those expressly stated, are possible and within the scope of the invention.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. In places where ranges of values are given, this disclosure explicitly contemplates other combinations of the lower and upper limits of those ranges that are not explicitly recited. For example, recitation of a value between 1 and 10 or between 2 and 9 also contemplates a value between 1 and 9 or between 2 and 10. Ranges identified as being "between" two values are inclusive of the end-point values. For example, recitation of a value between 1 and 10 includes the values 1 and 10.

Aspects of the present disclosure that are described with respect to methods can be utilized in the context of the compositions of matter or kits discussed in this disclosure. Similarly, aspects of the present disclosure that are described with respect to compositions of matter can be utilized in the context of the methods and kits, and aspects of the present disclosure that are described with respect to kits can be utilized in the context of the methods and compositions of matter.

The invention will be more fully understood upon consideration of the following non-limiting examples.

EXAMPLES

Example 1: Production of Lentiviral Vector

LV Construction

A DNA fragment comprising the cDNA of the human GLA gene encoding α-gal A was synthesized by GenScript. The cDNA of the GLA gene was codon-optimized for enhanced expression in human cells. The synthesized DNA fragment was sub-cloned into the 3' self-inactivating (3'SIN), HIV-1-based, lentiviral backbone plasmid pDY.cPPT-EF1α-MCS-WPRE previously generated in our laboratory between the EcoRI and XmaI restriction sites in the multiple cloning site (MCS). Following this we used site-directed mutagenesis using the QS site-directed mutagenesis kit (New England Biolabs) to edit the sequence upstream of the cDNA to create an optimal Kozak consensus sequence. These steps generated the plasmid pDY/CO.α-gal A (SEQ ID NO:2) which was used for all LV preparations in our studies. The plasmid sequence covering the proviral region was verified by DNA sequencing. This method was described in and is paraphrased from Huang et al., 2017, the contents of which are incorporated by reference in its entirety. Purification of Research-Grade and Near-Clinical-Grade LV along with Functional Titer Analyses Research-grade LV/AGA was prepared in our laboratory as described previously (Wang, J. C., Felizardo, T. C., Au, B. C., Fowler, D. H., Dekaban, G. A., and Medin, J. A. (2013). Engineering lentiviral vectors for modulation of dendritic cell apoptotic pathways. Virol. J. 10, 240.) Near-clinical-grade LV/AGA was produced, which meets current GMP requirements for potential human clinical trial use under an investigational new drug (IND) submission.

The LV particles were produced using HEK293T packaging cells. The packaging cells were expanded to a 4-L culture volume and transiently co-transfected with the LV packaging plasmids (pCMVΔR8.91 (packaging plasmid) and pMD.G (VSV-G envelope encoding plasmid)) and transfer plasmid (pDY/CO.α-gal A). The sequences of those plasmids that were expanded were verified by DNA sequencing. Culture supernatant was harvested twice, yielding a total of 8 L of unconcentrated LV-containing supernatant. The LV-containing supernatant was further purified by Mustang Q ion exchange chromatography, concentrated by tangential flow filtration, and buffer-exchanged into 100 mL GMP-grade Lonza X vivo 20 cell growth medium.

Figure 11:
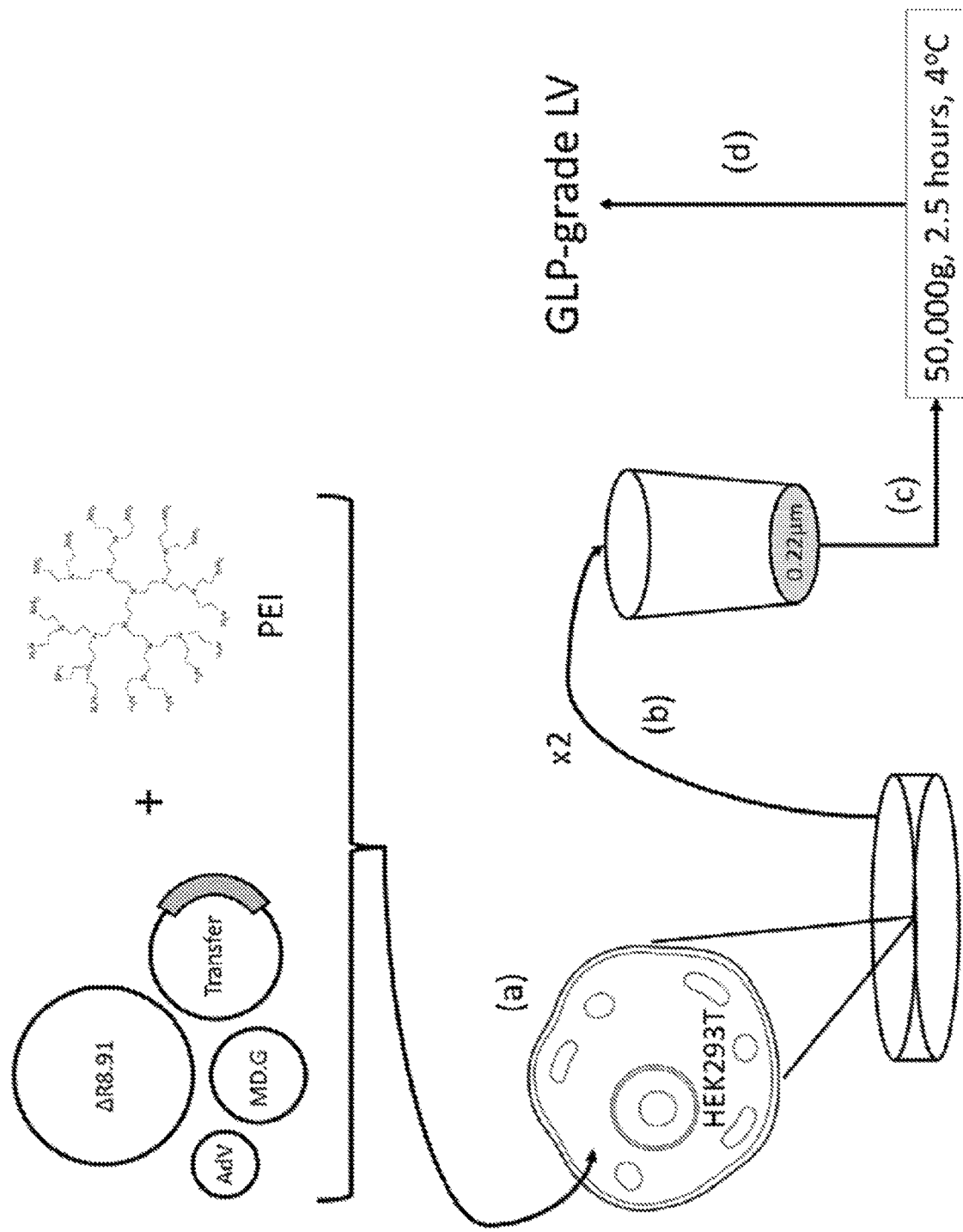
FIG. 11 is a cartoon depiction of one suitable method of making lentiviral vectors for use in the present methods.

Vesicular stomatitis virus glycoprotein-pseudotyped lentiviruses (VSVg-LVs), were generated. Briefly, HEK293T cells were seeded in 15 cm culture dishes and transfected 24 hours later with LV packaging plasmids and transfer plasmid. 16-17 hours later media on the cells was exchanged for fresh media. 24 hours later culture supernatant was collected and replaced with fresh media. A second collection was performed another 24 hours later. The culture supernatant was filtered through 0.22 µm vacuum-assisted filters, and ultra-centrifuged at 50,000 g for 2 and half hours. Residual liquid was removed from the viral pellets, and these were then resuspended in Lonza X Vivo 20 and stored at $-80°$ C. until use. Viral supernatants were harvested 24 and 48 hours later and concentrated by ultracentrifugation at 50,000 g for 2 hours as depicted in FIG. 11. Viral stocks were resuspended in lymphocyte culture medium (Lonza X Vivo 20) and stored at $-80°$ C. until use.

Sample vials of the final concentrated vector product underwent QC analyses, including vector identity confirmation by Southern blot analysis and titer by p24 ELISA, along with testing for aerobic and anaerobic sterility, mycoplasma levels, endotoxin levels, and residual DNA benzonase levels.

We performed infectious titer testing of all LV preparations by transduction of HEK293T cells using serial dilutions of the vector followed by measurement of average viral copy number per cell using quantitative real-time PCR analysis.

Example 2: Transduced T-Rapa Cell Manufacturing

Figure 9:
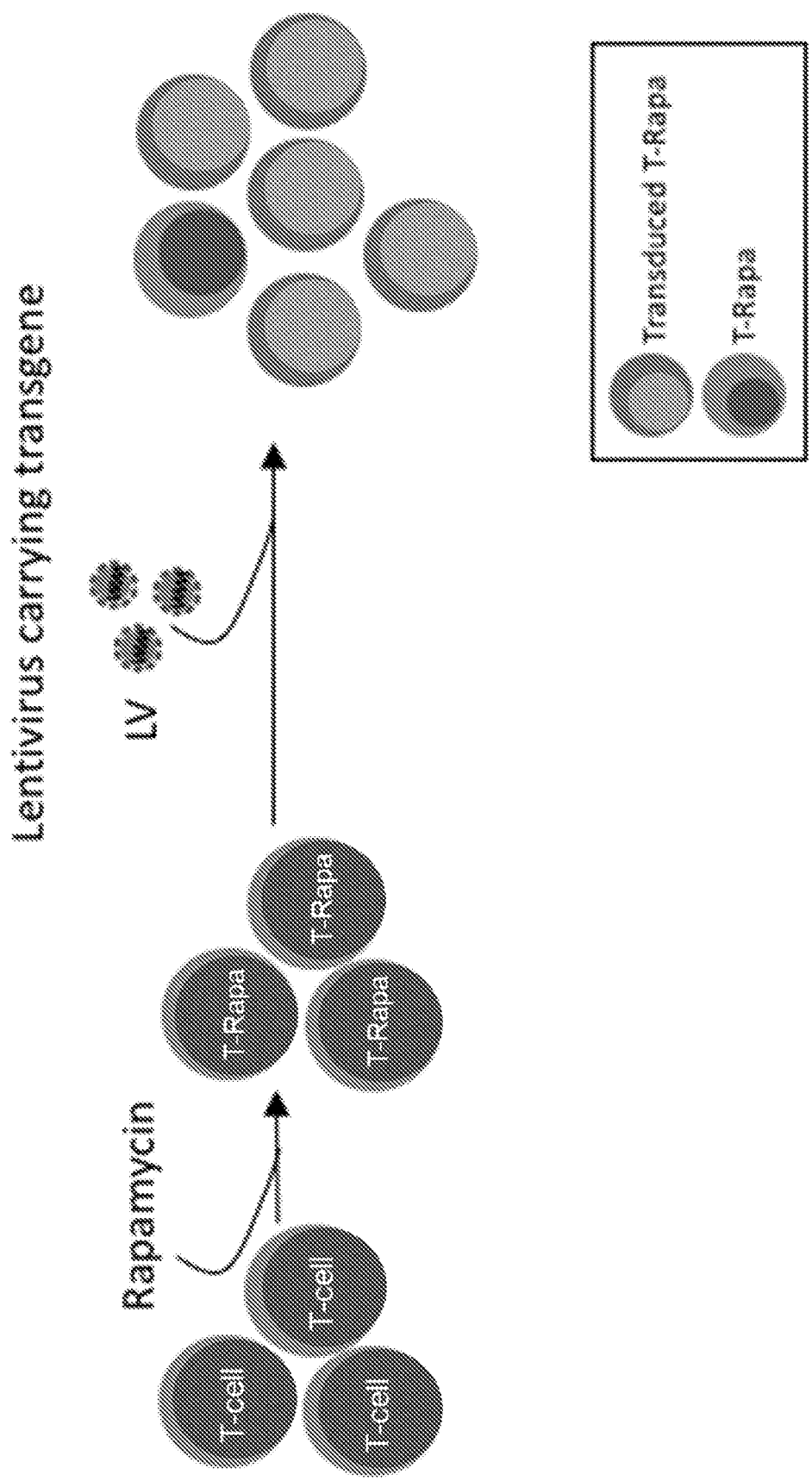
FIG. 9 is a schematic representing the method of producing transduced T-Rapa cells.

A schematic of making transduced T-Rapa cells is depicted in FIG. 9. Donor lymphocytes are collected by a 10-liter steady-state apheresis performed prior to stem cell mobilization. CD4 cells were positively selected (Miltenyi; CliniMACS® device, or laboratory equivalent) and co-stimulated (tosylated magnetic beads [Dynal] conjugated with GMP-grade anti-CD3 [OKT3; Ortho] and GMP-grade anti-CD28 9.3 antibodies [3:1 bead:cell ratio]). Alternatively, donor lymphocytes were obtained as CD34-depleted flow-through from CD34+ cliniMACS procedure from stem cell mobilized donors. CD4+ cells were obtained using magnetic enrichment as previously described.

Purified CD4+ cells will be cultured in polyolefin bags (Baxter) using X-VIVO 20 media (Lonza), 5% donor plasma, recombinant human (rhu) IL-4 (1000 I.U./mL; Schering), rhu IL-2 (20 I.U./mL; Chiron) and Sirolimus® oral solution (Wyeth; 1 µM) and anti-CD3/CD28 beads (3:1). After 3 days, T-cells will be washed and transduced with lentivirus vector able to express α-gal A at MOI of 30-60. After 18 hours, T-cells will be washed and propagated in supplemented X-VIVO 20 media without rapamycin. On day 6, beads will be removed; T-cells will be washed to remove cytokines, and then cryopreserved. All infused T-Rapa products will meet release criteria, which include: CD4 cell purity>70% (median CD4 purity was 99%), viability>70% (median viability was 95%), absence of bacterial and fungal growth, absence of endotoxin content by limulus assay, negative mycoplasma test, and <100 magnetic beads per $3\times10^6$ cells. T-Rapa cells are cultured, expanded and cryopreserved for use.

Figure 1:
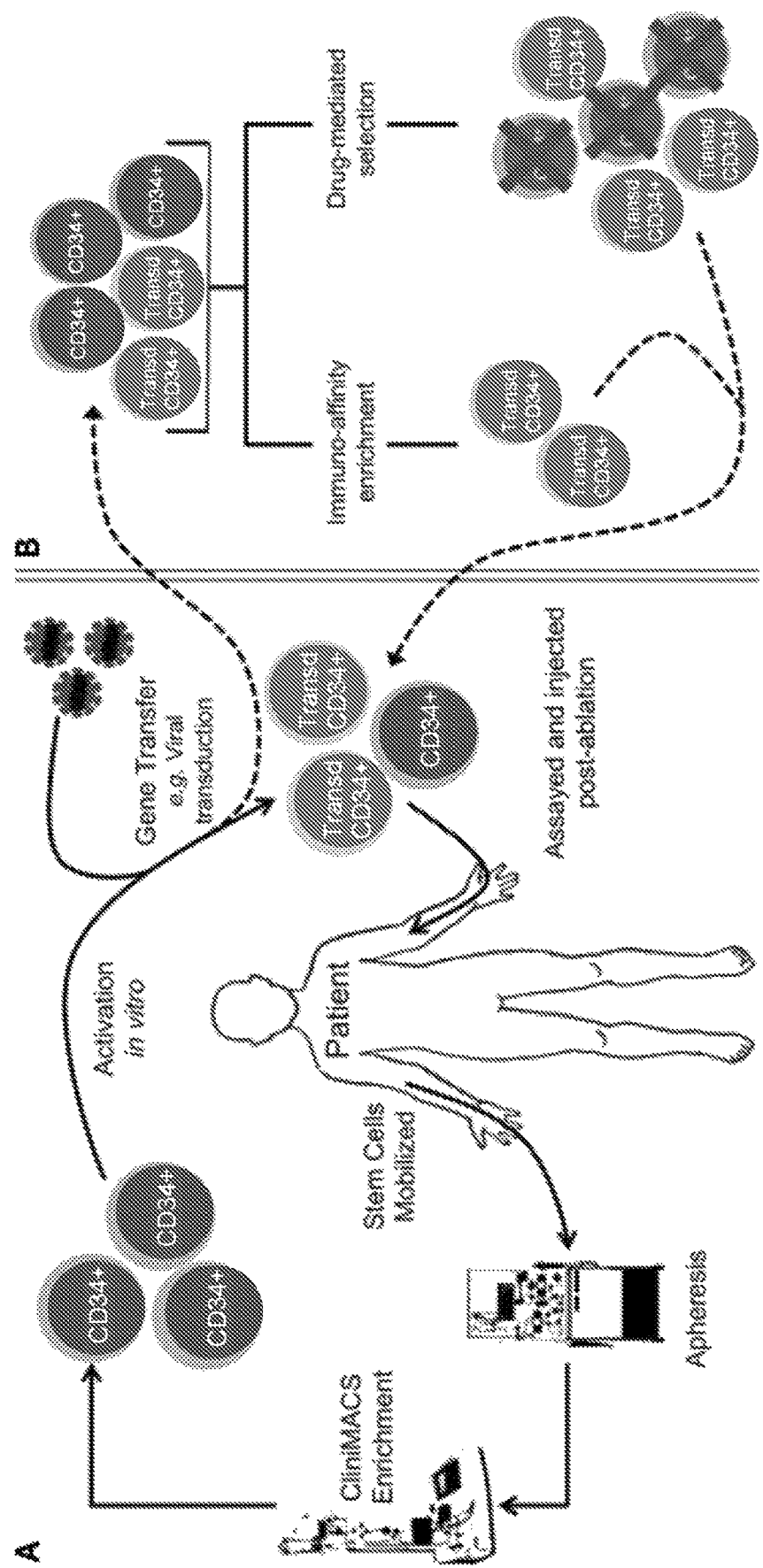
FIG. 1 is a schematic of prior methods of hematopoietic stem cell gene therapy.
Figure 2:
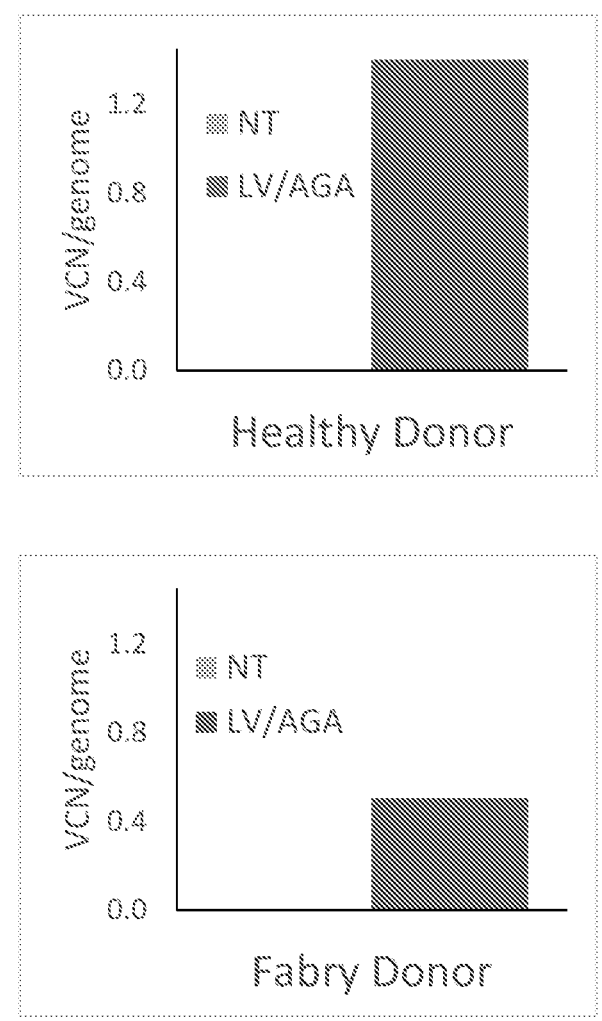
FIG. 2 are graphs depicting the transduction efficiency of T-Rapa cells isolated from healthy and Fabry donor using vehicle only (NT) or α-gal A-expressing lentiviral vector (LV/AGA).

As depicted in FIG. 2, both T-Rapa cells derived from a healthy donor (ND) and Fabry donor (FD) were efficiently transduced with the lentiviral vector.

Example 3: Expression of α-Gal a in T-Rapa Cells Transduced with LV

Figure 3A:
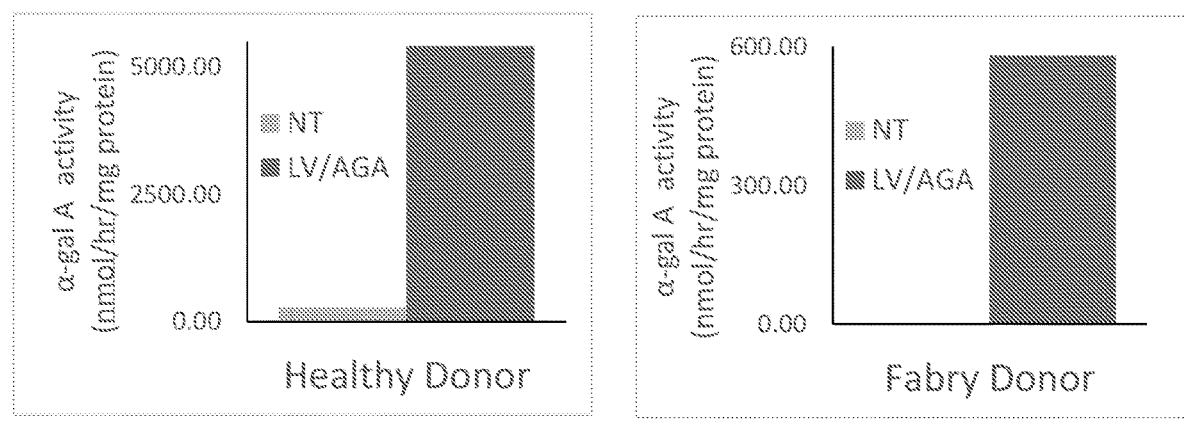
FIGS. 3A-3B depict the α-gal A expression in transduced T-Rapa cells from healthy and Fabry donors. Expression of α-gal A was determined both in the supernatant (B) or the cell lysates (A) of the transduced cells.
Figure 3B:
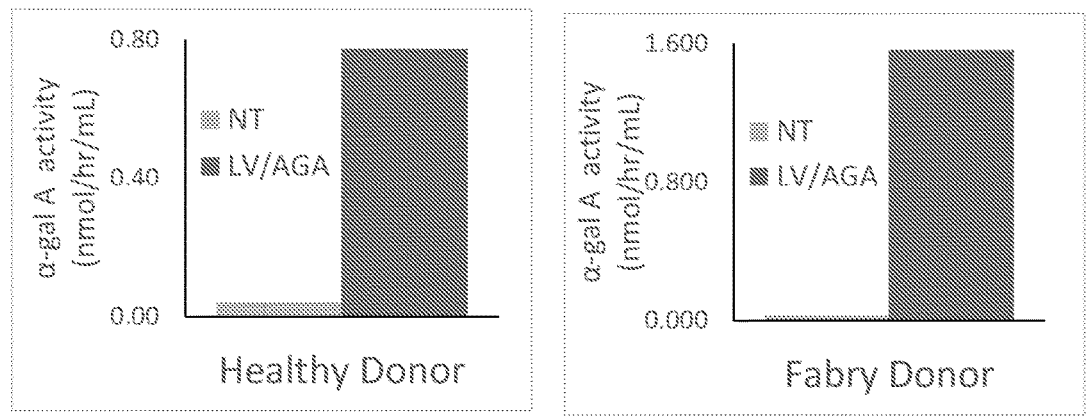

Levels of α-gal A were determined for the transduced T-Rapa cells from healthy and Fabry donors. The specific α-gal A activity was determined by fluorometric assay as previously described (Yoshimitsu et al. 2004, PNAS: 942540-2544). Briefly, plasma or cell/organ protein extracts were incubated with 4-methylumbelliferyl-α-D-galactopyranoside (5 mmol/L) in presence of the α-N-acetylgalactosaminidase inhibitor, N-acetyl-D-galactosamine (100 mmol/L) (Sigma Aldrich, St. Louis, Mo.). The product of the enzymatic reaction was quantified by comparison with known concentrations of 4-methylumbelliferone. Each measurement was assessed in triplicate and normalized to total protein concentration (BCA Protein Assay Kit; Pierce, Rockford, Ill.). Results are shown in FIGS. 3A and 3B, depicting the α-gal A content in cell lysates (A) and supernatants (B).

Figure 4:
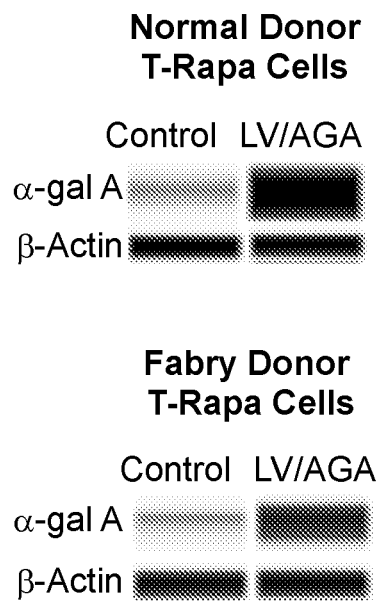
FIG. 4 is a representative western blot of α-gal A proteins level in normal donor- and Fabry Donor-derived transduced T-Rapa cells performed by Wes™ Western Blot System.
Figure 5:
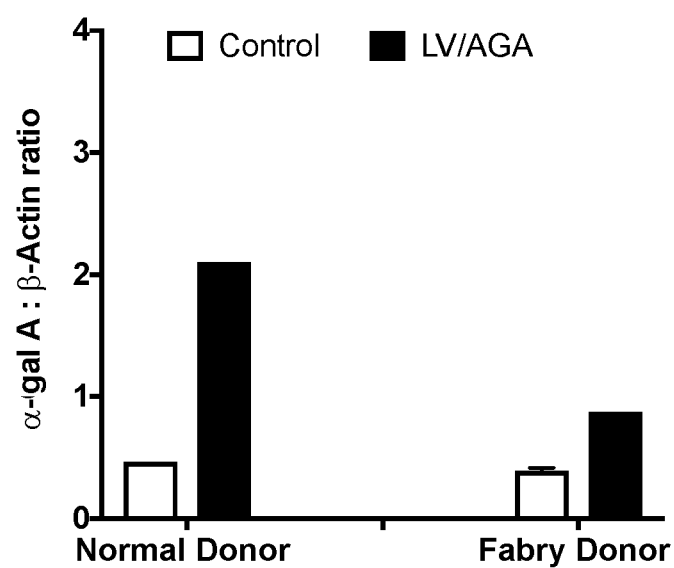
FIG. 5 is the quantitation of α-gal A in normal donor and Fabry donor transduced T-Rapa cells quantitated by Wes™ Western Blot System.

Levels of α-gal A were also detected by Wes' Simple Western System as shown in FIGS. 4 and 5.

Figure 6:
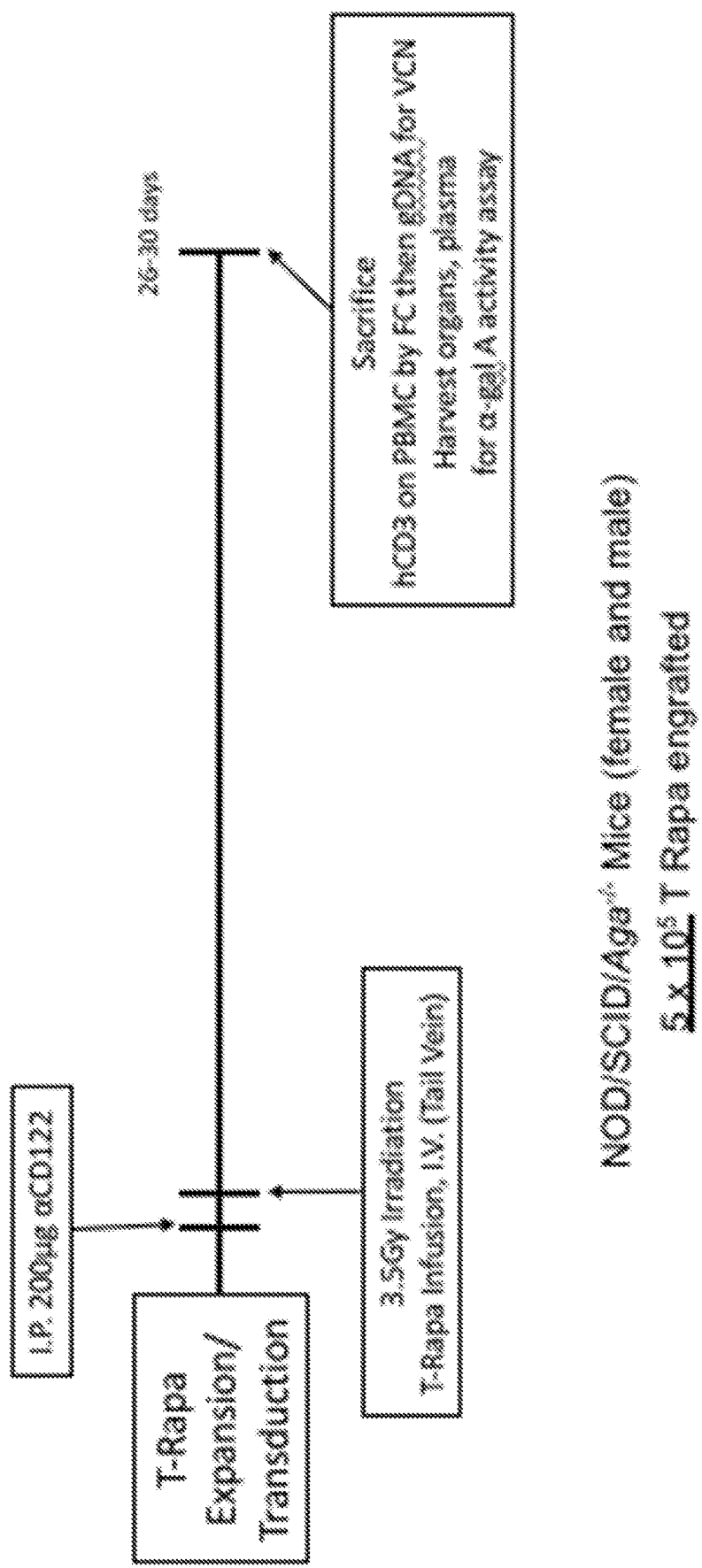
FIG. 6 is a schematic of the protocol for in vivo testing of the transduced T-Rapa cells in the NOD/SCID/Aga$^{-/-}$ Fabry mouse model.
Figure 7:
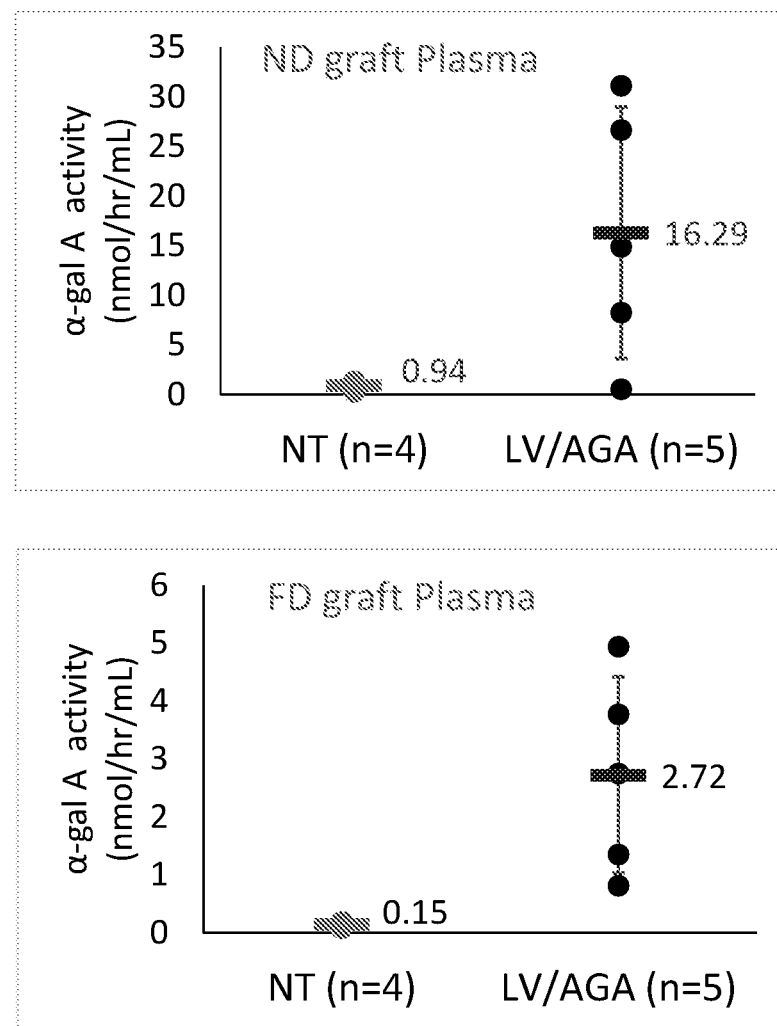
FIG. 7 are graphs depicting the enzyme activity levels of α-gal A in the plasma of mice engrafted with normal donor- or Fabry donor-derived transduced T-Rapa cells.

Example 4: In Vivo Treatment of a Mouse Model of Fabry Disease

α-gal A-deficient and immunocompromised Fabry mice (NOD/SCID/Aga$^{-/-}$) as described previously (Pacienza et al. 2012) were used to test the in vivo efficacy of using transduced T-Rapa cells for treatment of Fabry disease. NOD/SCID/Aga$^{-/-}$ mice were engrafted with $5\times10^5$ transduced human T-Rapa cells from either healthy or Fabry donors as depicted in FIG. 6. α-gal A activity in the engrafted animals was assayed 4 weeks after xeno-transplant. Liver, spleen heart, kidney, plasma and PB-WBCs were collected. PB-WBCs were assayed by flow cytometry and VCN for presence of transduced T-Rapa cells. Plasma was assessed for α-gal A activity, the results shown in FIG. 7 and the raw data shown in FIG. 8. FIG. 18 demonstrates α-gal A activity is detectable in the collected organs in vivo 4 weeks after xenograft of transduced healthy donor T Rapa (n=4-5).

Further, the ability of the transduced T-Rapa cells to reduce substrate in vivo was also assayed. Globotriaosylceramide (Gb$_3$), the primary substrate that accumulates in Fabry mice, and globotriaosylsphingosine (lyso-Gb$_3$) were quantified in plasma and tissue homogenates by UPLC-MS/MS after treatment with the healthy donor transduced T-Rapa cells. As shown in FIG. 19, substrate is reduced 4 weeks after transplant of transduced healthy donor T Rapa (n=4-5).

LV/AGA vector-transduced T-Rapa cells derived from healthy and Fabry donors produce and secrete active enzyme in vivo.

CD4+ T cells derived from Fabry patients were also transduced with the lentiviral vector encoding α-gal A as described above. First, we confirmed that the T-Rapa cells from 3 Fabry patients showed α-gal A activity, and measured enzyme activities both within the cell and in the cellular supernatants as shown in FIG. 17. We then treated immortalized Fabry patient-derived fibroblasts with T-Rapa-conditioned supernatant for 6 hours with or without 1 mM soluble mannose-6-phosphate to see if enzyme produced from T-Rapa cells can be taken up (FIG. 17).

These transduced T-Rapa cells derived from Fabry patients were also engrafted into the immunocompromised Fabry mouse model, and the α-gal A activity was measured. As shown in FIG. 20, α-gal A is detectable in vivo 4 weeks after xenograft of transduced Fabry donor T-Rapa (n=4-5). Further, these Fabry T-Rapa transduced cells were able to reduce substrate (Gb$_3$) in the Fabry mice, as depicted in FIG. 21. Substrate is reduced 4 weeks after transplant of transduced Fabry donor T-Rapa (n=4-5).

This Example demonstrates transduced T-Rapa express and secrete the enzymes necessary to counter lysosomal storage diseases (e.g., α-gal A and GCase). Further, this Example shows that transduced Fabry patient T-Rapa cells can be manufactured and transduced T-Rapa cells are able to function in vivo to reduce substrate.

Example 5: Treatment of Fabry Disease

Figure 10:
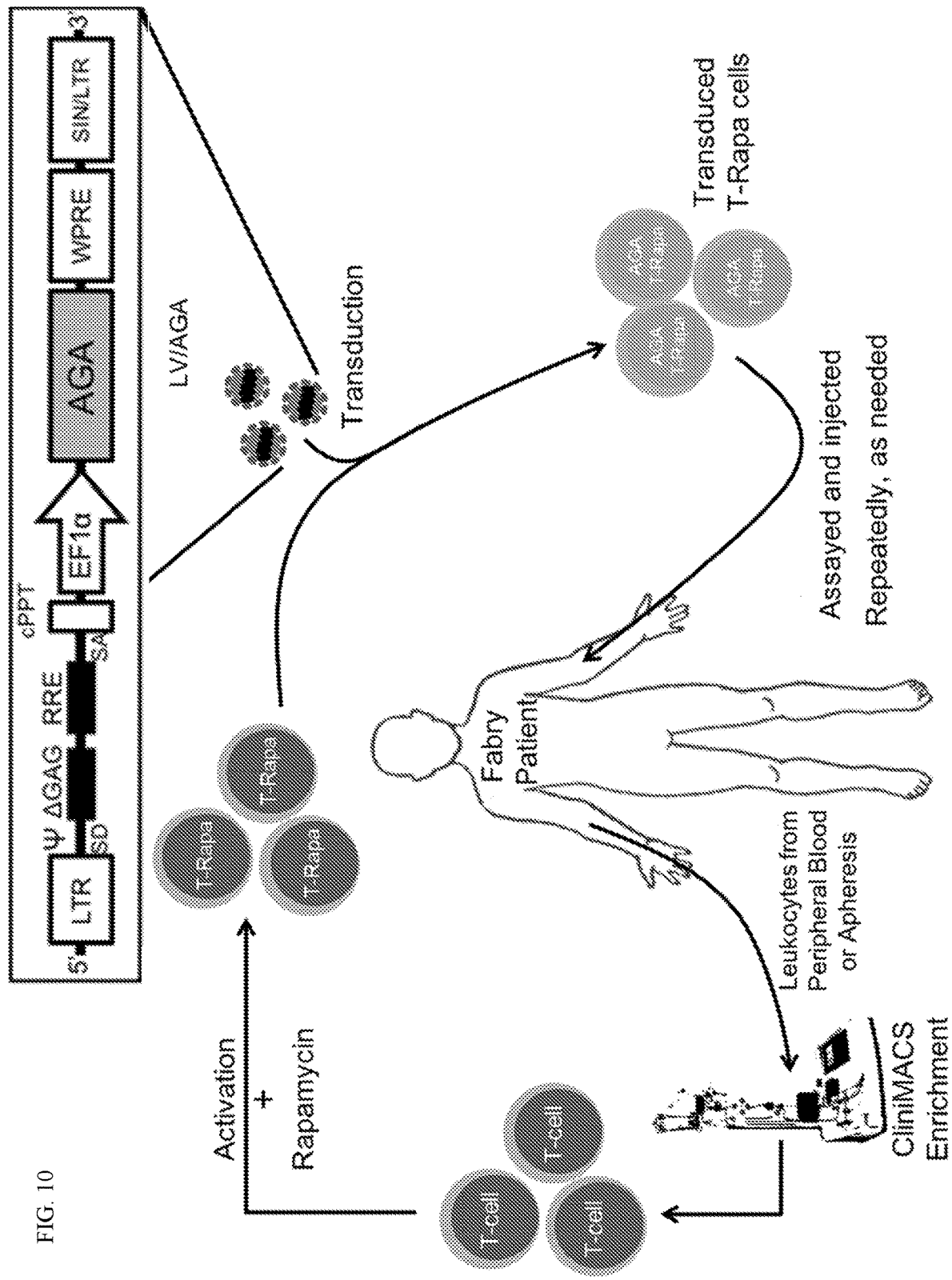
FIG. 10 is an exemplary schematic representing the method of treating a patient with Fabry disease according to the current invention. Alternative viruses used are contemplated and this is only exemplary.

FIG. 10 depicts a schematic of the overall protocol for treatment of a disorder by the methods described herein, specifically showing the steps for treatment of a lysosomal storage disorder, for example, Fabry disease using transduced T-Rapa cells.

Patients' peripheral blood is collected by known methods in the art. CD4+ T-cells are then isolated from peripheral blood using methods known in the art, for example, flow cytometric cell sorting or magnetic cell sorting using antibodies against CD4. Alternatively, CD4+ cells can be similarly isolated from apheresis products, which may be obtained using methods known in the art. Isolated CD4+ cells are cultured in the presence of cytokines (IL-2 and IL-4) as described above in the presence of rapamycin (for example, 1 micromolar) for 3 days. The T-Rapa cells are transduced using a lentivirus ex vivo at an MOI of 1-30 or 1-60 for 12-18 hours, after which they are cultured in cytokine-containing medium for an additional 3 days (can be cultured from 3 days to about 1 month).

Patients receiving T-Rapa cells will not be conditioned with myelo-ablative chemotherapy. Rather, the types of chemotherapy to be administered will be lymphocyte-specific and myeloid-sparing. Lymphocyte-specific chemotherapy may consist of the following regimens (although other regimens can be envisioned): (1) fludarabine plus low-dose, daily cyclophosphamide; or (2) pentostatin plus low-dose daily cyclophosphamide.

Patients are infused with about $2-10\times10^6$/kg transduced T-Rapa cells intravenously. Patients are monitored for expression of α-gal A. Cell administration may be repeated and cell dosage may be adjusted as recommended by appropriate physician.

Example 6: Production of Dual Promoter Lentivirus Vectors for Use in the Present Methods In some examples, the present invention may use dual promoter lentivirus vectors to transfer a transgene (e.g., AGA transgene) and a resistance gene (e.g., IMPDH2(IY)) to confer resistance to a drug (e.g., mycophenolate mofetil (MMF)) into the target T-cell. A dual promoter architecture (pDY-DP (SEQ ID NO:10)) was designed and constructed using pDY as a backbone using standard molecular biology techniques. Human-derived ubiquitous, constitutive promoters express transgenes of interest. For enrichment purposes, a vector with IMPDH2(IY) expressed from one promoter was constructed, with the ability to insert another transgene of interest from the other promoter (i.e. pDY-[MCS]+(IY), (SEQ ID NO:11)). A vector with AGA transgene was constructed to use in treating Fabry disease (SEQ ID NO:3). The titer for this vector is in the range of $1\times10^9$ infectious viral particles (IVP)/mL. A vector with enhanced green fluorescent protein (eGFP) instead of IMPDH2(IY) was used to measure expression and for use as a non-enrichment control. FIG. 13 show the vector maps of lentiviral vectors used in the present invention.

Suitable methods of producing lentiviral vectors are known in the art. A suitable protocol is shown in FIG. 11.

Production of lentivirus includes the following steps: (a) Three packaging plasmids, pCMVΔR8.91 (Zufferey, et al. Nature Biotechnology 15:871-874, 1997, incorporated by reference), pMD.G (Naldini et al., Science 272:263-267, 1996, incorporated by reference) and pAdV (Promega, USA) are mixed in appropriate ratios with a plasmid encoding the transfer vector of interest. These are complexed with polyethylenimine (PEI) and transfected into HEK293T cells. Media is replaced after 16 hours. (b) Culture supernatant containing virus particles is harvested approximately 40 and 64 hours after transfection. The supernatant is filtered through 0.22 μm membrane filters to remove contaminants. (c) Collected supernatant is subjected to ultracentrifugation as indicated to concentrate virus. (d) Viral pellets are resuspended in appropriate media in 2000-fold less volume than the original supernatant.

Example 7: Exemplary Treatment of Fabry Disease Using Dual Promoter Lentiviral Vectors Fabry patients will be treated as described in Example 5, with the exception that a dual promoter lentiviral vector, for example as described in Example 6 will be used in which the vector in addition to expressing α-gal A expresses IMPDH2 (IY), which presents a growth advantage to transduced T-Rapa cells when the patient is treated with low doses of MMF.

Enrichment can be initiated if required by treatment with mycophenolate mofetil (MMF; CellCept, Roche, or approved generic); transduced T-Rapa cells are resistant to the effects of this drug, providing them with a growth advantage. A low dose of oral MMF may be effective (0.1-5 mg/kg TID) but higher doses (5-10 mg/kg TID or 1000 mg BID) may also be tolerated, depending on the patient. As a general guideline, a blood concentration of 0.4-2 μM free mycophenolic acid (MPA) is desirable. MMF may be administered for the duration for which increased enzyme activity is desired, and doses adjusted to titrate the activity. MMF may also be substituted for MPA formulations (Myfortic, Novartis, or approved generic).

Each publication, patent, and patent publication cited in this disclosure is incorporated in reference herein in its entirety. The present invention is not intended to be limited to the foregoing examples but encompasses all such modifications and variations as come within the scope of the appended claims.

Sequence Listing Statement

The application includes the sequence listing that is concurrently filed in computer readable form. This sequence listing is incorporated by reference herein.

The following sequences correspond with the plasmid maps in FIG. 13.
Genetic Elements of Plasmids and Lentivirus Vectors
f1 ori: Origin of plasmid replication in bacteria
Amp(R): Ampicillin-resistance gene (beta-lactamase)
5' LTR: HIV1-derived 5' Long Terminal Repeat: Viral element required for integration into host genome
3' LTR/SIN: HIV1-derived 3' Long Terminal Repeat with a 133 bp deletion to inactivate the capacity for any viral replication after retrotranscription in the host cell
Psi sequence: Retroviral Psi packaging element
5'Gag(del3rdG): Viral element required in $2^{nd}$ generation lentivirus systems for proviral RNA transcription
RRE: Viral REV response element, required for nuclear export of proviral RNA cPPT: central polypurine tract, a lentiviral element that enhances nuclear import/export of viral RNA, consequently enhancing viral titer and transduction.

EF1a: Ubiquitous, constitutively expressing promoter derived from the human elongation factor 1 alpha gene WPRE: Woodchuck Hepatitis post-transcriptional regulatory element; potently terminates transcription and stabilizes mRNA.

hPGK: Ubiquitous, constitutively expressing promoter derived from the human phosphoglycerate kinase 1 gene CTE and polyA: C-Terminal end and polyA signal sequence for termination of transcription coIMPDH2(IY): codon optimized transgene expressing the T333I, S351Y mutant of human inosine-5'-monophosphate dehydrogenase 2

AGA/GBA/ASAH1/GAA: Codon optimized transgenes of interest encoding human α-galactosidase A, β-Glucocerebrosidase, N-acylsphingosine amidohydrolase 1, or acid α-glucosidase, respectively

```
SEQUENCES:
(AGA)
>co.hAGA
                                                                       SEQ ID NO: 1
ATGCAACTTCGAAACCCAGAGCTCCACCTCGGATGTGCCCTTGCTCTGAGGTTCCTGGCGCTG

GTGTCTTGGGATATACCCGGAGCACGCGCTCTGGACAACGGGCTGGCCCGGACTCCAACCATG

GGTTGGCTCCATTGGGAAAGGTTTATGTGCAACTTGGACTGCCAGGAAGAACCCGACTCCTG

TATTTCCGAGAAACTCTTCATGGAGATGGCCGAGCTGATGGTTAGCGAAGGCTGGAAGGATG

CCGGTTATGAATACTTGTGTATCGACGATTGTTGGATGGCTCCCCAGCGGGACAGTGAAGGA

CGACTCCAGGCAGATCCGCAACGGTTCCCTCATGGCATACGGCAGCTCGCCAATTACGTGCAC

AGCAAGGGTTTGAAGCTGGGGATATATGCTGACGTGGGCAACAAAACCTGTGCTGGTTTCCC

CGGCAGCTTCGGCTACTATGATATAGATGCACAAACCTTCGCTGATTGGGGCGTGGACCTGCT

TAAATTTGACGGCTGTTACTGCGACAGCTTGGAAAACCTCGCCGATGGATATAAACACATGA

GCCTTGCACTCAATCGGACTGGCCGGAGCATTGTCTACTCTTGCGAGTGGCCATTGTACATGT

GGCCTTTCCAGAAGCCTAACTATACGGAGATTAGACAGTATTGTAATCACTGGAGAAACTTT

GCAGATATCGACGACTCATGGAAGTCCATCAAATCTATTCTGGACTGGACTTCATTCAATCA

GGAGCGCATCGTCGATGTTGCCGGTCCAGGTGGATGGAACGACCCTGACATGCTCGTAATTG

GGAATTTCGGACTGTCCTGGAATCAGCAGGTCACACAGATGGCTTTGTGGGCTATCATGGCA

GCCCCACTCTTTATGTCTAACGATTTGCGGCATATTTCACCACAGGCCAAAGCCCTGCTGCAA

GATAAGGACGTCATAGCGATTAACCAGGACCCACTGGGAAAGCAGGGCTACCAGCTGAGACA

GGGCGACAATTTTGAGGTCTGGGAAAGACCTCTTAGCGGGCTGGCGTGGGCCGTAGCCATGA

TTAATCGCCAGGAAATTGGCGGCCCTCGCTCTTACACTATCGCGGTCGCCAGTCTGGGCAAGG

GAGTCGCTTGTAACCCCGCCTGCTTCATAACTCAGTTGCTGCCCGTGAAACGGAAGCTGGGCT

TCTATGAATGGACTAGCAGACTCCGCAGTCATATTAATCCGACTGGTACGGTGCTGCTGCAA

CTGGAGAATACCATGCAGATGTCACTTAAGGATCTTCTGTGA

>pDY co.hAGA
                                                                       SEQ ID NO: 2
AAATTGTAAGCGTTAATATTTTGTTAAAATTCGCGTTAAATTTTTGTTAAATCAGCTCATTT

TTTAACCAATAGGCCGAAATCGGCAAAATCCCTTATAAATCAAAAGAATAGACCGAGATAGG

GTTGAGTGTTGTTCCAGTTTGGAACAAGAGTCCACTATTAAAGAACGTGGACTCCAACGTCA

AAGGGCGAAAAACCGTCTATCAGGGCGATGGCCCACTACGTGAACCATCACCCTAATCAAGT

TTTTTGGGGTCGAGGTGCCGTAAAGCACTAAATCGGAACCCTAAAGGGAGCCCCCGATTTAG

AGCTTGACGGGGAAAGCCGGCGAACGTGGCGAGAAAGGAAGGGAAGAAAGCGAAAGGAGCG

GGCGCTAGGGCGCTGGCAAGTGTAGCGGTCACGCTGCGCGTAACCACCACACCCGCCGCGCTT

AATGCGCCGCTACAGGGCGCGTCCATTCGCCATTCAGGCTGCGCAACTGTTGGGAAGGGCGAT

CGGTGCGGGCCTCTTCGCTATTACGCCAGCTGGCGAAAGGGGGATGTGCTGCAAGGCGATTA

AGTTGGGTAACGCCAGGGTTTTCCCAGTCACGACGTTGTAAAACGACGGCCAGTGAATTGTA
```

-continued

```
ATACGACTCACTATAGGGCGAATTGGGCCCGACGTCGCATGCTTGGAAGGGCTAATTCACTCC
CAAAGAAGACAAGATATCCTTGATCTGTGGATCTACCACACACAAGGCTACTTCCCTGATTA
GCAGAACTACACACCAGGGCCAGGGGTCAGATATCCACTGACCTTTGGATGGTGCTACAAGC
TAGTACCAGTTGAGCCAGATAAGGTAGAAGAGGCCAATAAAGGAGAGAACACCAGCTTGTTA
CACCCTGTGAGCCTGCATGGGATGGATGACCCGGAGAGAGAAGTGTTAGAGTGGAGGTTTGA
CAGCCGCCTAGCATTTCATCACGTGGCCCGAGAGCTGCATCCGGAGTACTTCAAGAACTGCTG
ATATCGAGCTTGCTACAAGGGACTTTCCGCTGGGGACTTTCCAGGGAGGCGTGGCCTGGGCG
GGACTGGGGAGTGGCGAGCCCTCAGATCCTGCATATAAGCAGCTGCTTTTTGCCTGTACTGGG
TCTCTCTGGTTAGACCAGATCTGAGCCTGGGAGCTCTCTGGCTAACTAGGGAACCCACTGCTT
AAGCCTCAATAAAGCTTGCCTTGAGTGCTTCAAGTAGTGTGTGCCCGTCTGTTGTGTGACTCT
GGTAACTAGAGATCCCTCAGACCCTTTTAGTCAGTGTGGAAAATCTCTAGCAGTGGCGCCCG
AACAGGGACTTGAAAGCGAAAGGGAAACCAGAGGAGCTCTCTCGACGCAGGACTCGGCTTGC
TGAAGCGCGCACGGCAAGAGGCGAGGGGCGGCGACTGGTGAGTACGCCAAAAATTTTGACTA
GCGGAGGCTAGAAGGAGAGAGATGGGTGCGAGAGCGTCAGTATTAAGCGGGGGAGAATTAG
ATCGCGATGGGAAAAAATTCGGTTAAGGCCAGGGGGAAAGAAAAAATATAAATTAAAACAT
ATAGTATGGGCAAGCAGGGAGCTAGAACGATTCGCAGTTAATCCTGGCCTGTTAGAAACATC
AGAAGGCTGTAGACAAATACTGGGACAGCTACAACCATCCCTTCAGACAGGATCAGAAGAAC
TTAGATCATTATATAATACAGTAGCAACCCTCTATTGTGTGCATCAAAGGATAGAGATAAAA
GACACCAAGGAAGCTTTAGACAAGATAGAGGAAGAGCAAAACAAAAGTAAGACCACCGCACA
GCAAGCGGCCGCTGATCTTCAGACCTGGAGGAGGAGATATGAGGGACAATTGGAGAAGTGAA
TTATATAAATATAAAGTAGTAAAAATTGAACCATTAGGAGTAGCACCCACCAAGGCAAAGAG
AAGAGTGGTGCAGAGAGAAAAAAGAGCAGTGGGAATAGGAGCTTTGTTCCTTGGGTTCTTGG
GAGCAGCAGGAAGCACTATGGGCGCAGCGTCAATGACGCTGACGGTACAGGCCAGACAATTA
TTGTCTGGTATAGTGCAGCAGCAGAACAATTTGCTGAGGGCTATTGAGGCGCAACAGCATCT
GTTGCAACTCACAGTCTGGGGCATCAAGCAGCTCCAGGCAAGAATCCTGGCTGTGGAAAGAT
ACCTAAAGGATCAACAGCTCCTGGGGATTTGGGGTTGCTCTGGAAAACTCATTTGCACCACT
GCTGTGCCTTGGAATGCTAGTTGGAGTAATAAATCTCTGGAACAGATTTGGAATCACACGAC
CTGGATGGAGTGGGACAGAGAAATTAACAATTACACAAGCTTAATACACTCCTTAATTGAAG
AATCGCAAAACCAGCAAGAAAAGAATGAACAAGAATTATTGGAATTAGATAAATGGGCAAG
TTTGTGGAATTGGTTTAACATAACAAATTGGCTGTGGTATATAAAATTATTCATAATGATAG
TAGGAGGCTTGGTAGGTTTAAGAATAGTTTTTGCTGTACTTTCTATAGTGAATAGAGTTAGG
CAGGGATATTCACCATTATCGTTTCAGACCCACCTCCCAACCCCGAGGGGACCCGACAGGCCC
GAAGGAATAGAAGAAGAAGGTGGAGAGAGAGACAGAGACAGATCCATTCGATTAGTGAACG
GATCTCGACGGGATCGATTTTAAAAGAAAAGGGGGGATTGGGGGGTACAGTGCAGGGGAAA
GAATAGTAGACATAATAGCAACAGACATACAAACTAAAGAATTACAAAAACAAATTACAAA
AATTCAAAATTTTATCGATAAGCTTTGCAAAGATGGATAAAGTTTTAAACAGAGAGGAATCT
TTGCAGCTAATGGACCTTCTAGGTCTTGAAAGGAGTGGGAATTGGCTCCGGTGCCCGTCAGT
GGGCAGAGCGCACATCGCCCACAGTCCCCGAGAAGTTGGGGGAGGGGTCGGCAATTGAACC
GGTGCCTAGAGAAGGTGGCGCGGGGTAAACTGGGAAAGTGATGTCGTGTACTGGCTCCGCCT
TTTTCCCGAGGGTGGGGGAGAACCGTATATAAGTGCAGTAGTCGCCGTGAACGTTCTTTTTC
GCAACGGGTTTGCCGCCAGAACACAGGTAAGTGCCGTGTGTGGTTCCCGCGGGCCTGGCCTCT
```

```
TTACGGGTTATGGCCCTTGCGTGCCTTGAATTACTTCCACCTGGCTGCAGTACGTGATTCTTG

ATCCCGAGCTTCGGGTTGGAAGTGGGTGGGAGAGTTCGAGGCCTTGCGCTTAAGGAGCCCCT

TCGCCTCGTGCTTGAGTTGAGGCCTGGCCTGGGCGCTGGGGCCGCCGCGTGCGAATCTGGTGG

CACCTTCGCGCCTGTCTCGCTGCTTTCGATAAGTCTCTAGCCATTTAAAATTTTTGATGACCT

GCTGCGACGCTTTTTTTCTGGCAAGATAGTCTTGTAAATGCGGGCCAAGATCTGCACACTGG

TATTTCGGTTTTTGGGGCCGCGGGCGGCGACGGGGCCCGTGCGTCCCAGCGCACATGTTCGGC

GAGGCGGGGCCTGCGAGCGCGGCCACCGAGAATCGGACGGGGTAGTCTCAAGCTGGCCGGCC

TGCTCTGGTGCCTGGCCTCGCGCCGCCGTGTATCGCCCCGCCCTGGGCGGCAAGGCTGGCCCG

GTCGGCACCAGTTGCGTGAGCGGAAAGATGGCCGCTTCCCGGCCCTGCTGCAGGGAGCTCAAA

ATGGAGGACGCGGCGCTCGGGAGAGCGGGCGGGTGAGTCACCCACACAAAGGAAAAGGGCCT

TTCCGTCCTCAGCCGTCGCTTCATGTGACTCCACGGAGTACCGGGCGCCGTCCAGGCACCTCG

ATTAGTTCTCGAGCTTTTGGAGTACGTCGTCTTTAGGTTGGGGGGAGGGGTTTTATGCGATG

GAGTTTCCCCACACTGAGTGGGTGGAGACTGAAGTTAGGCCAGCTTGGCACTTGATGTAATT

CTCCTTGGAATTTGCCCTTTTTGAGTTTGGATCTTGGTTCATTCTCAAGCCTCAGACAGTGGT

TCAAAGTTTTTTTCTTCCATTTCAGGTGTCGTGAGGAATTCGCCACCATGCAACTTCGAAACC

CAGAGCTCCACCTCGGATGTGCCCTTGCTCTGAGGTTCCTGGCGCTGGTGTCTTGGGATATAC

CCGGAGCACGCGCTCTGGACAACGGGCTGGCCCGGACTCCAACCATGGGTTGGCTCCATTGGG

AAAGGTTTATGTGCAACTTGGACTGCCAGGAAGAACCCGACTCCTGTATTTCCGAGAAACTC

TTCATGGAGATGGCCGAGCTGATGGTTAGCGAAGGCTGGAAGGATGCCGGTTATGAATACTT

GTGTATCGACGATTGTTGGATGGCTCCCCAGCGGGACAGTGAAGGACGACTCCAGGCAGATC

CGCAACGGTTCCCTCATGGCATACGGCAGCTCGCCAATTACGTGCACAGCAAGGGTTTGAAGC

TGGGGATATATGCTGACGTGGGCAACAAAACCTGTGCTGGTTTCCCCGGCAGCTTCGGCTACT

ATGATATAGATGCACAAACCTTCGCTGATTGGGGCGTGGACCTGCTTAAATTTGACGGCTGT

TACTGCGACAGCTTGGAAAACCTCGCCGATGGATATAAACACATGAGCCTTGCACTCAATCG

GACTGGCCGGAGCATTGTCTACTCTTGCGAGTGGCCATTGTACATGTGGCCTTTCCAGAAGCC

TAACTATACGGAGATTAGACAGTATTGTAATCACTGGAGAAACTTTGCAGATATCGACGACT

CATGGAAGTCCATCAAATCTATTCTGGACTGGACTTCATTCAATCAGGAGCGCATCGTCGAT

GTTGCCGGTCCAGGTGGATGGAACGACCCTGACATGCTCGTAATTGGGAATTTCGGACTGTC

CTGGAATCAGCAGGTCACACAGATGGCTTTGTGGGCTATCATGGCAGCCCCACTCTTTATGTC

TAACGATTTGCGGCATATTTCACCACAGGCCAAAGCCCTGCTGCAAGATAAGGACGTCATAG

CGATTAACCAGGACCCACTGGGAAAGCAGGGCTACCAGCTGAGACAGGGCGACAATTTTGAG

GTCTGGGAAAGACCTCTTAGCGGGCTGGCGTGGGCCGTAGCCATGATTAATCGCCAGGAAAT

TGGCGGCCCTCGCTCTTACACTATCGCGGTCGCCAGTCTGGGCAAGGGAGTCGCTTGTAACCC

CGCCTGCTTCATAACTCAGTTGCTGCCCGTGAAACGGAAGCTGGGCTTCTATGAATGGACTAG

CAGACTCCGCAGTCATATTAATCCGACTGGTACGGTGCTGCTGCAACTGGAGAATACCATGC

AGATGTCACTTAAGGATCTTCTGTGAGAACCCGGGATCCAAGCTTCAATTGTGGTCACTCGA

CAATCAACCTCTGGATTACAAAATTTGTGAAAGATTGACTGGTATTCTTAACTATGTTGCTC

CTTTTACGCTATGTGGATACGCTGCTTTAATGCCTTTGTATCATGCTATTGCTTCCCGTATGG

CTTTCATTTTCTCCTCCTTGTATAAATCCTGGTTGCTGTCTCTTTATGAGGAGTTGTGGCCCG

TTGTCAGGCAACGTGGCGTGGTGTGCACTGTGTTTGCTGACGCAACCCCCACTGGTTGGGCA
```

-continued

```
TTGCCACCACCTGTCAGCTCCTTTCCGGGACTTTCGCTTTCCCCCTCCCTATTGCCACGGCGGA
ACTCATCGCCGCCTGCCTTGCCCGCTGCTGGACAGGGGCTCGGCTGTTGGGCACTGACAATTC
CGTGGTGTTGTCGGGGAAGCTGACGTCCTTTCCATGGCTGCTCGCCTGTGTTGCCACCTGGAT
TCTGCGCGGGACGTCCTTCTGCTACGTCCCTTCGGCCCTCAATCCAGCGGACCTTCCTTCCCGC
GGCCTGCTGCCGGCTCTGCGGCCTCTTCCGCGTCTTCGCCTTCGCCCTCAGACGAGTCGGATCT
CCCCTTTGGGCCGCCTCCCCGCCTGCTCGAGACCTAGAAAAACATGGAGCAATCACAAGTAGCA
ATACAGCAGCTACCAATGCTGATTGTGCCTGGCTAGAAGCACAAGAGGAGGAGGAGGTGGGT
TTTCCAGTCACACCTCAGGTACCTTTAAGACCAATGACTTACAAGGCAGCTGTAGATCTTAGC
CACTTTTTAAAAGAAAAGGGGGGACTGGAAGGGCTAATTCACTCCCAACGAAGACAAGATCT
GCTTTTTGCTTGTACTGGGTCTCTCTGGTTAGACCAGATCTGAGCCTGGGAGCTCTCTGGCTA
ACTAGGGAACCCACTGCTTAAGCCTCAATAAAGCTTGCCTTGAGTGCTTCAAGTAGTGTGTG
CCCGTCTGTTGTGTGACTCTGGTAACTAGAGATCCCTCAGACCCTTTTAGTCAGTGTGGAAAA
TCTCTAGCAGTAGTAGTTCATGTCATCTTATTATTCAGTATTTATAACTTGCAAAGAAATGA
ATATCAGAGAGTGAGAGGACGCGTTGGATGCATAGCTTGAGTATTCTATAGTGTCACCTAAA
TAGCTTGGCGTAATCATGGTCATAGCTGTTTCCTGTGTGAAATTGTTATCCGCTCACAATTCC
ACACAACATACGAGCCGGAAGCATAAAGTGTAAAGCCTGGGGTGCCTAATGAGTGAGCTAAC
TCACATTAATTGCGTTGCGCTCACTGCCCGCTTTCCAGTCGGGAAACCTGTCGTGCCAGCTGC
ATTAATGAATCGGCCAACGCGCGGGGAGAGGCGGTTTGCGTATTGGGCGCTCTTCCGCTTCCT
CGCTCACTGACTCGCTGCGCTCGGTCGTTCGGCTGCGGCGAGCGGTATCAGCTCACTCAAAGG
CGGTAATACGGTTATCCACAGAATCAGGGGATAACGCAGGAAAGAACATGTGAGCAAAAGGC
CAGCAAAAGGCCAGGAACCGTAAAAAGGCCGCGTTGCTGGCGTTTTTCCATAGGCTCCGCCCC
CCTGACGAGCATCACAAAAATCGACGCTCAAGTCAGAGGTGGCGAAACCCGACAGGACTATA
AAGATACCAGGCGTTTCCCCCTGGAAGCTCCCTCGTGCGCTCTCCTGTTCCGACCCTGCCGCT
TACCGGATACCTGTCCGCCTTTCTCCCTTCGGGAAGCGTGGCGCTTTCTCATAGCTCACGCTG
TAGGTATCTCAGTTCGGTGTAGGTCGTTCGCTCCAAGCTGGGCTGTGTGCACGAACCCCCCGT
TCAGCCCGACCGCTGCGCCTTATCCGGTAACTATCGTCTTGAGTCCAACCCGGTAAGACACGA
CTTATCGCCACTGGCAGCAGCCACTGGTAACAGGATTAGCAGAGCGAGGTATGTAGGCGGTG
CTACAGAGTTCTTGAAGTGGTGGCCTAACTACGGCTACACTAGAAGAACAGTATTTGGTATC
TGCGCTCTGCTGAAGCCAGTTACCTTCGGAAAAAGAGTTGGTAGCTCTTGATCCGGCAAACA
AACCACCGCTGGTAGCGGTGGTTTTTTTGTTTGCAAGCAGCAGATTACGCGCAGAAAAAAAG
GATCTCAAGAAGATCCTTTGATCTTTTCTACGGGGTCTGACGCTCAGTGGAACGAAAACTCA
CGTTAAGGGATTTTGGTCATGAGATTATCAAAAAGGATCTTCACCTAGATCCTTTTAAATTA
AAAATGAAGTTTTAAATCAATCTAAAGTATATATGAGTAAACTTGGTCTGACAGTTACCAAT
GCTTAATCAGTGAGGCACCTATCTCAGCGATCTGTCTATTTCGTTCATCCATAGTTGCCTGAC
TCCCCGTCGTGTAGATAACTACGATACGGGAGGGCTTACCATCTGGCCCCAGTGCTGCAATGA
TACCGCGAGACCCACGCTCACCGGCTCCAGATTTATCAGCAATAAACCAGCCAGCCGGAAGGG
CCGAGCGCAGAAGTGGTCCTGCAACTTTATCCGCCTCCATCCAGTCTATTAATTGTTGCCGGG
AAGCTAGAGTAAGTAGTTCGCCAGTTAATAGTTTGCGCAACGTTGTTGCCATTGCTACAGGC
ATCGTGGTGTCACGCTCGTCGTTTGGTATGGCTTCATTCAGCTCCGGTTCCCAACGATCAAGG
CGAGTTACATGATCCCCCATGTTGTGCAAAAAAGCGGTTAGCTCCTTCGGTCCTCCGATCGTT
GTCAGAAGTAAGTTGGCCGCAGTGTTATCACTCATGGTTATGGCAGCACTGCATAATTCTCT
```

-continued

```
TACTGTCATGCCATCCGTAAGATGCTTTTCTGTGACTGGTGAGTACTCAACCAAGTCATTCTG

AGAATAGTGTATGCGGCGACCGAGTTGCTCTTGCCCGGCGTCAATACGGGATAATACCGCGCC

ACATAGCAGAACTTTAAAAGTGCTCATCATTGGAAAACGTTCTTCGGGGCGAAAACTCTCAA

GGATCTTACCGCTGTTGAGATCCAGTTCGATGTAACCCACTCGTGCACCCAACTGATCTTCAG

CATCTTTTACTTTCACCAGCGTTTCTGGGTGAGCAAAAACAGGAAGGCAAAATGCCGCAAAA

AAGGGAATAAGGGCGACACGGAAATGTTGAATACTCATACTCTTCCTTTTTCAATATTATTG

AAGCATTTATCAGGGTTATTGTCTCATGAGCGGATACATATTTGAATGTATTTAGAAAAATA

AACAAATAGGGGTTCCGCGCACATTTCCCCGAAAAGTGCCACCTGATGCGGTGTGAAATACC

GCACAGATGCGTAAGGAGAAAATACCGCATCAGG
```

>pDY AGA + (IY) (SEQ ID NO: 3)                                                    SEQ ID NO: 3

```
AAATTGTAAGCGTTAATATTTTGTTAAAATTCGCGTTAAATTTTTGTTAAATCAGCTCATTT

TTTAACCAATAGGCCGAAATCGGCAAAATCCCTTATAAATCAAAAGAATAGACCGAGATAGG

GTTGAGTGTTGTTCCAGTTTGGAACAAGAGTCCACTATTAAAGAACGTGGACTCCAACGTCA

AAGGGCGAAAAACCGTCTATCAGGGCGATGGCCCACTACGTGAACCATCACCCTAATCAAGT

TTTTTGGGGTCGAGGTGCCGTAAAGCACTAAATCGGAACCCTAAAGGGAGCCCCCGATTTAG

AGCTTGACGGGGAAAGCCGGCGAACGTGGCGAGAAAGGAAGGGAAGAAAGCGAAAGGAGCG

GGCGCTAGGGCGCTGGCAAGTGTAGCGGTCACGCTGCGCGTAACCACCACACCCGCCGCGCTT

AATGCGCCGCTACAGGGCGCGTCCATTCGCCATTCAGGCTGCGCAACTGTTGGGAAGGGCGAT

CGGTGCGGGCCTCTTCGCTATTACGCCAGCTGGCGAAAGGGGGATGTGCTGCAAGGCGATTA

AGTTGGGTAACGCCAGGGTTTTCCCAGTCACGACGTTGTAAAACGACGGCCAGTGAATTGTA

ATACGACTCACTATAGGGCGAATTGGGCCCGACGTCGCATGCTTGGAAGGGCTAATTCACTCC

CAAAGAAGACAAGATATCCTTGATCTGTGGATCTACCACACACAAGGCTACTTCCCTGATTA

GCAGAACTACACACCAGGGCCAGGGGTCAGATATCCACTGACCTTTGGATGGTGCTACAAGC

TAGTACCAGTTGAGCCAGATAAGGTAGAAGAGGCCAATAAAGGAGAGAACACCAGCTTGTTA

CACCCTGTGAGCCTGCATGGGATGGATGACCCGGAGAGAGAAGTGTTAGAGTGGAGGTTTGA

CAGCCGCCTAGCATTTCATCACGTGGCCCGAGAGCTGCATCCGGAGTACTTCAAGAACTGCTG

ATATCGAGCTTGCTACAAGGGACTTTCCGCTGGGGACTTTCCAGGGAGGCGTGGCCTGGGCG

GGACTGGGGAGTGGCGAGCCCTCAGATCCTGCATATAAGCAGCTGCTTTTTGCCTGTACTGGG

TCTCTCTGGTTAGACCAGATCTGAGCCTGGGAGCTCTCTGGCTAACTAGGGAACCCACTGCTT

AAGCCTCAATAAAGCTTGCCTTGAGTGCTTCAAGTAGTGTGTGCCCGTCTGTTGTGTGACTCT

GGTAACTAGAGATCCCTCAGACCCTTTTAGTCAGTGTGGAAAATCTCTAGCAGTGGCGCCCG

AACAGGGACTTGAAAGCGAAAGGGAAACCAGAGGAGCTCTCTCGACGCAGGACTCGGCTTGC

TGAAGCGCGCACGGCAAGAGGCGAGGGGCGGCGACTGGTGAGTACGCCAAAAATTTTGACTA

GCGGAGGCTAGAAGGAGAGAGATGGGTGCGAGAGCGTCAGTATTAAGCGGGGGAGAATTAG

ATCGCGATGGGAAAAAATTCGGTTAAGGCCAGGGGGAAAGAAAAAATATAAATTAAAACAT

ATAGTATGGGCAAGCAGGGAGCTAGAACGATTCGCAGTTAATCCTGGCCTGTTAGAAACATC

AGAAGGCTGTAGACAAATACTGGGACAGCTACAACCATCCCTTCAGACAGGATCAGAAGAAC

TTAGATCATTATATAATACAGTAGCAACCCTCTATTGTGTGCATCAAAGGATAGAGATAAAA

GACACCAAGGAAGCTTTAGACAAGATAGAGGAAGAGCAAAACAAAAGTAAGACCACCGCACA

GCAAGCGGCCGCTGATCTTCAGACCTGGAGGAGGAGATATGAGGGACAATTGGAGAAGTGAA
```

-continued

```
TTATATAAATATAAAGTAGTAAAAATTGAACCATTAGGAGTAGCACCCACCAAGGCAAAGAG

AAGAGTGGTGCAGAGAGAAAAAAGAGCAGTGGGAATAGGAGCTTTGTTCCTTGGGTTCTTGG

GAGCAGCAGGAAGCACTATGGGCGCAGCGTCAATGACGCTGACGGTACAGGCCAGACAATTA

TTGTCTGGTATAGTGCAGCAGCAGAACAATTTGCTGAGGGCTATTGAGGCGCAACAGCATCT

GTTGCAACTCACAGTCTGGGGCATCAAGCAGCTCCAGGCAAGAATCCTGGCTGTGGAAAGAT

ACCTAAAGGATCAACAGCTCCTGGGGATTTGGGGTTGCTCTGGAAAACTCATTTGCACCACT

GCTGTGCCTTGGAATGCTAGTTGGAGTAATAAATCTCTGGAACAGATTTGGAATCACACGAC

CTGGATGGAGTGGGACAGAGAAATTAACAATTACACAAGCTTAATACACTCCTTAATTGAAG

AATCGCAAACCAGCAAGAAAAGAATGAACAAGAATTATTGGAATTAGATAAATGGGCAAG

TTTGTGGAATTGGTTTAACATAACAAATTGGCTGTGGTATATAAAATTATTCATAATGATAG

TAGGAGGCTTGGTAGGTTTAAGAATAGTTTTTGCTGTACTTTCTATAGTGAATAGAGTTAGG

CAGGGATATTCACCATTATCGTTTCAGACCCACCTCCCAACCCCGAGGGGACCCGACAGGCCC

GAAGGAATAGAAGAAGAAGGTGGAGAGAGAGACAGAGACAGATCCATTCGATTAGTGAACG

GATCTCGACGGGATCGATTTTAAAAGAAAAGGGGGGATTGGGGGGTACAGTGCAGGGGAAA

GAATAGTAGACATAATAGCAACAGACATACAAACTAAAGAATTACAAAAACAAATTACAAA

AATTCAAAATTTTATCGATAAGCTTTGCAAAGATGGATAAAGTTTTAAACAGAGAGGAATCT

TTGCAGCTAATGGACCTTCTAGGTCTGACCCCGTACGCCTCGAGAGATCTGATCATAATCAGC

CATACCACATTTGTAGAGGTTTTACTTGCTTTAAAAAACCTCCCACACCTCCCCCTGAACCTG

AAACATAAAATGAATGCAATTGTTGTTGTTAACTTGTTTATTGCAGCTTATAATGGTTACAA

ATAAGGCAATAGCATCACAAATTTCACAAATAAGGCATTTTTTTCACTGCATTCTAGTTTTG

GTTTGTCCAAACTCATCAATGTATCTTATCATGTCTGGATCTCAAATCCCTCGGAAGCTGCGC

CTGTCTTAGGTTGGAGTGATACATTTTTATCACTTTTACCCGTCTTTGGATTAGGCAGTAGC

TCTGACGGCCCTCCTGTCTTAGGTTAGTGAAAAATGTCACTCTCTTACCCGTCATTGGCTGTC

CAGCTTAGCTCGCAGGGGAGGTGGTCTGCCTGCAGGTTAGAACAGTCTCTTTTCGTATGAGT

GCAGTGAGTGGACGCCGCCTTCGACCTGGGCTGAAGAAGTTCTTTTCTCGAACTTCAGTTCGC

CGGAATACATCATTGCCCGCACCTGTGTCAGGCTCTTAGCGCCGATATCCTGGCATGAATGCT

GAATTCCGGCGATCAGGTAAGGCACGAATTTGTGAATACTGCCCTTATCCTGGACAGCTCCA

GACACGCCCTGTGCGACTTTGATCTTGTCTGCCTCGGAAAAATACCTGTTCTGAGAGGACAGA

TGCTTATCCATGGCGTCCAGTGACCCCATGCCCCTATATTTCTTCAGTCTGAACCCATCACTA

AAGAAGTACTCGCCGGGGGCTTCTGTGGTTGCAGCCAGCAGGCTGCCCATCATCACTGTGCTT

GCCCCCAGAGCCAGGGCTTTTGCGATGTGGCCCACATTCTGAATTCCCCCGTCAGCGATCACT

GGGACTCCGAATCTCCGGGCATACTCGTACACCTTGTAGACAGCAGTTGCCTGAGGTCGTCCA

CAGGCCAGCACTTCCTGAATGATGCAGATTGATCCACTCCCCATTCCGACCCTCAGAGCATCC

ACTCCTGCGTCAATCAGGTTTTTGGCCTGGGCTGCGGTCACGACATTGCCTCCGATGACCTGC

AGATTTGGGTACTTGTCCTTAATGTACTTGATCATATTAATCTGGAAGATGCTGTTTCCCTG

GCTTGAATCCAGCACGACCACGTCCACCCCTGCCTGAGCCAGCAGATCCAGGCGATATTTATC

GTCCTCGTGTGTGCCAATAGCGGCTCCACACAGCAGCTGTTTCTTTGCGTCCTTACTAGCCAG

AGGGTAATCTCGATTTTTCTTCAGGTCGGTGCGGGCAATGATTGCCACCAGCTCATCGTCTTC

ATTCACGATAGGCAGTTTTCCTTTCTTAGACCGCTGCAGAATCTCGTTGGCTTCCTTCAGTGT

GATGCCGGCAGGTGCGACCACCAGATCTTCGCGTTTGGTCATAATCTCTTCCAGAAAACAGTC

ATGCTCTTCCTCCTTCAGGAAATCGATGTCTCGACTAGAAATGATTCCCACCAGTCGGCTGCC
```

-continued

```
CATTCGTCCAGTATCTGTAATGGGGATGCCGCAAAATCCGTGCCTAGCTTTGGCCTCGAACAC

ATCGCGGACCCTGTCCTTGGGGCTCAGGACCACTGGGTCGGTGATAAAGCCCTGTTCGTATTT

CTTCACCTTTCTGACCTCATTGGCCTGAAATTCTGGAGTGCAGTTATGGTGAATGAACCCGAT

CCCGCCTGTCAGTGCCATAGCAATGGCCATGCCAGCCTCGGTGACAGTGTCCATAGGGGAGCT

CACCAGGGGTGTCTTCAGGGTGATTTTCTTGGTCAGGGCAGAAGTCAGATCCACCTGGTCTGC

GGTAAAATCAATATAGCCGGGCAGGATCAGGAAGTCGTTGTAAGTCAGCCCGTCTCCACAAT

TAAACAGCTGCTGGGCGGTCAGTCCATCATCAGGGACATAGGAAGTGCCTCCAGAAATCAGG

TAGTCGGCCATGGTGGCGCTAGCCCTGGGGAGAGAGGTCGGTGATTCGGTCAACGAGGGAGC

CGACTGCCGACGTGCGCTCCGGAGGCTTGCAGAATGCGGAACACCGCGCGGGCAGGAACAGG

GCCCACACTACCGCCCCACACCCCGCCTCCCGCACCGCCCCTTCCCGGCCGCTGCTCTCGGCGC

GCCCCGCTGAGCAGCCGCTATTGGCCACAGCCCATCGCGGTCGGCGCGCTGCCATTGCTCCCT

GGCGCTGTCCGTCTGCGAGGGTACTAGTGAGACGTGCGGCTTCCGTTTGTCACGTCCGGCACG

CCGCGAACCGCAAGGAACCTTCCCGACTTAGGGGCGGAGCAGGAAGCGTCGCCGGGGGCCCA

CAAGGGTAGCGGCGAAGATCCGGGTGACGCTGCGAACGGACGTGAAGAATGTGCGAGACCCA

GGGTCGGCGCCGCTGCGTTTCCCGGAACCACGCCCAGAGCAGCCGCGTCCCTGCGCAAACCCA

GGGCTGCCAAGGAAAAGGCGCAACCCCAACCCCGTGGTTAATTAAGGTGAAAGGAGTGGGAA

TTGGCTCCGGTGCCCGTCAGTGGGCAGAGCGCACATCGCCCACAGTCCCCGAGAAGTTGGGGG

GAGGGGTCGGCAATTGAACCGGTGCCTAGAGAAGGTGGCGCGGGGTAAACTGGGAAAGTGAT

GTCGTGTACTGGCTCCGCCTTTTTCCCGAGGGTGGGGGAGAACCGTATATAAGTGCAGTAGT

CGCCGTGAACGTTCTTTTTCGCAACGGGTTTGCCGCCAGAACACAGGTAAGTGCCGTGTGTGG

TTCCCGCGGGCCTGGCCTCTTTACGGGTTATGGCCCTTGCGTGCCTTGAATTACTTCCACCTG

GCTGCAGTACGTGATTCTTGATCCCGAGCTTCGGGTTGGAAGTGGGTGGGAGAGTTCGAGGC

CTTGCGCTTAAGGAGCCCCTTCGCCTCGTGCTTGAGTTGAGGCCTGGCCTGGGCGCTGGGGCC

GCCGCGTGCGAATCTGGTGGCACCTTCGCGCCTGTCTCGCTGCTTTCGATAAGTCTCTAGCCA

TTTAAAATTTTTGATGACCTGCTGCGACGCTTTTTTTCTGGCAAGATAGTCTTGTAAATGCG

GGCCAAGATCTGCACACTGGTATTTCGGTTTTTGGGGCCGCGGGCGGCGACGGGGCCCGTGCG

TCCCAGCGCACATGTTCGGCGAGGCGGGGCCTGCGAGCGCGGCCACCGAGAATCGGACGGGGG

TAGTCTCAAGCTGGCCGGCCTGCTCTGGTGCCTGGCCTCGCGCCGCCGTGTATCGCCCCGCCCT

GGGCGGCAAGGCTGGCCCGGTCGGCACCAGTTGCGTGAGCGGAAAGATGGCCGCTTCCCGGCC

CTGCTGCAGGGAGCTCAAAATGGAGGACGCGGCGCTCGGGAGAGCGGGCGGGTGAGTCACCC

ACACAAAGGAAAAGGGCCTTTCCGTCCTCAGCCGTCGCTTCATGTGACTCCACGGAGTACCGG

GCGCCGTCCAGGCACCTCGATTAGTTCTCGAGCTTTTGGAGTACGTCGTCTTTAGGTTGGGGG

GAGGGGTTTTATGCGATGGAGTTTCCCCACACTGAGTGGGTGGAGACTGAAGTTAGGCCAGC

TTGGCACTTGATGTAATTCTCCTTGGAATTTGCCCTTTTTGAGTTTGGATCTTGGTTCATTCT

CAAGCCTCAGACAGTGGTTCAAAGTTTTTTCTTCCATTTCAGGTGTCGTGAGGAATTCGCCA

CCATGCAACTTCGAAACCCAGAGCTCCACCTCGGATGTGCCCTTGCTCTGAGGTTCCTGGCGC

TGGTGTCTTGGGATATACCCGGAGCACGCGCTCTGGACAACGGGCTGGCCCGGACTCCAACCA

TGGGTTGGCTCCATTGGGAAAGGTTTATGTGCAACTTGGACTGCCAGGAAGAACCCGACTCC

TGTATTTCCGAGAAACTCTTCATGGAGATGGCCGAGCTGATGGTTAGCGAAGGCTGGAAGGA

TGCCGGTTATGAATACTTGTGTATCGACGATTGTTGGATGGCTCCCCAGCGGGACAGTGAAG
```

-continued

```
GACGACTCCAGGCAGATCCGCAACGGTTCCCTCATGGCATACGGCAGCTCGCCAATTACGTGC

ACAGCAAGGGTTTGAAGCTGGGGATATATGCTGACGTGGGCAACAAAACCTGTGCTGGTTTC

CCCGGCAGCTTCGGCTACTATGATATAGATGCACAAACCTTCGCTGATTGGGCGTGGACCTG

CTTAAATTTGACGGCTGTTACTGCGACAGCTTGGAAAACCTCGCCGATGGATATAAACACAT

GAGCCTTGCACTCAATCGGACTGGCCGGAGCATTGTCTACTCTTGCGAGTGGCCATTGTACAT

GTGGCCTTTCCAGAAGCCTAACTATACGGAGATTAGACAGTATTGTAATCACTGGAGAAACT

TTGCAGATATCGACGACTCATGGAAGTCCATCAAATCTATTCTGGACTGGACTTCATTCAAT

CAGGAGCGCATCGTCGATGTTGCCGGTCCAGGTGGATGGAACGACCCTGACATGCTCGTAAT

TGGGAATTTCGGACTGTCCTGGAATCAGCAGGTCACACAGATGGCTTTGTGGGCTATCATGG

CAGCCCCACTCTTTATGTCTAACGATTTGCGGCATATTTCACCACAGGCCAAAGCCCTGCTGC

AAGATAAGGACGTCATAGCGATTAACCAGGACCCACTGGGAAAGCAGGGCTACCAGCTGAGA

CAGGGCGACAATTTTGAGGTCTGGGAAAGACCTCTTAGCGGGCTGGCGTGGGCCGTAGCCAT

GATTAATCGCCAGGAAATTGGCGGCCCTCGCTCTTACACTATCGCGGTCGCCAGTCTGGGCAA

GGGAGTCGCTTGTAACCCCGCCTGCTTCATAACTCAGTTGCTGCCCGTGAAACGGAAGCTGGG

CTTCTATGAATGGACTAGCAGACTCCGCAGTCATATTAATCCGACTGGTACGGTGCTGCTGCA

ACTGGAGAATACCATGCAGATGTCACTTAAGGATCTTCTGTGAGAACCCGGGATCCAAGCTT

CAATTGTGGTCACTCGACAATCAACCTCTGGATTACAAAATTTGTGAAAGATTGACTGGTAT

TCTTAACTATGTTGCTCCTTTTACGCTATGTGGATACGCTGCTTTAATGCCTTTGTATCATGC

TATTGCTTCCCGTATGGCTTTCATTTTCTCCTCCTTGTATAAATCCTGGTTGCTGTCTCTTTA

TGAGGAGTTGTGGCCCGTTGTCAGGCAACGTGGCGTGGTGTGCACTGTGTTTGCTGACGCAA

CCCCCACTGGTTGGGGCATTGCCACCACCTGTCAGCTCCTTTCCGGGACTTTCGCTTTCCCCCT

CCCTATTGCCACGGCGGAACTCATCGCCGCCTGCCTTGCCCGCTGCTGGACAGGGGCTCGGCT

GTTGGGCACTGACAATTCCGTGGTGTTGTCGGGGAAGCTGACGTCCTTTCCATGGCTGCTCGC

CTGTGTTGCCACCTGGATTCTGCGCGGGACGTCCTTCTGCTACGTCCCTTCGGCCCTCAATCC

AGCGGACCTTCCTTCCCGCGGCCTGCTGCCGGCTCTGCGGCCTCTTCCGCGTCTTCGCCTTCGC

CCTCAGACGAGTCGGATCTCCCTTTGGGCCGCCTCCCCGCCTGCTCGAGACCTAGAAAAACAT

GGAGCAATCACAAGTAGCAATACAGCAGCTACCAATGCTGATTGTGCCTGGCTAGAAGCACA

AGAGGAGGAGGAGGTGGGTTTTCCAGTCACACCTCAGGTACCTTTAAGACCAATGACTTACA

AGGCAGCTGTAGATCTTAGCCACTTTTTAAAAGAAAAGGGGGACTGGAAGGGCTAATTCAC

TCCCAACGAAGACAAGATCTGCTTTTTGCTTGTACTGGGTCTCTCTGGTTAGACCAGATCTGA

GCCTGGGAGCTCTCTGGCTAACTAGGGAACCCACTGCTTAAGCCTCAATAAAGCTTGCCTTGA

GTGCTTCAAGTAGTGTGTGCCCGTCTGTTGTGTGACTCTGGTAACTAGAGATCCCTCAGACCC

TTTTAGTCAGTGTGGAAAATCTCTAGCAGTAGTAGTTCATGTCATCTTATTATTCAGTATTT

ATAACTTGCAAAGAAATGAATATCAGAGAGTGAGAGGACGCGTTGGATGCATAGCTTGAGTA

TTCTATAGTGTCACCTAAATAGCTTGGCGTAATCATGGTCATAGCTGTTTCCTGTGTGAAAT

TGTTATCCGCTCACAATTCCACACAACATACGAGCCGGAAGCATAAAGTGTAAAGCCTGGGG

TGCCTAATGAGTGAGCTAACTCACATTAATTGCGTTGCGCTCACTGCCCGCTTTCCAGTCGGG

AAACCTGTCGTGCCAGCTGCATTAATGAATCGGCCAACGCGCGGGGAGAGGCGGTTTGCGTA

TTGGGCGCTCTTCCGCTTCCTCGCTCACTGACTCGCTGCGCTCGGTCGTTCGGCTGCGGCGAG

CGGTATCAGCTCACTCAAAGGCGGTAATACGGTTATCCACAGAATCAGGGGATAACGCAGGA

AAGAACATGTGAGCAAAAGGCCAGCAAAAGGCCAGGAACCGTAAAAAGGCCGCGTTGCTGGC
```

-continued

```
GTTTTTCCATAGGCTCCGCCCCCCTGACGAGCATCACAAAAATCGACGCTCAAGTCAGAGGTG

GCGAAACCCGACAGGACTATAAAGATACCAGGCGTTTCCCCCTGGAAGCTCCCTCGTGCGCTC

TCCTGTTCCGACCCTGCCGCTTACCGGATACCTGTCCGCCTTTCTCCCTTCGGGAAGCGTGGC

GCTTTCTCATAGCTCACGCTGTAGGTATCTCAGTTCGGTGTAGGTCGTTCGCTCCAAGCTGGG

CTGTGTGCACGAACCCCCCGTTCAGCCCGACCGCTGCGCCTTATCCGGTAACTATCGTCTTGA

GTCCAACCCGGTAAGACACGACTTATCGCCACTGGCAGCAGCCACTGGTAACAGGATTAGCAG

AGCGAGGTATGTAGGCGGTGCTACAGAGTTCTTGAAGTGGTGGCCTAACTACGGCTACACTA

GAAGAACAGTATTTGGTATCTGCGCTCTGCTGAAGCCAGTTACCTTCGGAAAAAGAGTTGGT

AGCTCTTGATCCGGCAAACAAACCACCGCTGGTAGCGGTGGTTTTTTTGTTTGCAAGCAGCA

GATTACGCGCAGAAAAAAAGGATCTCAAGAAGATCCTTTGATCTTTTCTACGGGGTCTGACG

CTCAGTGGAACGAAAACTCACGTTAAGGGATTTTGGTCATGAGATTATCAAAAAGGATCTTC

ACCTAGATCCTTTTAAATTAAAAATGAAGTTTTAAATCAATCTAAAGTATATATGAGTAAAC

TTGGTCTGACAGTTACCAATGCTTAATCAGTGAGGCACCTATCTCAGCGATCTGTCTATTTCG

TTCATCCATAGTTGCCTGACTCCCCGTCGTGTAGATAACTACGATACGGGAGGGCTTACCATC

TGGCCCCAGTGCTGCAATGATACCGCGAGACCCACGCTCACCGGCTCCAGATTTATCAGCAAT

AAACCAGCCAGCCGGAAGGGCCGAGCGCAGAAGTGGTCCTGCAACTTTATCCGCCTCCATCCA

GTCTATTAATTGTTGCCGGGAAGCTAGAGTAAGTAGTTCGCCAGTTAATAGTTTGCGCAACG

TTGTTGCCATTGCTACAGGCATCGTGGTGTCACGCTCGTCGTTTGGTATGGCTTCATTCAGCT

CCGGTTCCCAACGATCAAGGCGAGTTACATGATCCCCCATGTTGTGCAAAAAAGCGGTTAGC

TCCTTCGGTCCTCCGATCGTTGTCAGAAGTAAGTTGGCCGCAGTGTTATCACTCATGGTTATG

GCAGCACTGCATAATTCTCTTACTGTCATGCCATCCGTAAGATGCTTTTCTGTGACTGGTGAG

TACTCAACCAAGTCATTCTGAGAATAGTGTATGCGGCGACCGAGTTGCTCTTGCCCGGCGTCA

ATACGGGATAATACCGCGCCACATAGCAGAACTTTAAAAGTGCTCATCATTGGAAAACGTTC

TTCGGGGCGAAAACTCTCAAGGATCTTACCGCTGTTGAGATCCAGTTCGATGTAACCCACTCG

TGCACCCAACTGATCTTCAGCATCTTTTACTTTCACCAGCGTTTCTGGGTGAGCAAAAACAGG

AAGGCAAAATGCCGCAAAAAAGGGAATAAGGGCGACACGGAAATGTTGAATACTCATACTCT

TCCTTTTTCAATATTATTGAAGCATTTATCAGGGTTATTGTCTCATGAGCGGATACATATTT

GAATGTATTTAGAAAAATAAACAAATAGGGGTTCCGCGCACATTTCCCCGAAAAGTGCCACC

TGATGCGGTGTGAAATACCGCACAGATGCGTAAGGAGAAAATACCGCATCAGG
```

Gaucher disease
>pDY co hGBA

SEQ ID NO: 4

```
AAATTGTAAGCGTTAATATTTTGTTAAAATTCGCGTTAAATTTTTGTTAAATCAGCTCATTT

TTTAACCAATAGGCCGAAATCGGCAAAATCCCTTATAAATCAAAAGAATAGACCGAGATAGG

GTTGAGTGTTGTTCCAGTTTGGAACAAGAGTCCACTATTAAAGAACGTGGACTCCAACGTCA

AAGGGCGAAAAACCGTCTATCAGGGCGATGGCCCACTACGTGAACCATCACCCTAATCAAGT

TTTTTGGGGTCGAGGTGCCGTAAAGCACTAAATCGGAACCCTAAAGGGAGCCCCCGATTTAG

AGCTTGACGGGGAAAGCCGGCGAACGTGGCGAGAAAGGAAGGGAAGAAAGCGAAAGGAGCG

GGCGCTAGGGCGCTGGCAAGTGTAGCGGTCACGCTGCGCGTAACCACCACACCCGCCGCGCTT

AATGCGCCGCTACAGGGCGCGTCCATTCGCCATTCAGGCTGCGCAACTGTTGGGAAGGGCGAT

CGGTGCGGGCCTCTTCGCTATTACGCCAGCTGGCGAAAGGGGGATGTGCTGCAAGGCGATTA

AGTTGGGTAACGCCAGGGTTTTCCCAGTCACGACGTTGTAAAACGACGGCCAGTGAATTGTA
```

-continued

```
ATACGACTCACTATAGGGCGAATTGGGCCCGACGTCGCATGCTTGGAAGGGCTAATTCACTCC

CAAAGAAGACAAGATATCCTTGATCTGTGGATCTACCACACACAAGGCTACTTCCCTGATTA

GCAGAACTACACACCAGGGCCAGGGGTCAGATATCCACTGACCTTTGGATGGTGCTACAAGC

TAGTACCAGTTGAGCCAGATAAGGTAGAAGAGGCCAATAAAGGAGAGAACACCAGCTTGTTA

CACCCTGTGAGCCTGCATGGGATGGATGACCCGGAGAGAGAAGTGTTAGAGTGGAGGTTTGA

CAGCCGCCTAGCATTTCATCACGTGGCCCGAGAGCTGCATCCGGAGTACTTCAAGAACTGCTG

ATATCGAGCTTGCTACAAGGGACTTTCCGCTGGGGACTTTCCAGGGAGGCGTGGCCTGGGCG

GGACTGGGGAGTGGCGAGCCCTCAGATCCTGCATATAAGCAGCTGCTTTTTGCCTGTACTGGG

TCTCTCTGGTTAGACCAGATCTGAGCCTGGGAGCTCTCTGGCTAACTAGGGAACCCACTGCTT

AAGCCTCAATAAAGCTTGCCTTGAGTGCTTCAAGTAGTGTGTGCCCGTCTGTTGTGTGACTCT

GGTAACTAGAGATCCCTCAGACCCTTTTAGTCAGTGTGGAAAATCTCTAGCAGTGGCGCCCG

AACAGGGACTTGAAAGCGAAAGGGAAACCAGAGGAGCTCTCTCGACGCAGGACTCGGCTTGC

TGAAGCGCGCACGGCAAGAGGCGAGGGGCGGCGACTGGTGAGTACGCCAAAAATTTTGACTA

GCGGAGGCTAGAAGGAGAGAGATGGGTGCGAGAGCGTCAGTATTAAGCGGGGGAGAATTAG

ATCGCGATGGGAAAAAATTCGGTTAAGGCCAGGGGGAAAGAAAAAATATAAATTAAAACAT

ATAGTATGGGCAAGCAGGGAGCTAGAACGATTCGCAGTTAATCCTGGCCTGTTAGAAACATC

AGAAGGCTGTAGACAAATACTGGGACAGCTACAACCATCCCTTCAGACAGGATCAGAAGAAC

TTAGATCATTATATAATACAGTAGCAACCCTCTATTGTGTGCATCAAAGGATAGAGATAAAA

GACACCAAGGAAGCTTTAGACAAGATAGAGGAAGAGCAAAACAAAGTAAGACCACCGCACA

GCAAGCGGCCGCTGATCTTCAGACCTGGAGGAGGAGATATGAGGGACAATTGGAGAAGTGAA

TTATATAAATATAAAGTAGTAAAAATTGAACCATTAGGAGTAGCACCCACCAAGGCAAAGAG

AAGAGTGGTGCAGAGAGAAAAAAGAGCAGTGGGAATAGGAGCTTTGTTCCTTGGGTTCTTGG

GAGCAGCAGGAAGCACTATGGGCGCAGCGTCAATGACGCTGACGGTACAGGCCAGACAATTA

TTGTCTGGTATAGTGCAGCAGCAGAACAATTTGCTGAGGGCTATTGAGGCGCAACAGCATCT

GTTGCAACTCACAGTCTGGGGCATCAAGCAGCTCCAGGCAAGAATCCTGGCTGTGGAAAGAT

ACCTAAAGGATCAACAGCTCCTGGGGATTTGGGGTTGCTCTGGAAAACTCATTTGCACCACT

GCTGTGCCTTGGAATGCTAGTTGGAGTAATAAATCTCTGGAACAGATTTGGAATCACACGAC

CTGGATGGAGTGGGACAGAGAAATTAACAATTACACAAGCTTAATACACTCCTTAATTGAAG

AATCGCAAAACCAGCAAGAAAAGAATGAACAAGAATTATTGGAATTAGATAAATGGGCAAG

TTTGTGGAATTGGTTTAACATAACAAATTGGCTGTGGTATATAAAATTATTCATAATGATAG

TAGGAGGCTTGGTAGGTTTAAGAATAGTTTTTGCTGTACTTTCTATAGTGAATAGAGTTAGG

CAGGGATATTCACCATTATCGTTTCAGACCCACCTCCCAACCCCGAGGGGACCCGACAGGCCC

GAAGGAATAGAAGAAGAAGGTGGAGAGAGAGACAGAGACAGATCCATTCGATTAGTGAACG

GATCTCGACGGGATCGATTTTAAAAGAAAAGGGGGATTGGGGGGTACAGTGCAGGGGAAA

GAATAGTAGACATAATAGCAACAGACATACAAACTAAAGAATTACAAAAACAAATTACAAA

AATTCAAAATTTTATCGATAAGCTTTGCAAAGATGGATAAAGTTTTAAACAGAGAGGAATCT

TTGCAGCTAATGGACCTTCTAGGTCTTGAAAGGAGTGGGAATTGGCTCCGGTGCCCGTCAGT

GGGCAGAGCGCACATCGCCCACAGTCCCCGAGAAGTTGGGGGGAGGGGTCGGCAATTGAACC

GGTGCCTAGAGAAGGTGGCGCGGGGTAAACTGGGAAAGTGATGTCGTGTACTGGCTCCGCCT

TTTTCCCGAGGGTGGGGGAGAACCGTATATAAGTGCAGTAGTCGCCGTGAACGTTCTTTTTC
```

-continued

```
GCAACGGGTTTGCCGCCAGAACACAGGTAAGTGCCGTGTGTGGTTCCCGCGGGCCTGGCCTCT
TTACGGGTTATGGCCCTTGCGTGCCTTGAATTACTTCCACCTGGCTGCAGTACGTGATTCTTG
ATCCCGAGCTTCGGGTTGGAAGTGGGTGGGAGAGTTCGAGGCCTTGCGCTTAAGGAGCCCCT
TCGCCTCGTGCTTGAGTTGAGGCCTGGCCTGGGCGCTGGGGCCGCCGCGTGCGAATCTGGTGG
CACCTTCGCGCCTGTCTCGCTGCTTTCGATAAGTCTCTAGCCATTTAAAATTTTTGATGACCT
GCTGCGACGCTTTTTTTCTGGCAAGATAGTCTTGTAAATGCGGGCCAAGATCTGCACACTGG
TATTTCGGTTTTTGGGGCCGCGGGCGGCGACGGGGCCCGTGCGTCCCAGCGCACATGTTCGGC
GAGGCGGGGCCTGCGAGCGCGGCCACCGAGAATCGGACGGGGGTAGTCTCAAGCTGGCCGGCC
TGCTCTGGTGCCTGGCCTCGCGCCGCCGTGTATCGCCCCGCCCTGGGCGGCAAGGCTGGCCCG
GTCGGCACCAGTTGCGTGAGCGGAAAGATGGCCGCTTCCCGGCCCTGCTGCAGGGAGCTCAAA
ATGGAGGACGCGGCGCTCGGGAGAGCGGGCGGGTGAGTCACCCACACAAAGGAAAAGGGCCT
TTCCGTCCTCAGCCGTCGCTTCATGTGACTCCACGGAGTACCGGGCGCCGTCCAGGCACCTCG
ATTAGTTCTCGAGCTTTTGGAGTACGTCGTCTTTAGGTTGGGGGGAGGGGTTTTATGCGATG
GAGTTTCCCCACACTGAGTGGGTGGAGACTGAAGTTAGGCCAGCTTGGCACTTGATGTAATT
CTCCTTGGAATTTGCCCTTTTTGAGTTTGGATCTTGGTTCATTCTCAAGCCTCAGACAGTGGT
TCAAAGTTTTTTTCTTCCATTTCAGGTGTCGTGAGGAATTCGCTAGCGCCACCATGGAGTTCT
CAAGCCCCTCTCGGGAAGAATGCCCAAAACCTCTGTCACGGGTGTCTATCATGGCTGGATCAC
TGACTGGCCTGCTGCTGCTGCAGGCCGTGAGCTGGGCCTCCGGAGCCCGGCCTTGCATCCCAA
AGTCTTTCGGCTACAGCTCCGTGGTGTGCGTGTGCAACGCCACCTATTGTGACTCCTTCGATC
CCCCTACCTTTCCCGCCCTGGGCACATTTTCTCGGTACGAGTCTACACGCAGCGGCAGGAGAA
TGGAGCTGAGCATGGGCCCTATCCAGGCCAATCACACCGGAACAGGCCTGCTGCTGACCCTGC
AGCCAGAGCAGAAGTTCCAGAAGGTGAAGGGCTTTGGAGGAGCAATGACAGACGCAGCCGCC
CTGAACATCCTGGCCCTGTCCCCACCCGCCCAGAATCTGCTGCTGAAGTCCTACTTCTCTGAG
GAGGGCATCGGCTATAACATCATCAGGGTGCCCATGGCCAGCTGCGACTTTTCCATCAGAACC
TACACATATGCCGATACCCCTGACGATTTCCAGCTGCACAATTTTTCCCTGCCAGAGGAGGAT
ACAAAGCTGAAGATCCCACTGATCCACAGGGCCCTGCAGCTGGCCCAGAGGCCCGTGAGCCTG
CTGGCCAGCCCCTGGACCTCCCCTACATGGCTGAAGACCAACGGCGCCGTGAATGGCAAGGGC
TCTCTGAAGGGACAGCCAGGCGACATCTACCACCAGACATGGGCCCGCTATTTCGTGAAGTTT
CTGGATGCCTACGCCGAGCACAAGCTGCAGTTCTGGGCCGTGACCGCAGAGAACGAGCCTTCT
GCCGGCCTGCTGAGCGGCTATCCCTTCCAGTGCCTGGGCTTTACACCTGAGCACCAGAGGGAC
TTTATCGCCAGAGATCTGGGCCCAACCCTGGCCAACTCCACACACCACAATGTGCGGCTGCTG
ATGCTGGACGATCAGCGCCTGCTGCTGCCTCACTGGGCCAAGGTGGTGCTGACCGACCCAGAG
GCCGCCAAGTACGTGCACGGCATCGCCGTGCACTGGTATCTGGATTTCCTGGCACCAGCAAAG
GCCACCCTGGGAGAGACACACAGGCTGTTCCCTAACACCATGCTGTTTGCCAGCGAGGCCTGC
GTGGGCTCCAAGTTTTGGGAGCAGTCCGTGCGGCTGGGCTCTTGGGACAGGGGCATGCAGTA
CTCCCACTCTATCATCACCAATCTGCTGTATCACGTGGTGGGCTGGACAGACTGGAACCTGGC
CCTGAATCCAGAGGGCGGCCCCAACTGGGTGAGAAATTTCGTGGATAGCCCCATCATCGTGG
ACATCACCAAGGATACATTCTACAAGCAGCCAATGTTTTATCACCTGGGCCACTTCTCTAAGT
TTATCCCAGAGGGCAGCCAGAGGGTGGGCCTGGTGGCCAGCCAGAAGAACGACCTGGATGCA
GTGGCCCTGATGCACCCTGACGGCTCCGCCGTGGTGGTGCTGAATCGCTCTAGCAAGGAC
GTGCCTCTGACCATCAAGGACCCCGCCGTGGGCTTTCTGGAGACCATTTCACCCGGCTATTCT
```

-continued

```
ATTCATACCTATCTGTGGAGGAGGCAGTAACCTGCAGGGGATCCAAGCTTCAATTGTGGTCA
CTCGACAATCAACCTCTGGATTACAAAATTTGTGAAAGATTGACTGGTATTCTTAACTATGT
TGCTCCTTTTACGCTATGTGGATACGCTGCTTTAATGCCTTTGTATCATGCTATTGCTTCCG
TATGGCTTTCATTTTCTCCTCCTTGTATAAATCCTGGTTGCTGTCTCTTTATGAGGAGTTGTG
GCCCGTTGTCAGGCAACGTGGCGTGGTGTGCACTGTGTTTGCTGACGCAACCCCCACTGGTTG
GGGCATTGCCACCACCTGTCAGCTCCTTTCCGGGACTTTCGCTTTCCCCCTCCCTATTGCCACG
GCGGAACTCATCGCCGCCTGCCTTGCCCGCTGCTGGACAGGGGCTCGGCTGTTGGGCACTGAC
AATTCCGTGGTGTTGTCGGGGAAGCTGACGTCCTTTCCATGGCTGCTCGCCTGTGTTGCCACC
TGGATTCTGCGCGGGACGTCCTTCTGCTACGTCCCTTCGGCCCTCAATCCAGCGGACCTTCCT
TCCCGCGGCCTGCTGCCGGCTCTGCGGCCTCTTCCGCGTCTTCGCCTTCGCCCTCAGACGAGTC
GGATCTCCCTTTGGGCCGCCTCCCCGCCTGCTCGAGACCTAGAAAAACATGGAGCAATCACAA
GTAGCAATACAGCAGCTACCAATGCTGATTGTGCCTGGCTAGAAGCACAAGAGGAGGAGGAG
GTGGGTTTTCCAGTCACACCTCAGGTACCTTTAAGACCAATGACTTACAAGGCAGCTGTAGA
TCTTAGCCACTTTTTAAAAGAAAAGGGGGGACTGGAAGGGCTAATTCACTCCCAACGAAGAC
AAGATCTGCTTTTTGCTTGTACTGGGTCTCTCTGGTTAGACCAGATCTGAGCCTGGGAGCTCT
CTGGCTAACTAGGGAACCCACTGCTTAAGCCTCAATAAAGCTTGCCTTGAGTGCTTCAAGTA
GTGTGTGCCCGTCTGTTGTGTGACTCTGGTAACTAGAGATCCCTCAGACCCTTTTAGTCAGTG
TGGAAAATCTCTAGCAGTAGTAGTTCATGTCATCTTATTATTCAGTATTTATAACTTGCAAA
GAAATGAATATCAGAGAGTGAGAGGACGCGTTGGATGCATAGCTTGAGTATTCTATAGTGTC
ACCTAAATAGCTTGGCGTAATCATGGTCATAGCTGTTTCCTGTGTGAAATTGTTATCCGCTC
ACAATTCCACACAACATACGAGCCGGAAGCATAAAGTGTAAAGCCTGGGGTGCCTAATGAGT
GAGCTAACTCACATTAATTGCGTTGCGCTCACTGCCCGCTTTCCAGTCGGGAAACCTGTCGTG
CCAGCTGCATTAATGAATCGGCCAACGCGCGGGGAGAGGCGGTTTGCGTATTGGGCGCTCTTC
CGCTTCCTCGCTCACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAAAGAACATGTGAG
CAAAAGGCCAGCAAAAGGCCAGGAACCGTAAAAAGGCCGCGTTGCTGGCGTTTTTCCATAGG
CTCCGCCCCCCTGACGAGCATCACAAAAATCGACGCTCAAGTCAGAGGTGGCGAAACCCGACA
GGACTATAAAGATACCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGGCGCTTTCTCATAGC
TCACGCTGTAGGTATCTCAGTTCGGTGTAGGTCGTTCGCTCCAAGCTGGGCTGTGTGCACGAA
CCCCCCGTTCAGCCCGACCGCTGCGCCTTATCCGGTAACTATCGTCTTGAGTCCAACCCGGTA
AGACACGACTTATCGCCACTGGCAGCAGCCACTGGTAACAGGATTAGCAGAGCGAGGTATGT
AGGCGGTGCTACAGAGTTCTTGAAGTGGTGGCCTAACTACGGCTACACTAGAAGAACAGTAT
TTGGTATCTGCGCTCTGCTGAAGCCAGTTACCTTCGGAAAAAGAGTTGGTAGCTCTTGATCC
GGCAAACAAACCACCGCTGGTAGCGGTGGTTTTTTTGTTTGCAAGCAGCAGATTACGCGCAG
AAAAAAAGGATCTCAAGAAGATCCTTTGATCTTTTCTACGGGGTCTGACGCTCAGTGGAACG
AAAACTCACGTTAAGGGATTTTGGTCATGAGATTATCAAAAAGGATCTTCACCTAGATCCTT
TTAAATTAAAAATGAAGTTTTAAATCAATCTAAAGTATATATGAGTAAACTTGGTCTGACAG
TTACCAATGCTTAATCAGTGAGGCACCTATCTCAGCGATCTGTCTATTTCGTTCATCCATAGT
TGCCTGACTCCCCGTCGTGTAGATAACTACGATACGGGAGGGCTTACCATCTGGCCCCAGTGC
```

-continued

```
TGCAATGATACCGCGAGACCCACGCTCACCGGCTCCAGATTTATCAGCAATAAACCAGCCAGC

CGGAAGGGCCGAGCGCAGAAGTGGTCCTGCAACTTTATCCGCCTCCATCCAGTCTATTAATTG

TTGCCGGGAAGCTAGAGTAAGTAGTTCGCCAGTTAATAGTTTGCGCAACGTTGTTGCCATTG

CTACAGGCATCGTGGTGTCACGCTCGTCGTTTGGTATGGCTTCATTCAGCTCCGGTTCCCAAC

GATCAAGGCGAGTTACATGATCCCCCATGTTGTGCAAAAAAGCGGTTAGCTCCTTCGGTCCTC

CGATCGTTGTCAGAAGTAAGTTGGCCGCAGTGTTATCACTCATGGTTATGGCAGCACTGCAT

AATTCTCTTACTGTCATGCCATCCGTAAGATGCTTTTCTGTGACTGGTGAGTACTCAACCAAG

TCATTCTGAGAATAGTGTATGCGGCGACCGAGTTGCTCTTGCCCGGCGTCAATACGGGATAA

TACCGCGCCACATAGCAGAACTTTAAAAGTGCTCATCATTGGAAAACGTTCTTCGGGGCGAA

AACTCTCAAGGATCTTACCGCTGTTGAGATCCAGTTCGATGTAACCCACTCGTGCACCCAACT

GATCTTCAGCATCTTTTACTTTCACCAGCGTTTCTGGGTGAGCAAAAACAGGAAGGCAAAAT

GCCGCAAAAAAGGGAATAAGGGCGACACGGAAATGTTGAATACTCATACTCTTCCTTTTTCA

ATATTATTGAAGCATTTATCAGGGTTATTGTCTCATGAGCGGATACATATTTGAATGTATTT

AGAAAAATAAACAAATAGGGGTTCCGCGCACATTTCCCCGAAAAGTGCCACCTGATGCGGTG

TGAAATACCGCACAGATGCGTAAGGAGAAAATACCGCATCAGG
```

```
Farber disease
>pDY hASAH1                                                    SEQ ID NO: 5
GGGCGAATTGGGCCCGACGTCGCATGCTTGGAAGGGCTAATTCACTCCCAAAGAAGACAAGA

TATCCTTGATCTGTGGATCTACCACACACAAGGCTACTTCCCTGATTAGCAGAACTACACACC

AGGGCCAGGGGTCAGATATCCACTGACCTTTGGATGGTGCTACAAGCTAGTACCAGTTGAGC

CAGATAAGGTAGAAGAGGCCAATAAAGGAGAGAACACCAGCTTGTTACACCCTGTGAGCCTG

CATGGGATGGATGACCCGGAGAGAGAAGTGTTAGAGTGGAGGTTTGACAGCCGCCTAGCATT

TCATCACGTGGCCCGAGAGCTGCATCCGGAGTACTTCAAGAACTGCTGATATCGAGCTTGCTA

CAAGGGACTTTCCGCTGGGGACTTTCCAGGGAGGCGTGGCCTGGGCGGGACTGGGGAGTGGC

GAGCCCTCAGATCCTGCATATAAGCAGCTGCTTTTTGCCTGTACTGGGTCTCTCTGGTTAGAC

CAGATCTGAGCCTGGGAGCTCTCTGGCTAACTAGGGAACCCACTGCTTAAGCCTCAATAAAGC

TTGCCTTGAGTGCTTCAAGTAGTGTGTGCCCGTCTGTTGTGTGACTCTGGTAACTAGAGATCC

CTCAGACCCTTTTAGTCAGTGTGGAAAATCTCTAGCAGTGGCGCCCGAACAGGGACTTGAAA

GCGAAAGGGAAACCAGAGGAGCTCTCTCGACGCAGGACTCGGCTTGCTGAAGCGCGCACGGC

AAGAGGCGAGGGGCGGCGACTGGTGAGTACGCCAAAAATTTTGACTAGCGGAGGCTAGAAGG

AGAGAGATGGGTGCGAGAGCGTCAGTATTAAGCGGGGAGAATTAGATCGCGATGGGAAAA

AATTCGGTTAAGGCCAGGGGGAAAGAAAAAATATAAATTAAAACATATAGTATGGGCAAGC

AGGGAGCTAGAACGATTCGCAGTTAATCCTGGCCTGTTAGAAACATCAGAAGGCTGTAGACA

AATACTGGGACAGCTACAACCATCCCTTCAGACAGGATCAGAAGAACTTAGATCATTATATA

ATACAGTAGCAACCCTCTATTGTGTGCATCAAAGGATAGAGATAAAAGACACCAAGGAAGCT

TTAGACAAGATAGAGGAAGAGCAAAACAAAAGTAAGACCACCGCACAGCAAGCGGCCGCTGA

TCTTCAGACCTGGAGGAGGAGATATGAGGGACAATTGGAGAAGTGAATTATATAAATATAA

AGTAGTAAAAATTGAACCATTAGGAGTAGCACCCACCAAGGCAAAGAGAAGAGTGGTGCAGA

GAGAAAAAAGAGCAGTGGGAATAGGAGCTTTGTTCCTTGGGTTCTTGGGAGCAGCAGGAAGC

ACTATGGGCGCAGCGTCAATGACGCTGACGGTACAGGCCAGACAATTATTGTCTGGTATAGT

GCAGCAGCAGAACAATTTGCTGAGGGCTATTGAGGCGCAACAGCATCTGTTGCAACTCACAG
```

-continued

```
TCTGGGGCATCAAGCAGCTCCAGGCAAGAATCCTGGCTGTGGAAAGATACCTAAAGGATCAA
CAGCTCCTGGGGATTTGGGGTTGCTCTGGAAAACTCATTTGCACCACTGCTGTGCCTTGGAAT
GCTAGTTGGAGTAATAAATCTCTGGAACAGATTTGGAATCACACGACCTGGATGGAGTGGGA
CAGAGAAATTAACAATTACACAAGCTTAATACACTCCTTAATTGAAGAATCGCAAAACCAGC
AAGAAAAGAATGAACAAGAATTATTGGAATTAGATAAATGGGCAAGTTTGTGGAATTGGTT
TAACATAACAAATTGGCTGTGGTATATAAAATTATTCATAATGATAGTAGGAGGCTTGGTAG
GTTTAAGAATAGTTTTTGCTGTACTTTCTATAGTGAATAGAGTTAGGCAGGGATATTCACCA
TTATCGTTTCAGACCCACCTCCCAACCCCGAGGGGACCCGACAGGCCCGAAGGAATAGAAGAA
GAAGGTGGAGAGAGAGACAGAGACAGATCCATTCGATTAGTGAACGGATCTCGACGGGATCG
ATTTTAAAAGAAAAGGGGGGATTGGGGGGTACAGTGCAGGGGAAAGAATAGTAGACATAAT
AGCAACAGACATACAAACTAAAGAATTACAAAAACAAATTACAAAAATTCAAAATTTTATCG
ATAAGCTTTGCAAAGATGGATAAAGTTTTAAACAGAGAGGAATCTTTGCAGCTAATGGACCT
TCTAGGTCTTGAAAGGAGTGGGAATTGGCTCCGGTGCCCGTCAGTGGGCAGAGCGCACATCG
CCCACAGTCCCCGAGAAGTTGGGGGGAGGGGTCGGCAATTGAACCGGTGCCTAGAGAAGGTG
GCGCGGGGTAAACTGGGAAAGTGATGTCGTGTACTGGCTCCGCCTTTTTCCCGAGGGTGGGG
GAGAACCGTATATAAGTGCAGTAGTCGCCGTGAACGTTCTTTTTCGCAACGGGTTTGCCGCC
AGAACACAGGTAAGTGCCGTGTGTGGTTCCCGCGGGCCTGGCCTCTTTACGGGTTATGGCCCT
TGCGTGCCTTGAATTACTTCCACCTGGCTGCAGTACGTGATTCTTGATCCCGAGCTTCGGGTT
GGAAGTGGGTGGGAGAGTTCGAGGCCTTGCGCTTAAGGAGCCCCTTCGCCTCGTGCTTGAGT
TGAGGCCTGGCCTGGGCGCTGGGGCCGCCGCGTGCGAATCTGGTGGCACCTTCGCGCCTGTCT
CGCTGCTTTCGATAAGTCTCTAGCCATTTAAAATTTTTGATGACCTGCTGCGACGCTTTTTTT
CTGGCAAGATAGTCTTGTAAATGCGGGCCAAGATCTGCACACTGGTATTTCGGTTTTTGGGG
CCGCGGGCGGCGACGGGGCCCGTGCGTCCCAGCGCACATGTTCGGCGAGGCGGGGCCTGCGAG
CGCGGCCACCGAGAATCGGACGGGGGTAGTCTCAAGCTGGCCGGCCTGCTCTGGTGCCTGGCC
TCGCGCCGCCGTGTATCGCCCCGCCCTGGGCGGCAAGGCTGGCCCGGTCGGCACCAGTTGCGT
GAGCGGAAAGATGGCCGCTTCCCGGCCCTGCTGCAGGGAGCTCAAAATGGAGGACGCGGCGC
TCGGGAGAGCGGGCGGGTGAGTCACCCACACAAAGGAAAAGGGCCTTTCCGTCCTCAGCCGTC
GCTTCATGTGACTCCACGGAGTACCGGGCGCCGTCCAGGCACCTCGATTAGTTCTCGAGCTTT
TGGAGTACGTCGTCTTTAGGTTGGGGGAGGGGTTTTATGCGATGGAGTTTCCCCACACTGA
GTGGGTGGAGACTGAAGTTAGGCCAGCTTGGCACTTGATGTAATTCTCCTTGGAATTTGCCC
TTTTTGAGTTTGGATCTTGGTTCATTCTCAAGCCTCAGACAGTGGTTCAAAGTTTTTTTCTTC
CATTTCAGGTGTCGTGAGGAATTCTGCAGTCGACGCCACCATGCCGGGCCGGAGTTGCGTCGC
CTTAGTCCTCCTGGCTGCCGCCGTCAGCTGTGCCGTCGCGCAGCACGCGCCGCCGTGGACAGA
GGACTGCAGAAAATCAACCTATCCTCCTTCAGGACCAACGTACAGAGGTGCAGTTCCATGGT
ACACCATAAATCTTGACTTACCACCCTACAAAAGATGGCATGAATTGATGCTTGACAAGGCA
CCAGTGCTAAAGGTTATAGTGAATTCTCTGAAGAATATGATAAATACATTCGTGCCAAGTGG
AAAAATTATGCAGGTGGTGGATGAAAAATTGCCTGGCCTACTTGGCAACTTTCCTGGCCCTT
TTGAAGAGGAAATGAAGGGTATTGCCGCTGTTACTGATATACCTTTAGGAGAGATTATTTCA
TTCAATATTTTTTATGAATTATTTACCATTTGTACTTCAATAGTAGCAGAAGACAAAAAAGG
TCATCTAATACATGGGAGAAACATGGATTTTGGAGTATTTCTTGGGTGGAACATAAATAATG
ATACCTGGGTCATAACTGAGCAACTAAAACCTTTAACAGTGAATTTGGATTTCCAAAGAAAC
```

-continued

```
AACAAAACTGTCTTCAAGGCTTCAAGCTTTGCTGGCTATGTGGGCATGTTAACAGGATTCAA

ACCAGGACTGTTCAGTCTTACACTGAATGAACGTTTCAGTATAAATGGTGGTTATCTGGGTA

TTCTAGAATGGATTCTGGGAAAGAAAGATGTCATGTGGATAGGGTTCCTCACTAGAACAGTT

CTGGAAAATAGCACAAGTTATGAAGAAGCCAAGAATTTATTGACCAAGACCAAGATATTGGC

CCCAGCCTACTTTATCCTGGGAGGCAACCAGTCTGGGGAAGGTTGTGTGATTACACGAGACA

GAAAGGAATCATTGGATGTATATGAACTCGATGCTAAGCAGGGTAGATGGTATGTGGTACAA

ACAAATTATGACCGTTGGAAACATCCCTTCTTCCTTGATGATCGCAGAACGCCTGCAAAGAT

GTGTCTGAACCGCACCAGCCAAGAGAATATCTCATTTGAAACCATGTATGATGTCCTGTCAA

CAAAACCTGTCCTCAACAAGCTGACCGTATACACAACCTTGATAGATGTTACCAAAGGTCAA

TTCGAAACTTACCTGCGGGACTGCCCTGACCCTTGTATAGGTTGGTGAGCGGCCGCCTCGAGG

ATCCAAGCTTCAATTGTGGTCACTCGACAATCAACCTCTGGATTACAAAATTTGTGAAAGAT

TGACTGGTATTCTTAACTATGTTGCTCCTTTTACGCTATGTGGATACGCTGCTTTAATGCCTT

TGTATCATGCTATTGCTTCCCGTATGGCTTTCATTTTCTCCTCCTTGTATAAATCCTGGTTGC

TGTCTCTTTATGAGGAGTTGTGGCCCGTTGTCAGGCAACGTGGCGTGGTGTGCACTGTGTTT

GCTGACGCAACCCCCACTGGTTGGGGCATTGCCACCACCTGTCAGCTCCTTTCCGGGACTTTC

GCTTTCCCCCTCCCTATTGCCACGGCGGAACTCATCGCCGCCTGCCTTGCCCGCTGCTGGACAG

GGGCTCGGCTGTTGGGCACTGACAATTCCGTGGTGTTGTCGGGGAAGCTGACGTCCTTTCCAT

GGCTGCTCGCCTGTGTTGCCACCTGGATTCTGCGCGGGACGTCCTTCTGCTACGTCCCTTCGG

CCCTCAATCCAGCGGACCTTCCTTCCCGCGGCCTGCTGCCGGCTCTGCGGCCTCTTCCGCGTCT

TCGCCTTCGCCCTCAGACGAGTCGGATCTCCCTTTGGGCCGCCTCCCCGCCTGCTCGAGACCTA

GAAAAACATGGAGCAATCACAAGTAGCAATACAGCAGCTACCAATGCTGATTGTGCCTGGCT

AGAAGCACAAGAGGAGGAGGAGGTGGGTTTTCCAGTCACACCTCAGGTACCTTTAAGACCAA

TGACTTACAAGGCAGCTGTAGATCTTAGCCACTTTTTAAAAGAAAAGGGGGGACTGGAAGGG

CTAATTCACTCCCAACGAAGACAAGATCTGCTTTTTGCTTGTACTGGGTCTCTCTGGTTAGAC

CAGATCTGAGCCTGGGAGCTCTCTGGCTAACTAGGGAACCCACTGCTTAAGCCTCAATAAAGC

TTGCCTTGAGTGCTTCAAGTAGTGTGTGCCCGTCTGTTGTGTGACTCTGGTAACTAGAGATCC

CTCAGACCCTTTTAGTCAGTGTGGAAAATCTCTAGCAGTAGTAGTTCATGTCATCTTATTAT

TCAGTATTTATAACTTGCAAAGAAATGAATATCAGAGAGTGAGAGGACGCGTTGGATGCATA

GCTTGAGTATTCTATAGTGTCACCTAAATAGCTTGGCGTAATCATGGTCATAGCTGTTTCCT

GTGTGAAATTGTTATCCGCTCACAATTCCACACAACATACGAGCCGGAAGCATAAAGTGTAA

AGCCTGGGGTGCCTAATGAGTGAGCTAACTCACATTAATTGCGTTGCGCTCACTGCCCGCTTT

CCAGTCGGGAAACCTGTCGTGCCAGCTGCATTAATGAATCGGCCAACGCGCGGGGAGAGGCG

GTTTGCGTATTGGGCGCTCTTCCGCTTCCTCGCTCACTGACTCGCTGCGCTCGGTCGTTCGGC

TGCGGCGAGCGGTATCAGCTCACTCAAAGGCGGTAATACGGTTATCCACAGAATCAGGGGAT

AACGCAGGAAAGAACATGTGAGCAAAAGGCCAGCAAAAGGCCAGGAACCGTAAAAAGGCCGC

GTTGCTGGCGTTTTTCCATAGGCTCCGCCCCCCTGACGAGCATCACAAAAATCGACGCTCAAG

TCAGAGGTGGCGAAACCCGACAGGACTATAAAGATACCAGGCGTTTCCCCCTGGAAGCTCCCT

CGTGCGCTCTCCTGTTCCGACCCTGCCGCTTACCGGATACCTGTCCGCCTTTCTCCCTTCGGGA

AGCGTGGCGCTTTCTCATAGCTCACGCTGTAGGTATCTCAGTTCGGTGTAGGTCGTTCGCTCC

AAGCTGGGCTGTGTGCACGAACCCCCCGTTCAGCCCGACCGCTGCGCCTTATCCGGTAACTAT
```

-continued

```
CGTCTTGAGTCCAACCCGGTAAGACACGACTTATCGCCACTGGCAGCAGCCACTGGTAACAGG

ATTAGCAGAGCGAGGTATGTAGGCGGTGCTACAGAGTTCTTGAAGTGGTGGCCTAACTACGG

CTACACTAGAAGAACAGTATTTGGTATCTGCGCTCTGCTGAAGCCAGTTACCTTCGGAAAAA

GAGTTGGTAGCTCTTGATCCGGCAAACAAACCACCGCTGGTAGCGGTGGTTTTTTTGTTTGC

AAGCAGCAGATTACGCGCAGAAAAAAAGGATCTCAAGAAGATCCTTTGATCTTTTCTACGGG

GTCTGACGCTCAGTGGAACGAAAACTCACGTTAAGGGATTTTGGTCATGAGATTATCAAAAA

GGATCTTCACCTAGATCCTTTTAAATTAAAAATGAAGTTTTAAATCAATCTAAAGTATATAT

GAGTAAACTTGGTCTGACAGTTACCAATGCTTAATCAGTGAGGCACCTATCTCAGCGATCTG

TCTATTTCGTTCATCCATAGTTGCCTGACTCCCCGTCGTGTAGATAACTACGATACGGGAGGG

CTTACCATCTGGCCCCAGTGCTGCAATGATACCGCGAGACCCACGCTCACCGGCTCCAGATTT

ATCAGCAATAAACCAGCCAGCCGGAAGGGCCGAGCGCAGAAGTGGTCCTGCAACTTTATCCG

CCTCCATCCAGTCTATTAATTGTTGCCGGGAAGCTAGAGTAAGTAGTTCGCCAGTTAATAGT

TTGCGCAACGTTGTTGCCATTGCTACAGGCATCGTGGTGTCACGCTCGTCGTTTGGTATGGCT

TCATTCAGCTCCGGTTCCCAACGATCAAGGCGAGTTACATGATCCCCCATGTTGTGCAAAAA

GCGGTTAGCTCCTTCGGTCCTCCGATCGTTGTCAGAAGTAAGTTGGCCGCAGTGTTATCACTC

ATGGTTATGGCAGCACTGCATAATTCTCTTACTGTCATGCCATCCGTAAGATGCTTTTCTGTG

ACTGGTGAGTACTCAACCAAGTCATTCTGAGAATAGTGTATGCGGCGACCGAGTTGCTCTTG

CCCGGCGTCAATACGGGATAATACCGCGCCACATAGCAGAACTTTAAAAGTGCTCATCATTG

GAAAACGTTCTTCGGGGCGAAAACTCTCAAGGATCTTACCGCTGTTGAGATCCAGTTCGATG

TAACCCACTCGTGCACCCAACTGATCTTCAGCATCTTTTACTTTCACCAGCGTTTCTGGGTGA

GCAAAAACAGGAAGGCAAAATGCCGCAAAAAAGGGAATAAGGGCGACACGGAAATGTTGAA

TACTCATACTCTTCCTTTTTCAATATTATTGAAGCATTTATCAGGGTTATTGTCTCATGAGCG

GATACATATTTGAATGTATTTAGAAAAATAAACAAATAGGGGTTCCGCGCACATTTCCCCGA

AAAGTGCCACCTGATGCGGTGTGAAATACCGCACAGATGCGTAAGGAGAAAATACCGCATCA

GGAAATTGTAAGCGTTAATATTTTGTTAAAATTCGCGTTAAATTTTTGTTAAATCAGCTCAT

TTTTTAACCAATAGGCCGAAATCGGCAAAATCCCTTATAAATCAAAAGAATAGACCGAGATA

GGGTTGAGTGTTGTTCCAGTTTGGAACAAGAGTCCACTATTAAAGAACGTGGACTCCAACGT

CAAAGGGCGAAAAACCGTCTATCAGGGCGATGGCCCACTACGTGAACCATCACCCTAATCAA

GTTTTTTGGGGTCGAGGTGCCGTAAAGCACTAAATCGGAACCCTAAAGGGAGCCCCCGATTT

AGAGCTTGACGGGGAAAGCCGGCGAACGTGGCGAGAAAGGAAGGGAAGAAAGCGAAAGGAG

CGGGCGCTAGGGCGCTGGCAAGTGTAGCGGTCACGCTGCGCGTAACCACCACACCCGCCGCGC

TTAATGCGCCGCTACAGGGCGCGTCCATTCGCCATTCAGGCTGCGCAACTGTTGGGAAGGGCG

ATCGGTGCGGGCCTCTTCGCTATTACGCCAGCTGGCGAAAGGGGGATGTGCTGCAAGGCGAT

TAAGTTGGGTAACGCCAGGGTTTTCCCAGTCACGACGTTGTAAAACGACGGCCAGTGAATTG

TAATACGACTCACTATA
```

Pompe disease (vector encoding GAA)
>pDY co hGAA

SEQ ID NO: 6

```
AAATTGTAAGCGTTAATATTTTGTTAAAATTCGCGTTAAATTTTTGTTAAATCAGCTCATTT

TTTAACCAATAGGCCGAAATCGGCAAAATCCCTTATAAATCAAAAGAATAGACCGAGATAGG

GTTGAGTGTTGTTCCAGTTTGGAACAAGAGTCCACTATTAAAGAACGTGGACTCCAACGTCA

AAGGGCGAAAAACCGTCTATCAGGGCGATGGCCCACTACGTGAACCATCACCCTAATCAAGT
```

-continued

```
TTTTTGGGGTCGAGGTGCCGTAAAGCACTAAATCGGAACCCTAAAGGGAGCCCCCGATTTAG
AGCTTGACGGGGAAAGCCGGCGAACGTGGCGAGAAAGGAAGGGAAGAAAGCGAAAGGAGCG
GGCGCTAGGGCGCTGGCAAGTGTAGCGGTCACGCTGCGCGTAACCACCACACCCGCCGCGCTT
AATGCGCCGCTACAGGGCGCGTCCATTCGCCATTCAGGCTGCGCAACTGTTGGGAAGGGCGAT
CGGTGCGGGCCTCTTCGCTATTACGCCAGCTGGCGAAAGGGGGATGTGCTGCAAGGCGATTA
AGTTGGGTAACGCCAGGGTTTTCCCAGTCACGACGTTGTAAAACGACGGCCAGTGAATTGTA
ATACGACTCACTATAGGGCGAATTGGGCCCGACGTCGCATGCTTGGAAGGGCTAATTCACTCC
CAAAGAAGACAAGATATCCTTGATCTGTGGATCTACCACACACAAGGCTACTTCCCTGATTA
GCAGAACTACACACCAGGGCCAGGGGTCAGATATCCACTGACCTTTGGATGGTGCTACAAGC
TAGTACCAGTTGAGCCAGATAAGGTAGAAGAGGCCAATAAAGGAGAGAACACCAGCTTGTTA
CACCCTGTGAGCCTGCATGGGATGGATGACCCGGAGAGAGAAGTGTTAGAGTGGAGGTTTGA
CAGCCGCCTAGCATTTCATCACGTGGCCCGAGAGCTGCATCCGGAGTACTTCAAGAACTGCTG
ATATCGAGCTTGCTACAAGGGACTTTCCGCTGGGGACTTTCCAGGGAGGCGTGGCCTGGGCG
GGACTGGGGAGTGGCGAGCCCTCAGATCCTGCATATAAGCAGCTGCTTTTTGCCTGTACTGGG
TCTCTCTGGTTAGACCAGATCTGAGCCTGGGAGCTCTCTGGCTAACTAGGGAACCCACTGCTT
AAGCCTCAATAAAGCTTGCCTTGAGTGCTTCAAGTAGTGTGTGCCCGTCTGTTGTGTGACTCT
GGTAACTAGAGATCCCTCAGACCCTTTTAGTCAGTGTGGAAAATCTCTAGCAGTGGCGCCCG
AACAGGGACTTGAAAGCGAAAGGGAAACCAGAGGAGCTCTCTCGACGCAGGACTCGGCTTGC
TGAAGCGCGCACGGCAAGAGGCGAGGGGCGGCGACTGGTGAGTACGCCAAAAATTTTGACTA
GCGGAGGCTAGAAGGAGAGAGATGGGTGCGAGAGCGTCAGTATTAAGCGGGGGAGAATTAG
ATCGCGATGGGAAAAAATTCGGTTAAGGCCAGGGGGAAAGAAAAAATATAAATTAAAACAT
ATAGTATGGGCAAGCAGGGAGCTAGAACGATTCGCAGTTAATCCTGGCCTGTTAGAAACATC
AGAAGGCTGTAGACAAATACTGGGACAGCTACAACCATCCCTTCAGACAGGATCAGAAGAAC
TTAGATCATTATATAATACAGTAGCAACCCTCTATTGTGTGCATCAAAGGATAGAGATAAAA
GACACCAAGGAAGCTTTAGACAAGATAGAGGAAGAGCAAAACAAAAGTAAGACCACCGCACA
GCAAGCGGCCGCTGATCTTCAGACCTGGAGGAGGAGATATGAGGGACAATTGGAGAAGTGAA
TTATATAAATATAAAGTAGTAAAAATTGAACCATTAGGAGTAGCACCCACCAAGGCAAAGAG
AAGAGTGGTGCAGAGAGAAAAAAGAGCAGTGGGAATAGGAGCTTTGTTCCTTGGGTTCTTGG
GAGCAGCAGGAAGCACTATGGGCGCAGCGTCAATGACGCTGACGGTACAGGCCAGACAATTA
TTGTCTGGTATAGTGCAGCAGCAGAACAATTTGCTGAGGGCTATTGAGGCGCAACAGCATCT
GTTGCAACTCACAGTCTGGGGCATCAAGCAGCTCCAGGCAAGAATCCTGGCTGTGGAAAGAT
ACCTAAAGGATCAACAGCTCCTGGGGATTTGGGGTTGCTCTGGAAAACTCATTTGCACCACT
GCTGTGCCTTGGAATGCTAGTTGGAGTAATAAATCTCTGGAACAGATTTGGAATCACACGAC
CTGGATGGAGTGGGACAGAGAAATTAACAATTACACAAGCTTAATACACTCCTTAATTGAAG
AATCGCAAAACCAGCAAGAAAAGAATGAACAAGAATTATTGGAATTAGATAAATGGGCAAG
TTTGTGGAATTGGTTTAACATAACAAATTGGCTGTGGTATATAAAATTATTCATAATGATAG
TAGGAGGCTTGGTAGGTTTAAGAATAGTTTTTGCTGTACTTTCTATAGTGAATAGAGTTAGG
CAGGGATATTCACCATTATCGTTTCAGACCCACCTCCCAACCCCGAGGGGACCCGACAGGCCC
GAAGGAATAGAAGAAGAAGGTGGAGAGAGAGACAGAGACAGATCCATTCGATTAGTGAACG
GATCTCGACGGGATCGATTTTAAAAGAAAAGGGGGGATTGGGGGGTACAGTGCAGGGGAAA
GAATAGTAGACATAATAGCAACAGACATACAAACTAAAGAATTACAAAAACAAATTACAAA
```

-continued

```
AATTCAAAATTTTATCGATAAGCTTTGCAAAGATGGATAAAGTTTTAAACAGAGAGGAATCT

TTGCAGCTAATGGACCTTCTAGGTCTTGAAAGGAGTGGGAATTGGCTCCGGTGCCCGTCAGT

GGGCAGAGCGCACATCGCCCACAGTCCCCGAGAAGTTGGGGGGAGGGGTCGGCAATTGAACC

GGTGCCTAGAGAAGGTGGCGCGGGGTAAACTGGGAAAGTGATGTCGTGTACTGGCTCCGCCT

TTTTCCCGAGGGTGGGGGAGAACCGTATATAAGTGCAGTAGTCGCCGTGAACGTTCTTTTTC

GCAACGGGTTTGCCGCCAGAACACAGGTAAGTGCCGTGTGTGGTTCCCGCGGGCCTGGCCTCT

TTACGGGTTATGGCCCTTGCGTGCCTTGAATTACTTCCACCTGGCTGCAGTACGTGATTCTTG

ATCCCGAGCTTCGGGTTGGAAGTGGGTGGGAGAGTTCGAGGCCTTGCGCTTAAGGAGCCCCT

TCGCCTCGTGCTTGAGTTGAGGCCTGGCCTGGGCGCTGGGGCCGCCGCGTGCGAATCTGGTGG

CACCTTCGCGCCTGTCTCGCTGCTTTCGATAAGTCTCTAGCCATTTAAAATTTTTGATGACCT

GCTGCGACGCTTTTTTTCTGGCAAGATAGTCTTGTAAATGCGGGCCAAGATCTGCACACTGG

TATTTCGGTTTTTGGGGCCGCGGGCGGCGACGGGGCCCGTGCGTCCCAGCGCACATGTTCGGC

GAGGCGGGGCCTGCGAGCGCGGCCACCGAGAATCGGACGGGGGTAGTCTCAAGCTGGCCGGCC

TGCTCTGGTGCCTGGCCTCGCGCCGCCGTGTATCGCCCCGCCCTGGGCGGCAAGGCTGGCCCG

GTCGGCACCAGTTGCGTGAGCGGAAAGATGGCCGCTTCCCGGCCCTGCTGCAGGGAGCTCAAA

ATGGAGGACGCGGCGCTCGGGAGAGCGGGCGGGTGAGTCACCCACACAAAGGAAAAGGGCCT

TTCCGTCCTCAGCCGTCGCTTCATGTGACTCCACGGAGTACCGGGCGCCGTCCAGGCACCTCG

ATTAGTTCTCGAGCTTTTGGAGTACGTCGTCTTTAGGTTGGGGGGAGGGGTTTTATGCGATG

GAGTTTCCCCACACTGAGTGGGTGGAGACTGAAGTTAGGCCAGCTTGGCACTTGATGTAATT

CTCCTTGGAATTTGCCCTTTTTGAGTTTGGATCTTGGTTCATTCTCAAGCCTCAGACAGTGGT

TCAAAGTTTTTTTCTTCCATTTCAGGTGTCGTGAGGAATTCGCCACCATGGGCGTGAGGCACC

CCCCTTGCTCTCACAGGCTGCTGGCCGTGTGCGCACTGGTGAGCCTGGCCACCGCCGCCCTGC

TGGGCCACATCCTGCTGCACGACTTCCTGCTGGTGCCCAGGGAGCTGTCCGGCAGCTCCCCAG

TGCTGGAGGAGACCCACCCAGCACACCAGCAGGGCGCCTCTCGGCCAGGCCCCCGCGATGCAC

AGGCACACCCAGGCCGGCCCCGCGCCGTGCCAACCCAGTGCGACGTGCCACCCAACAGCCGGT

TTGACTGTGCCCCCGATAAGGCCATCACACAGGAGCAGTGCGAGGCCAGGGGCTGCTGTTAT

ATCCCTGCAAAGCAGGGCCTCCAGGGCGCCCAGATGGGACAGCCATGGTGTTTCTTTCCTCCA

TCTTACCCCAGCTATAAGCTGGAGAATCTGTCTAGCTCCGAGATGGGCTACACAGCCACCCTG

ACAAGAACCACACCAACATTCTTTCCCAAGGACATCCTGACCCTGCGGCTGGACGTGATGATG

GAGACAGAGAACCGCCTGCACTTCACCATCAAGGACCCCGCCAATAGGAGATATGAGGTGCC

TCTGGAGACCCCACACGTGCACTCTCGGGCCCCTAGCCCACTGTACTCCGTGGAGTTCTCTGA

GGAGCCATTTGGCGTGATCGTGCGGCGCCAGCTGGATGGACGCGTGCTGCTGAACACCACAGT

GGCCCCCCTGTTCTTTGCCGACCAGTTCCTCCAGCTGAGCACATCCCTGCCCTCCCAGTATATC

ACCGGCCTGGCCGAGCACCTGTCTCCTCTGATGCTGTCTACCAGCTGGACAAGGATCACCCTG

TGGAACAGAGACCTGGCACCAACCCCTGGCGCAAATCTGTACGGCAGCCACCCTTTCTATCTG

GCCCTGGAGGATGGAGGCTCCGCCCACGGCGTGTTTCTGCTGAACTCTAATGCCATGGACGTG

GTGCTCCAGCCAAGCCCCGCCCTGTCCTGGCGGTCTACCGGCGGCATCCTGGACGTGTACATC

TTCCTGGGCCCTGAGCCAAAGTCCGTGGTGCAGCAGTACCTGGACGTGGTGGGCTATCCTTTC

ATGCCCCCTTACTGGGGACTGGGATTTCACCTGTGCCGCTGGGGCTATTCTAGCACAGCCATC

ACCCGGCAGGTGGTGGAGAACATGACCCGCGCCCACTTTCCACTGGATGTGCAGTGGAATGAC
```

-continued

```
CTGGATTACATGGACTCCAGGAGAGACTTCACCTTCAACAAGGACGGCTTCAGGGATTTTCCC

GCCATGGTGCAGGAGCTGCACCAGGGCGGCCGGCGCTACATGATGATCGTGGACCCCGCCATC

TCCTCTAGCGGACCTGCCGGCAGCTACAGACCATATGACGAGGGCCTGAGGAGAGGCGTGTTC

ATCACAAACGAGACCGGCCAGCCTCTGATCGGCAAGGTCTGGCCAGGCTCCACCGCCTTCCCA

GACTTCACCAATCCAACCGCCCTGGCCTGGTGGGAGGACATGGTGGCCGAGTTCCACGACCAG

GTGCCTTTTGATGGCATGTGGATCGACATGAACGAGCCATCTAATTTCATCAGGGGCAGCGA

GGACGGCTGCCCCAACAATGAGCTGGAGAACCCACCATATGTGCCTGGCGTGGTGGGAGGCA

CCCTCCAGGCAGCAACCATCTGTGCCTCCTCTCACCAGTTTCTGTCTACACACTATAACCTGC

ACAATCTGTACGGACTGACCGAGGCAATCGCCAGCCACAGAGCCCTGGTGAAGGCCAGGGGC

ACAAGACCTTTCGTGATCTCCAGGTCTACCTTTGCCGGACACGGCAGATACGCAGGACACTGG

ACCGGCGACGTGTGGAGCAGCTGGGAGCAGCTGGCCTCTAGCGTGCCAGAGATCCTCCAGTTC

AACCTGCTGGGCGTGCCCCTGGTGGGAGCAGACGTGTGCGGCTTTCTGGGCAATACATCCGAG

GAGCTGTGCGTGAGGTGGACCCAGCTGGGAGCCTTCTATCCCTTCATGCGCAACCACAATAGC

CTGCTGTCCCTGCCTCAGGAGCCATACAGCTTCTCCGAGCCTGCACAGCAGGCAATGAGGAAG

GCCCTGACACTGCGCTATGCCCTGCTGCCACACCTGTACACCCTGTTTCACCAGGCACACGTG

GCAGGAGAGACAGTGGCCCGGCCCCTGTTCCTGGAGTTTCCTAAGGATTCCTCTACCTGGACA

GTGGACCACCAGCTGCTGTGGGGAGAGGCCCTGCTGATCACCCCCGTGCTCCAGGCAGGCAAG

GCAGAGGTGACAGGCTATTTCCCTCTGGGCACATGGTACGACCTCCAGACCGTGCCAGTGGAG

GCCCTGGGCAGCCTGCCTCCACCACCTGCCGCCCCCCGCGAGCCTGCCATCCACTCCGAGGGAC

AGTGGGTGACACTGCCAGCACCTCTGGACACCATCAACGTGCACCTGAGGGCCGGCTATATCA

TCCCCCTCCAGGGCCCTGGCCTGACCACAACCGAGTCCAGACAGCAGCCAATGGCCCTGGCCG

TGGCCCTGACCAAGGGAGGCGAGGCCAGGGGCGAGCTGTTCTGGGACGATGGCGAGTCTCTG

GAGGTGCTGGAGAGAGGCGCCTACACACAGGTCATCTTCCTGGCCAGGAACAATACAATCGT

GAATGAGCTGGTGAGAGTGACCTCTGAGGGAGCAGGACTCCAGCTCCAGAAGGTGACAGTGC

TGGGAGTGGCAACCGCACCACAGCAGGTGCTGAGCAACGGCGTGCCCGTGAGCAATTTCACA

TACTCCCCTGATACCAAGGTGCTGGACATCTGCGTGAGCCTGCTGATGGGCGAGCAGTTTCTG

GTGTCCTGGTGTTGAGAACCCGGGATCCAAGCTTCAATTGTGGTCACTCGACAATCAACCTCT

GGATTACAAAATTTGTGAAAGATTGACTGGTATTCTTAACTATGTTGCTCCTTTTACGCTAT

GTGGATACGCTGCTTTAATGCCTTTGTATCATGCTATTGCTTCCCGTATGGCTTTCATTTTCT

CCTCCTTGTATAAATCCTGGTTGCTGTCTCTTTATGAGGAGTTGTGGCCCGTTGTCAGGCAAC

GTGGCGTGGTGTGCACTGTGTTTGCTGACGCAACCCCCACTGGTTGGGGCATTGCCACCACCT

GTCAGCTCCTTTCCGGGACTTTCGCTTTCCCCCTCCCTATTGCCACGGCGGAACTCATCGCCGC

CTGCCTTGCCCGCTGCTGGACAGGGGCTCGGCTGTTGGGCACTGACAATTCCGTGGTGTTGTC

GGGGAAGCTGACGTCCTTTCCATGGCTGCTCGCCTGTGTTGCCACCTGGATTCTGCGCGGGAC

GTCCTTCTGCTACGTCCCTTCGGCCCTCAATCCAGCGGACCTTCCTTCCCGCGGCCTGCTGCCG

GCTCTGCGGCCTCTTCCGCGTCTTCGCCTTCGCCCTCAGACGAGTCGGATCTCCCTTTGGGCCG

CCTCCCCGCCTGCTCGAGACCTAGAAAAACATGGAGCAATCACAAGTAGCAATACAGCAGCT

ACCAATGCTGATTGTGCCTGGCTAGAAGCACAAGAGGAGGAGGTGGGTTTTCCAGTCAC

ACCTCAGGTACCTTTAAGACCAATGACTTACAAGGCAGCTGTAGATCTTAGCCACTTTTTAA

AAGAAAAGGGGGGACTGGAAGGGCTAATTCACTCCCAACGAAGACAAGATCTGCTTTTTGCT

TGTACTGGGTCTCTCTGGTTAGACCAGATCTGAGCCTGGGAGCTCTCTGGCTAACTAGGGAAC
```

-continued

```
CCACTGCTTAAGCCTCAATAAAGCTTGCCTTGAGTGCTTCAAGTAGTGTGTGCCCGTCTGTTG
TGTGACTCTGGTAACTAGAGATCCCTCAGACCCTTTTAGTCAGTGTGGAAAATCTCTAGCAG
TAGTAGTTCATGTCATCTTATTATTCAGTATTTATAACTTGCAAAGAAATGAATATCAGAGA
GTGAGAGGACGCGTTGGATGCATAGCTTGAGTATTCTATAGTGTCACCTAAATAGCTTGGCG
TAATCATGGTCATAGCTGTTTCCTGTGTGAAATTGTTATCCGCTCACAATTCCACACAACATA
CGAGCCGGAAGCATAAAGTGTAAAGCCTGGGGTGCCTAATGAGTGAGCTAACTCACATTAAT
TGCGTTGCGCTCACTGCCCGCTTTCCAGTCGGGAAACCTGTCGTGCCAGCTGCATTAATGAAT
CGGCCAACGCGCGGGGAGAGGCGGTTTGCGTATTGGGCGCTCTTCCGCTTCCTCGCTCACTGA
CTCGCTGCGCTCGGTCGTTCGGCTGCGGCGAGCGGTATCAGCTCACTCAAAGGCGGTAATACG
GTTATCCACAGAATCAGGGGATAACGCAGGAAAGAACATGTGAGCAAAAGGCCAGCAAAAGG
CCAGGAACCGTAAAAAGGCCGCGTTGCTGGCGTTTTTCCATAGGCTCCGCCCCCCTGACGAGC
ATCACAAAAATCGACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGCCGCTTACCGGATACC
TGTCCGCCTTTCTCCCTTCGGGAAGCGTGGCGCTTTCTCATAGCTCACGCTGTAGGTATCTCA
GTTCGGTGTAGGTCGTTCGCTCCAAGCTGGGCTGTGTGCACGAACCCCCCGTTCAGCCCGACC
GCTGCGCCTTATCCGGTAACTATCGTCTTGAGTCCAACCCGGTAAGACACGACTTATCGCCAC
TGGCAGCAGCCACTGGTAACAGGATTAGCAGAGCGAGGTATGTAGGCGGTGCTACAGAGTTC
TTGAAGTGGTGGCCTAACTACGGCTACACTAGAAGAACAGTATTTGGTATCTGCGCTCTGCT
GAAGCCAGTTACCTTCGGAAAAAGAGTTGGTAGCTCTTGATCCGGCAAACAAACCACCGCTG
GTAGCGGTGGTTTTTTTGTTTGCAAGCAGCAGATTACGCGCAGAAAAAAAGGATCTCAAGAA
GATCCTTTGATCTTTTCTACGGGGTCTGACGCTCAGTGGAACGAAAACTCACGTTAAGGGAT
TTTGGTCATGAGATTATCAAAAAGGATCTTCACCTAGATCCTTTTAAATTAAAAATGAAGTT
TTAAATCAATCTAAAGTATATATGAGTAAACTTGGTCTGACAGTTACCAATGCTTAATCAGT
GAGGCACCTATCTCAGCGATCTGTCTATTTCGTTCATCCATAGTTGCCTGACTCCCCGTCGTG
TAGATAACTACGATACGGGAGGGCTTACCATCTGGCCCCAGTGCTGCAATGATACCGCGAGA
CCCACGCTCACCGGCTCCAGATTTATCAGCAATAAACCAGCCAGCCGGAAGGGCCGAGCGCAG
AAGTGGTCCTGCAACTTTATCCGCCTCCATCCAGTCTATTAATTGTTGCCGGGAAGCTAGAGT
AAGTAGTTCGCCAGTTAATAGTTTGCGCAACGTTGTTGCCATTGCTACAGGCATCGTGGTGT
CACGCTCGTCGTTTGGTATGGCTTCATTCAGCTCCGGTTCCCAACGATCAAGGCGAGTTACAT
GATCCCCCATGTTGTGCAAAAAAGCGGTTAGCTCCTTCGGTCCTCCGATCGTTGTCAGAAGTA
AGTTGGCCGCAGTGTTATCACTCATGGTTATGGCAGCACTGCATAATTCTCTTACTGTCATGC
CATCCGTAAGATGCTTTTCTGTGACTGGTGAGTACTCAACCAAGTCATTCTGAGAATAGTGT
ATGCGGCGACCGAGTTGCTCTTGCCCGGCGTCAATACGGGATAATACCGCGCCACATAGCAGA
ACTTTAAAAGTGCTCATCATTGGAAAACGTTCTTCGGGGCGAAAACTCTCAAGGATCTTACC
GCTGTTGAGATCCAGTTCGATGTAACCCACTCGTGCACCCAACTGATCTTCAGCATCTTTTAC
TTTCACCAGCGTTTCTGGGTGAGCAAAAACAGGAAGGCAAAATGCCGCAAAAAAGGGAATAA
GGGCGACACGGAAATGTTGAATACTCATACTCTTCCTTTTTCAATATTATTGAAGCATTTAT
CAGGGTTATTGTCTCATGAGCGGATACATATTTGAATGTATTTAGAAAAATAAACAAATAGG
GGTTCCGCGCACATTTCCCCGAAAAGTGCCACCTGATGCGGTGTGAAATACCGCACAGATGCG
TAAGGAGAAAATACCGCATCAGG
```

GBA transgene
>co.hGBA
SEQ ID NO: 7

ATGGAGTTCTCAAGCCCCTCTCGGGAAGAATGCCCAAAACCTCTGTCACGGGTGTCTATCATG

GCTGGATCACTGACTGGCCTGCTGCTGCTGCAGGCCGTGAGCTGGGCCTCCGGAGCCCGGCCT

TGCATCCCAAAGTCTTTCGGCTACAGCTCCGTGGTGTGCGTGTGCAACGCCACCTATTGTGAC

TCCTTCGATCCCCCTACCTTTCCCGCCCTGGGCACATTTTCTCGGTACGAGTCTACACGCAGC

GGCAGGAGAATGGAGCTGAGCATGGGCCCTATCCAGGCCAATCACACCGGAACAGGCCTGCT

GCTGACCCTGCAGCCAGAGCAGAAGTTCCAGAAGGTGAAGGGCTTTGGAGGAGCAATGACAG

ACGCAGCCGCCCTGAACATCCTGGCCCTGTCCCCACCCGCCCAGAATCTGCTGCTGAAGTCCT

ACTTCTCTGAGGAGGGCATCGGCTATAACATCATCAGGGTGCCCATGGCCAGCTGCGACTTTT

CCATCAGAACCTACACATATGCCGATACCCCTGACGATTTCCAGCTGCACAATTTTTCCCTGC

CAGAGGAGGATACAAAGCTGAAGATCCCACTGATCCACAGGGCCCTGCAGCTGGCCCAGAGG

CCCGTGAGCCTGCTGGCCAGCCCCTGGACCTCCCCTACATGGCTGAAGACCAACGGCGCCGTG

AATGGCAAGGGCTCTCTGAAGGGACAGCCAGGCGACATCTACCACCAGACATGGGCCCGCTAT

TTCGTGAAGTTTCTGGATGCCTACGCCGAGCACAAGCTGCAGTTCTGGGCCGTGACCGCAGAG

AACGAGCCTTCTGCCGGCCTGCTGAGCGGCTATCCCTTCCAGTGCCTGGGCTTTACACCTGAG

CACCAGAGGGACTTTATCGCCAGAGATCTGGGCCCAACCCTGGCCAACTCCACACACCACAAT

GTGCGGCTGCTGATGCTGGACGATCAGCGCCTGCTGCTGCCTCACTGGGCCAAGGTGGTGCTG

ACCGACCCAGAGGCCGCCAAGTACGTGCACGGCATCGCCGTGCACTGGTATCTGGATTTCCTG

GCACCAGCAAAGGCCACCCTGGGAGAGACACACAGGCTGTTCCCTAACACCATGCTGTTTGCC

AGCGAGGCCTGCGTGGGCTCCAAGTTTTGGGAGCAGTCCGTGCGGCTGGGCTCTTGGGACAG

GGGCATGCAGTACTCCCACTCTATCATCACCAATCTGCTGTATCACGTGGTGGGCTGGACAGA

CTGGAACCTGGCCCTGAATCCAGAGGGCGGCCCCAACTGGGTGAGAAATTTCGTGGATAGCCC

CATCATCGTGGACATCACCAAGGATACATTCTACAAGCAGCCAATGTTTTATCACCTGGGCCA

CTTCTCTAAGTTTATCCCAGAGGGCAGCCAGAGGGTGGGCCTGGTGGCCAGCCAGAAGAACG

ACCTGGATGCAGTGGCCCTGATGCACCCTGACGGCTCCGCCGTGGTGGTGGTGCTGAATCGCT

CTAGCAAGGACGTGCCTCTGACCATCAAGGACCCCGCCGTGGGCTTTCTGGAGACCATTTCAC

CCGGCTATTCTATTCATACCTATCTGTGGAGGAGGCAGTAA

ASAH1 transgene
>hASAH1
SEQ ID NO: 8

ATGCCGGGCCGGAGTTGCGTCGCCTTAGTCCTCCTGGCTGCCGCCGTCAGCTGTGCCGTCGCG

CAGCACGCGCCGCCGTGGACAGAGGACTGCAGAAAATCAACCTATCCTCCTTCAGGACCAACG

TACAGAGGTGCAGTTCCATGGTACACCATAAATCTTGACTTACCACCCTACAAAAGATGGCA

TGAATTGATGCTTGACAAGGCACCAGTGCTAAAGGTTATAGTGAATTCTCTGAAGAATATGA

TAAATACATTCGTGCCAAGTGGAAAAATTATGCAGGTGGTGGATGAAAAATTGCCTGGCCTA

CTTGGCAACTTTCCTGGCCCTTTTGAAGAGGAAATGAAGGGTATTGCCGCTGTTACTGATAT

ACCTTTAGGAGAGATTATTCATTCAATATTTTTTATGAATTATTTACCATTTGTACTTCAA

TAGTAGCAGAAGACAAAAAAGGTCATCTAATACATGGGAGAAACATGGATTTTGGAGTATTT

CTTGGGTGGAACATAAATAATGATACCTGGGTCATAACTGAGCAACTAAAACCTTTAACAGT

GAATTTGGATTTCCAAAGAAACAACAAAACTGTCTTCAAGGCTTCAAGCTTTGCTGGCTATG

TGGGCATGTTAACAGGATTCAAACCAGGACTGTTCAGTCTTACACTGAATGAACGTTTCAGT

ATAAATGGTGGTTATCTGGGTATTCTAGAATGGATTCTGGGAAAGAAAGATGTCATGTGGAT

-continued

```
AGGGTTCCTCACTAGAACAGTTCTGGAAAATAGCACAAGTTATGAAGAAGCCAAGAATTTAT

TGACCAAGACCAAGATATTGGCCCCAGCCTACTTTATCCTGGGAGGCAACCAGTCTGGGAA

GGTTGTGTGATTACACGAGACAGAAAGGAATCATTGGATGTATATGAACTCGATGCTAAGCA

GGGTAGATGGTATGTGGTACAAACAAATTATGACCGTTGGAAACATCCCTTCTTCCTTGATG

ATCGCAGAACGCCTGCAAAGATGTGTCTGAACCGCACCAGCCAAGAGAATATCTCATTTGAA

ACCATGTATGATGTCCTGTCAACAAAACCTGTCCTCAACAAGCTGACCGTATACACAACCTTG

ATAGATGTTACCAAAGGTCAATTCGAAACTTACCTGCGGGACTGCCCTGACCCTTGTATAGG

TTGGTGA
```

(GAA transgene)
>co.hGAA                                                              SEQ ID NO: 9

```
ATGGGCGTGAGGCACCCCCCTTGCTCTCACAGGCTGCTGGCCGTGTGCGCACTGGTGAGCCTG

GCCACCGCCGCCCTGCTGGGCCACATCCTGCTGCACGACTTCCTGCTGGTGCCCAGGGAGCTG

TCCGGCAGCTCCCCAGTGCTGGAGGAGACCCACCCAGCACACCAGCAGGGCGCCTCTCGGCCA

GGCCCCCGCGATGCACAGGCACACCCAGGCCGGCCCCGCGCCGTGCCAACCCAGTGCGACGTG

CCACCCAACAGCCGGTTTGACTGTGCCCCCGATAAGGCCATCACACAGGAGCAGTGCGAGGCC

AGGGGCTGCTGTTATATCCCTGCAAAGCAGGGCCTCCAGGGCGCCCAGATGGGACAGCCATGG

TGTTTCTTTCCTCCATCTTACCCCAGCTATAAGCTGGAGAATCTGTCTAGCTCCGAGATGGGC

TACACAGCCACCCTGACAAGAACCACACCAACATTCTTTCCCAAGGACATCCTGACCCTGCGG

CTGGACGTGATGATGGAGACAGAGAACCGCCTGCACTTCACCATCAAGGACCCCGCCAATAG

GAGATATGAGGTGCCTCTGGAGACCCCACACGTGCACTCTCGGGCCCCTAGCCCACTGTACTC

CGTGGAGTTCTCTGAGGAGCCATTTGGCGTGATCGTGCGGCGCCAGCTGGATGGACGCGTGCT

GCTGAACACCACAGTGGCCCCCCTGTTCTTTGCCGACCAGTTCCTCCAGCTGAGCACATCCCT

GCCCTCCCAGTATATCACCGGCCTGGCCGAGCACCTGTCTCCTCTGATGCTGTCTACCAGCTG

GACAAGGATCACCCTGTGGAACAGAGACCTGGCACCAACCCCTGGCGCAAATCTGTACGGCAG

CCACCCTTTCTATCTGGCCCTGGAGGATGGAGGCTCCGCCCACGGCGTGTTTCTGCTGAACTC

TAATGCCATGGACGTGGTGCTCCAGCCAAGCCCCGCCCTGTCCTGGCGGTCTACCGGCGGCAT

CCTGGACGTGTACATCTTCCTGGGCCCTGAGCCAAAGTCCGTGGTGCAGCAGTACCTGGACGT

GGTGGGCTATCCTTTCATGCCCCCTTACTGGGGACTGGGATTTCACCTGTGCCGCTGGGGCTA

TTCTAGCACAGCCATCACCCGGCAGGTGGTGGAGAACATGACCCGCGCCCACTTTCCACTGGA

TGTGCAGTGGAATGACCTGGATTACATGGACTCCAGGAGAGACTTCACCTTCAACAAGGACG

GCTTCAGGGATTTTCCCGCCATGGTGCAGGAGCTGCACCAGGGCGGCCGGCGCTACATGATGA

TCGTGGACCCCGCCATCTCCTCTAGCGGACCTGCCGGCAGCTACAGACCATATGACGAGGGCC

TGAGGAGAGGCGTGTTCATCACAAACGAGACCGGCCAGCCTCTGATCGGCAAGGTCTGGCCA

GGCTCCACCGCCTTCCCAGACTTCACCAATCCAACCGCCCTGGCCTGGTGGGAGGACATGGTG

GCCGAGTTCCACGACCAGGTGCCTTTTGATGGCATGTGGATCGACATGAACGAGCCATCTAA

TTTCATCAGGGGCAGCGAGGACGGCTGCCCCAACAATGAGCTGGAGAACCCACCATATGTGCC

TGGCGTGGTGGGAGGCACCCTCCAGGCAGCAACCATCTGTGCCTCCTCTCACCAGTTTCTGTC

TACACACTATAACCTGCACAATCTGTACGGACTGACCGAGGCAATCGCCAGCCACAGAGCCCT

GGTGAAGGCCAGGGGCACAAGACCTTTCGTGATCTCCAGGTCTACCTTTGCCGGACACGGCAG

ATACGCAGGACACTGGACCGGCGACGTGTGGAGCAGCTGGGAGCAGCTGGCCTCTAGCGTGCC

AGAGATCCTCCAGTTCAACCTGCTGGGCGTGCCCCTGGTGGGAGCAGACGTGTGCGGCTTTCT
```

-continued

```
GGGCAATACATCCGAGGAGCTGTGCGTGAGGTGGACCCAGCTGGGAGCCTTCTATCCCTTCAT

GCGCAACCACAATAGCCTGCTGTCCCTGCCTCAGGAGCCATACAGCTTCTCCGAGCCTGCACA

GCAGGCAATGAGGAAGGCCCTGACACTGCGCTATGCCCTGCTGCCACACCTGTACACCCTGTT

TCACCAGGCACACGTGGCAGGAGAGACAGTGGCCCGGCCCCTGTTCCTGGAGTTTCCTAAGGA

TTCCTCTACCTGGACAGTGGACCACCAGCTGCTGTGGGGAGAGGCCCTGCTGATCACCCCCGT

GCTCCAGGCAGGCAAGGCAGAGGTGACAGGCTATTTCCCTCTGGGCACATGGTACGACCTCCA

GACCGTGCCAGTGGAGGCCCTGGGCAGCCTGCCTCCACCACCTGCCGCCCCCGCGAGCCTGCC

ATCCACTCCGAGGGACAGTGGGTGACACTGCCAGCACCTCTGGACACCATCAACGTGCACCTG

AGGGCCGGCTATATCATCCCCCTCCAGGGCCCTGGCCTGACCACAACCGAGTCCAGACAGCAG

CCAATGGCCCTGGCCGTGGCCCTGACCAAGGGAGGCGAGGCCAGGGCGAGCTGTTCTGGGAC

GATGGCGAGTCTCTGGAGGTGCTGGAGAGAGGCGCCTACACACAGGTCATCTTCCTGGCCAG

GAACAATACAATCGTGAATGAGCTGGTGAGAGTGACCTCTGAGGGAGCAGGACTCCAGCTCC

AGAAGGTGACAGTGCTGGGAGTGGCAACCGCACCACAGCAGGTGCTGAGCAACGGCGTGCCC

GTGAGCAATTTCACATACTCCCCTGATACCAAGGTGCTGGACATCTGCGTGAGCCTGCTGATG

GGCGAGCAGTTTCTGGTGTCCTGGTGTTGA
```

(Dual promoter vector)
>pDY-DP
SEQ ID NO: 10

```
AAATTGTAAGCGTTAATATTTTGTTAAAATTCGCGTTAAATTTTGTTAAATCAGCTCATTTTTTAACCAATAGG

CCGAAATCGGCAAAATCCCTTATAAATCAAAAGAATAGACCGAGATAGGGTTGAGTGTTGTTCCAGTTTGGAA

CAAGAGTCCACTATTAAAGAACGTGGACTCCAACGTCAAAGGGCGAAAAACCGTCTATCAGGGCGATGGCCC

ACTACGTGAACCATCACCCTAATCAAGTTTTTTGGGGTCGAGGTGCCGTAAAGCACTAAATCGGAACCCTAAA

GGGAGCCCCCGATTTAGAGCTTGACGGGGAAAGCCGGCGAACGTGGCGAGAAAGGAAGGGAAGAAAGCGA

AAGGAGCGGGCGCTAGGGCGCTGGCAAGTGTAGCGGTCACGCTGCGCGTAACCACCACACCCGCCGCGCTT

AATGCGCCGCTACAGGGCGCGTCCATTCGCCATTCAGGCTGCGCAACTGTTGGGAAGGGCGATCGGTGCGGG

CCTCTTCGCTATTACGCCAGCTGGCGAAAGGGGGATGTGCTGCAAGGCGATTAAGTTGGGTAACGCCAGGGT

TTTCCCAGTCACGACGTTGTAAAACGACGGCCAGTGAATTGTAATACGACTCACTATAGGGCGAATTGGGCCC

GACGTCGCATGCTTGGAAGGGCTAATTCACTCCCAAAGAAGACAAGATATCCTTGATCTGTGGATCTACCACA

CACAAGGCTACTTCCCTGATTAGCAGAACTACACACCAGGGCCAGGGGTCAGATATCCACTGACCTTTGGATG

GTGCTACAAGCTAGTACCAGTTGAGCCAGATAAGGTAGAAGAGGCCAATAAAGGAGAGAACACCAGCTTGTT

ACACCCTGTGAGCCTGCATGGGATGGATGACCCGGAGAGAGAAGTGTTAGAGTGGAGGTTTGACAGCCGCC

TAGCATTTCATCACGTGGCCCGAGAGCTGCATCCGGAGTACTTCAAGAACTGCTGATATCGAGCTTGCTACAA

GGGACTTTCCGCTGGGGACTTTCCAGGGAGGCGTGGCCTGGGCGGGACTGGGGAGTGGCGAGCCCTCAGAT

CCTGCATATAAGCAGCTGCTTTTTGCCTGTACTGGGTCTCTCTGGTTAGACCAGATCTGAGCCTGGGAGCTCTC

TGGCTAACTAGGGAACCCACTGCTTAAGCCTCAATAAAGCTTGCCTTGAGTGCTTCAAGTAGTGTGTGCCCGT

CTGTTGTGTGACTCTGGTAACTAGAGATCCCTCAGACCCTTTTAGTCAGTGTGGAAAATCTCTAGCAGTGGCGC

CCGAACAGGGACTTGAAAGCGAAAGGGAAACCAGAGGAGCTCTCTCGACGCAGGACTCGGCTTGCTGAAGC

GCGCACGGCAAGAGGCGAGGGGCGGCGACTGGTGAGTACGCCAAAAATTTTGACTAGCGGAGGCTAGAAG

GAGAGAGATGGGTGCGAGAGCGTCAGTATTAAGCGGGGGAGAATTAGATCGCGATGGGAAAAAATTCGGTT

AAGGCCAGGGGGAAAGAAAAAATATAAATTAAAACATATAGTATGGGCAAGCAGGGAGCTAGAACGATTCG

CAGTTAATCCTGGCCTGTTAGAAACATCAGAAGGCTGTAGACAAATACTGGGACAGCTACAACCATCCCTTCA

GACAGGATCAGAAGAACTTAGATCATTATATAATAGAGTAGCAACCCTCTATTGTGTGCATCAAAGGATAGAG
```

-continued

```
ATAAAAGACACCAAGGAAGCTTTAGACAAGATAGAGGAAGAGCAAAACAAAAGTAAGACCACCGCACAGCA

AGCGGCCGCTGATCTTCAGACCTGGAGGAGGAGATATGAGGGACAATTGGAGAAGTGAATTATATAAATATA

AAGTAGTAAAAATTGAACCATTAGGAGTAGCACCCACCAAGGCAAAGAGAAGAGTGGTGCAGAGAGAAAA

AGAGCAGTGGAATAGGAGCTTTGTTCCTTGGGTTCTTGGGAGCAGCAGGAAGCACTATGGGCGCAGCGTCA

ATGACGCTGACGGTACAGGCCAGACAATTATTGTCTGGTATAGTGCAGCAGCAGAACAATTTGCTGAGGGCT

ATTGAGGCGCAACAGCATCTGTTGCAACTCACAGTCTGGGGCATCAAGCAGCTCCAGGCAAGAATCCTGGCT

GTGGAAAGATACCTAAAGGATCAACAGCTCCTGGGGATTTGGGGTTGCTCTGGAAAACTCATTTGCACCACTG

CTGTGCCTTGGAATGCTAGTTGGAGTAATAAATCTCTGGAACAGATTTGGAATCACACGACCTGGATGGAGTG

GGACAGAGAAATTAACAATTACACAAGCTTAATACACTCCTTAATTGAAGAATCGCAAAACCAGCAAGAAAAG

AATGAACAAGAATTATTGGAATTAGATAAATGGGCAAGTTTGTGGAATTGGTTTAACATAACAAATTGGCTGT

GGTATATAAAATTATTCATAATGATAGTAGGAGGCTTGGTAGGTTTAAGAATAGTTTTTGCTGTACTTTCTATA

GTGAATAGAGTTAGGCAGGGATATTCACCATTATCGTTTCAGACCCACCTCCCAACCCCGAGGGGACCCGACA

GGCCCGAAGGAATAGAAGAAGAAGGTGGAGAGAGAGACAGAGACAGATCCATTCGATTAGTGAACGGATCT

CGACGGGATCGATTTTAAAAGAAAAGGGGGGATTGGGGGGTACAGTGCAGGGGAAAGAATAGTAGACATA

ATAGCAACAGACATACAAACTAAAGAATTACAAAAACAAATTACAAAAATTCAAAATTTTATCGATAAGCTTTG

CAAAGATGGATAAAGTTTTAAACAGAGAGGAATCTTTGCAGCTAATGGACCTTCTAGGTCTGACCCCGTACGC

CTCGAGAGATCTGATCATAATCAGCCATACCACATTTGTAGAGGTTTTACTTGCTTTAAAAAACCTCCCACACCT

CCCCCTGAACCTGAAACATAAAATGAATGCAATTGTTGTTGTTAACTTGTTTATTGCAGCTTATAATGGTTACA

AATAAGGCAATAGCATCACAAATTTCACAAATAAGGCATTTTTTTCACTGCATTCTAGTTTTGGTTTGTCCAAAC

TCATCAATGTATCTTATCATGTCTGGATCTCAAATCCCTCGGAAGCTGCGCCTGTCTTAGGTTGGAGTGATACA

TTTTTATCACTTTTACCCGTCTTTGGATTAGGCAGTAGCTCTGACGGCCCTCCTGTCTTAGGTTAGTGAAAAATG

TCACTCTCTTACCCGTCATTGGCTGTCCAGCTTAGCTCGCAGGGGAGGTGGTCTGCCTGCAGGCGGATGGCGT

TAACATATGACAACTTTCTCCCGGGTAATCTGACCGTTCGCTAGCCCTGGGGAGAGAGGTCGGTGATTCGGTC

AACGAGGGAGCCGACTGCCGACGTGCGCTCCGGAGGCTTGCAGAATGCGGAACACCGCGCGGGCAGGAACA

GGGCCCACACTACCGCCCCACACCCCGCCTCCCGCACCGCCCCTTCCCGGCCGCTGCTCTCGGCGCGCCCCGCT

GAGCAGCCGCTATTGGCCACAGCCCATCGCGGTCGGCGCGCTGCCATTGCTCCCTGGCGCTGTCCGTCTGCGA

GGGTACTAGTGAGACGTGCGGCTTCCGTTTGTCACGTCCGGCACGCCGCGAACCGCAAGGAACCTTCCCGACT

TAGGGGCGGAGCAGGAAGCGTCGCCGGGGGGCCCACAAGGGTAGCGGCGAAGATCCGGGTGACGCTGCGA

ACGGACGTGAAGAATGTGCGAGACCCAGGGTCGGCGCCGCTGCGTTTCCCGGAACCACGCCCAGAGCAGCC

GCGTCCCTGCGCAAACCCAGGGCTGCCAAGGAAAAGGCGCAACCCCAACCCCGTGGTTAATTAAGGTGAAAG

GAGTGGGAATTGGCTCCGGTGCCCGTCAGTGGGCAGAGCGCACATCGCCCACAGTCCCCGAGAAGTTGGGG

GGAGGGGTCGGCAATTGAACCGGTGCCTAGAGAAGGTGGCGCGGGGTAAACTGGGAAAGTGATGTCGTGT

ACTGGCTCCGCCTTTTTCCCGAGGGTGGGGAGAACCGTATATAAGTGCAGTAGTCGCCGTGAACGTTCTTTT

TCGCAACGGGTTTGCCGCCAGAACACAGGTAAGTGCCGTGTGTGGTTCCCGCGGGCCTGGCCTCTTTACGGG

TTATGGCCCTTGCGTGCCTTGAATTACTTCCACCTGGCTGCAGTACGTGATTCTTGATCCCGAGCTTCGGGTTG

GAAGTGGGTGGGAGAGTTCGAGGCCTTGCGCTTAAGGAGCCCCTTCGCCTCGTGCTTGAGTTGAGGCCTGGC

CTGGGCGCTGGGGCCGCCGCGTGCGAATCGGTGGCACCTTCGCGCCTGTCTCGCTGCTTTCGATAAGTCTCT

AGCCATTTAAAATTTTTGATGACCTGCTGCGACGCTTTTTTTCTGGCAAGATAGTCTTGTAAATGCGGGCCAAG

ATCTGCACACTGGTATTTCGGTTTTTGGGGCCGCGGGCGGCGACGGGCCCGTGCGTCCCAGCGCACATGTT

CGGCGAGGCGGGCCTGCGAGCGCGGCCACCGAGAATCGGACGGGGGTAGTCTCAAGCTGGCCGGCCTGCT
```

-continued

```
CTGGTGCCTGGCCTCGCGCCGCCGTGTATCGCCCCGCCCTGGGCGGCAAGGCTGGCCCGGTCGGCACCAGTT

GCGTGAGCGGAAAGATGGCCGCTTCCCGGCCCTGCTGCAGGGAGCTCAAAATGGAGGACGCGGCGCTCGGG

AGAGCGGGCGGGTGAGTCACCCACACAAAGGAAAAGGGCCTTTCCGTCCTCAGCCGTCGCTTCATGTGACTC

CACGGAGTACCGGGCGCCGTCCAGGCACCTCGATTAGTTCTCGAGCTTTTGGAGTACGTCGTCTTTAGGTTGG

GGGGAGGGGTTTTATGCGATGGAGTTTCCCCACACTGAGTGGGTGGAGACTGAAGTTAGGCCAGCTTGGCAC

TTGATGTAATTCTCCTTGGAATTTGCCCTTTTTGAGTTTGGATCTTGGTTCATTCTCAAGCCTCAGACAGTGGTT

CAAAGTTTTTTTCTTCCATTTCAGGTGTCGTGAGGAATTCTGCAGTCGACGGTACCGCGGGCGCGCCCCGGGA

TCCAAGCTTCAATTGTGGTCACTCGACAATCAACCTCTGGATTACAAAATTTGTGAAAGATTGACTGGTATTCT

TAACTATGTTGCTCCTTTTACGCTATGTGGATACGCTGCTTTAATGCCTTTGTATCATGCTATTGCTTCCCGTATG

GCTTTCATTTTCTCCTCCTTGTATAAATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGGCATTGCCACCACCGTCAGCTCC

TTTCCGGGACTTTCGCTTTCCCCCTCCCTATTGCCACGGCGGAACTCATCGCCGCCTGCCTTGCCCGCTGCTGG

ACAGGGGCTCGGCTGTTGGGCACTGACAATTCCGTGGTGTTGTCGGGGAAGCTGACGTCCTTTCCATGGCTG

CTCGCCTGTGTTGCCACCTGGATTCTGCGCGGGACGTCCTTCTGCTACGTCCCTTCGGCCCTCAATCCAGCGGA

CCTTCCTTCCCGCGGCCTGCTGCCGGCTCTGCGGCCTCTTCCGCGTCTTCGCCTTCGCCCTCAGACGAGTCGGA

TCTCCCTTTGGGCCGCCTCCCCGCCTGCTCGAGACCTAGAAAAACATGGAGCAATCACAAGTAGCAATACAGC

AGCTACCAATGCTGATTGTGCCTGGCTAGAAGCACAAGAGGAGGAGGAGGTGGGTTTTCCAGTCACACCTCA

GGTACCTTTAAGACCAATGACTTACAAGGCAGCTGTAGATCTTAGCCACTTTTTAAAAGAAAAGGGGGGACTG

GAAGGGCTAATTCACTCCCAACGAAGACAAGATCTGCTTTTTGCTTGTACTGGGTCTCTCTGGTTAGACCAGAT

CTGAGCCTGGGAGCTCTCTGGCTAACTAGGGAACCCACTGCTTAAGCCTCAATAAAGCTTGCCTTGAGTGCTT

CAAGTAGTGTGTGCCCGTCTGTTGTGTGACTCTGGTAACTAGAGATCCCTCAGACCCTTTTAGTCAGTGTGGA

AAATCTCTAGCAGTAGTAGTTCATGTCATCTTATTATTCAGTATTTATAACTTGCAAAGAAATGAATATCAGAG

AGTGAGAGGACGCGTTGGATGCATAGCTTGAGTATTCTATAGTGTCACCTAAATAGCTTGGCGTAATCATGGT

CATAGCTGTTTCCTGTGTGAAATTGTTATCCGCTCACAATTCCACACAACATACGAGCCGGAAGCATAAAGTGT

AAAGCCTGGGGTGCCTAATGAGTGAGCTAACTCACATTAATTGCGTTGCGCTCACTGCCCGCTTTCCAGTCGG

GAAACCTGTCGTGCCAGCTGCATTAATGAATCGGCCAACGCGCGGGGAGAGGCGGTTTGCGTATTGGGCGCT

CTTCCGCTTCCTCGCTCACTGACTCGCTGCGCTCGGTCGTTCGGCTGCGGCGAGCGGTATCAGCTCACTCAAAG

GCGGTAATACGGTTATCCACAGAATCAGGGGATAACGCAGGAAAGAACATGTGAGCAAAAGGCCAGCAAAA

GGCCAGGAACCGTAAAAAGGCCGCGTTGCTGGCGTTTTTCCATAGGCTCCGCCCCCTGACGAGCATCACAAA

AATCGACGCTCAAGTCAGAGGTGGCGAAACCCGACAGGACTATAAAGATACCAGGCGTTTCCCCCTGGAAGC

TCCCTCGTGCGCTCTCCTGTTCCGACCCTGCCGCTTACCGGATACCTGTCCGCCTTTCTCCCTTCGGGAAGCGTG

GCGCTTTCTCATAGCTCACGCTGTAGGTATCTCAGTTCGGTGTAGGTCGTTCGCTCCAAGCTGGGCTGTGTGCA

CGAACCCCCCGTTCAGCCCGACCGCTGCGCCTTATCCGGTAACTATCGTCTTGAGTCCAACCCGGTAAGACAC

GACTTATCGCCACTGGCAGCAGCCACTGGTAACAGGATTAGCAGAGCGAGGTATGTAGGCGGTGCTACAGAG

TTCTTGAAGTGGTGGCCTAACTACGGCTACACTAGAAGAACAGTATTTGGTATCTGCGCTCTGCTGAAGCCAG

TTACCTTCGGAAAAAGAGTTGGTAGCTCTTGATCCGGCAAACAAACCACCGCTGGTAGCGGTGGTTTTTTTGTT

TGCAAGCAGCAGATTACGCGCAGAAAAAAAGGATCTCAAGAAGATCCTTTGATCTTTTCTACGGGGTCTGACG

CTCAGTGGAACGAAAACTCACGTTAAGGGATTTTGGTCATGAGATTATCAAAAGGATCTTCACCTAGATCCT

TTTAAATTAAAAATGAAGTTTTAAATCAATCTAAAGTATATATGAGTAAACTTGGTCTGACAGTTACCAATGCT

TAATCAGTGAGGCACCTATCTCAGCGATCTGTCTATTTCGTTCATCCATAGTTGCCTGACTCCCCGTCGTGTAG

ATAACTACGATACGGGAGGGCTTACCATCTGGCCCCAGTGCTGCAATGATACCGCGAGACCCACGCTCACCG
```

-continued

```
GCTCCAGATTTATCAGCAATAAACCAGCCAGCCGGAAGGGCCGAGCGCAGAAGTGGTCCTGCAACTTTATCC

GCCTCCATCCAGTCTATTAATTGTTGCCGGGAAGCTAGAGTAAGTAGTTCGCCAGTTAATAGTTTGCGCAACGT

TGTTGCCATTGCTACAGGCATCGTGGTGTCACGCTCGTCGTTTGGTATGGCTTCATTCAGCTCCGGTTCCCAAC

GATCAAGGCGAGTTACATGATCCCCCATGTTGTGCAAAAAAGCGGTTAGCTCCTTCGGTCCTCCGATCGTTGTC

AGAAGTAAGTTGGCCGCAGTGTTATCACTCATGGTTATGGCAGCACTGCATAATTCTCTTACTGTCATGCCATC

CGTAAGATGCTTTTCTGTGACTGGTGAGTACTCAACCAAGTCATTCTGAGAATAGTGTATGCGGCGACCGAGT

TGCTCTTGCCCGGCGTCAATACGGGATAATACCGCGCCACATAGCAGAACTTTAAAAGTGCTCATCATTGGAA

AACGTTCTTCGGGGCGAAAACTCTCAAGGATCTTACCGCTGTTGAGATCCAGTTCGATGTAACCCACTCGTGC

ACCCAACTGATCTTCAGCATCTTTTACTTTCACCAGCGTTTCTGGGTGAGCAAAAACAGGAAGGCAAAATGCC

GCAAAAAAGGGAATAAGGGCGACACGGAAATGTTGAATACTCATACTCTTCCTTTTTCAATATTATTGAAGCA

TTTATCAGGGTTATTGTCTCATGAGCGGATACATATTTGAATGTATTTAGAAAAATAAACAAATAGGGGTTCCG

CGCACATTTCCCCGAAAAGTGCCACCTGATGCGGTGTGAAATACCGCACAGATGCGTAAGGAGAAAATACCG

CATCAGG
```

>pDY-[MCS] + (IY)

SEQ ID NO: 11

```
AAATTGTAAGCGTTAATATTTTGTTAAAATTCGCGTTAAATTTTTGTTAAATCAGCTCATTTTTTAACCAATAGG

CCGAAATCGGCAAAATCCCTTATAAATCAAAAGAATAGACCGAGATAGGGTTGAGTGTTGTTCCAGTTTGGAA

CAAGAGTCCACTATTAAAGAACGTGGACTCCAACGTCAAAGGGCGAAAAACCGTCTATCAGGGCGATGGCCC

ACTACGTGAACCATCACCCTAATCAAGTTTTTTGGGGTCGAGGTGCCGTAAAGCACTAAATCGGAACCCTAAA

GGGAGCCCCCGATTTAGAGCTTGACGGGGAAAGCCGGCGAACGTGGCGAGAAAGGAAGGGAAGAAAGCGA

AAGGAGCGGGCGCTAGGGCGCTGGCAAGTGTAGCGGTCACGCTGCGCGTAACCACCACACCCGCCGCGCTT

AATGCGCCGCTACAGGGCGCGTCCATTCGCCATTCAGGCTGCGCAACTGTTGGGAAGGGCGATCGGTGCGGG

CCTCTTCGCTATTACGCCAGCTGGCGAAAGGGGGATGTGCTGCAAGGCGATTAAGTTGGGTAACGCCAGGGT

TTTCCCAGTCACGACGTTGTAAAACGACGGCCAGTGAATTGTAATACGACTCACTATAGGGCGAATTGGGCCC

GACGTCGCATGCTTGGAAGGGCTAATTCACTCCCAAAGAAGACAAGATATCCTTGATCTGTGGATCTACCACA

CACAAGGCTACTTCCCTGATTAGCAGAACTACACACCAGGGCCAGGGGTCAGATATCCACTGACCTTTGGATG

GTGCTACAAGCTAGTACCAGTTGAGCCAGATAAGGTAGAAGAGGCCAATAAAGGAGAGAACACCAGCTTGTT

ACACCCTGTGAGCCTGCATGGGATGGATGACCCGGAGAGAGAAGTGTTAGAGTGGAGGTTTGACAGCCGCC

TAGCATTTCATCACGTGGCCCGAGAGCTGCATCCGGAGTACTTCAAGAACTGCTGATATCGAGCTTGCTACAA

GGGACTTTCCGCTGGGGACTTTCCAGGGAGGCGTGGCCTGGGCGGGACTGGGGAGTGGCGAGCCCTCAGAT

CCTGCATATAAGCAGCTGCTTTTTGCCTGTACTGGGTCTCTCTGGTTAGACCAGATCTGAGCCTGGGAGCTCTC

TGGCTAACTAGGGAACCCACTGCTTAAGCCTCAATAAAGCTTGCCTTGAGTGCTTCAAGTAGTGTGTGCCCGT

CTGTTGTGTGACTCTGGTAACTAGAGATCCCTCAGACCCTTTTAGTCAGTGTGGAAAATCTCTAGCAGTGGCGC

CCGAACAGGGACTTGAAAGCGAAAGGGAAACCAGAGGAGCTCTCTCGACGCAGGACTCGGCTTGCTGAAGC

GCGCACGGCAAGAGGCGAGGGGCGGCGACTGGTGAGTACGCCAAAAATTTTGACTAGCGGAGGCTAGAAG

GAGAGAGATGGGTGCGAGAGCGTCAGTATTAAGCGGGGGAGAATTAGATCGCGATGGGAAAAAATTCGGTT

AAGGCCAGGGGGAAAGAAAAAATATAAATTAAAACATATAGTATGGGCAAGCAGGGAGCTAGAACGATTCG

CAGTTAATCCTGGCCTGTTAGAAACATCAGAAGGCTGTAGACAAATACTGGGACAGCTACAACCATCCCTTCA

GACAGGATCAGAAGAACTTAGATCATTATATAATACAGTAGCAACCCTCTATTGTGTGCATCAAAGGATAGAG

ATAAAAGACACCAAGGAAGCTTTAGACAAGATAGAGGAAGAGCAAAACAAAGTAAGACCACCGCACAGCA

AGCGGCCGCTGATCTTCAGACCTGGAGGAGGAGATATGAGGGACAATTGGAGAAGTGAATTATATAAATATA
```

-continued

```
AAGTAGTAAAAATTGAACCATTAGGAGTAGCACCCACCAAGGCAAAGAGAAGAGTGGTGCAGAGAGAAAA

AGAGCAGTGGGAATAGGAGCTTTGTTCCTTGGGTTCTTGGGAGCAGCAGGAAGCACTATGGGCGCAGCGTCA

ATGACGCTGACGGTACAGGCCAGACAATTATTGTCTGGTATAGTGCAGCAGCAGAACAATTTGCTGAGGGCT

ATTGAGGCGCAACAGCATCTGTTGCAACTCACAGTCTGGGGCATCAAGCAGCTCCAGGCAAGAATCCTGGCT

GTGGAAAGATACCTAAAGGATCAACAGCTCCTGGGGATTTGGGGTTGCTCTGGAAAACTCATTTGCACCACTG

CTGTGCCTTGGAATGCTAGTTGGAGTAATAAATCTCTGGAACAGATTTGGAATCACACGACCTGGATGGAGTG

GGACAGAGAAATTAACAATTACACAAGCTTAATACACTCCTTAATTGAAGAATCGCAAAACCAGCAAGAAAAG

AATGAACAAGAATTATTGGAATTAGATAAATGGGCAAGTTTGTGGAATTGGTTTAACATAACAAATTGGCTGT

GGTATATAAAATTATTCATAATGATAGTAGGAGGCTTGGTAGGTTTAAGAATAGTTTTTGCTGTACTTTCTATA

GTGAATAGAGTTAGGCAGGGATATTCACCATTATCGTTTCAGACCCACCTCCCAACCCCGAGGGGACCCGACA

GGCCCGAAGGAATAGAAGAAGAAGGTGGAGAGAGAGACAGAGACAGATCCATTCGATTAGTGAACGGATCT

CGACGGGATCGATTTTAAAAGAAAAGGGGGGATTGGGGGGTACAGTGCAGGGGAAAGAATAGTAGACATA

ATAGCAACAGACATACAAACTAAAGAATTACAAAAACAAATTACAAAAATTCAAAATTTTATCGATAAGCTTTG

CAAAGATGGATAAAGTTTTAAACAGAGAGGAATCTTTGCAGCTAATGGACCTTCTAGGTCTGACCCCGTACGC

CTCGAGAGATCTGATCATAATCAGCCATACCACATTTGTAGAGGTTTTACTTGCTTTAAAAAACCTCCCACACCT

CCCCCTGAACCTGAAACATAAAATGAATGCAATTGTTGTTGTTAACTTGTTTATTGCAGCTTATAATGGTTACA

AATAAGGCAATAGCATCACAAATTTCACAAATAAGGCATTTTTTTCACTGCATTCTAGTTTTGGTTTGTCCAAAC

TCATCAATGTATCTTATCATGTCTGGATCTCAAATCCCTCGGAAGCTGCGCCTGTCTTAGGTTGGAGTGATACA

TTTTTATCACTTTTACCCGTCTTTGGATTAGGCAGTAGCTCTGACGGCCCTCCTGTCTTAGGTTAGTGAAAAATG

TCACTCTCTTACCCGTCATTGGCTGTCCAGCTTAGCTCGCAGGGGAGGTGGTCTGCCTGCAGGTTAGAACAGT

CTCTTTTCGTATGAGTGCAGTGAGTGGACGCCGCCTTCGACCTGGGCTGAAGAAGTTCTTTTCTCGAACTTCAG

TTCGCCGGAATACATCATTGCCCGCACCTGTGTCAGGCTCTTAGCGCCGATATCCTGGCATGAATGCTGAATTC

CGGCGATCAGGTAAGGCACGAATTTGTGAATACTGCCCTTATCCTGGACAGCTCCAGACACGCCCTGTGCGAC

TTTGATCTTGTCTGCCTCGGAAAAATACCTGTTCTGAGAGGACAGATGCTTATCCATGGCGTCCAGTGACCCCA

TGCCCCTATATTTCTTCAGTCTGAACCCATCACTAAAGAAGTACTCGCCGGGGGCTTCTGTGGTTGCAGCCAGC

AGGCTGCCCATCATCACTGTGCTTGCCCCCAGAGCCAGGGCTTTTGCGATGTGGCCCACATTCTGAATTCCCCC

GTCAGCGATCACTGGGACTCCGAATCTCCGGGCATACTCGTACACCTTGTAGACAGCAGTTGCCTGAGGTCGT

CCACAGGCCAGCACTTCCTGAATGATGCAGATTGATCCACTCCCCATTCCGACCCTCAGAGCATCCACTCCTGC

GTCAATCAGGTTTTTGGCCTGGGCTGCGGTCACGACATTGCCTCCGATGACCTGCAGATTTGGGTACTTGTCCT

TAATGTACTTGATCATATTAATCTGGAAGATGCTGTTTCCCTGGCTTGAATCCAGCACGACCACGTCCACCCCT

GCCTGAGCCAGCAGATCCAGGCGATATTTATCGTCCTCGTGTGTGCCAATAGCGGCTCCACACAGCAGCTGTT

TCTTTGCGTCCTTACTAGCCAGAGGGTAATCTCGATTTTTCTTCAGGTCGGTGCGGGCAATGATTGCCACCAGC

TCATCGTCTTCATTCACGATAGGCAGTTTTCCTTTCTTAGACCGCTGCAGAATCTCGTTGGCTTCCTTCAGTGTG

ATGCCGGCAGGTGCGACCACCAGATCTTCGCGTTTGGTCATAATCTCTTCCAGAAAACAGTCATGCTCTTCCTC

CTTCAGGAAATCGATGTCTCGACTAGAAATGATTCCTCACCAGTCGGCTGCCCATTCGTCCAGTATCTGTAATGG

GGATGCCGCAAAATCCGTGCCTAGCTTTGGCCTCGAACACATCGCGGACCCTGTCCTTGGGGCTCAGGACCAC

TGGGTCGGTGATAAAGCCCTGTTCGTATTTCTTCACCTTTCTGACCTCATTGGCCTGAAATTCTGGAGTGCAGT

TATGGTGAATGAACCCGATCCCGCCTGTCAGTGCCATAGCAATGGCCATGCCAGCCTCGGTGACAGTGTCCAT

AGGGGAGCTCACCAGGGGTGTCTTCAGGGTGATTTTCTTGGTCAGGGCAGAAGTCAGATCCACCTGGTCTGC

GGTAAAATCAATATAGCCGGGCAGGATCAGGAAGTCGTTGTAAGTCAGCCCGTCTCCACAATTAAACAGCTG

CTGGGCGGTCAGTCCATCATCAGGGACATAGGAAGTGCCTCCAGAAATCAGGTAGTCGGCCATGGTGGCGCT
```

-continued

```
AGCCCTGGGGAGAGAGGTCGGTGATTCGGTCAACGAGGGAGCCGACTGCCGACGTGCGCTCCGGAGGCTTG
CAGAATGCGGAACACCGCGCGGGCAGGAACAGGGCCCACACTACCGCCCCTCACCCCGCCTCCCGCACCGCC
CCTTCCCGGCCGCTGCTCTCGGCGCGCCCCGCTGAGCAGCCGCTATTGGCCACAGCCCATCGCGGTCGGCGCG
CTGCCATTGCTCCCTGGCGCTGTCCGTCTGCGAGGGTACTAGTGAGACGTGCGGCTTCCGTTTGTCACGTCCG
GCACGCCGCGAACCGCAAGGAACCTTCCCGACTTAGGGGCGGAGCAGGAAGCGTCGCCGGGGGCCCACAA
GGGTAGCGGCGAAGATCCGGGTGACGCTGCGAACGGACGTGAAGAATGTGCGAGACCCAGGGTCGGCGCC
GCTGCGTTTCCCGGAACCACGCCCAGAGCAGCCGCGTCCCTGCGCAAACCCAGGGCTGCCAAGGAAAAGGCG
CAACCCCAACCCCGTGGTTAATTAAGGTGAAAGGAGTGGGAATTGGCTCCGGTGCCCGTCAGTGGGCAGAGC
GCACATCGCCCACAGTCCCCGAGAAGTTGGGGGGAGGGGTCGGCAATTGAACCGGTGCCTAGAGAAGGTGG
CGCGGGGTAAACTGGGAAAGTGATGTCGTGTACTGGCTCCGCCTTTTTCCCGAGGGTGGGGGAGAACCGTAT
ATAAGTGCAGTAGTCGCCGTGAACGTTCTTTTTCGCAACGGGTTTGCCGCCAGAACACAGGTAAGTGCCGTGT
GTGGTTCCCGCGGGCCTGGCCTCTTTACGGGTTATGGCCCTTGCGTGCCTTGAATTACTTCCACCTGGCTGCAG
TACGTGATTCTTGATCCCGAGCTTCGGGTTGGAAGTGGGTGGGAGAGTTCGAGGCCTTGCGCTTAAGGAGCC
CCTTCGCCTCGTGCTTGAGTTGAGGCCTGGCCTGGGCGCTGGGGCCGCCGCGTGCGAATCGGTGGCACCTTC
GCGCCTGTCTCGCTGCTTTCGATAAGTCTCTAGCCATTTAAAATTTTTGATGACCTGCTGCGACGGTTTTTTCT
GGCAAGATAGTCTTGTAAATGCGGGCCAAGATCTGCACACTGGTATTTCGGTTTTTGGGGCCGCGGGCGGCG
ACGGGGCCCGTGCGTCCCAGCGCACATGTTCGGCGAGGCGGGGCCTGCGAGCGCGGCCACCGAGAATCGGA
CGGGGGTAGTCTCAAGCTGGCCGGCCTGCTCTGGTGCCTGGCCTCGCGCCGCCGTGTATCGCCCCGCCCTGG
GCGGCAAGGCTGGCCCGGTCGGCACCAGTTGCGTGAGCGGAAAGATGGCCGCTTCCCGGCCCTGCTGCAGG
GAGCTCAAAATGGAGGACGCGCGCTCGGGAGAGCGGGCGGGTGAGTCACCCACACAAAGGAAAAGGGCC
TTTCCGTCCTCAGCCGTCGCTTCATGTGACTCCACGGAGTACCGGGCGCCGTCCAGGCACCTCGATTAGTTCTC
GAGCTTTTGGAGTACGTCGTCTTTAGGTTGGGGGGAGGGGTTTTATGCGATGGAGTTTCCCCACACTGAGTG
GGTGGAGACTGAAGTTAGGCCAGCTTGGCACTTGATGTAATTCTCCTTGGAATTTGCCCTTTTTGAGTTTGGAT
AGTCGACGGTACCGCGGGCGCGCCCCGGGATCCAAGCTTCAATTGTGGTCACTCGACAATCAACCTCTGGATT
ACAAAATTTGTGAAAGATTGACTGGTATTCTTAACTATGTTGCTCCTTTTACGCTATGTGGATACGCTGCTTTAA
TGCCTTTGTATCATGCTATTGCTTCCCGTATGGCTTTCAT-
TTTCTCCTCCTTGTATAAATCCTGGTTGCTGTCTCTT
TATGAGGAGTTGTGGCCCGTTGTCAGGCAACGTGGCGTGGTGTGCACTGTGTTTGCTGACGCAACCCCCACTG
GTTGGGGCATTGCCACCACCTGTCAGCTCCTTTCCGGGACTTTCGCTTTCCCCCTCCCTATTGCCACGGCGGAA
CTCATCGCCGCCTGCCTTGCCCGCTGCTGGACAGGGGCTCGGCTGTTGGGCACTGACAATTCCGTGGTGTTGT
CGGGGAAGCTGACGTCCTTTCCATGGCTGCTCGCCTGTGTTGCCACCTGGATTCTGCGCGGGACGTCCTTCTG
CTACGTCCCTTCGGCCCTCAATCCAGCGGACCTTCCTTCCCGCGGCCTGCTGCCGGCTCTGCGGCCTCTTCCGC
GTCTTCGCCTTCGCCCTCAGACGAGTCGGATCTCCCTTTGGGCCGCCTCCCCGCCTGCTCGAGACCTAGAAAAA
CATGGAGCAATCACAAGTAGCAATACAGCAGCTACCAATGCTGATTGTGCCTGGCTAGAAGCACAAGAGGAG
GAGGAGGTGGGTTTTCCAGTCACACCTCAGGTACCTTTAAGACCAATGACTTACAAGGCAGCTGTAGATCTTA
GCCACTTTTTAAAAGAAAAGGGGGGACTGGAAGGGCTAATTCACTCCCAACGAAGACAAGATCTGCTTTTTGC
TTGTACTGGGTCTCTCTGGTTAGACCAGATCTGAGCCTGGGAGCTCTCTGGCTAACTAGGGAACCCACTGCTT
AAGCCTCAATAAAGCTTGCCTTGAGTGCTTCAAGTAGTGTGTGCCCGTCTGTTGTGTGACTCTGGTAACTAGA
GATCCCTCAGACCCTTTTAGTCAGTGTGGAAAATCTCTAGCAGTAGTAGTTCATGTCATCTTATTATTCAGTATT
TATAACTTGCAAAGAAATGAATATCAGAGAGTGAGAGGACGCGTTGGATGCATAGCTTGAGTATTCTATAGT
GTCACCTAAATAGCTTGGCGTAATCATGGTCATAGCTGTTTCCTGTGTGAAATTGTTATCCGCTCACAATTCCAC
```

-continued

```
ACAACATACGAGCCGGAAGCATAAAGTGTAAAGCCTGGGGTGCCTAATGAGTGAGCTAACTCACATTAATTG
CGTTGCGCTCACTGCCCGCTTTCCAGTCGGGAAACCTGTCGTGCCAGCTGCATTAATGAATCGGCCAACGCGC
GGGGAGAGGCGGTTTGCGTATTGGGCGCTCTTCCGCTTCCTCGCTCACTGACTCGCTGCGCTCGGTCGTTCGG
CTGCGGCGAGCGGTATCAGCTCACTCAAAGGGGGTAATACGGTTATCCACAGAATCAGGGGATAACGCAGGA
AAGAACATGTGAGCAAAAGGCCAGCAAAAGGCCAGGAACCGTAAAAAGGCCGCGTTGCTGGCGTTTTTCCAT
AGGCTCCGCCCCCCTGACGAGCATCACAAAAATCGACGCTCAAGTCAGAGGTGGCGAAACCCGACAGGACTA
TAAAGATACCAGGCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGGTATCTCAGTTCGGTGT
AGGTCGTTCGCTCCAAGCTGGGCTGTGTGCACGAACCCCCCGTTCAGCCCGACCGCTGCGCCTTATCCGGTAA
CTATCGTCTTGAGTCCAACCCGGTAAGACACGACTTATCGCCACTGGCAGCAGCCACTGGTAACAGGATTAGC
AGAGCGAGGTATGTAGGCGGTGCTACAGAGTTCTTGAAGTGGTGGCCTAACTACGGCTACACTAGAAGAACA
GTATTTGGTATCTGCGCTCTGCTGAAGCCAGTTACCTTCGGAAAAAGAGTTGGTAGCTCTTGATCCGGCAAAC
AAACCACCGCTGGTAGCGGTGGTTTTTTTGTTTGCAAGCAGCAGATTACGCGCAGAAAAAAAGGATCTCAAG
AAGATCCTTTGATCTTTTCTACGGGGTCTGACGCTCAGTGGAACGAAAACTCACGTTAAGGGATTTTGGTCAT
GAGATTATCAAAAAGGATCTTCACCTAGATCCTTTTAAATTAAAAATGAAGTTTTAAATCAATCTAAAGTATAT
ATGAGTAAACTTGGTCTGACAGTTACCAATGCTTAATCAGTGAGGCACCTATCTCAGCGATCTGTCTATTTCGT
TCATCCATAGTTGCCTGACTCCCCGTCGTGTAGATAACTACGATACGGGAGGGCTTACCATCTGGCCCCAGTG
CTGCAATGATACCGCGAGACCCACGCTCACCGGCTCCAGATTTATCAGCAATAAACCAGCCAGCCGGAAGGG
CCGAGCGCAGAAGTGGTCCTGCAACTTTATCCGCCTCCATCCAGTCTATTAATTGTTGCCGGGAAGCTAGAGT
AAGTAGTTCGCCAGTTAATAGTTTGCGCAACGTTGTTGCCATTGCTACAGGCATCGTGGTGTCACGCTCGTCGT
TTGGTATGGCTTCATTCAGCTCCGGTTCCCAACGATCAAGGCGAGTTACATGATCCCCCATGTTGTGCAAAAAA
GCGGTTAGCTCCTTCGGTCCTCCGATCGTTGTCAGAAGTAAGTTGGCCGCAGTGTTATCACTCATGGTTATGGC
AGCACTGCATAATTCTCTTACTGTCATGCCATCCGTAAGATGCTTTTCTGTGACTGGTGAGTACTCAACCAAGT
CATTCTGAGAATAGTGTATGCGGCGACCGAGTTGCTCTTGCCCGGCGTCAATACGGGATAATACCGCGCCACA
TAGCAGAACTTTTAAAAGTGCTCATCATTGGAAAACGTTCTTCGGGGCGAAAACTCTCAAGGATCTTACCGCTG
TTGAGATCCAGTTCGATGTAACCCACTCGTGCACCCAACTGATCTTCAGCATCTTTTACTTTCACCAGCGTTTCT
GGGTGAGCAAAAACAGGAAGGCAAAATGCCGCAAAAAAGGGAATAAGGGCGACACGGAAATGTTGAATAC
TCATACTCTTCCTTTTTCAATATTATTGAAGCATTTATCAGGGTTATTGTCTCATGAGCGGATACATATTTGAAT
GTATTTAGAAAAATAAACAAATAGGGGTTCCGCGCACATTTCCCCGAAAAGTGCCACCTGATGCGGTGTGAAA
TACCGCACAGATGCGTAAGGAGAAAATACCGCATCAGG
```

The invention claimed is:

1. A method comprising:
(a) conditioning T-cells from a subject with rapamycin ex vivo to generate T-Rapa cells, wherein the subject is suffering from Fabry disease;
(b) transducing the T-Rapa cells in vitro with a vector comprising a transgene of interest that encodes an enzyme associated with a lysosomal storage disorder, wherein the enzyme associated with the lysosomal storage disorder is a-galactosidase A (α-gal A);
(c) expanding the vector-transduced T-Rapa cells by culturing in vitro; and
(d) administering the expanded transduced T-Rapa cells of step (c) derived from the subject to the subject by intravenous infusion, wherein the T-Rapa cells express the enzyme associated with the lysosomal storage disorder in the subject and reduce a level of globotriaosylceramide (Gb$_3$) in the subject.

2. The method of claim 1 further comprising cryopreserving a portion of the expanded transduced T-Rapa cells for future administration to the subject.

3. The method of claim 1 further comprising detecting and isolating CD4+ T-cells from the subject and culturing the CD4+ T-cells in vitro prior to step (a), wherein the purity of the isolated CD4+ T cells is at least 75%.

4. The method of claim 1, wherein step (a) comprises culturing the T-cells in chemically defined medium comprising about 0.1 to about 2 micromolar rapamycin.

5. The method of claim 4, wherein the chemically defined medium further comprises recombinant human interleukin 4 (IL-4) and recombinant human interleukin 2 (IL-2).

6. The method of claim 1, wherein the vector is a lentiviral vector.

7. The method of claim 6, wherein the lentiviral vector is a dual promoter lentivirus vector, and wherein the vector expresses the transgene of interest and a mutant form of inosine-5'-monophosphate dehydrogenase 2 (IMPDH2(IY)) when transduced into the T-Rapa cells.

8. The method of claim 7, wherein the vector comprises SEQ ID NO:11.

9. The method of claim 8, wherein the method further comprises administering to the subject an amount of mycophenolate mofetil (MMF) sufficient to enrich the population of transduced T-Rapa cells in the subject.

10. The method of claim 1, wherein the transgene is:
a) an a-galactosidase A (AGA) comprising SEQ ID NO: 1 or a sequence with at least 75% sequence identity to SEQ ID NO:1.

11. The method of claim 10, wherein the vector is a lentiviral vector that comprises:
SEQ ID NO:2 or a sequence with at least 75% sequence identity to SEQ ID NO:2.

12. The method of claim 1, wherein the reduced level of globotriaosylceramide (Gb$_3$) is detected in the blood, liver, spleen, heart or kidneys of the subject.

* * * * *

SEQUENCE LISTING

<160> NUMBER OF SEQ ID NOS: 11

<210> SEQ ID NO 1
<211> LENGTH: 1290
<212> TYPE: DNA
<213> ORGANISM: Artificial Sequence
<220> FEATURE:
<223> OTHER INFORMATION: AGA transgene

<400> SEQUENCE: 1

```
atgcaacttc gaaacccaga gctccacctc ggatgtgccc ttgctctgag gttcctggcg      60
ctggtgtctt gggatatacc cggagcacgc gctctggaca acgggctggc ccggactcca     120
```

```
accatgggtt ggctccattg ggaaaggttt atgtgcaact tggactgcca ggaagaaccc      180
gactcctgta tttccgagaa actcttcatg gagatggccg agctgatggt tagcgaaggc      240
tggaaggatg ccggttatga atacttgtgt atcgacgatt gttggatggc tccccagcgg      300
gacagtgaag gacgactcca ggcagatccg caacggttcc ctcatggcat acggcagctc      360
gccaattacg tgcacagcaa gggtttgaag ctggggatat atgctgacgt gggcaacaaa      420
acctgtgctg gtttccccgg cagcttcggc tactatgata tagatgcaca aaccttcgct      480
gattggggcg tggacctgct taaatttgac ggctgttact gcgacagctt ggaaaacctc      540
gccgatggat ataaacacat gagccttgca ctcaatcgga ctggccggag cattgtctac      600
tcttgcgagt ggccattgta catgtggcct ttccagaagc ctaactatac ggagattaga      660
cagtattgta atcactggag aaactttgca gatatcgacg actcatggaa gtccatcaaa      720
tctattctgg actggacttc attcaatcag gagcgcatcg tcgatgttgc cggtccaggt      780
ggatggaacg accctgacat gctcgtaatt gggaatttcg gactgtcctg gaatcagcag      840
gtcacacaga tggctttgtg ggctatcatg gcagccccac tctttatgtc taacgatttg      900
cggcatattt caccacaggc caaagccctg ctgcaagata aggacgtcat agcgattaac      960
caggacccac tgggaaagca gggctaccag ctgagacagg gcgacaattt tgaggtctgg     1020
gaaagacctc ttagcgggct ggcgtgggcc gtagccatga ttaatcgcca ggaaattggc     1080
ggccctcgct cttacactat cgcggtcgcc agtctgggca agggagtcgc ttgtaacccc     1140
gcctgcttca taactcagtt gctgcccgtg aaacggaagc tgggcttcta tgaatggact     1200
agcagactcc gcagtcatat taatccgact ggtacggtgc tgctgcaact ggagaatacc     1260
atgcagatgt cacttaagga tcttctgtga                                     1290
```

<210> SEQ ID NO 2
<211> LENGTH: 8767
<212> TYPE: DNA
<213> ORGANISM: Artificial Sequence
<220> FEATURE:
<223> OTHER INFORMATION: Lentiviral vector comprising AGA transgene

<400> SEQUENCE: 2

```
aaattgtaag cgttaatatt ttgttaaaat tcgcgttaaa ttttgttaa atcagctcat       60 tttttaacca ataggccgaa atcggcaaaa tcccttataa atcaaaagaa tagaccgaga      120
tagggttgag tgttgttcca gtttggaaca agagtccact attaaagaac gtggactcca      180
acgtcaaagg gcgaaaaacc gtctatcagg gcgatggccc actacgtgaa ccatcaccct      240
aatcaagttt ttggggtcg aggtgccgta agcactaaa tcggaaccct aaagggagcc       300
cccgatttag agcttgacgg ggaaagccgg cgaacgtggc gagaaaggaa gggaagaaag      360
cgaaaggagc gggcgctagg gcgctggcaa gtgtagcggt cacgctgcgc gtaaccacca      420
cacccgccgc gcttaatgcg ccgctacagg gcgcgtccat tcgccattca ggctgcgcaa      480
ctgttgggaa gggcgatcgg tgcgggcctc ttcgctatta cgccagctgg cgaaaggggg      540
atgtgctgca aggcgattaa gttgggtaac gccagggttt tcccagtcac gacgttgtaa      600
aacgacggcc agtgaattgt aatacgactc actatagggc gaattgggcc cgacgtcgca      660
tgcttggaag gctaattca ctcccaaaga agacaagata tccttgatct gtggatctac       720
cacacacaag gctacttccc tgattagcag aactacacac cagggccagg gtcagatat      780 ccactgacct ttggatggtg ctacaagcta gtaccagttg agccagataa ggtagaagag      840
```

```
gccaataaag gagagaacac cagcttgtta caccctgtga gcctgcatgg gatggatgac    900
ccggagagag aagtgttaga gtggaggttt gacagccgcc tagcatttca tcacgtggcc    960
cgagagctgc atccggagta cttcaagaac tgctgatatc gagcttgcta caagggactt   1020
tccgctgggg actttccagg gaggcgtggc ctggggcgga ctggggagtg gcgagccctc   1080
agatcctgca tataagcagc tgcttttttgc ctgtactggg tctctctggt tagaccagat   1140
ctgagcctgg gagctctctg gctaactagg gaacccactg cttaagcctc aataaagctt   1200
gccttgagtg cttcaagtag tgtgtgcccg tctgttgtgt gactctggta actagagatc   1260
cctcagaccc ttttagtcag tgtggaaaat ctctagcagt ggcgcccgaa cagggacttg   1320
aaagcgaaag ggaaaccaga ggagctctct cgacgcagga ctcggcttgc tgaagcgcgc   1380
acggcaagag gcgaggggcg cgactggtg agtacgccaa aaattttgac tagcggaggc    1440
tagaaggaga gagatgggtg cgagagcgtc agtattaagc gggggagaat tagatcgcga   1500
tgggaaaaaa ttcggttaag gccaggggga agaaaaaat ataaattaaa acatatagta    1560
tgggcaagca gggagctaga acgattcgca gttaatcctg gcctgttaga acatcagaa    1620
ggctgtagac aaatactggg acagctacaa ccatcccttc agacaggatc agaagaactt   1680
agatcattat ataatacagt agcaaccctc tattgtgtgc atcaaaggat agagataaaa   1740
gacaccaagg aagctttaga caagatagag gaagagcaaa acaaaagtaa gaccaccgca   1800
cagcaagcgg ccgctgatct tcagacctgg aggaggagat atgagggaca attggagaag   1860
tgaattatat aaatataaag tagtaaaaat tgaaccatta ggagtagcac ccaccaaggc   1920
aaagagaaga gtggtgcaga gagaaaaaag agcagtggga ataggagctt tgttccttgg   1980
gttcttggga gcagcaggaa gcactatggg cgcagcgtca atgacgctga cggtacaggc   2040
cagacaatta ttgtctggta tagtgcagca gcagaacaat ttgctgaggg ctattgaggc   2100
gcaacagcat ctgttgcaac tcacagtctg gggcatcaag cagctccagg caagaatcct   2160
ggctgtggaa agatacctaa aggatcaaca gctcctgggg atttggggtt gctctggaaa   2220
actcatttgc accactgctg tgccttggaa tgctagttgg agtaataaat ctctggaaca   2280
gatttggaat cacacgacct ggatggagtg ggacagagaa attaacaatt acacaagctt   2340
aatacactcc ttaattgaag aatcgcaaaa ccagcaagaa aagaatgaac aagaattatt   2400
ggaattagat aaatgggcaa gtttgtggaa ttggtttaac ataacaaatt ggctgtggta   2460
tataaaatta ttcataatga tagtaggagg cttggtaggt ttaagaatag ttttgctgt    2520
actttctata gtgaatagag ttaggcaggg atattcacca ttatcgtttc agacccacct   2580
cccaaccccg aggggacccg acaggcccga aggaatagaa gaagaaggtg gagagagaga   2640
cagagacaga tccattcgat tagtgaacgg atctcgacgg gatcgatttt aaaagaaaag   2700
gggggattgg ggggtacagt gcaggggaaa gaatagtaga cataatagca acagacatac   2760
aaactaaaga attacaaaaa caaattacaa aaattcaaaa tttttatcgat aagctttgca   2820
aagatggata aagtttttaaa cagagaggaa tctttgcagc taatgaccct tctaggtctt   2880
gaaaggagtg ggaattggct ccggtgcccg tcagtgggca gagcgcacat cgcccacagt   2940
ccccgagaag ttgggggag gggtcggcaa ttgaaccggt gcctagagaa ggtgcgcgcg    3000
ggtaaactgg gaaagtgatg tcgtgtactg gctccgcctt tttcccgagg gtggggagaa   3060
accgtatata agtgcagtag tcgccgtgaa cgttcttttt cgcaacgggt ttgccgccag   3120
aacacaggta agtgccgtgt gtggttcccg cgggcctggc ctctttacgg ttatggccc    3180
ttgcgtgcct tgaattactt ccacctggct gcagtacgtg attcttgatc ccgagcttcg   3240
```

```
ggttggaagt gggtgggaga gttcgaggcc ttgcgcttaa ggagcccctt cgcctcgtgc    3300
ttgagttgag gcctggcctg ggcgctgggg ccgccgcgtg cgaatctggt ggcaccttcg    3360
cgcctgtctc gctgctttcg ataagtctct agccatttaa aattttttgat gacctgctgc   3420 gacgctttt ttctggcaag atagtcttgt aaatgcgggc caagatctgc acactggtat    3480
ttcggttttt ggggccgcgg gcggcgacgg ggcccgtgcg tcccagcgca catgttcggc    3540
gaggcggggc ctgcgagcgc ggccaccgag aatcggacgg gggtagtctc aagctggccg    3600
gcctgctctg gtgcctggcc tcgcgccgcc gtgtatcgcc ccgccctggg cggcaaggct    3660
ggcccggtcg gcaccagttg cgtgagcgga aagatggccg cttcccggcc ctgctgcagg    3720
gagctcaaaa tggaggacgc ggcgctcggg agagcgggcg ggtgagtcac ccacacaaag    3780
gaaaagggcc tttccgtcct cagccgtcgc ttcatgtgac tccacggagt accgggcgcc    3840
gtccaggcac ctcgattagt tctcgagctt ttggagtacg tcgtctttag gttggggga    3900 ggggttttat gcgatggagt ttccccacac tgagtgggtg gagactgaag ttaggccagc    3960
ttggcacttg atgtaattct ccttggaatt tgccctttt gagtttggat cttggttcat     4020
tctcaagcct cagacagtgg ttcaaagttt ttttcttcca tttcaggtgt cgtgaggaat    4080
tcgccaccat gcaacttcga aacccagagc tccacctcgg atgtgcccctt gctctgaggt   4140 tcctggcgct ggtgtcttgg gatatacccg gagcacgcgc tctggacaac gggctggccc    4200
ggactccaac catgggttgg ctccattggg aaaggtttat gtgcaacttg gactgccagg    4260
aagaacccga ctcctgtatt tccgagaaac tcttcatgga gatggccgag ctgatggtta    4320
gcgaaggctg gaaggatgcc ggttatgaat acttgtgtat cgacgattgt tggatggctc    4380
cccagcggga cagtgaagga cgactccagg cagatccgca acggttccct catggcatac    4440
ggcagctcgc caattacgtg cacagcaagg gtttgaagct ggggatatat gctgacgtgg    4500
gcaacaaaac ctgtgctggt ttccccggca gcttcggcta ctatgatata gatgcacaaa    4560
ccttcgctga ttggggcgtg gacctgctta aatttgacgg ctgttactgc gacagcttgg    4620
aaaacctcgc cgatggatat aaacacatga gccttgcact caatcggact ggccggagca    4680
ttgtctactc ttgcgagtgg ccattgtaca tgtggccttt ccagaagcct aactatacgg    4740
agattagaca gtattgtaat cactggagaa actttgcaga tatcgacgac tcatggaagt    4800
ccatcaaatc tattctggac tggacttcat tcaatcagga gcgcatcgtc gatgttgccg    4860
gtccaggtgg atggaacgac cctgacatgc tcgtaattgg gaatttcgga ctgtcctgga    4920
atcagcaggt cacacagatg gctttgtggg ctatcatggc agccccactc tttatgtcta    4980
acgatttgcg gcatatttca ccacaggcca agccctgct gcaagataag gacgtcatag    5040
cgattaacca ggacccactg ggaaagcagg gctaccagct gagacagggc gacaattttg    5100
aggtctggga aagacctctt agcgggctgg cgtgggccgt agccatgatt aatcgccagg    5160
aaattggcgg ccctcgctct tacactatcg cggtcgccag tctgggcaag ggagtcgctt    5220 gtaacccgc ctgcttcata actcagttgc tgcccgtgaa acggaagctg ggcttctatg     5280
aatggactag cagactccgc agtcatatta atccgactgg tacggtgctg ctgcaactgg    5340
agaataccat gcagatgtca cttaaggatc ttctgtgaga acccgggatc caagcttcaa    5400
ttgtggtcac tcgacaatca acctctggat tacaaaattt gtgaaagatt gactggtatt    5460
cttaactatg ttgctccttt tacgctatgt ggatacgctg ctttaatgcc tttgtatcat    5520
gctattgctt cccgtatggc tttcatttc tcctccttgt ataaatcctg gttgctgtct     5580
```

```
ctttatgagg agttgtggcc cgttgtcagg caacgtggcg tggtgtgcac tgtgtttgct    5640
gacgcaaccc ccactggttg gggcattgcc accacctgtc agctcctttc cgggactttc    5700
gctttccccc tccctattgc cacggcggaa ctcatcgccg cctgccttgc ccgctgctgg    5760
acagggctc ggctgttggg cactgacaat tccgtggtgt tgtcggggaa gctgacgtcc     5820
tttccatggc tgctcgcctg tgttgccacc tggattctgc gcgggacgtc cttctgctac    5880
gtcccttcgg ccctcaatcc agcggacctt ccttcccgcg gcctgctgcc ggctctgcgg    5940
cctcttccgc gtcttcgcct tcgccctcag acagtcggga tctcccttttg gccgcctcc    6000
ccgcctgctc gagacctaga aaacatgga gcaatcacaa gtagcaatac agcagctacc     6060
aatgctgatt gtgcctggct agaagcacaa gaggaggagg aggtgggttt tccagtcaca    6120
cctcaggtac ctttaagacc aatgacttac aaggcagctg tagatcttag ccacttttta    6180
aaagaaaagg ggggactgga agggctaatt cactcccaac gaagacaaga tctgcttttt    6240
gcttgtactg ggtctctctg gttagaccag atctgagcct gggagctctc tggctaacta    6300
gggaacccac tgcttaagcc tcaataaagc ttgccttgag tgcttcaagt agtgtgtgcc    6360
cgtctgttgt gtgactctgg taactagaga tccctcagac ccttttagtc agtgtggaaa    6420
atctctagca gtagtagttc atgtcatctt attattcagt atttataact tgcaaagaaa    6480
tgaatatcag agagtgagag gacgcgttgg atgcatagct tgagtattct atagtgtcac    6540
ctaaatagct tggcgtaatc atggtcatag ctgtttcctg tgtgaaattg ttatccgctc    6600
acaattccac acaacatacg agccggaagc ataaagtgta aagcctgggg tgcctaatga    6660
gtgagctaac tcacattaat tgcgttgcgc tcactgcccg ctttccagtc gggaaacctg    6720
tcgtgccagc tgcattaatg aatcggccaa cgcgcgggga gaggcggttt gcgtattggg    6780
cgctcttccg cttcctcgct cactgactcg ctgcgctcgg tcgttcggct gcggcgagcg    6840
gtatcagctc actcaaaggc ggtaatacgg ttatccacag aatcaggggga taacgcagga    6900
aagaacatgt gagcaaaagg ccagcaaaag gccaggaacc gtaaaaaggc cgcgttgctg    6960
gcgttttttcc ataggctccg cccccctgac gagcatcaca aaaatcgacg ctcaagtcag    7020
aggtggcgaa acccgacagg actataaaga taccaggcgt ttccccctgg aagctccctc    7080
gtgcgctctc ctgttccgac cctgccgctt accggatacc tgtccgcctt tctcccttcg    7140
ggaagcgtgg cgctttctca tagctcacgc tgtaggtatc tcagttcggt gtaggtcgtt    7200
cgctccaagc tgggctgtgt gcacgaaccc cccgttcagc ccgaccgctg cgccttatcc    7260
ggtaactatc gtcttgagtc aacccggta agacacgact tatcgccact ggcagcagcc    7320
actggtaaca ggattagcag agcgaggtat gtaggcggtg ctacagagtt cttgaagtgg    7380
tggcctaact acggctacac tagaagaaca gtatttggta tctgcgctct gctgaagcca    7440
gttaccttcg gaaaaagagt tggtagctct tgatccggca acaaaccac cgctggtagc     7500
ggtggttttt ttgtttgcaa gcagcagatt acgcgcagaa aaaaaggatc tcaagaagat    7560
cctttgatct tttctacggg gtctgacgct cagtggaacg aaaactcacg ttaagggatt    7620
ttggtcatga gattatcaaa aaggatcttc acctagatcc ttttaaatta aaaatgaagt    7680
tttaaatcaa tctaaagtat atatgagtaa acttggtctg acagttacca atgcttaatc    7740
agtgaggcac ctatctcagc gatctgtcta tttcgttcat ccatagttgc ctgactcccc    7800
gtcgtgtaga taactacgat acgggagggc ttaccatctg gccccagtgc tgcaatgata    7860
ccgcgagacc cacgctcacc ggctccagat ttatcagcaa taaaccagcc agccggaagg    7920
gccgagcgca gaagtggtcc tgcaacttta tccgcctcca tccagtctat taattgttgc    7980
```

```
cgggaagcta gagtaagtag ttcgccagtt aatagtttgc gcaacgttgt tgccattgct    8040
acaggcatcg tggtgtcacg ctcgtcgttt ggtatggctt cattcagctc cggttcccaa    8100
cgatcaaggc gagttacatg atcccccatg ttgtgcaaaa aagcggttag ctccttcggt    8160
cctccgatcg ttgtcagaag taagttggcc gcagtgttat cactcatggt tatggcagca    8220
ctgcataatt ctcttactgt catgccatcc gtaagatgct tttctgtgac tggtgagtac    8280
tcaaccaagt cattctgaga atagtgtatg cggcgaccga gttgctcttg cccggcgtca    8340
atacgggata taccgcgcc acatagcaga actttaaaag tgctcatcat tggaaaacgt      8400
tcttcggggc gaaaactctc aaggatctta ccgctgttga tccagttc gatgtaaccc       8460 actcgtgcac ccaactgatc ttcagcatct tttactttca ccagcgtttc tgggtgagca    8520
aaaacaggaa ggcaaaatgc cgcaaaaaag gaataaggg cgacacggaa atgttgaata     8580
ctcatactct ccttttca atattattga agcatttatc agggttattg tctcatgagc      8640
ggatacatat ttgaatgtat ttagaaaaat aaacaaatag gggttccgcg cacatttccc    8700
cgaaaagtgc cacctgatgc ggtgtgaaat accgcacaga tgcgtaagga gaaaataccg    8760
catcagg                                                               8767
```

<210> SEQ ID NO 3
<211> LENGTH: 11298
<212> TYPE: DNA
<213> ORGANISM: Artificial Sequence
<220> FEATURE:
<223> OTHER INFORMATION: Dual promoter lentiviral vector comprising AGA
      transgene

<400> SEQUENCE: 3

```
aaattgtaag cgttaatatt ttgttaaaat tcgcgttaaa ttttttgttaa atcagctcat      60 tttttaacca ataggccgaa atcggcaaaa tcccttataa atcaaaagaa tagaccgaga     120
tagggttgag tgttgttcca gtttggaaca agagtccact attaaagaac gtggactcca    180
acgtcaaagg gcgaaaaacc gtctatcagg gcgatggccc actacgtgaa ccatcaccct    240
aatcaagttt ttttggggtcg aggtgccgta aagcactaaa tcggaaccct aaagggagcc    300
cccgatttag agcttgacgg ggaaagccgg cgaacgtggc gagaaaggaa gggaagaaag    360
cgaaaggagc gggcgctagg gcgctggcaa gtgtagcggt cacgctgcgc gtaaccacca    420
cacccgccgc gcttaatgcg ccgctacagg gcgcgtccat tcgccattca ggctgcgcaa    480
ctgttgggaa gggcgatcgg tgcgggcctc ttcgctatta cgccagctgg cgaaaggggg    540
atgtgctgca aggcgattaa gttgggtaac gccagggttt tcccagtcac gacgttgtaa    600
aacgacggcc agtgaattgt aatacgactc actatagggc gaattgggcc cgacgtcgca    660
tgcttggaag ggctaattca ctcccaaaga agacaagata tccttgatct gtggatctac    720
cacacacaag gctacttccc tgattagcag aactacacac cagggccagg gtcagatat     780 ccactgacct ttggatggtg ctacaagcta gtaccagttg agccagataa ggtagaagag    840
gccaataaag gagagaacac cagcttgtta caccctgtga gcctgcatgg gatggatgac    900
ccggagagag aagtgttaga gtggaggttt gacagccgcc tagcatttca tcacgtggcc    960
cgagagctgc atccggagta cttcaagaac tgctgatatc gagcttgcta acgggactt    1020 tccgctgggg actttccagg gaggcgtggc ctgggcggga ctggggagtg cgagccctc    1080 agatcctgca tataagcagc tgcttttgc ctgtactggg tctctctggt tagaccagat    1140
ctgagcctgg gagctctctg gctaactagg gaacccactg cttaagcctc aataaagctt    1200
```

```
gccttgagtg cttcaagtag tgtgtgcccg tctgttgtgt gactctggta actagagatc    1260
cctcagaccc ttttagtcag tgtggaaaat ctctagcagt ggcgcccgaa cagggacttg    1320
aaagcgaaag ggaaaccaga ggagctctct cgacgcagga ctcggcttgc tgaagcgcgc    1380
acggcaagag gcgaggggcg gcgactggtg agtacgccaa aaattttgac tagcggaggc    1440
tagaaggaga gagatgggtg cgagagcgtc agtattaagc ggggggagaat tagatcgcga    1500 tgggaaaaaa ttcggttaag gccagggggga aagaaaaaat ataaattaaa acatatagta    1560
tgggcaagca gggagctaga acgattcgca gttaatcctg gcctgttaga aacatcagaa    1620
ggctgtagac aaatactggg acagctacaa ccatcccttc agacaggatc agaagaactt    1680
agatcattat ataatacagt agcaaccctc tattgtgtgc atcaaaggat agagataaaa    1740
gacaccaagg aagctttaga caagatagag gaagagcaaa acaaaagtaa gaccaccgca    1800
cagcaagcgg ccgctgatct tcagacctgg aggaggagat atgagggaca attggagaag    1860
tgaattatat aaatataaag tagtaaaaat tgaaccatta ggagtagcac ccaccaaggc    1920
aaagagaaga gtggtgcaga gagaaaaaag agcagtggga ataggagctt tgttccttgg    1980
gttcttggga gcagcaggaa gcactatggg cgcagcgtca atgacgctga cggtacaggc    2040
cagacaatta ttgtctggta tagtgcagca gcagaacaat ttgctgaggg ctattgaggc    2100
gcaacagcat ctgttgcaac tcacagtctg gggcatcaag cagctccagg caagaatcct    2160
ggctgtggaa agatacctaa aggatcaaca gctcctgggg atttggggtt gctctggaaa    2220
actcatttgc accactgctg tgccttggaa tgctagttgg agtaataaat ctctggaaca    2280
gatttggaat cacacgacct ggatggagtg ggacagagaa attaacaatt acacaagctt    2340
aatacactcc ttaattgaag aatcgcaaaa ccagcaagaa aagaatgaac aagaattatt    2400
ggaattagat aaatgggcaa gtttgtggaa ttggtttaac ataacaaatt ggctgtggta    2460
tataaaatta ttcataatga tagtaggagg cttggtaggt ttaagaatag ttttgctgt    2520 actttctata gtgaatagag ttaggcaggg atattcacca ttatcgtttc agacccacct    2580
cccaaccccg aggggacccg acaggcccga aggaataga gaagaaggtg gagagagaga    2640
cagagacaga tccattcgat tagtgaacgg atctcgacgg gatcgatttt aaaagaaaag    2700
gggggattgg ggggtacagt gcaggggaaa gaatagtaga cataatagca acagacatac    2760
aaactaaaga attacaaaaa caaattacaa aaattcaaaa ttttatcgat aagctttgca    2820
aagatggata aagttttaaa cagagaggaa tctttgcagc taatggacct tctaggtctg    2880
accccgtacg cctcgagaga tctgatcata atcagccata ccacatttgt agaggtttta    2940
cttgctttaa aaaacctccc acacctcccc ctgaacctga aacataaaat gaatgcaatt    3000
gttgttgtta acttgtttat tgcagcttat aatggttaca aataaggcaa tagcatcaca    3060
aatttcacaa ataaggcatt tttttcactg cattctagtt ttggtttgtc caaactcatc    3120
aatgtatctt atcatgtctg gatctcaaat ccctcggaag ctgcgcctgt cttaggttgg    3180
agtgatacat ttttatcact tttacccgtc tttggattag gcagtagctc tgacggccct    3240
cctgtcttag gttagtgaaa aatgtcactc tcttacccgt cattggctgt ccagcttagc    3300
tcgcagggga ggtggtctgc ctgcaggtta gaacagtctc ttttcgtatg agtgcagtga    3360
gtggacgccg ccttcgacct gggctgaaga agttcttttc tcgaacttca gttcgccgga    3420
atacatcatt gcccgcacct gtgtcaggct cttagcgccg atatcctggc atgaatgctg    3480
aattccggcg atcaggtaag gcacgaattt gtgaatactg cccttatcct ggacagctcc    3540
```

```
agacacgccc tgtgcgactt tgatcttgtc tgcctcggaa aaatacctgt tctgagagga    3600
cagatgctta tccatggcgt ccagtgaccc catgcccta tatttcttca gtctgaaccc     3660
atcactaaag aagtactcgc cgggggcttc tgtggttgca gccagcaggc tgcccatcat    3720
cactgtgctt gccccagag ccagggcttt tgcgatgtgg cccacattct gaattccccc     3780
gtcagcgatc actgggactc cgaatctccg ggcatactcg tacaccttgt agacagcagt    3840
tgcctgaggt cgtccacagg ccagcacttc ctgaatgatg cagattgatc cactccccat    3900
tccgaccctc agagcatcca ctcctgcgtc aatcaggttt ttggcctggg ctgcggtcac    3960
gacattgcct ccgatgacct gcagatttgg gtacttgtcc ttaatgtact tgatcatatt    4020
aatctggaag atgctgtttc cctggcttga atccagcacg accacgtcca ccctgcctg     4080
agccagcaga tccaggcgat atttatcgtc ctcgtgtgtg ccaatagcgg ctccacacag    4140
cagctgtttc tttgcgtcct tactagccag agggtaatct cgattttttct tcaggtcggt   4200
gcgggcaatg attgccacca gctcatcgtc ttcattcacg ataggcagtt ttcctttctt    4260
agaccgctgc agaatctcgt tggcttcctt cagtgtgatg ccggcaggtg cgaccaccag    4320
atcttcgcgt ttggtcataa tctcttccag aaaacagtca tgctcttcct ccttcaggaa    4380
atcgatgtct cgactagaaa tgattcccac cagtcggctg cccattcgtc cagtatctgt    4440
aatggggatg ccgcaaaatc cgtgcctagc tttggcctcg aacacatcgc ggaccctgtc    4500
cttgggctc aggaccactg ggtcggtgat aaagccctgt tcgtatttct tcaccttttct    4560
gacctcattg gcctgaaatt ctggagtgca gttatggtga atgaacccga tcccgcctgt    4620
cagtgccata gcaatggcca tgccagcctc ggtgacagtg tccatagggg agctcaccag    4680
gggtgtcttc agggtgattt tcttggtcag ggcagaagtc agatccacct ggtctgcggt    4740
aaaatcaata tagccgggca ggatcaggaa gtcgttgtaa gtcagcccgt ctccacaatt    4800
aaacagctgc tgggcggtca gtccatcatc agggacatag gaagtgcctc cagaaatcag    4860
gtagtcggcc atggtggcgc tagccctggg gagagaggtc ggtgattcgg tcaacgaggg    4920
agccgactgc cgacgtgcgc tccggaggct tgcagaatgc ggaacaccgc gcgggcagga    4980
acagggccca cactaccgcc ccacacccg cctcccgcac cgccccttcc cggccgctgc     5040
tctcggcgcg ccccgctgag cagccgctat tggccacagc ccatcgcggt cggcgcgctg    5100
ccattgctcc ctggcgctgt ccgtctgcga gggtactagt gagacgtgcg gcttccgttt    5160
gtcacgtccg gcacgccgcg aaccgcaagg aaccttcccg acttaggggc ggagcaggaa    5220
gcgtcgccgg ggggcccaca agggtagcgg cgaagatccg ggtgacgctg cgaacggacg    5280
tgaagaatgt gcgagaccca gggtcggcgc cgctgcgttt cccggaacca cgcccagagc    5340
agccgcgtcc ctgcgcaaac ccagggctgc aaggaaaag gcgcaacccc aaccccgtgg     5400
ttaattaagg tgaaaggagt gggaattggc tccggtgccc gtcagtgggc agagcgcaca    5460
tcgcccacag tccccgagaa gttgggggga gggtcggca attgaaccgg tgcctagaga    5520
aggtggcgcg gggtaaactg ggaaagtgat gtcgtgtact ggctccgcct tttcccgag    5580
ggtgggggag aaccgtatat aagtgcagta gtcgccgtga acgttctttt tcgcaacggg    5640
tttgccgcca gaacacaggt aagtgccgtg tgtggttccc gcgggcctgg cctctttacg    5700
ggttatggcc cttgcgtgcc ttgaattact tccacctggc tgcagtacgt gattcttgat    5760
cccgagcttc gggttggaag tgggtgggag agttcgaggc cttgcgctta aggagcccct    5820
tcgcctcgtg cttgagttga ggcctggcct gggcgctggg gccgccgcgt gcgaatctgg    5880
tggcaccttc gcgcctgtct cgctgctttc gataagtctc tagccattta aaatttttga    5940
```

```
tgacctgctg cgacgctttt tttctggcaa gatagtcttg taaatgcggg ccaagatctg    6000
cacactggta tttcggtttt tggggccgcg ggcggcgacg gggcccgtgc gtcccagcgc    6060
acatgttcgg cgaggcgggg cctgcgagcg cggccaccga aatcggacg ggggtagtct     6120 caagctggcc ggcctgctct ggtgcctggc ctcgcgccgc cgtgtatcgc cccgccctgg    6180
gcggcaaggc tggcccggtc ggcaccagtt gcgtgagcgg aaagatggcc gcttcccggc    6240
cctgctgcag ggagctcaaa atggaggacg cggcgctcgg gagagcgggc gggtgagtca    6300
cccacacaaa ggaaaagggc ctttccgtcc tcagccgtcg cttcatgtga ctccacggag    6360
taccgggcgc cgtccaggca cctcgattag ttctcgagct tttggagtac gtcgtcttta    6420
ggttgggggg agggttttta tgcgatggag tttccccaca ctgagtgggt ggagactgaa    6480
gttaggccag cttggcactt gatgtaattc tccttggaat ttgcccttt tgagtttgga    6540 tcttggttca ttctcaagcc tcagacagtg gttcaaagtt ttttcttcc atttcaggtg    6600 tcgtgaggaa ttcgccacca tgcaacttcg aaacccagag ctccacctcg gatgtgccct    6660
tgctctgagg ttcctggcgc tggtgtcttg ggatataccc ggagcacgcg ctctggacaa    6720
cgggctggcc cggactccaa ccatgggttg gctccattgg gaaaggttta tgtgcaactt    6780
ggactgccag gaagaacccg actcctgtat ttccgagaaa ctcttcatgg agatggccga    6840
gctgatggtt agcgaaggct ggaaggatgc cggttatgaa tacttgtgta tcgacgattg    6900
ttggatggct ccccagcggg acagtgaagg acgactccag gcagatccgc aacggttccc    6960
tcatggcata cggcagctcg ccaattacgt gcacagcaag ggtttgaagc tggggatata    7020
tgctgacgtg ggcaacaaaa cctgtgctgg tttccccggc agcttcggct actatgatat    7080
agatgcacaa accttcgctg attggggcgt ggacctgctt aaatttgacg gctgttactg    7140
cgacagcttg gaaaacctcg ccgatggata taaacacatg agccttgcac tcaatcggac    7200
tggccggagc attgtctact cttgcgagtg gccattgtac atgtggcctt ccagaagcc    7260 taactatacg gagattagac agtattgtaa tcactggaga aactttgcag atatcgacga    7320
ctcatggaag tccatcaaat ctattctgga ctggacttca ttcaatcagg agcgcatcgt    7380
cgatgttgcc ggtccaggtg gatggaacga ccctgacatg ctcgtaattg ggaatttcgg    7440
actgtcctgg aatcagcagg tcacacagat ggctttgtgg gctatcatgg cagccccact    7500
ctttatgtct aacgatttgc ggcatatttc accacaggcc aaagccctgc tgcaagataa    7560
ggacgtcata gcgattaacc aggacccact gggaaagcag ggctaccagc tgagacaggg    7620
cgacaatttt gaggtctggg aaagacctct tagcgggctg gcgtgggccg tagccatgat    7680
taatcgccag gaaattggcg gccctcgctc ttacactatc gcggtcgcca gtctgggcaa    7740
gggagtcgct tgtaaccccg cctgcttcat aactcagttg ctgcccgtga aacgaaagct    7800
gggcttctat gaatggacta gcagactccg cagtcatatt aatccgactg gtacggtgct    7860
gctgcaactg gagaatacca tgcagatgtc acttaaggat cttctgtgag aacccgggat    7920
ccaagcttca attgtggtca ctcgacaatc aacctctgga ttacaaaatt tgtgaaagat    7980
tgactggtat tcttaactat gttgctcctt ttacgctatg tggatacgct gctttaatgc    8040
ctttgtatca tgctattgct tcccgtatgg ctttcatttt ctcctccttg tataaatcct    8100
ggttgctgtc tctttatgag gagttgtggc ccgttgtcag gcaacgtggc gtggtgtgca    8160
ctgtgtttgc tgacgcaacc cccactggtt ggggcattgc caccacctgt cagctccttt    8220
ccgggacttt cgctttcccc ctccctattg ccacggcgga actcatcgcc gcctgccttg    8280
```

```
cccgctgctg acaggggct cggctgttgg gcactgacaa ttccgtggtg ttgtcgggga      8340
agctgacgtc ctttccatgg ctgctcgcct gtgttgccac ctggattctg cgcgggacgt      8400
ccttctgcta cgtcccttcg gccctcaatc cagcggacct tccttcccgc ggcctgctgc      8460
cggctctgcg gcctcttccg cgtcttcgcc ttcgccctca gacgagtcgg atctcccttt      8520
gggccgcctc cccgcctgct cgagacctag aaaaacatgg agcaatcaca agtagcaata      8580
cagcagctac caatgctgat tgtgcctggc tagaagcaca agaggaggag gaggtggggtt     8640
ttccagtcac acctcaggta cctttaagac caatgactta caaggcagct gtagatctta      8700
gccactttt aaagaaaag gggggactgg aagggctaat tcactcccaa cgaagacaag       8760
atctgctttt tgcttgtact gggtctctct ggttagacca gatctgagcc tgggagctct      8820
ctggctaact agggaaccca ctgcttaagc ctcaataaag cttgccttga gtgcttcaag      8880
tagtgtgtgc ccgtctgttg tgtgactctg gtaactagag atccctcaga ccctttagt      8940
cagtgtggaa aatctctagc agtagtagtt catgtcatct tattattcag tatttataac      9000
ttgcaaagaa atgaatatca gagagtgaga ggacgcgttg gatgcatagc ttgagtattc      9060
tatagtgtca cctaaatagc ttggcgtaat catggtcata gctgtttcct gtgtgaaatt      9120
gttatccgct cacaattcca cacaacatac gagccggaag cataaagtgt aaagcctggg      9180
gtgcctaatg agtgagctaa ctcacattaa ttgcgttgcg ctcactgccc gctttccagt      9240
cgggaaacct gtcgtgccag ctgcattaat gaatcggcca acgcgcgggg agaggcggtt      9300
tgcgtattgg gcgctcttcc gcttcctcgc tcactgactc gctgcgctcg gtcgttcggc      9360
tgcggcgagc ggtatcagct cactcaaagg cggtaatacg gttatccaca gaatcagggg      9420
ataacgcagg aaagaacatg tgagcaaaag gccagcaaaa ggccaggaac cgtaaaaagg      9480
ccgcgttgct ggcgtttttc cataggctcc gcccccctga cgagcatcac aaaaatcgac      9540
gctcaagtca gaggtggcga aacccgacag gactataaag ataccaggcg tttccccctg      9600
gaagctccct cgtgcgctct cctgttccga ccctgccgct taccggatac ctgtccgcct      9660
ttctcccttc gggaagcgtg gcgctttctc atagctcacg ctgtaggtat ctcagttcgg      9720
tgtaggtcgt tcgctccaag ctgggctgtg tgcacgaacc ccccgttcag cccgaccgct      9780
gcgccttatc cggtaactat cgtcttgagt ccaacccggt aagacacgac ttatcgccac      9840
tggcagcagc cactggtaac aggattagca gagcgaggta tgtaggcggt gctacagagt      9900
tcttgaagtg gtggcctaac tacggctaca ctagaagaac agtatttggt atctgcgctc      9960
tgctgaagcc agttaccttc ggaaaaagag ttggtagctc ttgatccggc aaacaaacca     10020
ccgctggtag cggtggtttt tttgtttgca agcagcagat tacgcgcaga aaaaaggat      10080
ctcaagaaga tcctttgatc ttttctacgg ggtctgacgc tcagtggaac gaaaactcac     10140
gttaagggat tttggtcatg agattatcaa aaaggatctt cacctagatc cttttaaatt     10200
aaaaatgaag ttttaaatca atctaaagta tatatgagta aacttggtct gacagttacc     10260
aatgcttaat cagtgaggca cctatctcag cgatctgtct atttcgttca tccatagttg     10320
cctgactccc cgtcgtgtag ataactacga tacgggaggg cttaccatct ggccccagtg     10380
ctgcaatgat accgcgagac ccacgctcac cggctccaga tttatcagca ataaccagc     10440
cagccggaag ggccgagcgc agaagtggtc ctgcaacttt atccgcctcc atccagtcta    10500
ttaattgttg ccgggaagct agagtaagta gttcgccagt taatagtttg cgcaacgttg     10560
ttgccattgc tacaggcatc gtggtgtcac gctcgtcgtt tggtatggct tcattcagct    10620
ccggttccca acgatcaagg cgagttacat gatcccccat gttgtgcaaa aaagcggtta    10680
```

```
gctccttcgg tcctccgatc gttgtcagaa gtaagttggc cgcagtgtta tcactcatgg    10740
ttatggcagc actgcataat tctcttactg tcatgccatc cgtaagatgc ttttctgtga    10800
ctggtgagta ctcaaccaag tcattctgag aatagtgtat gcggcgaccg agttgctctt    10860
gcccggcgtc aatacgggat aataccgcgc cacatagcag aactttaaaa gtgctcatca    10920
ttggaaaacg ttcttcgggg cgaaaactct caaggatctt accgctgttg agatccagtt    10980
cgatgtaacc cactcgtgca cccaactgat cttcagcatc ttttactttc accagcgttt    11040
ctgggtgagc aaaaacagga aggcaaaatg ccgcaaaaaa gggaataagg gcgacacgga    11100
aatgttgaat actcatactc ttcctttttc aatattattg aagcatttat cagggttatt    11160
gtctcatgag cggatacata tttgaatgta tttagaaaaa taaacaaata ggggttccgc    11220
gcacatttcc ccgaaaagtg ccacctgatg cggtgtgaaa taccgcacag atgcgtaagg    11280
agaaaatacc gcatcagg                                                  11298
```

<210> SEQ ID NO 4
<211> LENGTH: 9095
<212> TYPE: DNA
<213> ORGANISM: Artificial Sequence
<220> FEATURE:
<223> OTHER INFORMATION: Lentiviral vector comprising GBA transgene

<400> SEQUENCE: 4

```
aaattgtaag cgttaatatt tgttaaaat tcgcgttaaa ttttgttaa atcagctcat       60 tttttaacca ataggccgaa atcggcaaaa tcccttataa atcaaaagaa tagaccgaga    120
tagggttgag tgttgttcca gtttggaaca agagtccact attaaagaac gtggactcca    180
acgtcaaagg gcgaaaaacc gtctatcagg gcgatggccc actacgtgaa ccatcaccct    240
aatcaagttt ttggggtcg aggtgccgta aagcactaaa tcggaaccct aaagggagcc    300
cccgatttag agcttgacgg ggaaagccgg cgaacgtggc gagaaaggaa gggaagaaag    360
cgaaaggagc gggcgctagg gcgctggcaa gtgtagcggt cacgctgcgc gtaaccacca    420
cacccgccgc gcttaatgcg ccgctacagg gcgcgtccat tcgccattca ggctgcgcaa    480
ctgttgggaa gggcgatcgg tgcgggcctc ttcgctatta cgccagctgg cgaaaggggg    540
atgtgctgca aggcgattaa gttgggtaac gccagggttt tcccagtcac gacgttgtaa    600
aacgacggcc agtgaattgt aatacgactc actatagggc gaattgggcc cgacgtcgca    660
tgcttggaag gctaattca ctcccaaaga agacaagata tccttgatct gtggatctac    720
cacacacaag gctacttccc tgattagcag aactacacac cagggccagg ggtcagatat    780
ccactgacct ttggatggtg ctacaagcta gtaccagttg agccagataa ggtagaagag    840
gccaataaag gagagaacac cagcttgtta caccctgtga gcctgcatgg gatggatgac    900
ccggagagag aagtgttaga gtggaggttt gacagccgcc tagcatttca tcacgtggcc    960
cgagagctgc atccggagta cttcaagaac tgctgatatc gagcttgcta caagggactt   1020
tccgctgggg actttccagg gaggcgtggc ctgggcggga ctggggagtg gcgagccctc   1080
agatcctgca tataagcagc tgcttttttgc ctgtactggg tctctctggt tagaccagat   1140
ctgagcctgg gagctctctg gctaactagg gaacccactg cttaagcctc aataaagctt   1200
gccttgagtg cttcaagtag tgtgtgcccg tctgttgtgt gactctggta actagagatc   1260
cctcagaccc ttttagtcag tgtggaaaat ctctagcagt ggcgcccgaa cagggacttg   1320
aaagcgaaag ggaaaccaga ggagctctct cgacgcagga ctcggcttgc tgaagcgcgc   1380
```

```
acggcaagag gcgaggggcg gcgactggtg agtacgccaa aaattttgac tagcggaggc    1440
tagaaggaga gagatgggtg cgagagcgtc agtattaagc gggggagaat tagatcgcga    1500
tgggaaaaaa ttcggttaag gccaggggga aagaaaaaat ataaattaaa acatatagta    1560
tgggcaagca gggagctaga acgattcgca gttaatcctg gcctgttaga aacatcagaa    1620
ggctgtagac aaatactggg acagctacaa ccatcccttc agacaggatc agaagaactt    1680
agatcattat ataatacagt agcaaccctc tattgtgtgc atcaaaggat agagataaaa    1740
gacaccaagg aagctttaga caagatagag gaagagcaaa acaaaagtaa gaccaccgca    1800
cagcaagcgg ccgctgatct tcagacctgg aggaggagat gagggaca attggagaag    1860 tgaattatat aaatataaag tagtaaaaat tgaaccatta ggagtagcac ccaccaaggc    1920
aaagagaaga gtggtgcaga gagaaaaaag agcagtggga ataggagctt tgttccttgg    1980
gttcttggga gcagcaggaa gcactatggg cgcagcgtca atgacgctga cggtacaggc    2040
cagacaatta ttgtctggta tagtgcagca gcagaacaat ttgctgaggg ctattgaggc    2100
gcaacagcat ctgttgcaac tcacagtctg gggcatcaag cagctccagg caagaatcct    2160
ggctgtggaa agatacctaa aggatcaaca gctcctgggg atttggggtt gctctggaaa    2220
actcatttgc accactgctg tgccttggaa tgctagttgg agtaataaat ctctggaaca    2280
gatttggaat cacacgacct ggatggagtg gacagagaa attaacaatt acacaagctt    2340
aatacactcc ttaattgaag aatcgcaaaa ccagcaagaa aagaatgaac aagaattatt    2400
ggaattagat aaatgggcaa gtttgtggaa ttggtttaac ataacaaatt ggctgtggta    2460
tataaaatta ttcataatga tagtaggagg cttggtaggt ttaagaatag ttttgctgt    2520 actttctata gtgaatagag ttaggcaggg atattcacca ttatcgtttc agacccacct    2580
cccaaccccg agggggacccg acaggcccga aggaatagaa gaagaaggtg gagagagaga    2640
cagagacaga tccattcgat tagtgaacgg atctcgacgg gatcgatttt aaaagaaaag    2700
gggggattgg ggggtacagt gcaggggaaa gaatagtaga cataatagca acagacatac    2760
aaactaaaga attacaaaaa caaattacaa aaattcaaaa ttttatcgat aagctttgca    2820
aagatggata agttttaaaa cagagaggaa tctttgcagc taatggacct tctaggtctt    2880
gaaaggagtg ggaattggct ccggtgcccg tcagtgggca gagcgcacat cgcccacagt    2940
ccccgagaag ttgggggggag gggtcggcaa ttgaaccggt gcctagagaa ggtgcgcgg    3000 ggtaaactgg gaaagtgatg tcgtgtactg gctccgcctt tttcccgagg gtggggagaa    3060
accgtatata agtgcagtag tcgccgtgaa cgttcttttt cgcaacgggt ttgccgccag    3120
aacacaggta agtgccgtgt gtggttcccg cgggcctggc ctctttacgg gttatggccc    3180
ttgcgtgcct tgaattactt ccacctggct gcagtacgtg attcttgatc ccgagcttcg    3240
ggttggaagt gggtgggaga gttcgaggcc ttgcgcttaa ggagcccctt cgcctcgtgc    3300
ttgagttgag gcctggcctg ggcgctgggg ccgccgcgtg cgaatctggt ggcaccttcg    3360
cgcctgtctc gctgctttcg ataagtctct agccatttaa aatttttgat gacctgctgc    3420
gacgcttttt ttctggcaag atagtcttgt aaatgcgggc caagatctgc acactggtat    3480
ttcggttttt ggggccgcgg gcggcgacgg ggcccgtgcg tcccagcgca catgttcggc    3540
gaggcggggc ctgcgagcgc ggccaccgag aatcggacgg gggtagtctc aagctggccg    3600
gcctgctctg tgcctggcc tcgcgccgcc gtgtatcgcc ccgccctggg cggcaaggct    3660
ggcccggtcg gcaccagttg cgtgagcgga agatggccg cttccggcc tgctgcagg    3720 gagctcaaaa tggaggacgc ggcgctcggg agagcgggcg ggtgagtcac ccacacaaag    3780
```

```
gaaaagggcc tttccgtcct cagccgtcgc ttcatgtgac tccacggagt accgggcgcc  3840
gtccaggcac ctcgattagt tctcgagctt ttggagtacg tcgtctttag gttgggggga  3900
ggggttttat gcgatggagt ttccccacac tgagtgggtg gagactgaag ttaggccagc  3960
ttggcacttg atgtaattct ccttggaatt tgccctttt gagtttggat cttggttcat   4020
tctcaagcct cagacagtgg ttcaaagttt ttttcttcca tttcaggtgt cgtgaggaat  4080
tcgctagcgc caccatggag ttctcaagcc cctctcggga agaatgccca aaacctctgt  4140
cacgggtgtc tatcatggct ggatcactga ctggcctgct gctgctgcag gccgtgagct  4200
gggcctccgg agcccggcct tgcatcccaa agtctttcgg ctacagctcc gtggtgtgcg  4260
tgtgcaacgc cacctattgt gactccttcg atcccctac cttcccgcc ctgggcacat    4320
tttctcggta cgagtctaca cgcagcggca ggagaatgga gctgagcatg gccctatcc   4380
aggccaatca caccggaaca ggcctgctgc tgaccctgca gccagagcag aagttccaga  4440
aggtgaaggg ctttggagga gcaatgacag acgcagccgc cctgaacatc ctggccctgt  4500
ccccacccgc ccagaatctg ctgctgaagt cctacttctc tgaggagggc atcggctata  4560
acatcatcag ggtgcccatg gccagctgcg acttttccat cagaacctac acatatgccg  4620
ataccctga cgatttccag ctgcacaatt tttccctgcc agaggaggat acaaagctga   4680
agatcccact gatccacagg gcctgcagc tggcccagag gccgtgagc ctgctggcca    4740
gcccctggac ctcccctaca tggctgaaga ccaacggcgc cgtgaatggc aagggctctc  4800
tgaagggaca gccaggcgac atctaccacc agacatgggc ccgctatttc gtgaagtttc  4860
tggatgccta cgccgagcac aagctgcagt tctgggccgt gaccgcagag aacgagcctt  4920
ctgccggcct gctgagcggc tatcccttcc agtgcctggg cttacacct gagcaccaga   4980
gggactttat cgccagagat ctgggcccaa ccctggccaa ctccacacac acaatgtgc   5040
ggctgctgat gctggacgat cagcgcctgc tgctgcctca ctgggccaag gtggtgctga  5100
ccgacccaga ggccgccaag tacgtgcacg gcatcgccgt gcactggtat ctggatttcc  5160
tggcaccagc aaaggccacc ctgggagaga cacacaggct gttccctaac accatgctgt  5220
tgccagcga ggcctgcgtg ggctccaagt tttgggagca gtccgtgcgg ctgggctctt   5280
gggacagggg catgcagtac tcccactcta tcatccacaa tctgctgtat cacgtggtgg  5340
gctgacaga ctggaacctg gccctgaatc cagagggcgg ccccaactgg gtgagaaatt   5400
tcgtggatag ccccatcatc gtggacatca ccaaggatac attctacaag cagccaatgt  5460
tttatcacct gggccacttc tctaagttta tcccagaggg cagccagagg gtgggcctgg  5520
tggccagcca gaagaacgac ctggatgcag tggccctgat gcaccctgac ggctccgccg  5580
tggtggtggt gctgaatcgc tctagcaagg acgtgcctct gaccatcaag gaccccgccg  5640
tgggctttct ggagaccatt tcacccggct attctattca tacctatctg tggaggaggc  5700
agtaacctgc aggggatcca agcttcaatt gtggtcactc gacaatcaac ctctggatta  5760
caaaatttgt gaaagattga ctggtattct taactatgtt gctccttta cgctatgtgg   5820
atacgctgct ttaatgcctt tgtatcatgc tattgcttcc cgtatggctt tcattttctc  5880
ctccttgtat aaatcctggt tgctgtctct ttatgaggag ttgtgcccg ttgtcaggca   5940
acgtggcgtg gtgtgcactg tgtttgctga cgcaaccccc actggttggg gcattgccac  6000
cacctgtcag ctcctttccg ggactttcgc tttcccctc cctattgcca cggcggaact   6060
catcgccgcc tgccttgccc gctgctggac aggggctcgg ctgttgggca ctgacaattc  6120
```

```
cgtggtgttg tcggggaagc tgacgtcctt ccatggctg ctcgcctgtg ttgccacctg      6180
gattctgcgc gggacgtcct tctgctacgt cccttcggcc ctcaatccag cggaccttcc      6240
ttcccgcggc ctgctgccgg ctctgcggcc tcttccgcgt cttcgccttc gccctcagac      6300
gagtcggatc tcccctttggg ccgcctcccc ggctgctcga gacctagaaa acatggagc      6360 aatcacaagt agcaatacag cagctaccaa tgctgattgt gcctggctag aagcacaaga      6420
ggaggaggag gtgggttttc cagtcacacc tcaggtacct ttaagaccaa tgacttacaa      6480
ggcagctgta gatcttagcc acttttttaaa agaaaagggg ggactggaag ggctaattca      6540
ctcccaacga agacaagatc tgcttttttgc ttgtactggg tctctctggt tagaccagat      6600
ctgagcctgg gagctctctg gctaactagg gaacccactg cttaagcctc aataaagctt      6660
gccttgagtg cttcaagtag tgtgtgcccg tctgttgtgt gactctggta actagagatc      6720
cctcagaccc ttttagtcag tgtggaaaat ctctagcagt agtagttcat gtcatcttat      6780
tattcagtat ttataacttg caaagaaatg aatatcagag agtgagagga cgcgttggat      6840
gcatagcttg agtattctat agtgtcacct aaatagcttg gcgtaatcat ggtcatagct      6900
gtttcctgtg tgaaattgtt atccgctcac aattccacac aacatacgag ccggaagcat      6960
aaagtgtaaa gcctggggtg cctaatgagt gagctaactc acattaattg cgttgcgctc      7020
actgcccgct ttccagtcgg gaaacctgtc gtgccagctg cattaatgaa tcggccaacg      7080
cgcggggaga ggcggtttgc gtattgggcg ctcttccgct tcctcgctca ctgactcgct      7140
gcgctcggtc gttcggctgc ggcgagcggt atcagctcac tcaaaggcgg taatacggtt      7200
atccacagaa tcaggggata acgcaggaaa gaacatgtga gcaaaaggcc agcaaaaggc      7260
caggaaccgt aaaaaggccg cgttgctggc gtttttccat aggctccgcc cccctgacga      7320
gcatcacaaa aatcgacgct caagtcagag gtggcgaaac ccgacaggac tataaagata      7380
ccaggcgttt ccccctggaa gctccctcgt gcgctctcct gttccgaccc tgccgcttac      7440
cggatacctg tccgcctttc tcccttcggg aagcgtggcg ctttctcata gctcacgctg      7500
taggtatctc agttcggtgt aggtcgttcg ctccaagctg ggctgtgtgc acgaaccccc      7560
cgttcagccc gaccgctgcg ccttatccgg taactatcgt cttgagtcca acccggtaag      7620
acacgactta tcgccactgg cagcagccac tggtaacagg attagcagag cgaggtatgt      7680
aggcggtgct acagagttct tgaagtggtg gcctaactac ggctacacta agaacagt      7740 atttggtatc tgcgctctgc tgaagccagt taccttcgga aaaagagttg gtagctcttg      7800
atccggcaaa caaaccaccg ctggtagcgg tggttttttt gtttgcaagc agcagattac      7860
gcgcagaaaa aaaggatctc aagaagatcc tttgatcttt tctacggggt ctgacgctca      7920
gtggaacgaa aactcacgtt aagggatttt ggtcatgaga ttatcaaaaa ggatcttcac      7980
ctagatcctt ttaaattaaa aatgaagttt taaatcaatc taaagtatat atgagtaaac      8040
ttggtctgac agttaccaat gcttaatcag tgaggcacct atctcagcga tctgtctatt      8100
tcgttcatcc atagttgcct gactccccgt cgtgtagata actacgatac gggagggctt      8160
accatctggc cccagtgctg caatgatacc gcgagaccca cgctcaccgg ctccagattt      8220
atcagcaata aaccagccag ccggaagggc cgagcgcaga agtggtcctg caactttatc      8280
cgcctccatc cagtctatta attgttgccg ggaagctaga gtaagtagtt cgccagttaa      8340 tagtttcgc aacgttgttg ccattgctac aggcatcgtg gtgtcacgct cgtcgtttgg      8400
tatggcttca ttcagctccg gttcccaacg atcaaggcga gttacatgat cccccatgtt      8460
gtgcaaaaaa gcggttagct ccttcggtcc tccgatcgtt gtcagaagta agttggccgc      8520
```

```
agtgttatca ctcatggtta tggcagcact gcataattct cttactgtca tgccatccgt    8580
aagatgcttt tctgtgactg gtgagtactc aaccaagtca ttctgagaat agtgtatgcg    8640
gcgaccgagt tgctcttgcc cggcgtcaat acgggataat accgcgccac atagcagaac    8700
tttaaaagtg ctcatcattg gaaaacgttc ttcggggcga aaactctcaa ggatcttacc    8760
gctgttgaga tccagttcga tgtaacccac tcgtgcaccc aactgatctt cagcatcttt    8820
tactttcacc agcgtttctg ggtgagcaaa acaggaagg  caaaatgccg caaaaaggg     8880 aataagggcg acacggaaat gttgaatact catactcttc cttttcaat  attattgaag    8940 catttatcag ggttattgtc tcatgagcgg atacatattt gaatgtattt agaaaaataa    9000
acaaataggg gttccgcgca catttccccg aaaagtgcca cctgatgcgg tgtgaaatac    9060
cgcacagatg cgtaaggaga aaataccgca tcagg                               9095
```

<210> SEQ ID NO 5
<211> LENGTH: 8681
<212> TYPE: DNA
<213> ORGANISM: Artificial Sequence
<220> FEATURE:
<223> OTHER INFORMATION: Lentiviral vector comprising ASAH1 transgene

<400> SEQUENCE: 5

```
gggcgaattg ggcccgacgt cgcatgcttg aagggctaa  ttcactccca aagaagacaa      60
gatatccttg atctgtggat ctaccacaca caaggctact ccctgatta  gcagaactac    120 acaccagggc caggggtcag atatccactg acctttggat ggtgctacaa gctagtacca    180
gttgagccag ataaggtaga agaggccaat aaaggagaga acaccagctt gttacaccct    240
gtgagcctgc atgggatgga tgaccccgag agagaagtgt tagagtggag gtttgacagc    300
cgcctagcat ttcatcacgt ggcccgagag ctgcatccgg agtacttcaa gaactgctga    360
tatcgagctt gctacaaggg actttccgct ggggactttc cagggaggcg tggcctgggc    420
gggactgggg agtggcgagc cctcagatcc tgcatataag cagctgcttt ttgcctgtac    480
tgggtctctc tggttagacc agatctgagc ctgggagctc tctggctaac tagggaaccc    540
actgcttaag cctcaataaa gcttgccttg agtgcttcaa gtagtgtgtg cccgtctgtt    600
gtgtgactct ggtaactaga gatccctcag acccttttag tcagtgtgga aaatctctag    660
cagtggcgcc cgaacaggga cttgaaagcg aaagggaaac cagaggagct ctctcgacgc    720
aggactcggc ttgctgaagc gcgcacggca agaggcgagg ggcggcgact ggtgagtacg    780
ccaaaaattt tgactagcgg aggctagaag gagagagatg ggtgcgagag cgtcagtatt    840
aagcggggga gaattagatc gcgatgggaa aaaattcggt taaggccagg gggaaagaaa    900
aaatataaat taaaacatat agtatgggca agcagggagc tagaacgatt cgcagttaat    960
cctggcctgt tagaaacatc agaaggctgt agacaaatac tgggacagct acaaccatcc   1020
cttcagacag gatcagaaga acttagatca ttatataata cagtagcaac cctctattgt   1080
gtgcatcaaa ggatagagat aaaagacacc aaggaagctt tagacaagat agaggaagag   1140
caaaacaaaa gtaagaccac cgcacagcaa gcggccgctg atcttcagac ctggaggagg   1200
agatatgagg gacaattgga gaagtgaatt atataaatat aaagtagtaa aaattgaacc   1260
attaggagta gcacccacca aggcaaagag aagagtggtg cagagagaaa aaagagcagt   1320
gggaatagga gctttgttcc ttgggttctt gggagcagca ggaagcacta tgggcgcagc   1380
gtcaatgacg ctgacggtac aggccagaca attattgtct ggtatagtgc agcagcagaa   1440
```

```
caatttgctg agggctattg aggcgcaaca gcatctgttg caactcacag tctgggcat    1500
caagcagctc caggcaagaa tcctggctgt ggaaagatac ctaaaggatc aacagctcct   1560
ggggatttgg ggttgctctg gaaaactcat ttgcaccact gctgtgcctt ggaatgctag   1620
ttggagtaat aaatctctgg aacagatttg gaatcacacg acctggatgg agtgggacag   1680
agaaattaac aattacacaa gcttaataca ctccttaatt gaagaatcgc aaaaccagca   1740
agaaaagaat gaacaagaat tattggaatt agataaatgg gcaagtttgt ggaattggtt   1800
taacataaca aattggctgt ggtatataaa attattcata atgatagtag gaggcttggt   1860
aggtttaaga atagttttg ctgtactttc tatagtgaat agagttaggc agggatattc    1920
accattatcg tttcagaccc acctcccaac cccgaggga cccgacaggc ccgaaggaat    1980
agaagaagaa ggtggagaga gagacagaga cagatccatt cgattagtga acggatctcg   2040
acgggatcga ttttaaaaga aaaggggga ttggggggta cagtgcaggg gaaagaatag    2100
tagacataat agcaacagac atacaaacta agaattaca aaaacaaatt acaaaaattc    2160
aaaattttat cgataagctt tgcaaagatg gataaagttt aaacagaga ggaatctttg    2220
cagctaatgg accttctagg tcttgaaagg agtgggaatt ggctccggtg cccgtcagtg   2280
ggcagagcgc acatcgccca cagtccccga aagttgggg ggagggggtcg gcaattgaac   2340
cggtgcctag agaaggtggc gcggggtaaa ctgggaaagt gatgtcgtgt actggctccg   2400
ccttttccc gagggtgggg gagaaccgta tataagtgca gtagtcgccg tgaacgttct    2460
ttttcgcaac gggtttgccg ccagaacaca ggtaagtgcc gtgtgtggtt cccgcgggcc   2520
tggcctcttt acgggttatg gcccttgcgt gccttgaatt acttccacct ggctgcagta   2580
cgtgattctt gatcccgagc ttcggttgg aagtgggtgg gagagttcga ggccttgcgc    2640
ttaaggagcc ccttcgcctc gtgcttgagt tgaggcctgg cctgggcgct ggggccgccg   2700
cgtgcgaatc tggtggcacc ttcgcgcctg tctcgctgct ttcgataagt ctctagccat   2760
ttaaaatttt tgatgacctg ctgcgacgct ttttttctgg caagatagtc ttgtaaatgc   2820
gggccaagat ctgcacactg gtatttcggt ttttggggcc gcgggcggcg acggggcccg   2880
tgcgtcccag cgcacatgtt cggcgaggcg gggcctgcga gcgcggccac cgagaatcgg   2940
acggggggtag tctcaagctg gccggcctgc tctggtgcct ggcctcgcgc cgccgtgtat   3000
cgccccgccc tggcggcaa ggctggcccg gtcggcacca gttgcgtgag cggaaagatg    3060
gccgcttccc ggccctgctg cagggagctc aaaatggagg acgcggcgct cgggagagcg   3120
ggcgggtgag tcacccacac aaaggaaaag ggccttttcg tcctcagccg tcgcttcatg   3180
tgactccacg gagtaccggg cgccgtccag gcacctcgat tagttctcga gcttttggag   3240
tacgtcgtct ttaggttggg gggagggtt ttatgcgatg gagtttcccc acactgagtg    3300
ggtggagact gaagttaggc cagcttggca cttgatgtaa ttctccttgg aatttgccct   3360
ttttgagttt ggatcttggt tcattctcaa gcctcagaca gtggttcaaa gttttttct    3420
tccatttcag gtgtcgtgag gaattctgca gtcgacgcca ccatgccggg ccggagttgc   3480
gtcgccttag tcctcctggc tgccgccgtc agctgtgccg tcgcgcagca cgcgccgccg   3540
tggacagagg actgcagaaa atcaacctat cctccttcag gaccaacgta cagaggtgca   3600
gttccatggt acaccataaa tcttgactta ccaccctaca aagatggca tgaattgatg    3660
cttgacaagg caccagtgct aaaggttata gtgaattctc tgaagaatat gataaataca   3720
ttcgtgccaa gtggaaaaat tatgcaggtg gtggatgaaa aattgcctgg cctacttggc   3780
aactttcctg gcccttttga agaggaaatg aagggtattg ccgctgttac tgatatacct   3840
```

```
ttaggagaga ttatttcatt caatattttt tatgaattat ttaccatttg tacttcaata    3900
gtagcagaag acaaaaaagg tcatctaata catgggagaa acatggattt tggagtattt    3960
cttgggtgga acataaataa tgatacctgg gtcataactg agcaactaaa acctttaaca    4020
gtgaatttgg atttccaaag aaacaacaaa actgtcttca aggcttcaag ctttgctggc    4080
tatgtgggca tgttaacagg attcaaacca ggactgttca gtcttacact gaatgaacgt    4140
ttcagtataa atggtggtta tctgggtatt ctagaatgga ttctgggaaa gaaagatgtc    4200
atgtggatag ggttcctcac tagaacagtt ctggaaaata gcacaagtta tgaagaagcc    4260
aagaatttat tgaccaagac caagatattg gccccagcct actttatcct gggaggcaac    4320
cagtctgggg aaggttgtgt gattacacga gacagaaagg aatcattgga tgtatatgaa    4380
ctcgatgcta agcagggtag atggtatgtg gtacaaacaa attatgaccg ttggaaacat    4440
cccttcttcc ttgatgatcg cagaacgcct gcaaagatgt gtctgaaccg caccagccaa    4500
gagaatatct catttgaaac catgtatgat gtcctgtcaa caaaacctgt cctcaacaag    4560
ctgaccgtat acacaacctt gatagatgtt accaaaggtc aattcgaaac ttacctgcgg    4620
gactgccctg acccttgtat aggttggtga gcggccgcct cgaggatcca agcttcaatt    4680
gtggtcactc gacaatcaac ctctggatta caaaatttgt gaaagattga ctggtattct    4740
taactatgtt gctccttta cgctatgtgg atacgctgct ttaatgcctt tgtatcatgc    4800
tattgcttcc cgtatggctt tcattttctc ctccttgtat aaatcctggt tgctgtctct    4860
ttatgaggag ttgtggcccg ttgtcaggca acgtggcgtg gtgtgcactg tgtttgctga    4920
cgcaaccccc actggttggg gcattgccac cacctgtcag ctcctttccg ggactttcgc    4980
tttccccctc cctattgcca cggcggaact catcgccgcc tgccttgccc gctgctggac    5040
aggggctcgg ctgttgggca ctgacaattc cgtggtgttg tcggggaagc tgacgtcctt    5100
tccatggctg ctcgcctgtg ttgccacctg gattctgcgc gggacgtcct tctgctacgt    5160
cccttcggcc ctcaatccag cggaccttcc ttcccgcggc ctgctgccgg ctctgcggcc    5220
tcttccgcgt cttcgccttc gccctcagac gagtcggatc tccctttggg ccgcctcccc    5280
gcctgctcga gacctagaaa aacatggagc aatcacaagt agcaatacag cagctaccaa    5340
tgctgattgt gcctggctag aagcacaaga ggaggaggag gtgggttttc cagtcacacc    5400
tcaggtacct ttaagaccaa tgacttacaa ggcagctgta gatcttagcc acttttaaa    5460 agaaaagggg ggactggaag ggctaattca ctcccaacga agacaagatc tgcttttgc    5520 ttgtactggg tctctctggt tagaccagat ctgagcctgg gagctctctg ctaactaggg    5580
gaacccactg cttaagcctc aataaagctt gccttgagtg cttcaagtag tgtgtgcccg    5640
tctgttgtgt gactctggta actagagatc cctcagaccc ttttagtcag tgtggaaaat    5700
ctctagcagt agtagttcat gtcatcttat tattcagtat ttataacttg caaagaaatg    5760
aatatcagag agtgagagga cgcgttggat gcatagcttg agtattctat agtgtcacct    5820
aaatagcttg gcgtaatcat ggtcatagct gtttcctgtg tgaaattgtt atccgctcac    5880
aattccacac aacatacgag ccggaagcat aaagtgtaaa gcctggggtg cctaatgagt    5940
gagctaactc acattaattg cgttgcgctc actgcccgct ttccagtcgg gaaacctgtc    6000
gtgccagctg cattaatgaa tcggccaacg cgcgggagga ggcggtttgc gtattgggcg    6060
ctcttccgct tcctcgctca ctgactcgct gcgctcggtc gttcggctgc ggcgagcggt    6120
atcagctcac tcaaaggcgg taatacggtt atccacagaa tcaggggata acgcaggaaa    6180
```

```
gaacatgtga gcaaaaggcc agcaaaaggc caggaaccgt aaaaaggccg cgttgctggc     6240
gttttccat aggctccgcc cccctgacga gcatcacaaa aatcgacgct caagtcagag      6300
gtggcgaaac ccgacaggac tataaagata ccaggcgttt ccccctggaa gctccctcgt    6360
gcgctctcct gttccgaccc tgccgcttac cggatacctg tccgcctttc tcccttcggg    6420
aagcgtggcg ctttctcata gctcacgctg taggtatctc agttcggtgt aggtcgttcg    6480
ctccaagctg ggctgtgtgc acgaaccccc cgttcagccc gaccgctgcg ccttatccgg    6540
taactatcgt cttgagtcca acccggtaag acacgactta tcgccactgg cagcagccac    6600
tggtaacagg attagcagag cgaggtatgt aggcggtgct acagagttct tgaagtggtg    6660
gcctaactac ggctacacta agaacagt atttggtatc tgcgctctgc tgaagccagt      6720
taccttcgga aaaagagttg gtagctcttg atccggcaaa caaaccaccg ctggtagcgg    6780
tggtttttt gtttgcaagc agcagattac gcgcagaaaa aaaggatctc aagaagatcc     6840
tttgatcttt tctacggggt ctgacgctca gtggaacgaa aactcacgtt aagggatttt    6900
ggtcatgaga ttatcaaaaa ggatcttcac ctagatcctt ttaaattaaa aatgaagttt    6960
taaatcaatc taaagtatat atgagtaaac ttggtctgac agttaccaat gcttaatcag    7020
tgaggcacct atctcagcga tctgtctatt tcgttcatcc atagttgcct gactccccgt    7080
cgtgtagata actacgatac gggagggctt accatctggc cccagtgctg caatgatacc    7140
gcgagaccca cgctcaccgg ctccagattt atcagcaata aaccagccag ccggaagggc    7200
cgagcgcaga agtggtcctg caactttatc cgcctccatc cagtctatta attgttgccg    7260
ggaagctaga gtaagtagtt cgccagttaa tagtttgcgc aacgttgttg ccattgctac    7320
aggcatcgtg gtgtcacgct cgtcgtttgg tatggcttca ttcagctccg gttcccaacg    7380
atcaaggcga gttacatgat cccccatgtt gtgcaaaaaa gcggttagct ccttcggtcc    7440
tccgatcgtt gtcagaagta agttggccgc agtgttatca ctcatggtta tggcagcact    7500
gcataattct cttactgtca tgccatccgt aagatgcttt tctgtgactg gtgagtactc    7560
aaccaagtca ttctgagaat agtgtatgcg gcgaccgagt tgctcttgcc cggcgtcaat    7620
acgggataat accgcgccac atagcagaac tttaaaagtg ctcatcattg gaaaacgttc    7680
ttcggggcga aaactctcaa ggatcttacc gctgttgaga tccagttcga tgtaacccac    7740
tcgtgcaccc aactgatctt cagcatcttt tactttcacc agcgtttctg ggtgagcaaa    7800
aacaggaagg caaaatgccg caaaaaaggg aataagggcg acacggaaat gttgaatact    7860
catactcttc ctttttcaat attattgaag catttatcag ggttattgtc tcatgagcgg    7920
atacatattt gaatgtattt agaaaaataa acaaataggg gttccgcgca catttccccg    7980
aaaagtgcca cctgatgcgg tgtgaaatac cgcacagatg cgtaaggaga aaataccgca    8040
tcaggaaatt gtaagcgtta atattttgtt aaaattcgcg ttaaattttt gttaaatcag    8100
ctcattttt aaccaatagg ccgaaatcgg caaaatccct tataaatcaa agaatagac      8160
cgagataggg ttgagtgttg ttccagtttg gaacaagagt ccactattaa agaacgtgga    8220
ctccaacgtc aaagggcgaa aaaccgtcta tcagggcgat ggcccactac gtgaaccatc    8280
accctaatca agttttttgg ggtcgaggtg ccgtaaagca ctaaatcgga acccaaaagg    8340
gagcccccga tttagagctt gacggggaaa gccggcgaac gtggcgagaa aggaagggaa    8400
gaaagcgaaa ggagcgggcg ctagggcgct ggcaagtgta gcggtcacgc tgcgcgtaac    8460
caccacaccc gccgcgctta atgcgccgct acagggcgcg tccattcgcc attcaggctg    8520
cgcaactgtt gggaagggcg atcggtgcgg gcctcttcgc tattacgcca gctggcgaaa    8580
```

```
gggggatgtg ctgcaaggcg attaagttgg gtaacgccag gttttccca gtcacgacgt    8640 tgtaaaacga cggccagtga attgtaatac gactcactat a                       8681

<210> SEQ ID NO 6
<211> LENGTH: 10336
<212> TYPE: DNA
<213> ORGANISM: Artificial Sequence
<220> FEATURE:
<223> OTHER INFORMATION: Lentiviral vector comprising GAA transgene

<400> SEQUENCE: 6
aaattgtaag cgttaatatt ttgttaaaat tcgcgttaaa ttttttgttaa atcagctcat     60 tttttaacca ataggccgaa atcggcaaaa tcccttataa atcaaaagaa tagaccgaga    120
tagggttgag tgttgttcca gtttggaaca agagtccact attaaagaac gtggactcca    180
acgtcaaagg gcgaaaaacc gtctatcagg gcgatggccc actacgtgaa ccatcaccct    240
aatcaagttt tttggggtcg aggtgccgta aagcactaaa tcggaaccct aaagggagcc    300
cccgatttag agcttgacgg ggaaagccgg cgaacgtggc gagaaaggaa gggaagaaag    360
cgaaaggagc gggcgctagg gcgctggcaa gtgtagcggt cacgctgcgc gtaaccacca    420
cacccgccgc gcttaatgcg ccgctacagg gcgcgtccat tcgccattca ggctgcgcaa    480
ctgttgggaa gggcgatcgg tgcgggcctc ttcgctatta cgccagctgg cgaaaggggg    540
atgtgctgca aggcgattaa gttgggtaac gccagggttt tcccagtcac gacgttgtaa    600
aacgacggcc agtgaattgt aatacgactc actatagggc gaattgggcc cgacgtcgca    660
tgcttggaag ggctaattca ctcccaaaga agacaagata tccttgatct gtggatctac    720
cacacacaag gctacttccc tgattagcag aactacacac cagggccagg ggtcagatat    780
ccactgacct ttggatggtg ctacaagcta gtaccagttg agccagataa ggtagaagag    840
gccaataaag gagagaacac cagcttgtta caccctgtga gcctgcatgg gatggatgac    900
ccggagagag aagtgttaga gtggaggttt gacagccgcc tagcatttca tcacgtggcc    960
cgagagctgc atccggagta cttcaagaac tgctgatatc gagcttgcta caagggactt   1020
tccgctgggg actttccagg gaggcgtggc ctgggcggga ctggggagtg gcgagccctc   1080
agatcctgca tataagcagc tgctttttgc ctgtactggg tctctctggt tagaccagat   1140
ctgagcctgg gagctctctg gctaactagg gaacccactg cttaagcctc aataaagctt   1200
gccttgagtg cttcaagtag tgtgtgcccg tctgttgtgt gactctggta actagagatc   1260
cctcagaccc ttttagtcag tgtggaaaat ctctagcagt ggcgcccgaa cagggacttg   1320
aaagcgaaag ggaaaccaga ggagctctct cgacgcagga ctcggcttgc tgaagcgcgc   1380
acggcaagag gcgaggggcg gcgactggtg agtacgccaa aaattttgac tagcggaggc   1440
tagaaggaga gagatgggtg cgagagcgtc agtattaagc gggggagaat tagatcgcga   1500
tgggaaaaaa ttcggttaag gccaggggga agaaaaaaat ataattaaa acatatagta   1560 tgggcaagca gggagctaga acgattcgca gttaatcctg gcctgttaga acatcagaa    1620 ggctgtagac aaatactggg acagctacaa ccatcccttc agacaggatc agaagaactt   1680
agatcattat ataatacagt agcaaccctc tattgtgtgc atcaaaggat agagataaaa   1740
gacaccaagg aagctttaga caagatagag gaagagcaaa acaaaagtaa gaccaccgca   1800
cagcaagcgg ccgctgatct tcagacctgg aggaggagat atgagggaca attggagaag   1860
tgaattatat aaatataaag tagtaaaaat tgaaccatta ggagtagcac ccaccaaggc   1920
```

```
aaagagaaga gtggtgcaga gagaaaaaag agcagtggga ataggagctt tgttccttgg      1980
gttcttggga gcagcaggaa gcactatggg cgcagcgtca atgacgctga cggtacaggc      2040
cagacaatta ttgtctggta tagtgcagca gcagaacaat ttgctgaggg ctattgaggc      2100
gcaacagcat ctgttgcaac tcacagtctg gggcatcaag cagctccagg caagaatcct      2160
ggctgtggaa agatacctaa aggatcaaca gctcctgggg atttggggtt gctctggaaa      2220
actcatttgc accactgctg tgccttggaa tgctagttgg agtaataaat ctctggaaca      2280
gatttggaat cacacgacct ggatggagtg ggacagagaa attaacaatt acacaagctt      2340
aatacactcc ttaattgaag aatcgcaaaa ccagcaagaa aagaatgaac aagaattatt      2400
ggaattagat aaatgggcaa gtttgtggaa ttggtttaac ataacaaatt ggctgtggta      2460
tataaaatta ttcataatga tagtaggagg cttggtaggt ttaagaatag ttttttgctgt      2520 actttctata gtgaatagag ttaggcaggg atattcacca ttatcgtttc agacccacct      2580
cccaaccccg aggggacccg acaggcccga aggaatagaa gaagaaggtg gagagagaga      2640
cagagacaga tccattcgat tagtgaacgg atctcgacgg gatcgatttt aaaagaaaag      2700
gggggattgg ggggtacagt gcaggggaaa gaatagtaga cataatagca acagacatac      2760
aaactaaaga attacaaaaa caaattacaa aaattcaaaa ttttatcgat aagctttgca      2820
aagatggata aagttttaaa cagagaggaa tctttgcagc taatggacct tctaggtctt      2880
gaaaggagtg gaattggct ccggtgcccg tcagtgggca gagcgcacat cgcccacagt       2940
ccccgagaag ttgggggggag gggtcggcaa ttgaaccggt gcctagagaa ggtggcgcgg      3000
ggtaaactgg gaaagtgatg tcgtgtactg gctccgcctt ttttcccgagg gtgggggaga     3060 accgtatata agtgcagtag tcgccgtgaa cgttctttttt cgcaacgggt ttgccgccag     3120
aacacaggta agtgccgtgt gtggttcccg cgggcctggc ctctttacgg ttatggccc       3180 ttgcgtgcct tgaattactt ccacctggct gcagtacgtg attcttgatc ccgagcttcg      3240
ggttggaagt gggtgggaga gttcgaggcc ttgcgcttaa ggagcccctt cgcctcgtgc      3300
ttgagttgag gcctggcctg ggcgctgggg ccgccgcgtg cgaatctggt ggcaccttcg      3360
cgcctgtctc gctgctttcg ataagtctct agccatttaa aatttttgat gacctgctgc      3420
gacgcttttt ttctggcaag atagtcttgt aaatgcgggc caagatctgc acactggtat      3480
ttcggttttt ggggccgcgg gcggcgacgg ggcccgtgcg tcccagcgca catgttcggc      3540
gaggcggggc ctgcgagcgc ggccaccgag aatcggacgg gggtagtctc aagctggccg      3600
gcctgctctg tgcctggcc tcgcgccgcc gtgtatcgcc ccgccctggg cggcaaggct       3660
ggcccggtcg gcaccagttg cgtgagcgga aagatggccg cttcccggcc ctgctgcagg     3720
gagctcaaaa tggaggacgc ggcgctcggg agagcgggcg ggtgagtcac ccacacaaag     3780
gaaaagggcc tttccgtcct cagccgtcgc ttcatgtgac tccacggagt accgggcgcc      3840
gtccaggcac ctcgattagt tctcgagctt ttggagtacg tcgtctttag gttgggggga     3900
ggggttttat gcgatggagt ttccccacac tgagtgggtg gagactgaag ttaggccagc      3960
ttggcacttg atgtaattct ccttggaatt tgcccttttt gagtttggat cttggttcat      4020
tctcaagcct cagacagtgg ttcaaagttt ttttcttcca tttcaggtgt cgtgaggaat     4080
tcgccaccat gggcgtgagg caccccctt gctctcacag gctgctggcc gtgtgcgcac      4140
tggtgagcct ggccaccgcc gccctgctgg ccacatcct gctgcacgac ttcctgctgg      4200
tgcccaggga gctgtccggc agctccccag tgctggagga gacccacccca gcacaccagc    4260 agggcgcctc tcggccaggc ccccgcgatg cacaggcaca cccaggccgg ccccgcgccg     4320
```

```
tgccaaccca gtgcgacgtg ccacccaaca gccggtttga ctgtgccccc gataaggcca    4380
tcacacagga gcagtgcgag gccagggget gctgttatat ccctgcaaag cagggcctcc    4440
agggcgccca gatgggacag ccatggtgtt tctttcctcc atcttacccc agctataagc    4500
tggagaatct gtctagctcc gagatgggct acacagccac cctgacaaga accacaccaa    4560
cattctttcc caaggacatc ctgaccctgc ggctggacgt gatgatggag acagagaacc    4620
gcctgcactt caccatcaag gaccccgcca ataggagata tgaggtgcct ctggagaccc    4680
cacacgtgca ctctcgggcc cctagccacc tgtactccgt ggagttctct gaggagccat    4740
ttggcgtgat cgtgcggcgc cagctggatg gacgcgtgct gctgaacacc acagtggccc    4800
ccctgttctt tgccgaccag ttcctccagc tgagcacatc cctgccctcc cagtatatca    4860
ccggcctggc cgagcacctg tctcctctga tgctgtctac cagctggaca aggatcaccc    4920
tgtggaacag agacctggca ccaacccctg gcgcaaatct gtacggcagc cacccttct    4980 atctggccct ggaggatgga ggctccgccc acggcgtgtt tctgctgaac tctaatgcca    5040
tggacgtggt gctccagcca agccccgccc tgtcctggcg gtctaccggc ggcatcctgg    5100
acgtgtacat cttcctgggc cctgagccaa agtccgtggt gcagcagtac ctggacgtgg    5160
tgggctatcc tttcatgccc ccttactggg gactgggatt tcacctgtgc cgctggggct    5220
attctagcac agccatcacc cggcaggtgg tggagaacat gacccgcgcc cactttccac    5280
tggatgtgca gtggaatgac ctggattaca tggactccag gagagacttc accttcaaca    5340
aggacggctt cagggatttt cccgccatgg tgcaggagct gcaccagggc ggccggcgct    5400
acatgatgat cgtggacccc gccatctcct ctagcggacc tgccggcagc tacagaccat    5460
atgacgaggg cctgaggaga ggcgtgttca tcacaaacga gaccggccag cctctgatcg    5520
gcaaggtctg gccaggctcc accgccttcc cagacttcac caatccaacc gccctggcct    5580
ggtgggagga catggtggcc gagttccacg accaggtgcc ttttgatggc atgtggatcg    5640
acatgaacga gccatctaat ttcatcaggg gcagcgagga cggctgcccc aacaatgagc    5700
tggagaaccc accatatgtg cctggcgtgg tgggaggcac cctccaggca gcaaccatct    5760
gtgcctcctc tcaccagttt ctgtctacac actataacct gcacaatctg tacggactga    5820
ccgaggcaat cgccagccac agagccctgg tgaaggccag gggcacaaga cctttcgtga    5880
tctccaggtc tacctttgcc ggacacggca gatacgcagg acactggacc ggcgacgtgt    5940
ggagcagctg ggagcagctg gcctctagcg tgccagagat cctccagttc aacctgctgg    6000 gcgtgccccct ggtgggagca gacgtgtgcg gctttctggg caatacatcc gaggagctgt    6060
gcgtgaggtg gacccagctg ggagccttct atcccttcat gcgcaaccac aatagcctgc    6120
tgtccctgcc tcaggagcca tacagcttct ccgagcctgc acagcaggca atgaggaagg    6180
ccctgacact gcgctatgcc ctgctgccac acctgtacac cctgtttcac caggcacacg    6240
tggcaggaga gacagtggcc cggccccgt tcctggagtt tcctaaggat cctctacct    6300 ggacagtgga ccaccagctg ctgtggggag aggccctgct gatcaccccc gtgctccagg    6360
caggcaaggc agaggtgaca ggctattcc ctctgggcac atggtacgac ctccagaccg    6420
tgccagtgga ggccctgggc agcctgcctc caccacctgc cgcccccgc gagcctgcca    6480 tccactccga gggacagtgg gtgacactgc cagcacctct ggacaccatc aacgtgcacc    6540
tgagggccgg ctatatcatc ccctccagg gccctggcct gaccacaacc gagtccagac    6600
agcagccaat ggccctggcc gtggccctga ccaagggagg cgaggccagg ggcgagctgt    6660
```

```
tctgggacga tggcgagtct ctggaggtgc tggagagagg cgcctacaca caggtcatct    6720
tcctggccag gaacaataca atcgtgaatg agctggtgag agtgacctct gagggagcag    6780
gactccagct ccagaaggtg acagtgctgg gagtggcaac cgcaccacag caggtgctga    6840
gcaacggcgt gcccgtgagc aatttcacat actcccctga taccaaggtg ctggacatct    6900
gcgtgagcct gctgatgggc gagcagtttc tggtgtcctg gtgttgagaa cccgggatcc    6960
aagcttcaat tgtggtcact cgacaatcaa cctctggatt acaaaatttg tgaaagattg    7020
actggtattc ttaactatgt tgctcctttt acgctatgtg gatacgctgc tttaatgcct    7080
ttgtatcatg ctattgcttc ccgtatggct ttcattttct cctccttgta taaatcctgg    7140
ttgctgtctc tttatgagga gttgtggccc gttgtcaggc aacgtggcgt ggtgtgcact    7200
gtgtttgctg acgcaacccc cactggttgg ggcattgcca ccacctgtca gctccttttcc   7260 gggactttcg ctttcccccct ccctattgcc acggcggaac tcatcgccgc ctgccttgcc   7320
cgctgctgga caggggctcg gctgttgggc actgacaatt ccgtggtgtt gtcggggaag   7380
ctgacgtcct ttccatggct gctcgcctgt gttgccacct ggattctgcg cgggacgtcc   7440
ttctgctacg tcccttcggc cctcaatcca gcggaccttc cttcccgcgg cctgctgccg   7500
gctctgcggc ctcttccgcg tcttcgcctt cgccctcaga cgagtcggat ctcccttttgg   7560 gccgcctccc cgcctgctcg agacctagaa aaacatggag caatcacaag tagcaataca   7620
gcagctacca atgctgattg tgcctggcta gaagcacaag aggaggagga ggtgggtttt   7680
ccagtcacac ctcaggtacc tttaagacca atgacttaca aggcagctgt agatcttagc   7740 cacttttttaa aagaaaaggg gggactgaa gggctaattc actcccaacg aagacaagat   7800 ctgcttttg cttgtactgg gtctctctgg ttagaccaga tctgagcctg ggagctctct    7860
ggctaactag ggaacccact gcttaagcct caataaagct tgccttgagt gcttcaagta   7920
gtgtgtgccc gtctgttgtg tgactctggt aactagagat ccctcagacc cttttagtca   7980
gtgtggaaaa tctctagcag tagtagttca tgtcatctta ttattcagta tttataactt    8040
gcaaagaaat gaatatcaga gagtgagagg acgcgttgga tgcatagctt gagtattcta    8100
tagtgtcacc taaatagctt ggcgtaatca tggtcatagc tgtttcctgt gtgaaattgt    8160
tatccgctca caattccaca acatacga gccggaagca taaagtgtaa agcctggggt    8220
gcctaatgag tgagctaact cacattaatt gcgttgcgct cactgcccgc tttccagtcg    8280
ggaaacctgt cgtgccagct gcattaatga atcggccaac gcgcgggag aggcggtttg    8340 cgtattgggc gctcttccgc ttcctcgctc actgactcgc tgcgctcggt cgttcggctg    8400
cggcgagcgg tatcagctca ctcaaaggcg gtaatacggt tatccacaga atcaggggat    8460
aacgcaggaa agaacatgtg agcaaaaggc cagcaaaagg ccaggaaccg taaaaaggcc    8520
gcgttgctgg cgtttttcca taggctccgc cccctgacg agcatcacaa aaatcgacgc    8580
tcaagtcaga ggtggcgaaa cccgacagga ctataaagat accaggcgtt ccccctggaa    8640
agctccctcg tgcgctctcc tgttccgacc ctgccgctta ccggatacct gtccgccttt    8700
ctcccttcgg gaagcgtggc gctttctcat agctcacgct gtaggtatct cagttcggtg    8760
taggtcgttc gctccaagct gggctgtgtg cacgaacccc ccgttcagcc cgaccgctgc    8820
gccttatccg gtaactatcg tcttgagtcc aacccggtaa gacacgactt atcgccactg    8880
gcagcagcca ctggtaacag gattagcaga gcgaggtatg taggcggtgc tacagagttc    8940
ttgaagtggt ggcctaacta cggctacact agaagaacag tatttggtat ctgcgctctg    9000
ctgaagccag ttaccttcgg aaaaagagtt ggtagctctt gatccggcaa acaaaccacc    9060
```

```
gctggtagcg gtggttttt tgtttgcaag cagcagatta cgcgcagaaa aaaaggatct    9120
caagaagatc ctttgatctt ttctacgggg tctgacgctc agtggaacga aaactcacgt    9180
taagggattt tggtcatgag attatcaaaa aggatcttca cctagatcct tttaaattaa    9240
aaatgaagtt ttaaatcaat ctaaagtata tatgagtaaa cttggtctga cagttaccaa    9300
tgcttaatca gtgaggcacc tatctcagcg atctgtctat ttcgttcatc catagttgcc    9360
tgactccccg tcgtgtagat aactacgata cgggagggct taccatctgg ccccagtgct    9420
gcaatgatac cgcgagaccc acgctcaccg gctccagatt tatcagcaat aaaccagcca    9480
gccgaagggc cgagcgcag aagtggtcct gcaactttat ccgcctccat ccagtctatt    9540
aattgttgcc gggaagctag agtaagtagt tcgccagtta atagtttgcg caacgttgtt    9600
gccattgcta caggcatcgt ggtgtcacgc tcgtcgtttg gtatggcttc attcagctcc    9660
ggttcccaac gatcaaggcg agttacatga tcccccatgt tgtgcaaaaa agcggttagc    9720
tccttcggtc ctccgatcgt tgtcagaagt aagttggccg cagtgttatc actcatggtt    9780
atggcagcac tgcataattc tcttactgtc atgccatccg taagatgctt ttctgtgact    9840
ggtgagtact caaccaagtc attctgagaa tagtgtatgc ggcgaccgag ttgctcttgc    9900
ccggcgtcaa tacgggataa taccgcgcca catagcagaa ctttaaaagt gctcatcatt    9960
ggaaaacgtt cttcggggcg aaaactctca aggatcttac cgctgttgag atccagttcg   10020
atgtaaccca ctcgtgcacc caactgatct tcagcatctt ttactttcac cagcgtttct   10080
gggtgagcaa aaacaggaag gcaaaatgcc gcaaaaaagg gataagggc gacacggaaa   10140 tgttgaatac tcatactctt cctttttcaa tattattgaa gcatttatca gggttattgt   10200
ctcatgagcg gatacatatt tgaatgtatt tagaaaaata acaaataggg gttccgcgc   10260 acatttcccc gaaaagtgcc acctgatgcg gtgtgaaata ccgcacagat gcgtaaggag   10320
aaaataccgc atcagg                                                   10336
```

<210> SEQ ID NO 7
<211> LENGTH: 1611
<212> TYPE: DNA
<213> ORGANISM: Artificial Sequence
<220> FEATURE:
<223> OTHER INFORMATION: GBA transgene

<400> SEQUENCE: 7

```
atggagttct caagcccctc tcgggaagaa tgcccaaaac ctctgtcacg ggtgtctatc      60
atggctggat cactgactgg cctgctgctg ctgcaggccg tgagctgggc ctccggagcc     120
cggccttgca tcccaaagtc tttcggctac agctccgtgg tgtgcgtgtg caacgccacc     180
tattgtgact ccttcgatcc ccctaccttt cccgccctgg gcacattttc tcggtacgag     240
tctacacgca gcggcaggag aatggagctg agcatgggcc ctatccaggc caatcacacc     300
ggaacaggcc tgctgctgac cctgcagcca gagcagaagt tccagaaggt gaagggcttt     360
ggaggagcaa tgacagacgc agccgccctg aacatcctgg ccctgtcccc acccgcccag     420
aatctgctgc tgaagtccta cttctctgag gagggcatcg gctataacat catcagggtg     480
cccatggcca gctgcgactt ttccatcaga acctacacat atgccgatac ccctgacgat     540
ttccagctgc acaatttttc cctgccagag gaggatacaa agctgaagat cccactgatc     600
cacagggccc tgcagctggc ccagaggccc gtgagcctgc tggccagccc ctggaccctc     660
cctacatggc tgaagaccaa cggcgccgtg aatggcaagg ctctctgaa gggacagcca     720
```

```
ggcgacatct accaccagac atgggcccgc tatttcgtga agtttctgga tgcctacgcc    780
gagcacaagc tgcagttctg ggccgtgacc gcagagaacg agccttctgc cggcctgctg    840
agcggctatc ccttccagtg cctgggcttt acacctgagc accagaggga ctttatcgcc    900
agagatctgg gcccaaccct ggccaactcc acacaccaca atgtgcggct gctgatgctg    960
gacgatcagc gcctgctgct gcctcactgg gccaaggtgg tgctgaccga cccagaggcc   1020
gccaagtacg tgcacggcat cgccgtgcac tggtatctgg atttcctggc caccagcaaag  1080
gccaccctgg agagacaca caggctgttc cctaacacca tgctgtttgc cagcgaggcc   1140
tgcgtgggct ccaagttttg ggagcagtcc gtgcggctgg gctcttggga caggggcatg   1200
cagtactccc actctatcat caccaatctg ctgtatcacg tggtgggctg acagactgg    1260
aacctggccc tgaatccaga gggcggcccc aactgggtga aaatttcgt ggatagcccc    1320
atcatcgtgg acatcaccaa ggatacattc tacaagcagc caatgttttta tcacctgggc   1380
cacttctcta gtttatccc agagggcagc cagagggtgg gcctggtggc cagccagaag   1440
aacgacctgg atgcagtggc cctgatgcac cctgacggct ccgccgtggt ggtggtgctg   1500
aatcgctcta gcaaggacgt gcctctgacc atcaaggacc ccgccgtggg ctttctggag   1560
accatttcac ccggctattc tattcatacc tatctgtgga ggaggcagta a            1611

<210> SEQ ID NO 8
<211> LENGTH: 1188
<212> TYPE: DNA
<213> ORGANISM: Artificial Sequence
<220> FEATURE:
<223> OTHER INFORMATION: ASAH1 transgene

<400> SEQUENCE: 8
atgccgggcc ggagttgcgt cgccttagtc ctcctggctg ccgccgtcag ctgtgccgtc     60
gcgcagcacg cgccgccgtg gacagaggac tgcagaaaat caacctatcc tccttcagga   120
ccaacgtaca gaggtgcagt tccatggtac accataaatc ttgacttacc accctacaaa   180
agatggcatg aattgatgct tgacaaggca ccagtgctaa aggttatagt gaattctctg   240
aagaatatga taaatacatt cgtgccaagt ggaaaaatta tgcaggtggt ggatgaaaaa   300
ttgcctggcc tacttggcaa cttttcctggc ccttttgaag aggaaatgaa gggtattgcc   360
gctgttactg atataccttt aggagagatt atttcattca atatttttta tgaattattt   420
accatttgta cttcaatagt agcagaagac aaaaaaggtc atctaataca tgggagaaac   480
atggattttg gagtatttct tgggtggaac ataaataatg ataccctggt cataactgag   540
caactaaaac ctttaacagt gaatttggat ttccaaagaa caacaaaac tgtcttcaag   600
gcttcaagct tgctggcta tgtgggcatg ttaacaggat tcaaaccagg actgttcagt   660
cttacactga atgaacgttt cagtataaat ggtggttatc tgggtattct agaatggatt   720
ctgggaaaga aagatgtcat gtggataggg ttcctcacta gaacagttct ggaaatagc   780
acaagttatg aagaagccaa gaattattg accaagacca gatattggc cccagcctac    840
tttatcctgg gaggcaacca gtctgggaa ggttgtgtga ttacacgaga cagaaaggaa    900
tcattggatg tatatgaact cgatgctaag cagggtagag ggtatgtggt acaaacaaat   960
tatgaccgtt ggaaacatcc cttcttcctt gatgatcgca gaacgcctgc aaagatgtgt  1020
ctgaaccgca ccagccaaga gaatatctca tttgaaacca tgtatgatgt cctgtcaaca  1080
aaacctgtcc tcaacaagct gaccgtatac acaaccttga tagatgttac caaaggtcaa  1140
ttcgaaactt acctgcggga ctgccctgac ccttgtatag gttggtga              1188
```

<210> SEQ ID NO 9
<211> LENGTH: 2859
<212> TYPE: DNA
<213> ORGANISM: Artificial Sequence
<220> FEATURE:
<223> OTHER INFORMATION: GAA transgene

<400> SEQUENCE: 9

```
atgggcgtga ggcacccccc ttgctctcac aggctgctgg ccgtgtgcgc actggtgagc      60
ctggccaccg ccgccctgct gggccacatc ctgctgcacg acttcctgct ggtgcccagg     120
gagctgtccg gcagctcccc agtgctggag gagacccacc cagcacacca gcagggcgcc     180
tctcggccag gccccgcga tgcacaggca cacccaggcc ggccccgcgc cgtgccaacc     240
cagtgcgacg tgccacccaa cagccggttt gactgtgccc ccgataaggc catcacacag     300
gagcagtgcg aggccagggg ctgctgttat atccctgcaa gcagggcct ccagggcgcc      360
cagatgggac agccatggtg tttctttcct ccatcttacc ccagctataa gctggagaat     420
ctgtctagct ccgagatggg ctacacagcc accctgacaa gaaccacacc aacattcttt     480
cccaaggaca tcctgaccct gcggctggac gtgatgatgg agacagagaa ccgcctgcac     540
ttcaccatca aggaccccgc aataggaga tatgaggtgc ctctggagac cccacacgtg     600
cactctcggg ccctagccc actgtactcc gtggagttct ctgaggagcc atttggcgtg     660
atcgtgcggc gccagctgga tggacgcgtg ctgctgaaca ccacagtggc cccctgttc     720
tttgccgacc agttcctcca gctgagcaca tccctgccct cccagtatat caccggcctg     780
gccgagcacc tgtctcctct gatgctgtct accagctgga caaggatcac cctgtggaac     840
agagacctgg caccaacccc tggcgcaaat ctgtacggca gccacccttt ctatctggcc     900
ctggaggatg gaggctccgc ccacggcgtg tttctgctga actctaatgc catggacgtg     960
gtgctccagc aagcccgc cctgtcctgg cggtctaccg gcggcatcct ggacgtgtac    1020
atcttcctgg gccctgagcc aaagtccgtg gtgcagcagt acctggacgt ggtgggctat    1080
cctttcatgc ccccttactg gggactggga tttcacctgt gccgctgggg ctattctagc    1140
acagccatca cccggcaggt ggtggagaac atgacccgcg cccactttcc actggatgtg    1200
cagtggaatg acctggatta catggactcc aggagagact tcaccttcaa caaggacggc    1260
ttcagggatt tcccgccat ggtgcaggag ctgcaccagg gcggcggcg ctacatgatg    1320
atcgtggacc ccgccatctc ctctagcgga cctgccggca gctacagacc atatgacgag    1380
ggcctgagga gaggcgtgtt catcacaaac gagaccggcc agcctctgat cggcaaggtc    1440
tggccaggct ccaccgcctt cccagacttc accaatccaa ccgccctggc ctggtgggag    1500
gacatggtgg ccgagttcca cgaccagtg cctttttgatg gcatgtggat cgacatgaac    1560
gagccatcta atttcatcag gggcagcgag gacggctgcc ccaacaatga gctggagaac    1620
ccaccatatg tgcctggcgt ggtgggaggc accctccagg cagcaaccat ctgtgcctcc    1680
tctcaccagt ttctgtctac acactataac ctgcacaatc tgtacggact gaccgaggca    1740
atcgccagcc acagagccct ggtgaaggcc aggggcacaa gaccttcgt gatctccagg    1800
tctaccttg ccggacacgg cagatacgca ggacactgga ccggcgacgt gtggagcagc    1860
tgggagcagc tggcctctag cgtgccagag atcctccagt tcaacctgct gggcgtgccc    1920
ctggtgggag cagacgtgtg cggctttctg ggcaatacat ccgaggagct gtgcgtgagg    1980
tggacccagc tgggagcctt ctatcccttc atgcgcaacc acaatagcct gctgtccctg    2040
```

| | |
|---|---|
| cctcaggagc catacagctt ctccgagcct gcacagcagg caatgaggaa ggccctgaca | 2100 |
| ctgcgctatg ccctgctgcc acacctgtac accctgtttc accaggcaca cgtggcagga | 2160 |
| gagacagtgg cccggcccct gttcctggag tttcctaagg attcctctac ctggacagtg | 2220 |
| gaccaccagc tgctgtgggg agaggccctg ctgatcaccc ccgtgctcca ggcaggcaag | 2280 |
| gcagaggtga caggctattt ccctctgggc acatggtacg acctccagac cgtgccagtg | 2340 |
| gaggccctgg gcagcctgcc tccaccacct gccgccccc gcgagcctgc catccactcc | 2400 |
| gagggacagt gggtgacact gccagcacct ctggacacca tcaacgtgca cctgagggcc | 2460 |
| ggctatatca tccccctcca gggccctggc ctgaccacaa ccgagtccag acagcagcca | 2520 |
| atggccctgg ccgtggccct gaccaaggga ggcgaggcca ggggcgagct gttctgggac | 2580 |
| gatggcgagt ctctggaggt gctggagaga ggcgcctaca cacaggtcat cttcctggcc | 2640 |
| aggaacaata caatcgtgaa tgagctggtg agagtgacct ctgagggagc aggactccag | 2700 |
| ctccagaagg tgacagtgct gggagtggca accgcaccac agcaggtgct gagcaacggc | 2760 |
| gtgcccgtga gcaatttcac atactcccct gataccaagg tgctggacat ctgcgtgagc | 2820 |
| ctgctgatgg gcgagcagtt tctggtgtcc tggtgttga | 2859 |

<210> SEQ ID NO 10
<211> LENGTH: 8523
<212> TYPE: DNA
<213> ORGANISM: Artificial Sequence
<220> FEATURE:
<223> OTHER INFORMATION: Dual promoter lentiviral vector

<400> SEQUENCE: 10

| | |
|---|---|
| aaattgtaag cgttaatatt ttgttaaaat tcgcgttaaa ttttttgttaa atcagctcat | 60 |
| tttttaacca ataggccgaa atcggcaaaa tcccttataa atcaaaagaa tagaccgaga | 120 |
| tagggttgag tgttgttcca gtttggaaca agagtccact attaaagaac gtggactcca | 180 |
| acgtcaaagg gcgaaaaacc gtctatcagg gcgatggccc actacgtgaa ccatcaccct | 240 |
| aatcaagttt tttggggtcg aggtgccgta agcactaaa tcggaaccct aaagggagcc | 300 |
| cccgatttag agcttgacgg ggaaagccgg cgaacgtggc gagaaaggaa gggaagaaag | 360 |
| cgaaaggagc gggcgctagg gcgctggcaa gtgtagcggt cacgctgcgc gtaaccacca | 420 |
| cacccgccgc gcttaatgcg ccgctacagg gcgcgtccat tcgccattca ggctgcgcaa | 480 |
| ctgttgggaa gggcgatcgg tgcgggcctc ttcgctatta cgccagctgg cgaaaggggg | 540 |
| atgtgctgca aggcgattaa gttgggtaac gccagggttt cccagtcac gacgttgtaa | 600 |
| aacgacggcc agtgaattgt aatacgactc actatagggc gaattgggcc cgacgtcgca | 660 |
| tgcttggaag gctaattca ctcccaaaga agacaagata tccttgatct gtggatctac | 720 |
| cacacacaag gctacttccc tgattagcag aactacacac cagggccagg ggtcagatat | 780 |
| ccactgacct ttggatggtg ctacaagcta gtaccagttg agccagataa ggtagaagag | 840 |
| gccaataaag gagagaacac cagcttgtta caccctgtga gcctgcatgg gatggatgac | 900 |
| ccggagagag aagtgttaga gtggaggttt gacagccgcc tagcatttca tcacgtggcc | 960 |
| cgagagctgc atccggagta cttcaagaac tgctgatatc gagcttgcta caagggactt | 1020 |
| tccgctgggg actttccagg gaggcgtggc ctgggcggga ctggggagtg gcgagccctc | 1080 |
| agatcctgca tataagcagc tgctttttgc ctgtactggg tctctctggt tagaccagat | 1140 |
| ctgagcctgg gagctctctg gctaactagg gaacccactg cttaagcctc aataaagctt | 1200 |
| gccttgagtg cttcaagtag tgtgtgcccg tctgttgtgt gactctggta actagagatc | 1260 |

```
cctcagaccc ttttagtcag tgtggaaaat ctctagcagt ggcgcccgaa cagggacttg    1320
aaagcgaaag ggaaaccaga ggagctctct cgacgcagga ctcggcttgc tgaagcgcgc    1380
acggcaagag gcgaggggcg gcgactggtg agtacgccaa aaattttgac tagcggaggc    1440
tagaaggaga gagatgggtg cgagagcgtc agtattaagc gggggagaat tagatcgcga    1500
tgggaaaaaa ttcggttaag gccagggggA agaaaaaat ataaattaaa acatatagta    1560
tgggcaagca gggagctaga acgattcgca gttaatcctg gcctgttaga acatcagaa    1620 ggctgtagac aaatactggg acagctacaa ccatcccttc agacaggatc agaagaactt    1680
agatcattat ataatacagt agcaaccctc tattgtgtgc atcaaaggat agagataaaa    1740
gacaccaagg aagctttaga caagatagag gaagagcaaa acaaaagtaa gaccaccgca    1800
cagcaagcgg ccgctgatct tcagacctgg aggaggagat atgagggaca attggagaag    1860
tgaattatat aaatataaag tagtaaaaat tgaaccatta ggagtagcac ccaccaaggc    1920
aaagagaaga gtggtgcaga gagaaaaaag agcagtggga ataggagctt tgttccttgg    1980
gttcttggga gcagcaggaa gcactatggg cgcagcgtca atgacgctga cggtacaggc    2040
cagacaatta ttgtctggta tagtgcagca gcagaacaat ttgctgaggg ctattgaggc    2100
gcaacagcat ctgttgcaac tcacagtctg ggcatcaag cagctccagg caagaatcct    2160
ggctgtggaa agatacctaa aggatcaaca gctcctgggg atttggggtt gctctggaaa    2220
actcatttgc accactgctg tgccttggaa tgctagttgg agtaataaat ctctggaaca    2280
gatttggaat cacacgacct ggatggagtg ggacagagaa attaacaatt acacaagctt    2340
aatacactcc ttaattgaag aatcgcaaaa ccagcaagaa aagaatgaac aagaattatt    2400
ggaattagat aaatgggcaa gtttgtggaa ttggtttaac ataacaaatt ggctgtggta    2460
tataaaatta ttcataatga tagtaggagg cttggtaggt ttaagaatag ttttgctgt    2520 actttctata gtgaatagag ttaggcaggg atattcacca ttatcgtttc agacccacct    2580
cccaaccccg aggggacccg acaggcccga aggaatagaa gaagaaggtg gagagagaga    2640
cagagacaga tccattcgat tagtgaacgg atctcgacgg gatcgatttt aaaagaaaag    2700
gggggattgg ggggtacagt gcaggggaaa gaatagtaga cataatagca acagacatac    2760
aaactaaaga attacaaaaa caaattacaa aaattcaaaa ttttatcgat aagctttgca    2820
aagatggata agttttaaa cagagaggaa tctttgcagc taatggacct tctaggtctg    2880
accccgtacg cctcgagaga tctgatcata atcagccata ccacatttgt agaggtttta    2940
cttgctttaa aaaacctccc acacctcccc ctgaacctga aacataaaat gaatgcaatt    3000
gttgttgtta acttgtttat tgcagcttat aatggttaca ataaggcaa tagcatcaca    3060 aatttcacaa ataaggcatt ttttcactg cattctagtt ttggtttgtc caactcatc    3120 aatgtatctt atcatgtctg gatctcaaat ccctcggaag ctgcgcctgt cttaggttgg    3180
agtgatacat tttatcact tttacccgtc tttggattag cagtagctc tgacggccct    3240 cctgtcttag gttagtgaaa atgtcactc tcttacccgt cattggctgt ccagcttagc    3300
tcgcagggga ggtggtctgc ctgcaggcgg atggcgttaa catatgacaa ctttctcccg    3360
ggtaatctga ccgttcgcta gccctgggga gagaggtcg tgattcggtc aacgagggag    3420
ccgactgccg acgtgcgctc cggaggcttg cagaatgcgg aacaccgcgc gggcaggaac    3480
agggcccaca ctaccgcccc acaccccgcc tcccgcaccg ccccttcccg gccgctgctc    3540
tcggcgcgcc ccgctgagca gccgctattg gccacagccc atcgcggtcg gcgcgctgcc    3600
```

```
attgctccct ggcgctgtcc gtctgcgagg gtactagtga gacgtgcggc ttccgtttgt    3660
cacgtccggc acgccgcgaa ccgcaaggaa ccttcccgac ttaggggcgg agcaggaagc    3720
gtcgccgggg ggcccacaag ggtagcggcg aagatccggg tgacgctgcg aacggacgtg    3780
aagaatgtgc gagacccagg gtcggcgccg ctgcgtttcc cggaaccacg cccagagcag    3840
ccgcgtccct gcgcaaaccc agggctgcca aggaaaaggc gcaaccccaa ccccgtggtt    3900
aattaaggtg aaaggagtgg gaattggctc cggtgcccgt cagtgggcag agcgcacatc    3960
gcccacagtc cccgagaagt tgggggaggg ggtcggcaat tgaaccggtg cctagagaag    4020
gtggcgcggg gtaaactggg aaagtgatgt cgtgtactgg ctccgccttt ttcccgaggg    4080
tgggggagaa ccgtatataa gtgcagtagt cgccgtgaac gttctttttc gcaacgggtt    4140
tgccgccaga acacaggtaa gtgccgtgtg tggttcccgc gggcctggcc tctttacggg    4200
ttatggccct tgcgtgcctt gaattacttc cacctggctg cagtacgtga ttcttgatcc    4260
cgagcttcgg gttggaagtg ggtgggagag ttcgaggcct tgcgcttaag gagcccttc    4320 gcctcgtgct tgagttgagg cctggcctgg gcgctggggc cgccgcgtgc gaatctggtg    4380
gcaccttcgc gcctgtctcg ctgctttcga taagtctcta gccatttaaa attttttgatg  4440 acctgctgcg acgcttttttt tctggcaaga tagtcttgta aatgcgggcc aagatctgca   4500
cactggtatt tcggttttttg gggccgcggg cggcgacggg gcccgtgcgt cccagcgcac    4560
atgttcggcg aggcggggcc tgcgagcgcg gccaccgaga tcggacgggg ggtagtctca    4620
agctggccgg cctgctctgg tgcctggcct cgcgccgccg tgtatcgccc cgccctgggc    4680
ggcaaggctg gccgggtcgg caccagttgc gtgagcggaa agatgccgc ttcccggccc    4740 tgctgcaggg agctcaaaat ggaggacgcg gcgctcggga gagcgggcgg gtgagtcacc    4800
cacacaaagg aaaagggcct ttccgtcctc agccgtcgct tcatgtgact ccacggagta    4860
ccgggcgccg tccaggcacc tcgattagtt ctcgagcttt tggagtacgt cgtctttagg    4920 ttgggggggag gggttttatg cgatggagtt tccccacact gagtgggtgg agactgaagt    4980
taggccagct tggcacttga tgtaattctc cttggaattt gccctttttg agtttggatc    5040
ttggttcatt ctcaagcctc agacagtggt tcaaagtttt tttcttccat ttcaggtgtc    5100
gtgaggaatt ctgcagtcga cggtaccgcg ggcgcgcccc gggatccaag cttcaattgt    5160
ggtcactcga caatcaacct ctggattaca aaatttgtga agattgact ggtattctta    5220 actatgttgc tccttttacg ctatgtggat acgctgcttt aatgcctttg tatcatgcta    5280
ttgcttcccg tatggctttc attttctcct ccttgtataa atcctggttg ctgtctcttt    5340
atgaggagtt gtggcccgtt gtcaggcaac gtggcgtggt gtgcactgtg tttgctgacg    5400 caaccccac tggttgggc attgccacca cctgtcagct cctttccggg actttcgctt    5460
tccccctccc tattgccacg gcggaactca tcgccgcctg ccttgcccgc tgctggacag    5520
gggctcggct gttgggcact gacaattccg tggtgttgtc ggggaagctg acgtcctttc    5580
catggctgct cgcctgtgtt gccacctgga ttctgcgcgg gacgtccttc tgctacgtcc    5640
cttcggccct caatccagcg gaccttcctt cccgcggcct gctgccggct ctgcggcctc    5700
ttccgcgtct tcgccttcgc cctcagacga gtcggatctc cctttgggcc gcctccccgc    5760
ctgctcgaga cctagaaaaa catggagcaa tcacaagtag caatacagca gctaccaatg    5820
ctgattgtgc ctggctagaa gcacaagagg aggaggaggt gggttttcca gtcacacctc    5880
aggtaccttt aagaccaatg acttacaagg cagctgtaga tcttagccac tttttaaaag    5940 aaaaggggggg actggaaggg ctaattcact cccaacgaag acaagatctg cttttttgctt   6000
```

```
gtactgggtc tctctggtta gaccagatct gagcctggga gctctctggc taactaggga    6060
acccactgct taagcctcaa taaagcttgc cttgagtgct tcaagtagtg tgtgcccgtc    6120
tgttgtgtga ctctggtaac tagagatccc tcagacccct ttagtcagtg tggaaaatct    6180
ctagcagtag tagttcatgt catcttatta ttcagtattt ataacttgca aagaaatgaa    6240
tatcagagag tgagaggacg cgttggatgc atagcttgag tattctatag tgtcacctaa    6300
atagcttggc gtaatcatgg tcatagctgt ttcctgtgtg aaattgttat ccgctcacaa    6360
ttccacacaa catacgagcc ggaagcataa agtgtaaagc ctggggtgcc taatgagtga    6420
gctaactcac attaattgcg ttgcgctcac tgcccgcttt ccagtcggga aacctgtcgt    6480
gccagctgca ttaatgaatc ggccaacgcg cggggagagg cggtttgcgt attgggcgct    6540
cttccgcttc ctcgctcact gactcgctgc gctcggtcgt tcggctgcgg cgagcggtat    6600
cagctcactc aaaggcggta atacggttat ccacagaatc aggggataac gcaggaaaga    6660
acatgtgagc aaaaggccag caaaaggcca ggaaccgtaa aaaggccgcg ttgctggcgt    6720
ttttccatag gctccgcccc cctgacgagc atcacaaaaa tcgacgctca agtcagaggt    6780
ggcgaaaccc gacaggacta taaagatacc aggcgtttcc ccctggaagc tccctcgtgc    6840
gctctcctgt tccgaccctg ccgcttaccg gatacctgtc cgcctttctc ccttcgggaa    6900
gcgtggcgct ttctcatagc tcacgctgta ggtatctcag ttcggtgtag tcgttcgct    6960
ccaagctggg ctgtgtgcac gaaccccccg ttcagcccga ccgctgcgcc ttatccggta    7020
actatcgtct tgagtccaac ccggtaagac acgacttatc gccactggca gcagccactg    7080
gtaacaggat tagcagagcg aggtatgtag gcggtgctac agagttcttg aagtggtggc    7140
ctaactacgg ctacactaga agaacagtat ttggtatctg cgctctgctg aagccagtta    7200
ccttcggaaa aagagttggt agctcttgat ccggcaaaca aaccaccgct ggtagcggtg    7260
gtttttttgt ttgcaagcag cagattacgc gcagaaaaaa aggatctcaa gaagatcctt    7320
tgatcttttc tacggggtct gacgctcagt ggaacgaaaa ctcacgttaa gggattttgg    7380
tcatgagatt atcaaaaagg atcttcacct agatcctttt aaattaaaaa tgaagtttta    7440
aatcaatcta agtatatat gagtaaactt ggtctgacag ttaccaatgc ttaatcagtg    7500
aggcacctat ctcagcgatc tgtctatttc gttcatccat agttgcctga ctccccgtcg    7560
tgtagataac tacgatacgg gagggcttac catctggccc cagtgctgca atgataccgc    7620
gagacccacg ctcaccggct ccagatttat cagcaataaa ccagccagcc ggaagggccg    7680
agcgcagaag tggtcctgca actttatccg cctccatcca gtctattaat tgttgccggg    7740
aagctagagt aagtagttcg ccagttaata gtttgcgcaa cgttgttgcc attgctacag    7800
gcatcgtggt gtcacgctcg tcgtttggta tggcttcatt cagctccggt tcccaacgat    7860
caaggcgagt tacatgatcc cccatgttgt gcaaaaaagc ggttagctcc ttcggtcctc    7920
cgatcgttgt cagaagtaag ttggccgcag tgttatcact catggttatg gcagcactgc    7980
ataattctct tactgtcatg ccatccgtaa gatgcttttc tgtgactggt gagtactcaa    8040
ccaagtcatt ctgagaatag tgtatgcggc gaccgagttg ctcttgcccg gcgtcaatac    8100
gggataatac cgcgccacat agcagaactt taaaagtgct catcattgga aaacgttctt    8160
cggggcgaaa actctcaagg atcttaccgc tgttgagatc cagttcgatg taacccactc    8220
gtgcacccaa ctgatcttca gcatctttta ctttcaccag cgtttctggg tgagcaaaaa    8280
caggaaggca aaatgccgca aaaaagggaa taagggcgac acggaaatgt tgaatactca    8340
```

| | |
|---|---:|
| tactcttcct ttttcaatat tattgaagca tttatcaggg ttattgtctc atgagcggat | 8400 |
| acatatttga atgtatttag aaaaataaac aaatagggt tccgcgcaca tttccccgaa | 8460 |
| aagtgccacc tgatgcggtg tgaaataccg cacagatgcg taaggagaaa ataccgcatc | 8520 |
| agg | 8523 |

<210> SEQ ID NO 11
<211> LENGTH: 10025
<212> TYPE: DNA
<213> ORGANISM: Artificial Sequence
<220> FEATURE:
<223> OTHER INFORMATION: Dual promoter lentiviral vector comprising
      IMPDH2(IY) resistance gene

<400> SEQUENCE: 11

| | |
|---|---:|
| aaattgtaag cgttaatatt ttgttaaaat tcgcgttaaa ttttgttaa atcagctcat | 60 |
| tttttaacca ataggccgaa atcggcaaaa tcccttataa atcaaaagaa tagaccgaga | 120 |
| tagggttgag tgttgttcca gtttggaaca agagtccact attaaagaac gtggactcca | 180 |
| acgtcaaagg gcgaaaaacc gtctatcagg gcgatggccc actacgtgaa ccatcaccct | 240 |
| aatcaagttt ttggggtcg aggtgccgta aagcactaaa tcggaaccct aaagggagcc | 300 |
| cccgatttag agcttgacgg ggaaagccgg cgaacgtggc gagaaaggaa gggaagaaag | 360 |
| cgaaaggagc gggcgctagg gcgctggcaa gtgtagcggt cacgctgcgc gtaaccacca | 420 |
| cacccgccgc gcttaatgcg ccgctacagg gcgcgtccat tcgccattca ggctgcgcaa | 480 |
| ctgttgggaa gggcgatcgg tgcgggcctc ttcgctatta cgccagctgg cgaaaggggg | 540 |
| atgtgctgca aggcgattaa gttgggtaac gccagggttt tcccagtcac gacgttgtaa | 600 |
| aacgacggcc agtgaattgt aatacgactc actatagggc gaattgggcc cgacgtcgca | 660 |
| tgcttggaag ggctaattca ctcccaaaga agacaagata tccttgatct gtggatctac | 720 |
| cacacacaag gctacttccc tgattagcag aactacacac cagggccagg ggtcagatat | 780 |
| ccactgacct ttggatggtg ctacaagcta gtaccagttg agccagataa ggtagaagag | 840 |
| gccaataaag gagagaacac cagcttgtta caccctgtga gcctgcatgg gatggatgac | 900 |
| ccggagagag aagtgttaga gtggaggttt gacagccgcc tagcatttca tcacgtggcc | 960 |
| cgagagctgc atccggagta cttcaagaac tgctgatatc gagcttgcta caagggactt | 1020 |
| tccgctgggg actttccagg gaggcgtggc ctgggcggga ctggggagtg gcgagccctc | 1080 |
| agatcctgca tataagcagc tgctttttgc ctgtactggg tctctctggt tagaccagat | 1140 |
| ctgagcctgg gagctctctg gctaactagg gaacccactg cttaagcctc aataaagctt | 1200 |
| gccttgagtg cttcaagtag tgtgtgcccg tctgttgtgt gactctggta actagagatc | 1260 |
| cctcagaccc ttttagtcag tgtggaaaat ctctagcagt ggcgcccgaa cagggacttg | 1320 |
| aaagcgaaag ggaaaccaga ggagctctct cgacgcagga ctcggcttgc tgaagcgcgc | 1380 |
| acggcaagag gcgaggggcg gcgactggtg agtacgccaa aattttgac tagcggaggc | 1440 |
| tagaaggaga gagatgggtg cgagagcgtc agtattaagc gggggagaat tagatcgcga | 1500 |
| tgggaaaaaa ttcggttaag gccagggga aagaaaaaat ataaattaaa acatatagta | 1560 |
| tgggcaagca gggagctaga acgattcgca gttaatcctg gcctgttaga acatcagaa | 1620 |
| ggctgtagac aaatactggg acagctacaa ccatcccttc agacaggatc agaagaactt | 1680 |
| agatcattat ataatacagt agcaaccctc tattgtgtgc atcaaaggat agagataaaa | 1740 |
| gacaccaagg aagctttaga caagatagag gaagagcaaa acaaaagtaa gaccaccgca | 1800 |

```
cagcaagcgg ccgctgatct tcagacctgg aggaggagat atgagggaca attggagaag    1860
tgaattatat aaatataaag tagtaaaaat tgaaccatta ggagtagcac ccaccaaggc    1920
aaagagaaga gtggtgcaga gagaaaaaag agcagtggga ataggagctt tgttccttgg    1980
gttcttggga gcagcaggaa gcactatggg cgcagcgtca atgacgctga cggtacaggc    2040
cagacaatta ttgtctggta tagtgcagca gcagaacaat ttgctgaggg ctattgaggc    2100
gcaacagcat ctgttgcaac tcacagtctg gggcatcaag cagctccagg caagaatcct    2160
ggctgtggaa agatacctaa aggatcaaca gctcctgggg atttggggtt gctctggaaa    2220
actcatttgc accactgctg tgccttggaa tgctagttgg agtaataaat ctctggaaca    2280
gatttggaat cacacgacct ggatggagtg ggacagagaa attaacaatt acacaagctt    2340
aatacactcc ttaattgaag aatcgcaaaa ccagcaagaa aagaatgaac aagaattatt    2400
ggaattagat aaatgggcaa gtttgtggaa ttggtttaac ataacaaatt ggctgtggta    2460
tataaaatta ttcataatga tagtaggagg cttggtaggt ttaagaatag ttttgctgt    2520 actttctata gtgaatagag ttaggcaggg atattcacca ttatcgtttc agacccacct    2580
cccaaccccg aggggacccg acaggcccga aggaatagaa gaagaaggtg gagagagaga    2640
cagagacaga tccattcgat tagtgaacgg atctcgacgg gatcgatttt aaaagaaaag    2700
gggggattgg ggggtacagt gcaggggaaa gaatagtaga cataatagca acagacatac    2760
aaactaaaga attacaaaaa caaattacaa aaattcaaaa ttttatcgat aagctttgca    2820
aagatggata agttttaaa cagagaggaa tctttgcagc taatggacct tctaggtctg    2880
accccgtacg cctcgagaga tctgatcata atcagccata ccacatttgt agaggtttta    2940
cttgctttaa aaaacctccc acacctcccc ctgaacctga acataaaat gaatgcaatt    3000 gttgttgtta acttgtttat tgcagcttat aatggttaca aataaggcaa tagcatcaca    3060
aatttcacaa ataaggcatt tttttcactg cattctagtt ttggtttgtc caaactcatc    3120
aatgtatctt atcatgtctg gatctcaaat ccctcggaag ctgcgcctgt cttaggttgg    3180
agtgatacat ttttatcact tttacccgtc tttggattag gcagtagctc tgacggccct    3240
cctgtcttag gttagtgaaa aatgtcactc tcttacccgt cattggctgt ccagcttagc    3300
tcgcagggga ggtggtctgc ctgcaggtta gaacagtctc ttttcgtatg agtgcagtga    3360
gtggacgccg ccttcgacct gggctgaaga agttcttttc tcgaacttca gttcgccgga    3420
atacatcatt gcccgcacct gtgtcaggct cttagcgccg atatcctggc atgaatgctg    3480
aattccggcg atcaggtaag gcacgaattt gtgaatactg cccttatcct ggacagctcc    3540
agacacgccc tgtgcgactt tgatcttgtc tgcctcggaa aaataccgt tctgagagga    3600 cagatgctta tccatggcgt ccagtgaccc catgccccta tatttcttca gtctgaaccc    3660
atcactaaag aagtactcgc cgggggcttc tgtggttgca gccagcaggc tgcccatcat    3720
cactgtgctt gccccagag ccagggcttt tgcgatgtgg cccacattct gaattccccc    3780
gtcagcgatc actgggactc cgaatctccg ggcatactcg tacaccttgt agacagcagt    3840
tgcctgaggt cgtccacagg ccagcacttc ctgaatgatg cagattgatc cactccccat    3900
tccgaccctc agagcatcca ctcctgcgtc aatcaggttt ttggcctggg ctgcggtcac    3960
gacattgcct ccgatgacct gcagatttgg gtacttgtcc ttaatgtact tgatcatatt    4020
aatctggaag atgctgtttc cctggcttga atccagcacg accacgtcca cccctgcctg    4080
agccagcaga tccaggcgat atttatcgtc ctcgtgtgtg ccaatagcgg ctccacacag    4140
cagctgtttc tttgcgtcct tactagccag agggtaatct cgatttttct tcaggtcggt    4200
```

```
gcgggcaatg attgccacca gctcatcgtc ttcattcacg ataggcagtt ttcctttctt    4260
agaccgctgc agaatctcgt tggcttcctt cagtgtgatg ccggcaggtg cgaccaccag    4320
atcttcgcgt ttggtcataa tctcttccag aaaacagtca tgctcttcct ccttcaggaa    4380
atcgatgtct cgactagaaa tgattccac cagtcggctg cccattcgtc cagtatctgt     4440
aatggggatg ccgcaaaatc cgtgcctagc tttggcctcg aacacatcgc ggaccctgtc    4500 cttgggctc aggaccactg ggtcggtgat aaagccctgt tcgtatttct tcacctttct     4560
gacctcattg gcctgaaatt ctggagtgca gttatggtga atgaaccga tcccgcctgt     4620 cagtgccata gcaatggcca tgccagcctc ggtgacagtg tccatagggg agctcaccag    4680
gggtgtcttc agggtgattt tcttggtcag ggcagaagtc agatccacct ggtctgcggt    4740
aaaatcaata tagccgggca ggatcaggaa gtcgttgtaa gtcagcccgt ctccacaatt    4800
aaacagctgc tgggcggtca gtccatcatc agggacatag aagtgcctc cagaaatcag    4860 gtagtcggcc atggtggcgc tagccctggg gagagaggtc ggtgattcgg tcaacgaggg    4920
agccgactgc cgacgtgcgc tccggaggct tgcagaatgc ggaacaccgc gcgggcagga    4980
acagggccca cactaccgcc ccacacccg cctcccgcac cgcccttcc cggccgctgc      5040 tctcggcgcg ccccgctgag cagccgctat tggccacagc ccatcgcggt cggcgcgctg    5100
ccattgctcc ctggcgctgt ccgtctgcga gggtactagt gagacgtgcg gcttccgttt    5160
gtcacgtccg gcacgccgcg aaccgcaagg aaccttcccg acttaggggc ggagcaggaa    5220
gcgtcgccgg ggggcccaca agggtagcgg cgaagatccg ggtgacgctg cgaacggacg    5280
tgaagaatgt gcgagaccca gggtcggcgc cgctgcgttt cccggaacca cgcccagagc    5340
agccgcgtcc ctgcgcaaac ccagggctgc caaggaaaag gcgcaacccc aaccccgtgg    5400
ttaattaagg tgaaaggagt gggaattggc tccggtgccc gtcagtgggc agagcgcaca    5460
tcgcccacag tccccgagaa gttgggggga ggggtcggca attgaaccgg tgcctagaga    5520
aggtggcgcg gggtaaactg ggaaagtgat gtcgtgtact ggctccgcct ttttcccgag    5580
ggtgggggag aaccgtatat aagtgcagta gtcgccgtga acgttctttt tcgcaacggg    5640
tttgccgcca gaacacaggt aagtgccgtg tgtggttccc gcgggcctgg cctctttacg    5700
ggttatggcc cttgcgtgcc ttgaattact tccacctggc tgcagtacgt gattcttgat    5760
cccgagcttc gggttggaag tgggtgggag agttcgaggc cttgcgctta aggagccccct   5820 tcgcctcgtg cttgagttga ggcctggcct gggcgctggg gccgccgcgt gcgaatctgg    5880
tggcaccttc gcgcctgtct cgctgctttc gataagtctc tagccattta aaattttga     5940 tgacctgctg cgacgctttt tttctggcaa gatagtcttg taaatgcggg ccaagatctg    6000
cacactggta tttcggtttt tggggccgcg ggcggcgacg gggcccgtgc gtcccagcgc    6060
acatgttcgg cgaggcgggg cctgcgagcg cggccaccga gaatcggacg ggggtagtct    6120
caagctggcc ggcctgctct ggtgcctggc ctcgcgccgc cgtgtatcgc ccgcccctgg    6180
gcggcaaggc tggcccggtc ggcaccagtt gcgtgagcgg aaagatggcc gcttcccggc    6240
cctgctgcag ggagctcaaa atggaggacg cggcgctcgg gagagcgggc gggtgagtca    6300
cccacacaaa ggaaaagggc cttccgtcc tcagccgtcg cttcatgtga ctccacggag     6360
taccgggcgc cgtccaggca cctcgattag ttctcgagct tttggagtac gtcgtcttta    6420
ggttgggggg aggggttta tgcgatgag tttccccaca ctgagtgggt ggagactgaa      6480
gttaggccag cttggcactt gatgtaattc tccttggaat ttgcccttt tgagtttgga    6540
```

```
tcttggttca ttctcaagcc tcagacagtg gttcaaagtt ttttctcc  atttcaggtg    6600
tcgtgaggaa ttctgcagtc gacggtaccg cgggcgcgcc ccgggatcca agcttcaatt    6660
gtggtcactc gacaatcaac ctctggatta caaaatttgt gaaagattga ctggtattct    6720
taactatgtt gctccttta cgctatgtgg atacgctgct ttaatgcctt tgtatcatgc    6780
tattgcttcc cgtatggctt tcattttctc ctccttgtat aaatcctggt tgctgtctct    6840
ttatgaggag ttgtggcccg ttgtcaggca acgtggcgtg gtgtgcactg tgtttgctga    6900
cgcaaccccc actggttggg gcattgccac cacctgtcag ctccttccg  ggactttcgc    6960
tttcccctc  cctattgcca cggcggaact catcgccgcc tgccttgccc gctgctggac    7020
aggggctcgg ctgttgggca ctgacaattc cgtggtgttg tcggggaagc tgacgtcctt    7080
tccatggctg ctcgcctgtg ttgccacctg gattctgcgc gggacgtcct tctgctacgt    7140
cccttcggcc ctcaatccag cggaccttcc ttcccgcggc ctgctgccgg ctctgcggcc    7200
tcttccgcgt cttcgccttc gccctcagac gagtcggatc tccctttggg ccgcctcccc    7260
gcctgctcga gacctagaaa aacatggagc aatcacaagt agcaatacag cagctaccaa    7320
tgctgattgt gcctggctag aagcacaaga ggaggaggag gtgggttttc cagtcacacc    7380
tcaggtacct ttaagaccaa tgacttacaa ggcagctgta gatcttagcc acttttaaa    7440
agaaaagggg ggactggaag ggctaattca ctcccaacga agacaagatc tgcttttgc    7500
ttgtactggg tctctctggt tagaccagat ctgagcctgg gagctctctg ctaactagg    7560
gaacccactg cttaagcctc aataaagctt gccttgagtg cttcaagtag tgtgtgcccg    7620
tctgttgtgt gactctggta actagagatc cctcagaccc ttttagtcag tgtggaaaat    7680
ctctagcagt agtagttcat gtcatcttat tattcagtat ttataacttg caaagaaatg    7740
aatatcagag agtgagagga cgcgttggat gcatagcttg agtattctat agtgtcacct    7800
aaatagcttg gcgtaatcat ggtcatagct gttttcctgtg tgaaattgtt atccgctcac    7860
aattccacac aacatacgag ccggaagcat aaagtgtaaa gcctggggtg cctaatgagt    7920
gagctaactc acattaattg cgttgcgctc actgcccgct ttccagtcgg gaaacctgtc    7980
gtgccagctg cattaatgaa tcggccaacg cgcggggaga ggcggtttgc gtattgggcg    8040
ctcttccgct tcctcgctca ctgactcgct gcgctcggtc gttcggctgc ggcgagcggt    8100
atcagctcac tcaaaggcgg taatacggtt atccacagaa tcaggggata acgcaggaaa    8160
gaacatgtga gcaaaaggcc agcaaaaggc caggaaccgt aaaaaggccg cgttgctggc    8220
gttttccat aggctccgcc cccctgacga gcatcacaaa aatcgacgct caagtcagag    8280
gtggcgaaac ccgacaggac tataaagata ccaggcgttt ccccctggaa gctccctcgt    8340
gcgctctcct gttccgaccc tgccgcttac cggatacctg tccgcctttc tcccttcggg    8400
aagcgtggcg ctttctcata gctcacgctg taggtatctc agttcggtgt aggtcgttcg    8460
ctccaagctg ggctgtgtgc acgaaccccc cgttcagccc gaccgctgcg ccttatccgg    8520
taactatcgt cttgagtcca acccggtaag acacgactta tcgccactgg cagcagccac    8580
tggtaacagg attagcagag cgaggtatgt aggcggtgct acagagttct tgaagtggtg    8640
gcctaactac ggctacacta gaagaacagt atttggtatc tgcgctctgc tgaagccagt    8700
taccttcgga aaaagagttg gtagctcttg atccggcaaa caaaccaccg ctggtagcgg    8760
tggtttttt gtttgcaagc agcagattac gcgcagaaaa aaggatctc  aagaagatcc    8820
tttgatcttt tctacggggt ctgacgctca gtggaacgaa aactcacgtt aagggatttt    8880
ggtcatgaga ttatcaaaaa ggatcttcac ctagatcctt ttaaattaaa aatgaagttt    8940
```

```
taaatcaatc taaagtatat atgagtaaac ttggtctgac agttaccaat gcttaatcag    9000
tgaggcacct atctcagcga tctgtctatt tcgttcatcc atagttgcct gactcccgt    9060 cgtgtagata actacgatac gggagggctt accatctggc cccagtgctg caatgatacc    9120
gcgagaccca cgctcaccgg ctccagattt atcagcaata aaccagccag ccggaagggc    9180
cgagcgcaga agtggtcctg caactttatc cgcctccatc cagtctatta attgttgccg    9240
ggaagctaga gtaagtagtt cgccagttaa tagtttgcgc aacgttgttg ccattgctac    9300
aggcatcgtg gtgtcacgct cgtcgtttgg tatggcttca ttcagctccg gttcccaacg    9360
atcaaggcga gttacatgat cccccatgtt gtgcaaaaaa gcggttagct ccttcggtcc    9420
tccgatcgtt gtcagaagta agttggccgc agtgttatca ctcatggtta tggcagcact    9480
gcataattct cttactgtca tgccatccgt aagatgcttt tctgtgactg gtgagtactc    9540
aaccaagtca ttctgagaat agtgtatgcg gcgaccgagt tgctcttgcc cggcgtcaat    9600
acgggataat accgcgccac atagcagaac tttaaaagtg ctcatcattg gaaaacgttc    9660
ttcggggcga aaactctcaa ggatcttacc gctgttgaga tccagttcga tgtaacccac    9720
tcgtgcaccc aactgatctt cagcatcttt tactttcacc agcgtttctg ggtgagcaaa    9780
aacaggaagg caaaatgccg caaaaaaggg aataagggcg acacggaaat gttgaatact    9840
catactcttc cttttttcaat attattgaag catttatcag ggttattgtc tcatgagcgg    9900
atacatattt gaatgtattt agaaaaataa acaaataggg gttccgcgca catttccccg    9960
aaaagtgcca cctgatgcgg tgtgaaatac cgcacagatg cgtaaggaga aaataccgca   10020
tcagg                                                                10025
```